US012428450B2

(12) United States Patent
Yamada et al.

(10) Patent No.: US 12,428,450 B2
(45) Date of Patent: Sep. 30, 2025

(54) COMPOUND HAVING AFFINITY SUBSTANCE TO ANTIBODY, CLEAVABLE PORTION, AND REACTIVE GROUP, OR SALT THEREOF

(71) Applicant: Ajinomoto Co., Inc., Tokyo (JP)

(72) Inventors: Kei Yamada, Kawasaki (JP); Yoshihiko Matsuda, Kawasaki (JP); Kazutoshi Takahashi, Kawasaki (JP); Natsuki Shikida, Kawasaki (JP); Kazutaka Shimbo, Kawasaki (JP); Hayato Nagano, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1123 days.

(21) Appl. No.: 17/241,585

(22) Filed: Apr. 27, 2021

(65) Prior Publication Data

US 2021/0300972 A1    Sep. 30, 2021

Related U.S. Application Data

(63) Continuation of application No. PCT/JP2019/042785, filed on Oct. 31, 2019.

(30) Foreign Application Priority Data

Oct. 31, 2018   (JP) ................................. 2018-205225

(51) Int. Cl.
    *C07K 14/31* (2006.01)
    *A61K 47/68* (2017.01)
    *C07K 16/32* (2006.01)

(52) U.S. Cl.
    CPC .............. *C07K 14/31* (2013.01); *C07K 16/32* (2013.01); *C07K 2317/24* (2013.01); *C07K 2319/00* (2013.01)

(58) Field of Classification Search
    None
    See application file for complete search history.

(56) References Cited

U.S. PATENT DOCUMENTS

| 5,122,368 A | 6/1992 | Greenfield et al. |
| 5,622,929 A | 4/1997 | Willner et al. |
| 5,824,805 A | 10/1998 | King et al. |
| 6,013,763 A | 1/2000 | Braisted et al. |
| 6,090,597 A | 7/2000 | Hirano et al. |
| 6,197,927 B1 | 3/2001 | Braisted et al. |
| 6,214,345 B1 | 4/2001 | Firestone et al. |
| 10,835,585 B2* | 11/2020 | Fritsch ............... A61K 39/0011 |
| 12,024,549 B2* | 7/2024 | Yamada ............ A61K 47/68033 |
| 2003/0175285 A1 | 9/2003 | Klinguer-Hamour et al. |
| 2005/0238649 A1 | 10/2005 | Doronina et al. |
| 2006/0074008 A1 | 4/2006 | Senter et al. |
| 2007/0160534 A1 | 7/2007 | Dennis et al. |
| 2011/0293644 A1 | 12/2011 | Anderson et al. |
| 2018/0141976 A1 | 5/2018 | Ito |
| 2020/0190165 A1 | 6/2020 | Yamada et al. |
| 2021/0139541 A1* | 5/2021 | Matsuda ............... C07K 14/001 |
| 2021/0139549 A1* | 5/2021 | Yamada .................... C07K 7/08 |
| 2024/0000964 A1* | 1/2024 | Fujii ................... A61K 49/0058 |
| 2024/0000965 A1* | 1/2024 | Hatada .................... A61K 47/65 |
| 2024/0115719 A1* | 4/2024 | Fujii .................... C07K 14/001 |

FOREIGN PATENT DOCUMENTS

| CN | 108101825 A | 6/2018 |
| EP | 3470418 | 4/2019 |
| JP | 09-322774 | 12/1997 |
| JP | 2003-528112 | 9/2003 |
| JP | 2007-289200 | 11/2007 |
| JP | 2012-510431 | 5/2012 |
| WO | 02/083180 | 10/2002 |
| WO | 2004/010957 | 2/2004 |
| WO | 2004/043493 | 5/2004 |
| WO | 2005/112919 | 12/2005 |
| WO | 2016/186206 | 11/2016 |
| WO | 2017/217347 | 12/2017 |
| WO | 2018/199337 | 11/2018 |
| WO | 2018/230257 | 12/2018 |

OTHER PUBLICATIONS

Combined Chinese Office Action and Search Report issued Jun. 29, 2024 in Chinese Patent Application No. 201980070996.4 (with unedited, machine-generated English translation), 17 pages.
International Search Report in Application PCT/JP2019/042785 issued Feb. 4, 2020.
Reichert JM, et al., "Monoclonal antibody successes in the clinic". Nature Biotechnol, vol. 23 (2005), pp. 1073-1078.
Kubota T, et al. "Engineered therapeutic antibodies with improved effector functions", Cancer Science, vol. 100, No. 9 (2009) pp. 1566-1572.
Wu AM, et al. "Arming antibodies: prospects and challenges for immunoconjugates", Nature Biotechnol, vol. 23, No. 9 (2005) pp. 1137-1146
Junutula JR, et al. "Site-specific conjugation of a cytotoxic drug to an antibody improves the therapeutic index" Nature Biotechnology, vol. 28, No. 8 (2008) pp. 925-932.

(Continued)

*Primary Examiner* — Ilia I Ouspenski
(74) *Attorney, Agent, or Firm* — Oblon, McClelland, Maier &Neustadt, L.L.P.

(57) ABSTRACT

Compounds having an affinity substance to an antibody, a cleavable portion, and a reactive group, or a salt thereof, are represented by the following Formula (I):

A-L-B—R    (I)

wherein
A is an affinity substance to an antibody,
L is a cleavable linker that is a divalent group comprising a cleavable portion,
B is (a) a divalent group comprising a bioorthogonal functional group or (b) a divalent group comprising no bioorthogonal functional group, and
R is a reactive group to the antibody,
wherein the affinity substance to an antibody is a polypeptide comprising a glutamine residue (Q) at an N-terminal.

6 Claims, 39 Drawing Sheets

Specification includes a Sequence Listing.

(56) References Cited

OTHER PUBLICATIONS

Shen BQ, et al. "Conjugation site modulates the in vivo stability and therapeutic activity of antibody-drug conjugates" Nature Biotechnology, vol. 30, No. 2 (2012) pp. 184-189.
Hofer T, et al. "Molecularly defined antibody conjugation through a selenocysteine interface" Biochemistry (2009) vol. 48 pp. 12047-12057.
Liu W, et al. "Genetic incorporation of unnatural amino acids into proteins in mammalian cells", Nature Methods, vol. 4, No. 3 (2007), pp. 239-244.
S.T. Laughlin, et al. "In Vivo Imaging of Membrane-Associated Glycans in Developing Zebrafish" Science (2008) vol. 320, pp. 664-667.
A.E. Speers, et al. "Chemical Strategies for Activity-Based Proteomics" ChemBioChem (2004) vol. 5, pp. 41-47.
Y. Takaoka, et al. "Protein Organic Chemistry and Applications for Labeling and Engineering in Live-Cell Systems" Angew. Chem. Int. Ed., (2013), vol. 52, pp. 4088-4106.
Dubowchik et al., "Receptor-mediated and enzyme-dependent targeting of cytotoxic anticancer drugs" Pharmacology & Therapeutics (1999) vol. 83 pp. 67-123.

* cited by examiner

FIG. 3

PKSCDKTHTCPPCPAPEXXGXPSVFLFPPKPKDTLMISRTPEVTCVVVDV
SHEDPEVKFNWYVDGVEVHNAKTKPREEQYDSTYRVVSVLTVLHQDWL
NGKEYKCKVSNKALPAPIEKTISKAKGQPREPQVYTLPPSRXEXTKNQVS
LTCLVKGFYPSDIAVEWESNGQPENNYKXTPPVLDSDGSFFLYSKLTVDK
SRWQQGNVFSCSVMHEALHNHYTQKSLSLSPG (SEQ ID NO: 1)

FIG. 4

(1) Amino acid sequence of heavy chain of trastuzumab
EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSRW
GGDGFYAMDYWGQGTLVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREE
QYDSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLS
LSPG (SEQ ID NO: 2)

(2) Amino acid sequence of IgG1 Fc region
IEGRMDPKSCDKTHTCPPCPAPEAEGAPSVFLFPPKPKDTLMISRTPEVT
CVVVDVSHEDPEVKFNWYVDGVEVHNAKTKPREEQYDSTYRVVSVLTVL
HQDWLNGKEYKCKVSNKALPAPIEKTISKAKGQPREPQVYTLPPSRDELT
KNQVSLTCLVKGFYPSDIAVEWESNGQPENNYKATPPVLDSDGSFFLYSK
LTVDKSRWQQGNVFSCSVMHEALHNHYTQKSLSLSPGK (SEQ ID NO: 3)

(3) Amino acid sequence of light chain of trastuzumab
DIQMTQSPSSLSASVGDRVTITCRASQDVNTAVAWYQQKPGKAPKLLIYS
ASFLYSGVPSRFSGSRSGTDFTLTISSLQPEDFATYYCQQHYTTPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC (SEQ ID NO: 4)

SEQUENCE LISTING

```
<160> NUMBER OF SEQ ID NOS: 62

<210> SEQ ID NO 1
<211> LENGTH: 230
<212> TYPE: PRT
<213> ORGANISM: Artificial Sequence
<220> FEATURE:
<223> OTHER INFORMATION: Fc region of human IgG1
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid

<400> SEQUENCE: 1

Pro Lys Ser Cys Asp Lys Thr His Thr Cys Pro Pro Cys Pro Ala Pro
1               5                   10                  15

Glu Xaa Xaa Gly Xaa Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asp Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110
```

```
Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Xaa Glu Xaa Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Xaa Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
            210                 215                 220

Leu Ser Leu Ser Pro Gly
225                 230

<210> SEQ ID NO 2
<211> LENGTH: 449
<212> TYPE: PRT
<213> ORGANISM: Artificial Sequence
<220> FEATURE:
<223> OTHER INFORMATION: Heavy chain of Trastuzumab (humanized IgG1
      monoclonal antibody)

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asp Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 3
<211> LENGTH: 237
<212> TYPE: PRT
<213> ORGANISM: Artificial Sequence
<220> FEATURE:
<223> OTHER INFORMATION: Fc region of human IgG1 antibody

<400> SEQUENCE: 3

Ile Glu Gly Arg Met Asp Pro Lys Ser Cys Asp Lys Thr His Thr Cys
1               5                   10                  15

Pro Pro Cys Pro Ala Pro Glu Ala Glu Gly Ala Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asp Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140
```

-continued

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Ala Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 4
<211> LENGTH: 214
<212> TYPE: PRT
<213> ORGANISM: Artificial Sequence
<220> FEATURE:
<223> OTHER INFORMATION: Light chain of Trastuzumab (humanized IgG1
      monoclonal antibody)

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 34
<212> TYPE: PRT
<213> ORGANISM: Artificial Sequence
<220> FEATURE:
<223> OTHER INFORMATION: Peptide having an affinity to Fc region of
      human IgG.  Two cysteine residues may be linked by disulfide

```
                              bridge.
<220> FEATURE:
<221> NAME/KEY: MISC_FEATURE
<222> LOCATION: (26)..(26)
<223> OTHER INFORMATION: arginine, glutamic acid, or glutamine
<220> FEATURE:
<221> NAME/KEY: MISC_FEATURE
<222> LOCATION: (28)..(28)
<223> OTHER INFORMATION: arginine, glutamic acid, or glutamine

<400> SEQUENCE: 5

Phe Asn Met Gln Cys Gln Arg Arg Phe Tyr Glu Ala Leu His Asp Pro
1               5                   10                  15

Asn Leu Asn Glu Glu Gln Arg Asn Ala Xaa Ile Xaa Ser Ile Arg Asp
            20                  25                  30

Asp Cys

<210> SEQ ID NO 6
<211> LENGTH: 34
<212> TYPE: PRT
<213> ORGANISM: Artificial Sequence
<220> FEATURE:
<223> OTHER INFORMATION: Peptide having an affinity to Fc region of
      human IgG.  Two cysteine residues may be linked by disulfide
      bridge.

<400> SEQUENCE: 6

Phe Asn Met Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

Asp Cys

<210> SEQ ID NO 7
<211> LENGTH: 47
<212> TYPE: PRT
<213> ORGANISM: Artificial Sequence
<220> FEATURE:
<223> OTHER INFORMATION: Peptide having an affinity to Fc region of
      human IgG (CspB6Tev-QZ34C).  Two cysteine residues may be linked
      by disulfide bridge.

<400> SEQUENCE: 7

Gln Glu Thr Asn Pro Thr Glu Asn Leu Tyr Phe Gln Gln Lys Asn Met
1               5                   10                  15

Gln Cys Gln Arg Arg Phe Tyr Glu Ala Leu His Asp Pro Asn Leu Asn
            20                  25                  30

Glu Glu Gln Arg Asn Ala Arg Ile Arg Ser Ile Arg Asp Asp Cys
        35                  40                  45

<210> SEQ ID NO 8
<211> LENGTH: 61
<212> TYPE: PRT
<213> ORGANISM: Artificial Sequence
<220> FEATURE:
<223> OTHER INFORMATION: Peptide having an affinity to Fc region of
      human IgG (QZ34C-60). Two cysteine residues may be linked by
      disulfide bridge.

<400> SEQUENCE: 8

Gln Thr Ala Asn Asp Gln Lys Asn Met Gln Cys Gln Arg Arg Phe Tyr
1               5                   10                  15

Glu Ala Leu His Asp Pro Asn Leu Asn Glu Glu Gln Arg Asn Ala Arg
            20                  25                  30
```

-continued

```
Ile Arg Ser Ile Arg Asp Asp Cys Ser Gln Ser Ala Asn Leu Leu Ala
        35                  40                  45

Glu Ala Gln Gln Leu Asn Asp Ala Gln Ala Pro Gln Ala
    50                  55                  60

<210> SEQ ID NO 9
<211> LENGTH: 37
<212> TYPE: PRT
<213> ORGANISM: Artificial Sequence
<220> FEATURE:
<223> OTHER INFORMATION: Peptide having an affinity to Fc region of
      human IgG (QET-Z34C). Two cysteine residues may be linked by
      disulfide bridge.

<400> SEQUENCE: 9

Gln Glu Thr Lys Asn Met Gln Cys Gln Arg Arg Phe Tyr Glu Ala Leu
1               5                   10                  15

His Asp Pro Asn Leu Asn Glu Glu Gln Arg Asn Ala Arg Ile Arg Ser
            20                  25                  30

Ile Arg Asp Asp Cys
        35

<210> SEQ ID NO 10
<211> LENGTH: 37
<212> TYPE: PRT
<213> ORGANISM: Artificial Sequence
<220> FEATURE:
<223> OTHER INFORMATION: Peptide having an affinity to Fc region of
      human IgG (QET-FNK-Z34C). Two cysteine residues may be linked by
      disulfide bridge.

<400> SEQUENCE: 10

Gln Glu Thr Phe Asn Lys Gln Cys Gln Arg Arg Phe Tyr Glu Ala Leu
1               5                   10                  15

His Asp Pro Asn Leu Asn Glu Glu Gln Arg Asn Ala Arg Ile Arg Ser
            20                  25                  30

Ile Arg Asp Asp Cys
        35

<210> SEQ ID NO 11
<211> LENGTH: 6
<212> TYPE: PRT
<213> ORGANISM: Artificial Sequence
<220> FEATURE:
<223> OTHER INFORMATION: N-terminal six amino acid residues of CspB
      mature protein

<400> SEQUENCE: 11

Gln Glu Thr Asn Pro Thr
1               5

<210> SEQ ID NO 12
<211> LENGTH: 6
<212> TYPE: PRT
<213> ORGANISM: Artificial Sequence
<220> FEATURE:
<223> OTHER INFORMATION: Amino acid sequence of proTev protease
      recognition site

<400> SEQUENCE: 12

Glu Asn Leu Tyr Phe Gln
1               5

<210> SEQ ID NO 13
<211> LENGTH: 234
```

```
<212> TYPE: DNA
<213> ORGANISM: Artificial Sequence
<220> FEATURE:
<223> OTHER INFORMATION: Nucleotide sequence of CspBss-CspB6Tev-QZ34C

<400> SEQUENCE: 13
atgtttaaca accgtatccg cactgcagct ctcgctggtg caatcgcaat ctccaccgca      60
gcttccggcg tagctatccc agcattcgct caggagacca acccaaccga gaacctgtac     120
ttccagcaga gaacatgca gtgtcagcgt cgcttctacg aggccctcca cgaccctaac     180
ctcaacgagg aacagcgtaa cgcgcgtatt cgctccatcc gcgatgactg ctaa           234

<210> SEQ ID NO 14
<211> LENGTH: 77
<212> TYPE: PRT
<213> ORGANISM: Artificial Sequence
<220> FEATURE:
<223> OTHER INFORMATION: Amino acid sequence of CspBss-CspB6Tev-QZ34C

<400> SEQUENCE: 14

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Asn Pro Thr Glu Asn Leu Tyr Phe Gln Gln Lys Asn Met Gln Cys
        35                  40                  45

Gln Arg Arg Phe Tyr Glu Ala Leu His Asp Pro Asn Leu Asn Glu Glu
    50                  55                  60

Gln Arg Asn Ala Arg Ile Arg Ser Ile Arg Asp Asp Cys
65                  70                  75

<210> SEQ ID NO 15
<211> LENGTH: 12
<212> TYPE: PRT
<213> ORGANISM: Artificial Sequence
<220> FEATURE:
<223> OTHER INFORMATION: Fusion amino acid sequence of (a) N-terminal
      six amino acid residues of CspB mature protein (SEQ ID NO:11) and
      (b) amino acid sequence of proTev protease recognition (SEQ ID
      NO:12)

<400> SEQUENCE: 15

Gln Glu Thr Asn Pro Thr Glu Asn Leu Tyr Phe Gln
1               5                   10

<210> SEQ ID NO 16
<211> LENGTH: 261
<212> TYPE: DNA
<213> ORGANISM: Artificial Sequence
<220> FEATURE:
<223> OTHER INFORMATION: Nucleotide sequence of CspAss-QZ34C-60

<400> SEQUENCE: 16
atgaaacgca tgaaatcgct ggctgcggcg ctcaccgtcg ctggggccat gctgccgca      60 cctgtggcaa cggcacagac cgcagacaac cagaagaaca tgcagtgtca gcgtcgcttc    120
tacgaggccc tccacgaccc taacctcaac gaggaacagc gtaacgcgcg tattcgctcc    180
atccgcgatg actgctccca gtccgcaaac ctcctcgcag aggcacagca gctcaacgac    240
gcacaggcac acaggcata a                                               261

<210> SEQ ID NO 17
<211> LENGTH: 86
```

```
<212> TYPE: PRT
<213> ORGANISM: Artificial Sequence
<220> FEATURE:
<223> OTHER INFORMATION: Amino acid sequence of CspAss-QZ34C-60

<400> SEQUENCE: 17

Met Lys Arg Met Lys Ser Leu Ala Ala Ala Leu Thr Val Ala Gly Ala
1               5                   10                  15

Met Leu Ala Ala Pro Val Ala Thr Ala Gln Thr Ala Asp Asn Gln Lys
            20                  25                  30

Asn Met Gln Cys Gln Arg Arg Phe Tyr Glu Ala Leu His Asp Pro Asn
        35                  40                  45

Leu Asn Glu Glu Gln Arg Asn Ala Arg Ile Arg Ser Ile Arg Asp Asp
    50                  55                  60

Cys Ser Gln Ser Ala Asn Leu Leu Ala Glu Ala Gln Leu Asn Asp
65                  70                  75                  80

Ala Gln Ala Pro Gln Ala
                85

<210> SEQ ID NO 18
<211> LENGTH: 204
<212> TYPE: DNA
<213> ORGANISM: Artificial Sequence
<220> FEATURE:
<223> OTHER INFORMATION: Nucleotide sequence of CspBss-QET-Z34C

<400> SEQUENCE: 18
atgtttaaca accgtatccg cactgcagct ctcgctggtg caatcgcaat ctccaccgca      60
gcttccggcg tagctatccc agcattcgct caggagacca agaacatgca gtgtcagcgt    120
cgcttctacg aggccctcca cgaccctaac ctcaacgagg aacagcgtaa cgcgcgtatt    180
cgctccatcc gcgatgactg ctaa                                           204

<210> SEQ ID NO 19
<211> LENGTH: 67
<212> TYPE: PRT
<213> ORGANISM: Artificial Sequence
<220> FEATURE:
<223> OTHER INFORMATION: Amino acid sequence of CspBss-QET-Z34C

<400> SEQUENCE: 19

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Lys Asn Met Gln Cys Gln Arg Arg Phe Tyr Glu Ala Leu His Asp
        35                  40                  45

Pro Asn Leu Asn Glu Glu Gln Arg Asn Ala Arg Ile Arg Ser Ile Arg
    50                  55                  60

Asp Asp Cys
65

<210> SEQ ID NO 20
<211> LENGTH: 204
<212> TYPE: DNA
<213> ORGANISM: Artificial Sequence
<220> FEATURE:
<223> OTHER INFORMATION: Nucleotide sequence of CspBss-QET-FNK-Z34C

<400> SEQUENCE: 20
atgtttaaca accgtatccg cactgcagct ctcgctggtg caatcgcaat ctccaccgca      60
```

```
gcttccggcg tagctatccc agcattcgct caggagacct tcaacaagca gtgtcagcgt    120
cgcttctacg aggccctcca cgaccctaac ctcaacgagg aacagcgtaa cgcgcgtatt    180
cgctccatcc gcgatgactg ctaa                                          204
```

```
<210> SEQ ID NO 21
<211> LENGTH: 67
<212> TYPE: PRT
<213> ORGANISM: Artificial Sequence
<220> FEATURE:
<223> OTHER INFORMATION: Amino acid sequence of CspBss-QET-FNK-Z34C

<400> SEQUENCE: 21

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Phe Asn Lys Gln Cys Gln Arg Arg Phe Tyr Glu Ala Leu His Asp
        35                  40                  45

Pro Asn Leu Asn Glu Glu Gln Arg Asn Ala Arg Ile Arg Ser Ile Arg
    50                  55                  60

Asp Asp Cys
65
```

```
<210> SEQ ID NO 22
<211> LENGTH: 37
<212> TYPE: PRT
<213> ORGANISM: Artificial Sequence
<220> FEATURE:
<223> OTHER INFORMATION: Peptide having an affinity to Fc region of
      human IgG.  Two cysteine residues may be linked by disulfide
      bridge.

<400> SEQUENCE: 22

Gln Glu Thr Phe Asn Met Gln Cys Gln Arg Arg Phe Tyr Glu Ala Leu
1               5                   10                  15

His Asp Pro Asn Leu Asn Lys Glu Gln Arg Asn Ala Arg Ile Arg Ser
            20                  25                  30

Ile Arg Asp Asp Cys
        35
```

```
<210> SEQ ID NO 23
<211> LENGTH: 37
<212> TYPE: PRT
<213> ORGANISM: Artificial Sequence
<220> FEATURE:
<223> OTHER INFORMATION: Peptide having an affinity to Fc region of
      human IgG.  Two cysteine residues may be linked by disulfide
      bridge.

<400> SEQUENCE: 23

Gln Glu Thr Phe Asn Met Gln Cys Gln Arg Arg Phe Tyr Glu Ala Leu
1               5                   10                  15

His Asp Pro Asn Leu Asn Glu Glu Gln Arg Asn Ala Arg Ile Arg Ser
            20                  25                  30

Ile Lys Asp Asp Cys
        35
```

```
<210> SEQ ID NO 24
<211> LENGTH: 20
<212> TYPE: PRT
<213> ORGANISM: Artificial Sequence
```

```
<220> FEATURE:
<223> OTHER INFORMATION: Peptide having an affinity to Fc region of
      human IgG.  Two cysteine residues may be linked by disulfide
      bridge.

<400> SEQUENCE: 24

Gln Glu Thr Arg Gly Asn Cys Ala Tyr His Lys Gly Gln Leu Val Trp
1               5                   10                  15

Cys Thr Tyr His
            20

<210> SEQ ID NO 25
<211> LENGTH: 20
<212> TYPE: PRT
<213> ORGANISM: Artificial Sequence
<220> FEATURE:
<223> OTHER INFORMATION: Peptide having an affinity to Fc region of
      human IgG.  Two cysteine residues may be linked by disulfide
      bridge.

<400> SEQUENCE: 25

Gln Glu Thr Arg Gly Asn Cys Ala Tyr His Lys Gly Gln Ile Ile Trp
1               5                   10                  15

Cys Thr Tyr His
            20

<210> SEQ ID NO 26
<211> LENGTH: 33
<212> TYPE: PRT
<213> ORGANISM: Artificial Sequence
<220> FEATURE:
<223> OTHER INFORMATION: Fragment of trastuzumab

<400> SEQUENCE: 26

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg

<210> SEQ ID NO 27
<211> LENGTH: 58
<212> TYPE: PRT
<213> ORGANISM: Artificial Sequence
<220> FEATURE:
<223> OTHER INFORMATION: Domain A of Protein A derived from
      Staphylococcus aureus

<400> SEQUENCE: 27

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
            35                  40                  45

Lys Lys Leu Asn Glu Ser Gln Ala Pro Lys
        50                  55

<210> SEQ ID NO 28
<211> LENGTH: 58
<212> TYPE: PRT
<213> ORGANISM: Artificial Sequence
<220> FEATURE:
<223> OTHER INFORMATION: Domain B of Protein A derived from
```

Staphylococcus aureus

<400> SEQUENCE: 28

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 29
<211> LENGTH: 58
<212> TYPE: PRT
<213> ORGANISM: Artificial Sequence
<220> FEATURE:
<223> OTHER INFORMATION: Domain C of Protein A which from Staphylococcus
      aureus

<400> SEQUENCE: 29

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 30
<211> LENGTH: 61
<212> TYPE: PRT
<213> ORGANISM: Artificial Sequence
<220> FEATURE:
<223> OTHER INFORMATION: Domain D of Protein A derived from
      Staphylococcus aureus

<400> SEQUENCE: 30

Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 31
<211> LENGTH: 60
<212> TYPE: PRT
<213> ORGANISM: Artificial Sequence
<220> FEATURE:
<223> OTHER INFORMATION: Domain E of Protein A derived from
      Staphylococcus aureus

<400> SEQUENCE: 31

Ala Ala Asn Ala Ala Gln His Asp Glu Ala Gln Gln Asn Ala Phe Tyr
1               5                   10                  15

Gln Val Leu Asn Met Pro Asn Leu Asn Ala Asp Gln Arg Asn Gly Phe
            20                  25                  30

Ile Gln Ser Leu Lys Asp Asp Pro Ser Gln Ser Ala Asn Val Leu Gly
            35                  40                  45

Glu Ala Gln Lys Leu Asn Asp Ser Gln Ala Pro Lys
        50                  55                  60

<210> SEQ ID NO 32
<211> LENGTH: 60
<212> TYPE: PRT
<213> ORGANISM: Artificial Sequence
<220> FEATURE:
<223> OTHER INFORMATION: Domain C2 of Protein G derived from group G
      streptococci

<400> SEQUENCE: 32

Thr Pro Ala Val Thr Thr Tyr Lys Leu Val Ile Asn Gly Lys Thr Leu
1               5                   10                  15

Lys Gly Glu Thr Thr Thr Glu Ala Val Asp Ala Ala Thr Ala Glu Lys
            20                  25                  30

Val Phe Lys Gln Tyr Ala Asn Asp Asn Gly Val Asp Gly Glu Trp Thr
        35                  40                  45

Tyr Asp Asp Ala Thr Lys Thr Phe Thr Val Thr Glu
    50                  55                  60

<210> SEQ ID NO 33
<211> LENGTH: 60
<212> TYPE: PRT
<213> ORGANISM: Artificial Sequence
<220> FEATURE:
<223> OTHER INFORMATION: Domain C3 of Protein G derived from group G
      streptococci

<400> SEQUENCE: 33

Thr Pro Ala Val Thr Thr Tyr Lys Leu Val Ile Asn Gly Lys Thr Leu
1               5                   10                  15

Lys Gly Glu Thr Thr Thr Lys Ala Val Asp Ala Glu Thr Ala Glu Lys
            20                  25                  30

Ala Phe Lys Gln Tyr Ala Asn Asp Asn Gly Val Asp Gly Val Trp Thr
        35                  40                  45

Tyr Asp Asp Ala Thr Lys Thr Phe Thr Val Thr Glu
    50                  55                  60

<210> SEQ ID NO 34
<211> LENGTH: 61
<212> TYPE: PRT
<213> ORGANISM: Artificial Sequence
<220> FEATURE:
<223> OTHER INFORMATION: Domain C of Protein L derived from
      Peptostreptococcus magnus

<400> SEQUENCE: 34

Glu Val Thr Ile Lys Val Asn Leu Ile Phe Ala Asp Gly Lys Ile Gln
1               5                   10                  15

Thr Ala Glu Phe Lys Gly Thr Phe Glu Glu Ala Thr Ala Glu Ala Tyr
            20                  25                  30

Arg Tyr Ala Asp Leu Leu Ala Lys Val Asn Gly Glu Tyr Thr Ala Asp
        35                  40                  45

Leu Glu Asp Gly Gly Asn His Met Asn Ile Lys Phe Ala
    50                  55                  60

<210> SEQ ID NO 35
<211> LENGTH: 61
<212> TYPE: PRT

```
<213> ORGANISM: Artificial Sequence
<220> FEATURE:
<223> OTHER INFORMATION: Domain C1 of Protein L derived from
      Peptostreptococcus magnus

<400> SEQUENCE: 35

Glu Val Thr Ile Lys Ala Asn Leu Ile Phe Ala Asp Gly Ser Thr Gln
1               5                   10                  15

Asn Ala Glu Phe Lys Gly Thr Phe Ala Lys Ala Val Ser Asp Ala Tyr
            20                  25                  30

Ala Tyr Ala Asp Ala Leu Lys Lys Asp Asn Gly Glu Tyr Thr Val Asp
        35                  40                  45

Val Ala Asp Lys Gly Leu Thr Leu Asn Ile Lys Phe Ala
    50                  55                  60

<210> SEQ ID NO 36
<211> LENGTH: 61
<212> TYPE: PRT
<213> ORGANISM: Artificial Sequence
<220> FEATURE:
<223> OTHER INFORMATION: Domain C2 of Protein L derived from
      Peptostreptococcus magnus

<400> SEQUENCE: 36

Glu Val Thr Ile Lys Val Asn Leu Ile Phe Ala Asp Gly Lys Thr Gln
1               5                   10                  15

Thr Ala Glu Phe Lys Gly Thr Phe Glu Glu Ala Thr Ala Lys Ala Tyr
            20                  25                  30

Ala Tyr Ala Asp Leu Leu Ala Lys Glu Asn Gly Glu Tyr Thr Ala Asp
        35                  40                  45

Leu Glu Asp Gly Gly Asn Thr Ile Asn Ile Lys Phe Ala
    50                  55                  60

<210> SEQ ID NO 37
<211> LENGTH: 61
<212> TYPE: PRT
<213> ORGANISM: Artificial Sequence
<220> FEATURE:
<223> OTHER INFORMATION: Domain C3 of Protein L derived from
      Peptostreptococcus magnus

<400> SEQUENCE: 37

Glu Val Thr Ile Lys Val Asn Leu Ile Phe Ala Asp Gly Lys Ile Gln
1               5                   10                  15

Thr Ala Glu Phe Lys Gly Thr Phe Glu Glu Ala Thr Ala Lys Ala Tyr
            20                  25                  30

Ala Tyr Ala Asn Leu Leu Ala Lys Glu Asn Gly Glu Tyr Thr Ala Asp
        35                  40                  45

Leu Glu Asp Gly Gly Asn Thr Ile Asn Ile Lys Phe Ala
    50                  55                  60

<210> SEQ ID NO 38
<211> LENGTH: 61
<212> TYPE: PRT
<213> ORGANISM: Artificial Sequence
<220> FEATURE:
<223> OTHER INFORMATION: Domain C4 of Protein L derived from
      Peptostreptococcus magnus

<400> SEQUENCE: 38

Glu Val Thr Ile Lys Val Asn Leu Ile Phe Ala Asp Gly Lys Thr Gln
1               5                   10                  15
```

```
Thr Ala Glu Phe Lys Gly Thr Phe Glu Ala Thr Ala Glu Ala Tyr
            20                  25                  30

Arg Tyr Ala Asp Leu Leu Ala Lys Val Asn Gly Glu Tyr Thr Ala Asp
            35                  40                  45

Leu Glu Asp Gly Gly Tyr Thr Ile Asn Ile Lys Phe Ala
    50                  55                  60

<210> SEQ ID NO 39
<211> LENGTH: 61
<212> TYPE: PRT
<213> ORGANISM: Artificial Sequence
<220> FEATURE:
<223> OTHER INFORMATION: Domain B1 of Protein L derived from
      Peptostreptococcus magnus

<400> SEQUENCE: 39

Glu Val Thr Ile Lys Ala Asn Leu Ile Phe Ala Asn Gly Ser Thr Gln
1               5                   10                  15

Thr Ala Glu Phe Lys Gly Thr Phe Glu Lys Ala Thr Ser Glu Ala Tyr
            20                  25                  30

Ala Tyr Ala Asp Thr Leu Lys Lys Asp Asn Gly Glu Tyr Thr Val Asp
            35                  40                  45

Val Ala Asp Lys Gly Tyr Thr Leu Asn Ile Lys Phe Ala
    50                  55                  60

<210> SEQ ID NO 40
<211> LENGTH: 61
<212> TYPE: PRT
<213> ORGANISM: Artificial Sequence
<220> FEATURE:
<223> OTHER INFORMATION: Domain B2 of Protein L derived from
      Peptostreptococcus magnus

<400> SEQUENCE: 40

Glu Val Thr Ile Lys Ala Asn Leu Ile Tyr Ala Asp Gly Lys Thr Gln
1               5                   10                  15

Thr Ala Glu Phe Lys Gly Thr Phe Glu Glu Ala Thr Ala Glu Ala Tyr
            20                  25                  30

Arg Tyr Ala Asp Ala Leu Lys Lys Asp Asn Gly Glu Tyr Thr Val Asp
            35                  40                  45

Val Ala Asp Lys Gly Tyr Thr Leu Asn Ile Lys Phe Ala
    50                  55                  60

<210> SEQ ID NO 41
<211> LENGTH: 61
<212> TYPE: PRT
<213> ORGANISM: Artificial Sequence
<220> FEATURE:
<223> OTHER INFORMATION: Domain B3 of Protein L derived from
      Peptostreptococcus magnus

<400> SEQUENCE: 41

Glu Val Thr Ile Lys Ala Asn Leu Ile Tyr Ala Asp Gly Lys Thr Gln
1               5                   10                  15

Thr Ala Glu Phe Lys Gly Thr Phe Glu Glu Ala Thr Ala Glu Ala Tyr
            20                  25                  30

Arg Tyr Ala Asp Leu Leu Ala Lys Glu Asn Gly Lys Tyr Thr Val Asp
            35                  40                  45

Val Ala Asp Lys Gly Tyr Thr Leu Asn Ile Lys Phe Ala
    50                  55                  60
```

```
<210> SEQ ID NO 42
<211> LENGTH: 61
<212> TYPE: PRT
<213> ORGANISM: Artificial Sequence
<220> FEATURE:
<223> OTHER INFORMATION: Domain B4 of Protein L derived from
      Peptostreptococcus magnus

<400> SEQUENCE: 42

Glu Val Thr Ile Lys Ala Asn Leu Ile Tyr Ala Asp Gly Lys Thr Gln
1               5                   10                  15

Thr Ala Glu Phe Lys Gly Thr Phe Ala Glu Ala Thr Ala Glu Ala Tyr
                20                  25                  30

Arg Tyr Ala Asp Leu Leu Ala Lys Glu Asn Gly Lys Tyr Thr Ala Asp
            35                  40                  45

Leu Glu Asp Gly Gly Tyr Thr Ile Asn Ile Arg Phe Ala
        50                  55                  60

<210> SEQ ID NO 43
<211> LENGTH: 61
<212> TYPE: PRT
<213> ORGANISM: Artificial Sequence
<220> FEATURE:
<223> OTHER INFORMATION: Domain B5 of Protein L derived from
      Peptostreptococcus magnus

<400> SEQUENCE: 43

Gln Val Thr Ile Lys Glu Asn Ile Tyr Phe Glu Asp Gly Thr Val Gln
1               5                   10                  15

Thr Ala Thr Phe Lys Gly Thr Phe Ala Glu Ala Thr Ala Glu Ala Tyr
                20                  25                  30

Arg Tyr Ala Asp Leu Leu Ser Lys Glu His Gly Lys Tyr Thr Ala Asp
            35                  40                  45

Leu Glu Asp Gly Gly Tyr Thr Ile Asn Ile Arg Phe Ala
        50                  55                  60

<210> SEQ ID NO 44
<211> LENGTH: 58
<212> TYPE: PRT
<213> ORGANISM: Artificial Sequence
<220> FEATURE:
<223> OTHER INFORMATION: Protein Z which is artificially designed based
      on Protein A derived from Staphylococcus aureus

<400> SEQUENCE: 44

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 45
<211> LENGTH: 34
<212> TYPE: PRT
<213> ORGANISM: Artificial Sequence
<220> FEATURE:
<223> OTHER INFORMATION: Polypeptide Z34C which is artificially designed
      based on Protein A derived from Staphylococcus aureus

<400> SEQUENCE: 45
```

```
Phe Asn Met Gln Cys Gln Arg Arg Phe Tyr Glu Ala Leu His Asp Pro
1               5                   10                  15

Asn Leu Asn Glu Glu Gln Arg Asn Ala Lys Ile Lys Ser Ile Arg Asp
            20                  25                  30

Asp Cys
```

<210> SEQ ID NO 46
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 46

```
Phe Asn Met Gln Cys Gln Arg Arg Phe Tyr Glu Ala Leu His Asp Pro
1               5                   10                  15

Asn Leu Asn Lys Glu Gln Arg Asn Ala Arg Ile Arg Ser Ile Arg Asp
            20                  25                  30

Asp Cys
```

<210> SEQ ID NO 47
<211> LENGTH: 19
<212> TYPE: PRT
<213> ORGANISM: Artificial Sequence
<220> FEATURE:
<223> OTHER INFORMATION: Polypeptide fragment

<400> SEQUENCE: 47

```
Val Val Ser Val Leu Thr Val Leu His Gln Asp Trp Leu Asn Gly Lys
1               5                   10                  15

Glu Tyr Lys
```

<210> SEQ ID NO 48
<211> LENGTH: 28
<212> TYPE: PRT
<213> ORGANISM: Artificial Sequence
<220> FEATURE:
<223> OTHER INFORMATION: Polypeptide fragment

<400> SEQUENCE: 48

```
Glu Glu Gln Tyr Asp Ser Thr Tyr Arg Val Val Ser Val Leu Thr Val
1               5                   10                  15

Leu His Gln Asp Trp Leu Asn Gly Lys Glu Tyr Lys
            20                  25
```

<210> SEQ ID NO 49
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 49

```
Phe Asn Met Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Lys Asp
            20                  25                  30

Asp Cys
```

```
<210> SEQ ID NO 50
<211> LENGTH: 18
<212> TYPE: PRT
<213> ORGANISM: Artificial Sequence
<220> FEATURE:
<223> OTHER INFORMATION: Polypeptide fragment

<400> SEQUENCE: 50

Phe Asn Trp Tyr Val Asp Gly Val Glu Val His Asn Ala Lys Thr Lys
1               5                   10                  15

Pro Arg

<210> SEQ ID NO 51
<211> LENGTH: 35
<212> TYPE: PRT
<213> ORGANISM: Artificial Sequence
<220> FEATURE:
<223> OTHER INFORMATION: Peptide having an affinity to Fc region of
      human IgG.  Two cysteine residues may be linked by disulfide
      bridge.

<400> SEQUENCE: 51

Gln Glu Thr Met Gln Cys Gln Arg Arg Phe Tyr Glu Ala Leu His Asp
1               5                   10                  15

Pro Asn Leu Asn Glu Glu Gln Arg Asn Ala Arg Ile Arg Ser Ile Lys
            20                  25                  30

Asp Asp Cys
        35

<210> SEQ ID NO 52
<211> LENGTH: 34
<212> TYPE: PRT
<213> ORGANISM: Artificial Sequence
<220> FEATURE:
<223> OTHER INFORMATION: Peptide having an affinity to Fc region of
      human IgG.  Two cysteine residues may be linked by disulfide
      bridge.

<400> SEQUENCE: 52

Gln Glu Thr Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Lys Asp
            20                  25                  30

Asp Cys

<210> SEQ ID NO 53
<211> LENGTH: 33
<212> TYPE: PRT
<213> ORGANISM: Artificial Sequence
<220> FEATURE:
<223> OTHER INFORMATION: Peptide having an affinity to Fc region of
      human IgG.  Two cysteine residues may be linked by disulfide
      bridge.

<400> SEQUENCE: 53

Gln Glu Thr Cys Gln Arg Arg Phe Tyr Glu Ala Leu His Asp Pro Asn
1               5                   10                  15

Leu Asn Glu Glu Gln Arg Asn Ala Arg Ile Arg Ser Ile Lys Asp Asp
            20                  25                  30

Cys

<210> SEQ ID NO 54
<211> LENGTH: 13
```

```
<212> TYPE: PRT
<213> ORGANISM: Artificial Sequence
<220> FEATURE:
<223> OTHER INFORMATION: Peptide having an affinity to Fc region of
      human IgG (peptide known as Fc-III).  Two cysteine residues may be
      linked by disulfide bridge.

<400> SEQUENCE: 54

Asp Cys Ala Trp His Leu Gly Glu Leu Val Trp Cys Thr
1               5                   10

<210> SEQ ID NO 55
<211> LENGTH: 204
<212> TYPE: DNA
<213> ORGANISM: Artificial Sequence
<220> FEATURE:
<223> OTHER INFORMATION: Nucleotide sequence encoding the amino acid
      sequence of CspBss-QET-Z34C3

<400> SEQUENCE: 55
atgtttaaca accgtatccg cactgcagct ctcgctggtg caatcgcaat ctccaccgca       60
gcttccggcg tagctatccc agcattcgct caggagacct tcaacatgca gtgtcagcgt      120
cgcttctacg aggccctcca cgaccctaac ctcaacaagg aacagcgtaa cgcgcgtatt      180
cgctccatcc gcgatgactg ctaa                                             204

<210> SEQ ID NO 56
<211> LENGTH: 67
<212> TYPE: PRT
<213> ORGANISM: Artificial Sequence
<220> FEATURE:
<223> OTHER INFORMATION: Amino acid sequence of CspBss-QET-Z34C3

<400> SEQUENCE: 56

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Phe Asn Met Gln Cys Gln Arg Arg Phe Tyr Glu Ala Leu His Asp
        35                  40                  45

Pro Asn Leu Asn Lys Glu Gln Arg Asn Ala Arg Ile Arg Ser Ile Arg
    50                  55                  60

Asp Asp Cys
65

<210> SEQ ID NO 57
<211> LENGTH: 204
<212> TYPE: DNA
<213> ORGANISM: Artificial Sequence
<220> FEATURE:
<223> OTHER INFORMATION: Nucleotide sequence encoding the amino acid
      sequence of CspBss-QET-Z34C4

<400> SEQUENCE: 57
atgtttaaca accgtatccg cactgcagct ctcgctggtg caatcgcaat ctccaccgca       60
gcttccggcg tagctatccc agcattcgct caggagacct tcaacatgca gtgtcagcgt      120
cgcttctacg aggccctcca cgaccctaac ctcaacgagg aacagcgtaa cgcgcgtatt      180
cgctccatca aggatgactg ctaa                                             204

<210> SEQ ID NO 58
<211> LENGTH: 67
<212> TYPE: PRT
```

<213> ORGANISM: Artificial Sequence
<220> FEATURE:
<223> OTHER INFORMATION: Amino acid sequence of CspBss-QET-Z34C4

<400> SEQUENCE: 58

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Phe Asn Met Gln Cys Gln Arg Arg Phe Tyr Glu Ala Leu His Asp
        35                  40                  45

Pro Asn Leu Asn Glu Glu Gln Arg Asn Ala Arg Ile Arg Ser Ile Lys
    50                  55                  60

Asp Asp Cys
65

<210> SEQ ID NO 59
<211> LENGTH: 153
<212> TYPE: DNA
<213> ORGANISM: Artificial Sequence
<220> FEATURE:
<223> OTHER INFORMATION: Nucleotide sequence encoding the amino acid
      sequence of CspBss-QET-LV

<400> SEQUENCE: 59
atgtttaaca accgtatccg cactgcagct ctcgctggtg caatcgcaat ctccaccgca    60
gcttccggcg tagctatccc agcattcgct caggagaccc gcggcaactg cgcataccac   120
aagggccagc tggtgtggtg cacctaccac taa                                153

<210> SEQ ID NO 60
<211> LENGTH: 50
<212> TYPE: PRT
<213> ORGANISM: Artificial Sequence
<220> FEATURE:
<223> OTHER INFORMATION: Amino acid sequence of CspBss-QET-LV

<400> SEQUENCE: 60

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Arg Gly Asn Cys Ala Tyr His Lys Gly Gln Leu Val Trp Cys Thr
        35                  40                  45

Tyr His
    50

<210> SEQ ID NO 61
<211> LENGTH: 153
<212> TYPE: DNA
<213> ORGANISM: Artificial Sequence
<220> FEATURE:
<223> OTHER INFORMATION: Nucleotide sequence encoding the amino acid
      sequence of CspBss-QET-II

<400> SEQUENCE: 61
atgtttaaca accgtatccg cactgcagct ctcgctggtg caatcgcaat ctccaccgca    60
gcttccggcg tagctatccc agcattcgct caggagaccc gcggcaactg cgcataccac   120
aagggccaga tcatctggtg cacctaccac taa                                153

<210> SEQ ID NO 62

```
<211> LENGTH: 50
<212> TYPE: PRT
<213> ORGANISM: Artificial Sequence
<220> FEATURE:
<223> OTHER INFORMATION: Amino acid sequence of CspBss-QET-II

<400> SEQUENCE: 62

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Arg Gly Asn Cys Ala Tyr His Lys Gly Gln Ile Ile Trp Cys Thr
        35                  40                  45

Tyr His
    50
```

COMPOUND HAVING AFFINITY SUBSTANCE TO ANTIBODY, CLEAVABLE PORTION, AND REACTIVE GROUP, OR SALT THEREOF

CROSS REFERENCES TO RELATED APPLICATIONS

This application is a continuation of International Patent Application No. PCT/JP2019/042785, filed on Oct. 31, 2019, and claims priority to Japanese Patent Application No. 2018-205225, filed on Oct. 31, 2018, both of which are incorporated herein by reference in their entireties.

BACKGROUND OF THE INVENTION

Field of the Invention

The present invention relates to compounds having an affinity substance to an antibody, a cleavable portion, and a reactive group, and salts thereof, and the like.

Discussion of the Background

In recent years, research and development of an antibody drug conjugation (ADC) have been actively performed. An ADC, as implied by the name, is a medicine in which a drug (e.g., an anti-cancer agent) is conjugated with an antibody and has a direct cytotoxic activity on cancer cells and the like. A typical ADC is T-DM1 (trade name: Kadcyla (registered trademark)) jointly developed by Immunogene Inc. and Roche Inc. (see Reichert J M et al., Nat Biotechnol 2005; 23: 1073-8; Kubota T et al., Cancer Sci 2009; 100: 1566-72; and Wu A M et al., Nat Biotechnol 2005; 23: 1137-46, all of which are incorporated herein by reference in their entireties).

ADCs including T-DM1 have had a problem of their nonuniformity from the beginning of their development. That is, a small compound drug is randomly reacted with about 70 to 80 Lys residues in an antibody, and thus a drug antibody ratio (DAR) and a conjugation position are not constant. It is known that such a random conjugation method normally provides a DAR within a range of 0 to 8, producing a plurality of medicines having different numbers of bonds of a drug. In recent years, it has been reported that when the number of bonds and the binding positions of a drug of an ADC are changed, pharmacokinetics, and a releasing rate and effects of the drug change. Under these circumstances, next-generation ADCs are required to control the number and positions of a drug to be conjugated. It is believed that when the number and positions are fixed, problems of expected efficacy, variations in conjugation medicines, and lot difference, or what is called regulation, will be solved (see Junutula J R et al., Nat Biotechnol 2008; 26: 925-32, which is incorporated herein by reference in its entirety).

Although methods for regioselectively modifying antibodies are being investigated worldwide, most of them are modification methods using genetic engineering techniques or enzymes. For the genetic engineering modification methods, problems have been pointed out such as reductions in expression efficiency of antibodies themselves (reductions in total yield when ADCs are prepared), although regioselectivity and number selectivity can be controlled. In addition, there is a problem in that it takes long years to construct an antibody expression system and the like (see Shen B Q et al., Nat Biotechnol 2012; 30: 184-9; Hofer T et al., Biochemistry 2009; 48: 12047-57; and Liu W et al., Nat Methods 2007; 4: 239-44, all of which are incorporated herein by reference in their entireties).

In recent years, a method for chemically modifying a protein under complicated environments such as intracellular ones using a low molecule probe has been reported. This method is used for imaging or identification of a receptor in repositioning a low molecular drug. In the field of chemical biology, a method for organic chemically modifying a protein using a synthesized low molecular probe is attracting attention (see S. T. Laughlin et al., Science 2008; 320,664; A. E. Speers et al., Chem BioChem 2004; 5,41; and Y. Takaoka et al., Angew. Chem. Int. Ed. 2013; 52,4088, all of which are incorporated herein by reference in their entireties).

A chemical conjugation by affinity peptide (C-CAP) method has been recently developed. This method has succeeded in regioselective modification of an antibody by a method for causing a reaction between a peptide reagent in which an NHS-activated ester and a drug are coupled with an affinity peptide and an antibody (that is, a method for producing an ADC through a linker comprising a peptide portion). This method has succeeded in regioselectively modifying an antibody Fc region with a drug by a chemical synthetic technique first in the world, and besides, practically favorable results [reaction time: 30 minutes, yield: 70% (for DAR 1), and regioselectivity: 100%] have been determined. It has been demonstrated that control with a DAR of 2 can be achieved by adding about five equivalents of the peptide reagent, which is epoch-making in that a modified position can also be controlled (see WO 2016/186206 A, which is incorporated herein by reference in its entirety).

SUMMARY OF THE INVENTION

Accordingly, it is one object of the present invention to provide novel techniques that make modification of an antibody, particularly regioselective modification of an antibody possible.

These and other objects, which will become apparent during the following detailed description, have been achieved by the inventors' discovery that a compound developed based on a novel and original design concept with structural features of having (1) an affinity substance to an antibody, (2) a reactive group to an amino acid residue in the antibody, and (3) a cleavable portion between the affinity substance and the reactive group, and (4) being capable of forming a structural unit having a bioorthogonal functional group or bioorthogonal functional groups on a reactive group side by cleavage at the cleavable portion (that is, a structural unit comprising a bioorthogonal functional group and a reactive group) is useful for regiospecific modification of an antibody (see, e.g., FIGS. 1-1, 1-2, 1-3, and 2).

The present inventors have also found that use of such a compound can prepare an antibody comprising no peptide portion as a linker and regioselectively having a functional substance or functional substances (e.g., a drug or drugs) (e.g., antibody drug conjugate (ADC)). Avoidance of use of a linker comprising a peptide portion, which has potential immunogenicity and is easily hydrolyzed in the blood, is desirable in a clinical application of ADC. That is, it can be said that the method developed by the present inventors has succeeded in regioselectively modifying an antibody Fc region with a drug by a chemical synthetic technique, and besides, without using any linker comprising a peptide portion first in the world. According to such a method, it is possible to develop various compounds having the structural features as described in (1) to (4) above (see, e.g., FIGS. 1-1, 1-2, 1-3, and 2).

The present inventors have also found the following. That is, by using a polypeptide comprising a glutamine residue (Q) at an N-terminal as an affinity substance to an antibody, an amino group (—NH$_2$) in the glutamine residue (Q) at the N-terminal reacts (is pyroglutamylated) with an amide group (e.g., —CONH$_2$ in the glutamine residue (Q) when QET is comprised at the N-terminal) present in a side chain thereof, and therefore the amino group can be protected. Therefore, a linker that mediates a binding of the affinity substance to an antibody can be specifically added to a specific amino acid residue (lysine residue having an amino group) in the affinity substance. As a result, the polypeptide comprising the glutamine residue (Q) at the N-terminal is useful as the affinity substance to an antibody.

The present inventors have also found that a polypeptide secretion production method using a coryneform bacterium as a host (see WO 2013/062029 A, which is incorporated herein by reference in its entirety) is useful in order to easily and in large quantities prepare the polypeptide comprising a glutamine residue (Q) at an N-terminal. According to this method, by adding N-terminal three residues Gln-Glu-Thr (QET) of a Csp mature protein to an N-terminal of a target polypeptide, an advantage of the polypeptide secretion production method can be enjoyed. Therefore, this method is suitable for preparing a polypeptide comprising a glutamine residue (Q) at an N-terminal (affinity substance to an antibody).

Specifically, the present invention is as follows.

According to a first embodiment, the present invention provides a compound having an affinity substance to an antibody, a cleavable portion, and a reactive group, or a salt thereof, and a reagent of regioselectively modifying an antibody, the reagent comprising the compound or a salt thereof.

(1) A compound having an affinity substance to an antibody, a cleavable portion, and a reactive group, or a salt thereof, the compound being represented by the following Formula (I):

A-L-B—R   (I)

wherein
A is an affinity substance to an antibody,
L is a cleavable linker that is a divalent group comprising a cleavable portion,
B is (a) a divalent group comprising a bioorthogonal functional group or (b) a divalent group comprising no bioorthogonal functional group, and
R is a reactive group to the antibody, wherein
the affinity substance to an antibody is a polypeptide comprising a glutamine residue (Q) at an N-terminal.

(2) The compound or salt thereof according to (1), wherein the polypeptide comprises a tripeptide (QET) consisting of glutamine residue (Q)—glutamic acid (E)—threonine residue (T) at an N-terminal.

(3) The compound or salt thereof according to (1) or (2), wherein the glutamine residue is pyroglutamylated.

(4) The compound or salt thereof according to any one of (1) to (3), wherein the polypeptide comprises 16 or more and 123 or less amino acid residues.

(5) The compound or salt thereof according to any one of (1) to (3), wherein the polypeptide comprises 20 or more and 70 or less amino acid residues.

[6] The compound or salt thereof according to any one of [1] to [5], wherein the polypeptide is selected from the group consisting of the following (1) to (4):

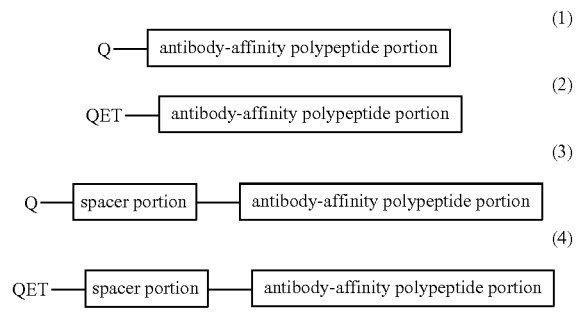

wherein Q is a glutamine residue at an N-terminal, E is a glutamic acid residue, T is a threonine residue, the solid line is a bond, the spacer portion consists of 1 or more and 50 or less amino acid residues, and the affinity substance to an antibody consists of 15 or more and 70 or less amino acid residues.

(7) The compound or salt thereof according to (6), wherein the antibody-affinity polypeptide portion is selected from the group consisting of protein A, protein G, protein L, protein Z, fragments thereof having affinity to an antibody, and variants thereof having affinity to an antibody.

(8) The compound or salt thereof according to (6) or (7), wherein the antibody-affinity polypeptide portion comprises an amino acid sequence with any one amino acid residue substituted with a lysine residue in an amino acid sequence of FNMQCQRRFYEALHDPNLNEEQRNAXIXSIRDDC (SEQ ID NO: 5) (two Xs are each independently one amino acid residue selected from the group consisting of an arginine residue, a glutamic acid residue, and a glutamine residue) and having 90% or more identity to the amino acid sequence of SEQ ID NO: 5.

(9) The compound or salt thereof according to any one of (6) to (8), wherein the antibody-affinity polypeptide portion comprises an amino acid sequence with any one amino acid residue substituted with a lysine residue in an amino acid sequence of FNMQCQRRFYEALHDPNLNEEQRNARIRSIRDDC (SEQ ID NO: 6) and having 90% or more identity to the amino acid sequence of SEQ ID NO: 6.

(10) The compound or salt thereof according to any one of (1) to (9), wherein the affinity substance to an antibody comprises an amino acid sequence selected from the group consisting of the following:

(1)
```
                                         (SEQ ID NO: 7)
QETNPTENLYFQQKNMQCQRRFYEALHDPNLNEEQRNARIRSIRDDC;
```

(2)
```
                                         (SEQ ID NO: 8)
QTADNQKNMQCQRRFYEALHDPNLNEEQRNARIRSIRDDCSQSANLLAE
AQQLNDAQAPQA;
```

(3)
```
                                         (SEQ ID NO: 9)
QETKNMQCQRRFYEALHDPNLNEEQRNARIRSIRDDC;
```

(4)
```
                                         (SEQ ID NO: 10)
QETFNKQCQRRFYEALHDPNLNEEQRNARIRSIRDDC;
```

-continued (5)
(SEQ ID NO: 22)
QETENMQCQRRFYEALHDPNLNKEQRNARIRSIRDDC;

(6)
(SEQ ID NO: 23)
QETENMQCQRRFYEALHDPNLNEEQRNARIRSIKDDC;

(7)
(SEQ ID NO: 51)
QETMQCQRRFYEALHDPNLNEEQRNARIRSIKDDC;

(8)
(SEQ ID NO: 52)
QETQCQRRFYEALHDPNLNEEQRNARIRSIKDDC;

(9)
(SEQ ID NO: 53)
QETCQRRFYEALHDPNLNEEQRNARIRSIKDDC;

(10)
(SEQ ID NO: 24)
QETRGNCAYHKGQLVWCTYH; and

(11)
(SEQ ID NO: 25)
QETRGNCAYHKGQIIWCTYH.

(11) The compound or salt thereof according to any one of (1) to (10), wherein L is (i) a cleavable linker that is a divalent group comprising a cleavable portion capable of forming a bioorthogonal functional group on a reactive group side by cleavage, or (ii) a cleavable linker that is a divalent group comprising a cleavable portion not capable of forming a bioorthogonal functional group on a reactive group side by cleavage.

(12) The compound or salt thereof according to (11), wherein L is the cleavable linker of the above (i).

(13) The compound or salt thereof according to (11) or (12), wherein L is the cleavable linker of the above (i) and B is the divalent group of the above (b).

(14) The compound or salt thereof according to (11), wherein L is the cleavable linker of the above (ii) and B is the divalent group of the above (a).

(15) The compound or salt thereof according to any one of (1) to (14), wherein the polypeptide is a binding peptide to an Fc region of a monoclonal antibody.

(16) The compound or salt thereof according to (15), wherein the polypeptide is a binding peptide to an Fc region of IgG.

(17) The compound or salt thereof according to any one of (1) to (16), wherein the affinity substance is an affinity substance to an antibody, comprising any one Fc region protein selected from the group consisting of the following (A) to (C) and having an antigen-binding ability:
  (A) an Fc region protein comprising an amino acid sequence of SEQ ID NO: 1;
  (B) an Fc region protein comprising an amino acid sequence with one or several amino acid residues inserted, added, deleted, or substituted in the amino acid sequence of SEQ ID NO: 1; or
  (C) an Fc region protein comprising an amino acid sequence having 90% or more identity to the amino acid sequence of SEQ ID NO: 1.

(18) The compound or salt thereof according to any one of (1) to (17), wherein the polypeptide is capable of binding to human IgG.

(19) The compound or salt thereof according to any one of (1) to (18), wherein the cleavable portion is cleavable by any of (a) a treatment with one or more substances selected from the group consisting of an acidic substance, a basic substance, a reducing agent, an oxidizing agent, and an enzyme, (b) a treatment with a physical and chemical stimulus selected from the group consisting of light, and (c) leaving a cleavable linker as it is when the cleavable linker comprises a self-degradable cleavable portion.

(20) The compound or salt thereof according to any one of (1) to (19), wherein the cleavable portion is selected from the group consisting of a disulfide residue, an acetal residue, a ketal residue, an ester residue, a carbamoyl residue, an alkoxyalkyl residue, an imine residue, a tertiary alkyloxycarbamate residue, a silane residue, a hydrazone-containing residue, a phosphoramidate residue, an aconityl residue, a trityl residue, an azo residue, a vicinaldiol residue, a selenium residue, an aromatic ring-containing residue with an electron-withdrawing group, a coumarin-containing residue, a sulfone-containing residue, an unsaturated bond-containing chain residue, and a glycosyl residue.

(21) The compound or salt thereof according to any one of (11) to (20), wherein the cleavable portion of the above (i) is selected from the group consisting of a disulfide residue, an ester residue, an acetal residue, a ketal residue, an imine residue, and a vicinaldiol residue.

(22) The compound or salt thereof according to any one of (11) to (20), wherein the cleavable portion of the above (ii) is selected from the group consisting of an ester residue, a carbamoyl residue, an alkoxyalkyl residue, an imine residue, a tertiary alkyloxycarbamate residue, a silane residue, a hydrazone-containing residue, a phosphoramidate residue, an aconityl residue, a trityl residue, an azo residue, a vicinaldiol residue, a selenium residue, an aromatic ring-containing residue with an electron-withdrawing group, a coumarin-containing residue, a sulfone-containing residue, an unsaturated bond-containing chain residue, and a glycosyl residue.

(23) The compound or salt thereof according to any one of (1) to (22), wherein the cleavable portion corresponds to any one chemical structure selected from the group consisting of the following:

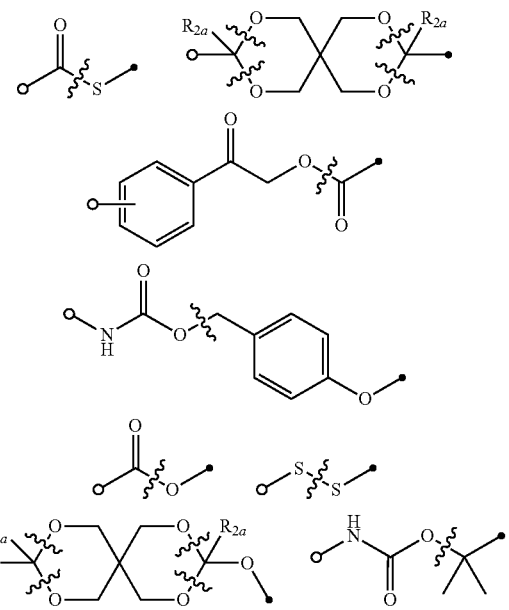

-continued

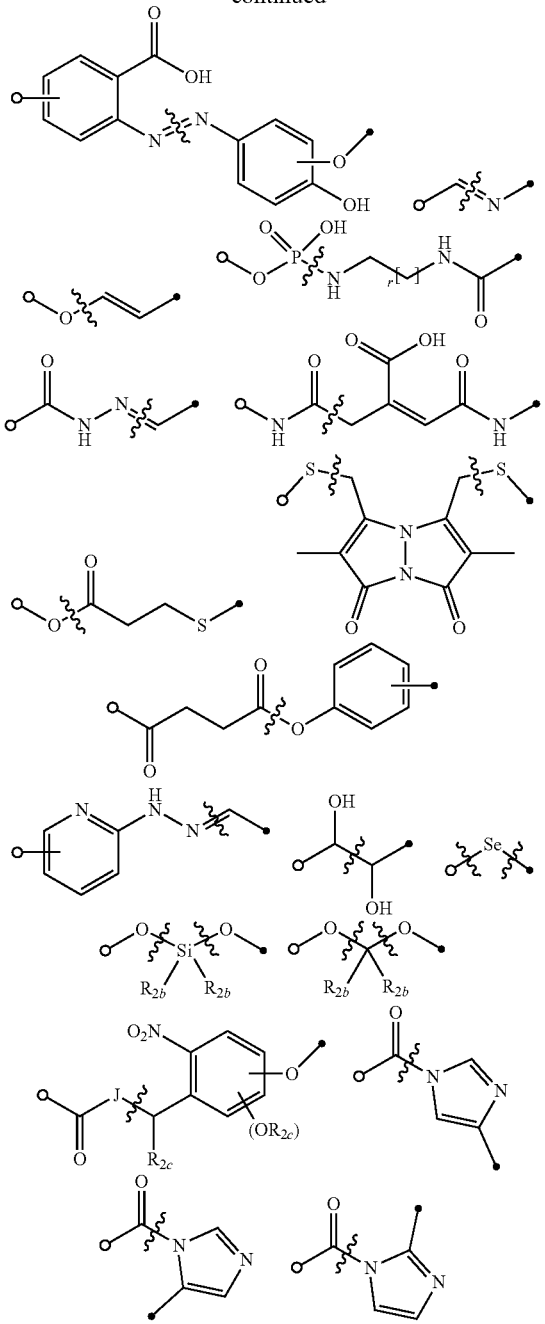

wherein the wavy line orthogonal to the bond indicates a cleavage site,
a plurality of $R_{2a}$s, a plurality of $R_{2b}$s, and a plurality of $R_{2c}$s are the same as or different from each other, and are each selected from the group consisting of:
(i) a hydrogen atom or a halogen atom;
(ii) a monovalent hydrocarbon group;
(iii) an aralkyl;
(iv) a monovalent heterocyclic group;
(v) $R_c$—O—, $R_c$—C(=O)—, $R_c$—O—C(=O)—, or $R_c$—C(=O)—O— (where $R_c$ represents a hydrogen atom or a monovalent hydrocarbon group);
(vi) $NR_dR_e$—, $N_dR_e$—C(=O)—, $NR_dR_e$—C(=O)—O—, or $R_d$—C(=O)—$NR_e$—, (where $R_d$ and $R_e$ are the same as or different from each other and each represent a hydrogen atom or a monovalent hydrocarbon group); and
(vii) a nitro group, a sulfate group, a sulfonate group, a cyano group, or a carboxyl group,
J is —CH$_2$—, —O—, or —S—,
r is any integer of 1 to 4
○ (white circle) indicates a bond to A, and ● (black circle) indicates a bond to B, and
when the chemical structure is asymmetrical about the cleavage site, ● may indicate a bond to A, and n may indicate a bond to B.

(24) The compound or salt thereof according to any one of (11) to (19), (21), and (230), wherein the cleavable portion of the above (i) corresponds to any one chemical structure selected from the group consisting of the following:

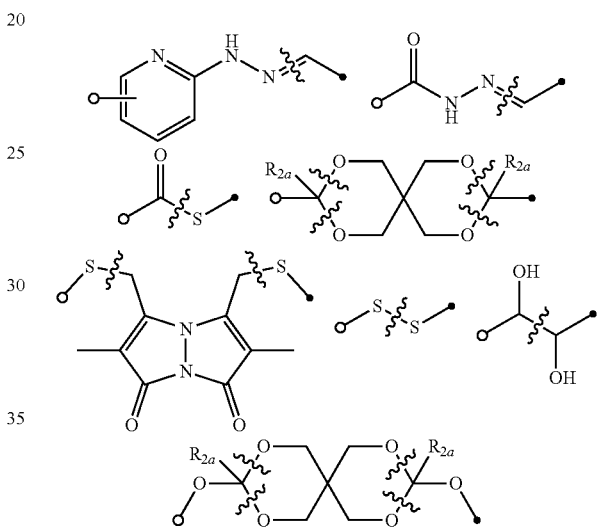

wherein the wavy line orthogonal to the bond indicates a cleavage site,
$R_{2a}$ is the same as that in (23),
○ (white circle) indicates a bond to A, and ● (black circle) indicates a bond to B, and
when the chemical structure is asymmetrical about the cleavage site, ● may indicate a bond to A, and ○ may indicate a bond to B.

(25) The compound or salt thereof according to any one of (11) to (19), (22), and (23), wherein the cleavable portion of the above (ii) corresponds to any one chemical structure selected from the group consisting of the following:

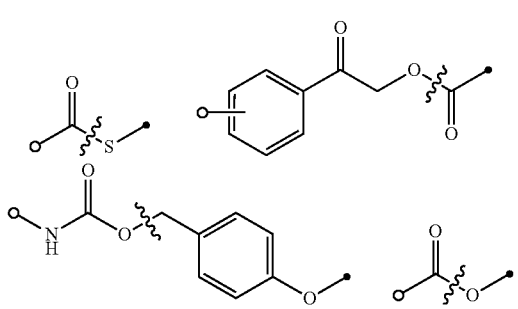

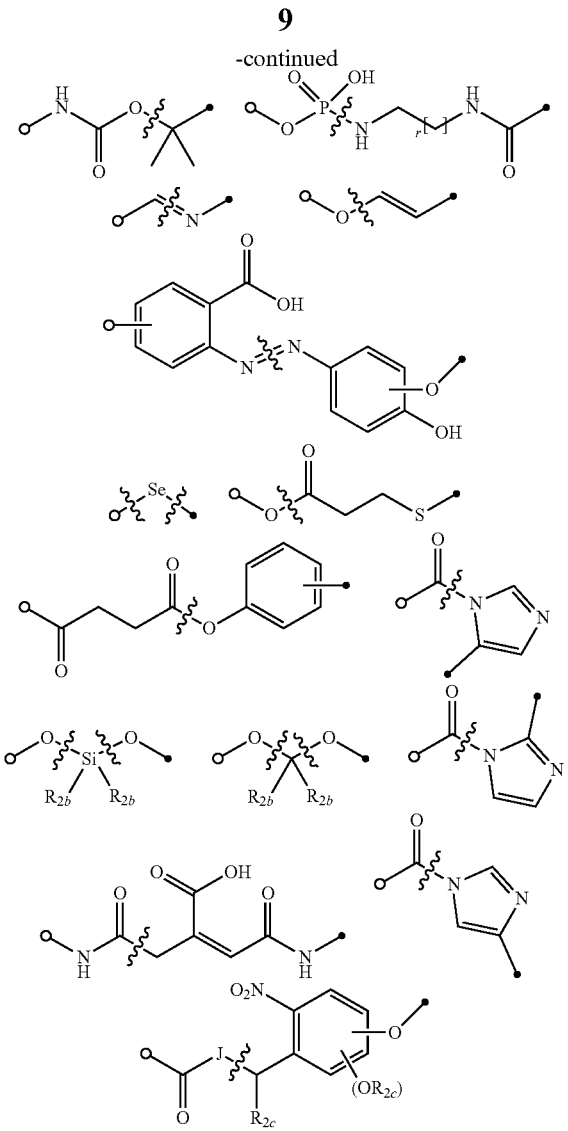

wherein the wavy line orthogonal to the bond indicates a cleavage site, $R_{2b}$, $R_{2c}$, J, and r are the same as those in (23), ○ (white circle) indicates a bond to A, and ● (black circle) indicates a bond to B, and when the chemical structure is asymmetrical about the cleavage site, ● may indicate a bond to A, and ○ may indicate a bond to B.

(26) The compound or salt thereof according to any one of (1) to (25), wherein L is represented by any one of the following Formulae (L1) to (L3):

 (L1)

 (L2)

 (L3)

wherein

La and Lb are each a divalent group, and

C is a cleavable portion.

(27) The compound or salt thereof according to (26), wherein the La and Lb are represented by the following (La') and (Lb'), respectively:

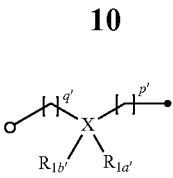

and

wherein p and p' are the same as or different from each other and are each any integer of 0 to 10, q and q' are the same as or different from each other and are each any integer of 0 to 10, X and X' are the same as or different from each other and are each a carbon atom, a nitrogen atom, or a single bond (where $R_{1b}$ is absent when X is a nitrogen atom, $R_{1b'}$ is absent when X' is a nitrogen atom, $R_{1a}$ and $R_{1b}$ are absent when X is a single bond, and $R_{1a'}$ and $R_{1b'}$ are absent when X' is a single bond), and $R_{1a}$, $R_{1b}$, $R_{1a'}$, and $R_{1b'}$ are the same as or different from each other and are each an atom or a group selected from the group consisting of the above (i) to (vii).

(28) The compound or salt thereof according to any one of (1) to (27), wherein the divalent group comprising a bioorthogonal functional group is a divalent group comprising, in a main chain thereof, a bioorthogonal functional group selected from the group consisting of an azide residue, an aldehyde residue, a thiol residue, an alkyne residue, an alkene residue, a tetrazine residue, a nitron residue, a hydroxylamine residue, a nitrile residue, a hydrazine residue, a ketone residue, a boronic acid residue, a cyanobenzothiazole residue, an allyl residue, a phosphine residue, a maleimide residue, a disulfide residue, a thioester residue, an α-halocarbonyl residue, an isonitrile residue, a sydnone residue, and a selenium residue.

(29) The compound or salt thereof according to any one of (1) to (27), wherein the divalent group comprising a bioorthogonal functional group is a divalent group comprising, in a side chain thereof, a bioorthogonal functional group selected from the group consisting of an azide residue, an aldehyde residue, a thiol residue, an alkyne residue, an alkene residue, a halogen residue, a tetrazine residue, a nitron residue, a hydroxylamine residue, a nitrile residue, a hydrazine residue, a ketone residue, a boronic acid residue, a cyanobenzothiazole residue, an allyl residue, a phosphine residue, a maleimide residue, a disulfide residue, an α-halocarbonyl residue, an isonitrile residue, a sydnone residue, and a selenium residue.

(30) The compound or salt thereof according to any one of (1) to (29), wherein the bioorthogonal functional group is any one represented by the following:

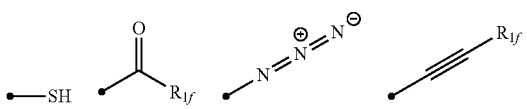

-continued

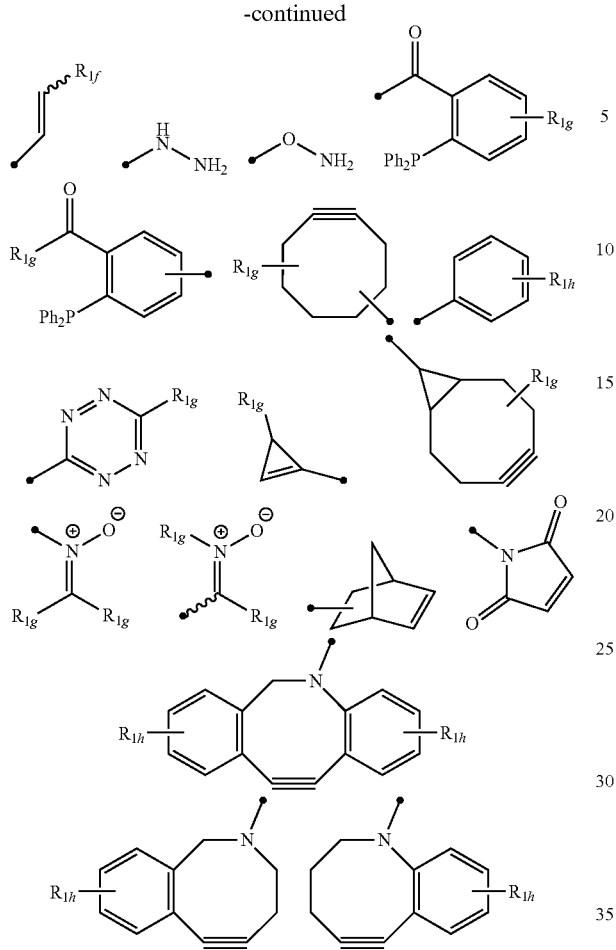

wherein

R$_{1f}$, one or a plurality of R$_{1g}$s, and one or a plurality of R$_{1h}$s are the same as or different from each other, and each an atom or a group selected from the group consisting of the above (i) to (vii) or an electron-withdrawing group, and

• is a bond.

(31) The compound or salt thereof according to any one of (1) to (30), wherein the divalent group of the above (b) is selected from the group consisting of an alkylene optionally having a substituent, a cycloalkylene optionally having a substituent, an aryl optionally having a substituent, a divalent heterocyclic group optionally having a substituent, —NR$_a$— (where R$_a$ represents a hydrogen atom or a substituent), —O—, and a combination of two or more of these.

(32) The compound or salt thereof according to any one of (1) to (31), wherein B is represented by the following Formula (B-1)

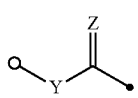

(B-1)

wherein

Y is —NH—, —O—, —CH$_2$—, or a group represented by the following Formula (B-2):

(B-2)

wherein

V and V' are the same as or different from each other and are each —NH—, —O—, —CH$_2$—, or a single bond, V1 is a divalent group comprising a bioorthogonal functional group, s is any integer of 0 to 10, and ○ and ● in Formula (B-2) have the same orientation as ○ and ● in Formula (B-1), respectively, Z is an oxygen atom, a sulfur atom, or a hydrogen atom (—C(=Z)— represents —CH$_2$—when Z is a hydrogen atom), and in Formula (B-1), ○ (white circle) indicates a bond to an L-side portion, and ● (black circle) indicates a bond to an R-side portion.

(33) The compound or salt thereof according to any one of (1) to (32), wherein the reactive group is a reactive group specific to any one side chain of a lysine residue, a tyrosine residue, and a tryptophan residue.

(34) The compound or salt thereof according to (33), wherein the reactive group is a reactive group specific to a side chain of a lysine residue.

(35) The compound or salt thereof according to any one of (1) to (34), wherein the reactive group corresponds to any one chemical structure selected from the group consisting of the following:

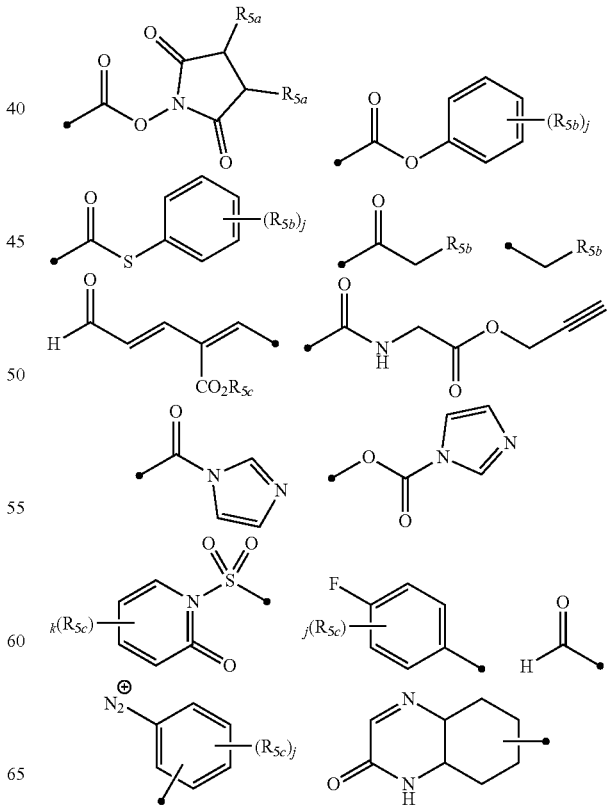

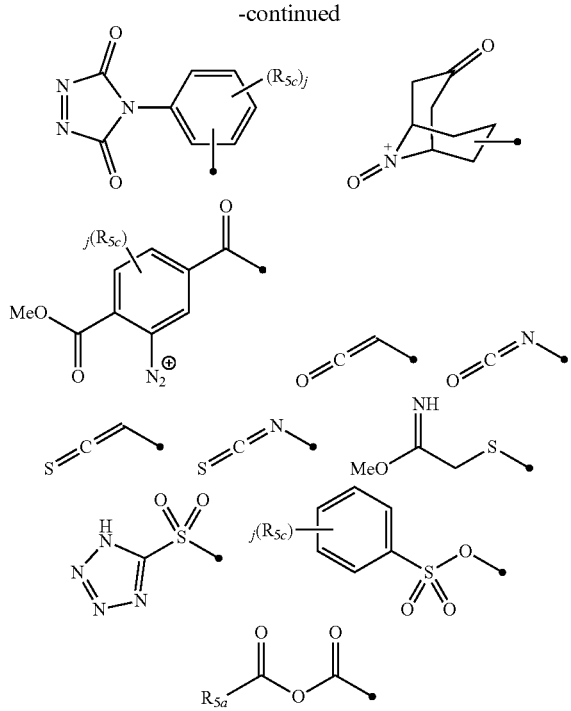

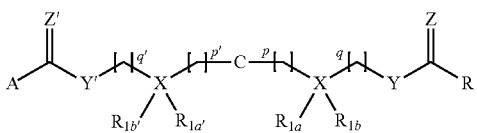

wherein

A and R are the same as those in Formula (I) described in (1),

C is a cleavable portion, p, p', q, q', X, X', $R_{1a}$, $R_{1a'}$, $R_{1b}$, and $R_{1b'}$ are the same as those in Formulae (La') and (Lb') described in (19), Y and Y' are the same as or different from each other and are the same as Y in Formula (B-1) described in (32), and Z and Z' are the same as or different from each other and are the same as Z in the above Formula (B-1).

(41) A reagent of regioselectively modifying an antibody, the compound comprising a compound having an affinity substance to an antibody, a cleavable portion, and a reactive group, or a salt thereof, represented by the following Formula (I):

A-L-B—P        (i)

wherein

A is an affinity substance to an antibody,

L is a cleavable linker that is a divalent group comprising a cleavable portion, B is (a) a divalent group comprising a bioorthogonal functional group or (b) a divalent group comprising no bioorthogonal functional group, and R is a reactive group to the antibody, wherein the affinity substance to an antibody is a polypeptide comprising a glutamine residue (Q) at an N-terminal (preferably comprising the compound or salt thereof according to any one of (2) to (40)).

(42) A compound having an affinity substance to an antibody, a cleavable portion, and a reactive group, or a salt thereof, represented by the following Formula (I):

A-L-B—R        (I)

wherein

A is an affinity substance to an antibody,

L is a cleavable linker that is a divalent group comprising a cleavable portion, B is (a) a divalent group comprising a bioorthogonal functional group or (b) a divalent group comprising no bioorthogonal functional group, and R is a reactive group specific to a side chain of a lysine residue, wherein the affinity substance to an antibody is a polypeptide comprising a glutamine residue (Q) at an N-terminal.

(43) A reagent of regioselectively modifying an antibody, the reagent comprising a compound having an affinity substance to an antibody, a cleavable portion, and a reactive group, or a salt thereof, represented by the following Formula (I):

A-L-B—R        (I)

wherein

A is an affinity substance to an antibody,

L is a cleavable linker that is a divalent group comprising a cleavable portion, B is (a) a divalent group comprising a bioorthogonal functional group or (b) a divalent group comprising no bioorthogonal functional group, and wherein $R_{5a}$ and $R_{5c}$ are each an atom or a group selected from the group consisting of the above (i) to (vii), $R_{5b}$ is an electron-withdrawing group, j is any integer of 1 to 5, and k is any integer of 1 to 4.

(36) The compound or salt thereof according to any one of (1) to (35), wherein a main chain coupling A with R has 4 to 20 atoms.

(37) The compound or salt thereof according to any one of (1) to (36), wherein a main chain coupling A with R comprises no cyclic structure.

(38) The compound or salt thereof according to any one of (1) to (37), wherein the partial structure represented by L-B comprises no peptide portion.

(39) The compound or salt thereof according to any one of (1) to (38), wherein the compound represented by the above Formula (I) is represented by the following (I'):

A-B2-L'-B1-R        (I')

wherein

A and R are the same as those in the above Formula (I),

L' is a cleavable linker that is a divalent group comprising a cleavable portion, B1 and B2 are the same as or different from each other and are each (a) a divalent group comprising a bioorthogonal functional group or (b) a divalent group comprising no bioorthogonal functional group, and B1 and B2 may have a symmetrical structure about L'.

(40) The compound or salt thereof according to (39), wherein the compound represented by the above Formula (I') is represented by the following (I"):

R is a reactive group specific to a side chain of a lysine residue, wherein the affinity substance to an antibody is a polypeptide comprising a glutamine residue (Q) at an N-terminal.

According to a second embodiment, the present invention provides an antibody having an affinity substance to an antibody and a cleavable portion, or a salt thereof, and a method for producing the same.

Antibody having affinity substance to antibody and cleavable portion, or salt thereof.

(1) An antibody having an affinity substance to an antibody and a cleavable portion, or a salt thereof, represented by the following Formula (II):

A-L-B—R'-T    (II)

wherein

A is an affinity substance to an antibody,

L is a cleavable linker that is a divalent group comprising a cleavable portion, B is (a) a divalent group comprising a bioorthogonal functional group or (b) a divalent group comprising no bioorthogonal functional group, R' is a portion formed by a reaction between an antibody and a reactive group, and T is an antibody, wherein the affinity substance to an antibody is a polypeptide comprising a glutamine residue (Q) at an N-terminal.

(2) The antibody or salt thereof according to (1), wherein the antibody is a monoclonal antibody.

(3) The antibody or salt thereof according to (1) or (2), wherein the antibody is an IgG antibody.

(4) The antibody or salt thereof according to any one of (1) to (3), wherein the antibody is derived from a human.

(5) The antibody or salt thereof according to any one of (1) to (4), wherein the antibody comprises any one Fc region protein selected from the group consisting of the following (A) to (C) and has an antigen-binding ability:

(A) an Fc region protein comprising an amino acid sequence of SEQ ID NO: 1;

(B) an Fc region protein comprising an amino acid sequence with one or several amino acid residues inserted, added, deleted, or substituted in the amino acid sequence of SEQ ID NO: 1; or (C) an Fc region protein comprising an amino acid sequence having 90% or more identity to the amino acid sequence of SEQ ID NO: 1.

(6) The antibody or salt thereof according to any one of (1) to (5), wherein the antibody comprises one or more specific amino acid residues in a target region consisting of 1 to 50 consecutive amino acid residues and comprises five or more of the specific amino acid residues in a non-target region other than the target region, and the structural unit represented by A-L-B—R' is bound to the one or more specific amino acid residues comprised in the target region with 30% or more regioselectivity.

(7) The antibody or salt thereof according to (6), wherein the target region consists of 1 to 10 consecutive amino acid residues.

(8) The antibody or salt thereof according to (7), wherein the target region consists of 1 to 3 consecutive amino acid residues.

(9) The antibody or salt thereof according to (8), wherein the target region consists of amino acid residues at positions 246 to 248 in a human IgG Fc region.

(10) The antibody or salt thereof according to any one of (6) to (9), wherein the regioselectivity is 50% or more.

(11) The antibody or salt thereof according to (10), wherein the regioselectivity is 70% or more.

(12) The antibody or salt thereof according to (10), wherein the regioselectivity is 90% or more.

(13) The antibody or salt thereof according to any one of (6) to (12), wherein the same type of amino acid residue as the specific amino acid residue other than the specific amino acid residue present at the specific position is not comprised in a region up to a remote position of "a" (where "a" is any integer of 1 to 10) amino acid residues to an N-terminal side and a C-terminal side each with respect to the specific amino acid present at the specific position.

(14) The antibody or salt thereof according to any one of (1) to (13), wherein the antibody comprises a plurality of heavy chains, and T has a structural unit represented by A-L-B—R' in a plurality of corresponding target regions in the plurality of heavy chains, and as a result, the antibody has a plurality of structural units represented by A-L-B—R'.

(15) The antibody or salt thereof according to (14), comprising two heavy chains.

(16) The antibody or salt thereof according to any one of (1) to (15), wherein the portion formed by a reaction between an antibody and a reactive group is formed by a reaction of a reactive group specific to a side chain of any one of a lysine residue, a tyrosine residue, and a tryptophan residue with the lysine residue, the tyrosine residue, or the tryptophan residue.

(17) The antibody or salt thereof according to any one of (1) to (16), wherein the portion formed by a reaction between an antibody and a reactive group is formed by a reaction between a lysine residue and a reactive group specific to a side chain of the lysine residue.

(18) The antibody or salt thereof according to any one of (1) to (17), wherein the portion formed by the reaction corresponds to any one chemical structure selected from the group consisting of the following:

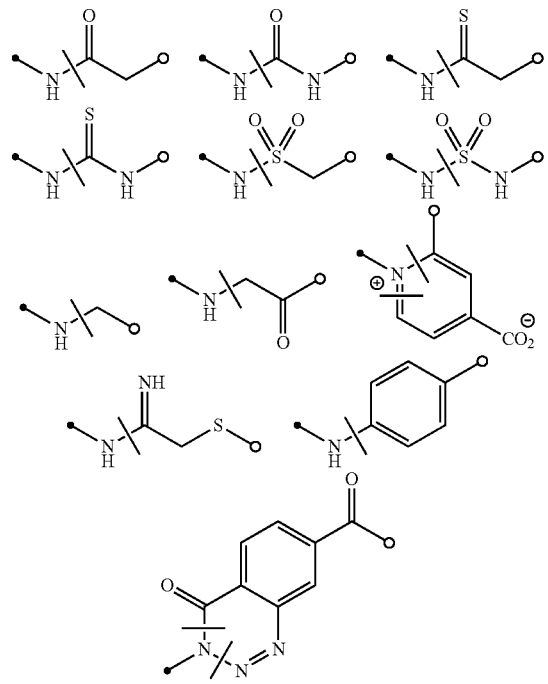

wherein ● (black circle) indicates a bond to a T-side portion, and ○ (white circle) indicates a bond to a B-side portion, and the straight line orthogonal to the bond indicates a bond formed by the reaction.

(19) The antibody or salt thereof according to any one of (1) to (18), wherein a main chain coupling A with R' has 4 to 20 atoms.

(20) The antibody or salt thereof according to any one of (1) to (19), wherein a main chain coupling A with R comprises no cyclic structure.

(21) The antibody or salt thereof according to any one of (1) to (20), wherein the partial structure represented by L-B comprises no peptide portion.

(22) The antibody or salt thereof according to any one of (1) to (21), wherein the compound represented by the above Formula (II) is represented by the following (II'):

A-B2-L'-B1-R'-T          (II')

wherein

A, R', and T are the same as those in the above Formula (II),

L' is a cleavable linker that is a divalent group comprising a cleavable portion, B1 and B2 are the same as or different from each other and are each (a) a divalent group comprising a bioorthogonal functional group or (b) a divalent group comprising no bioorthogonal functional group, and B1 and B2 may have a symmetrical structure about L'.

(23) The antibody or salt thereof according to (22), wherein the compound represented by the above Formula (II') is represented by the following (II"):

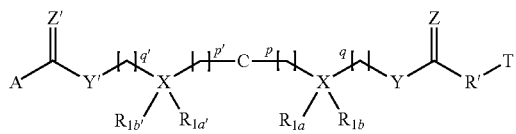

(II")

wherein

A, R', and T are the same as those in the above Formula (II),

C is a cleavable portion, p and p' are the same as or different from each other and are each any integer of 0 to 10, q and q' are the same as or different from each other and are each any integer of 0 to 10, X and X' are the same as or different from each other and are each a carbon atom, a nitrogen atom, or a single bond (where $P_{1b}$ is absent when X is a nitrogen atom, $R_{1b'}$ is absent when X' is a nitrogen atom, $R_{1a}$ and $R_{1b}$ are absent when X is a single bond, and $R_{1a'}$ and $R_{1b'}$ are absent when X' is a single bond), and $R_{1a}$, $R_{1b}$, $R_{1a'}$, and $R_{1b'}$ are the same as or different from each other and are each selected from the group consisting of:

(i) a hydrogen atom or a halogen atom;
(ii) a monovalent hydrocarbon group;
(iii) an aralkyl;
(iv) a monovalent heterocyclic group;
(v) $R_c$—O—, $R_c$—C(=O)—, $R_c$—O—C(=O)—, or $R_c$—C(=O)—O—, (where $R_c$ represents a hydrogen atom or a monovalent hydrocarbon group);
(vi) $NR_dR_e$—, $NR_dR_e$—C(=O)—, $NR_dR_e$—C(=O)—O—, or $R_d$—C(=O)—$NR_e$—, (where $R_d$ and $R_e$ are the same or different and each represent a hydrogen atom or a monovalent hydrocarbon group); and
(vii) a nitro group, a sulfate group, a sulfonate group, a cyano group, or a carboxyl group, Y and Y' are the same as or different from each other and are the same as Y in the above Formula (B-1), and Z and Z' are the same as or different from each other and are the same as Z in the above Formula (B-1).

(24) An antibody having an affinity substance to an antibody and a cleavable portion, or a salt thereof, represented by the following Formula (II):

A-L-B—R'-T          (II)

wherein

A is an affinity substance to an antibody,

L is a cleavable linker that is a divalent group comprising a cleavable portion, B is (a) a divalent group comprising a bioorthogonal functional group or (b) a divalent group comprising no bioorthogonal functional group, R' is a portion formed by a reaction between an antibody and a reactive group specific to a side chain of a lysine residue, and T is an antibody, wherein the affinity substance to an antibody is a polypeptide comprising a glutamine residue (Q) at an N-terminal.

Method for producing antibody having affinity substance to antibody and cleavable portion, or salt thereof.

(25) A method for producing an antibody having an affinity substance to an antibody and a cleavable portion, or a salt thereof, the method comprising reacting a compound having an affinity substance to an antibody, a cleavable portion, and a reactive group, or a salt thereof, represented by the following Formula (I):

A-L-B—R          (I)

wherein

A is an affinity substance to an antibody,

L is a cleavable linker that is a divalent group comprising a cleavable portion, B is (a) a divalent group comprising a bioorthogonal functional group or (b) a divalent group comprising no bioorthogonal functional group, and R is a reactive group to the antibody, with an antibody to form an antibody having an affinity substance to an antibody and a cleavable portion, or a salt thereof, represented by the following Formula (II):

A-L-B—R'-T          (II)

wherein

A, L, and B are the same as those in the above Formula (I),

R' is a portion formed by a reaction between an antibody and a reactive group, and T is an antibody, wherein the affinity substance to an antibody is a polypeptide comprising a glutamine residue (Q) at an N-terminal.

(26) The method according to (25), wherein the reactive group is specific to a side chain of a lysine residue.

According to a third embodiment, the present invention provides a conjugate having an affinity substance to an antibody, a cleavable portion, a functional substance, and an antibody, or a salt thereof, and a method for producing the same.

Conjugate having affinity substance to antibody, cleavable portion, functional substance, and antibody, or salt thereof)

(1) A conjugate having an affinity substance to an antibody, a cleavable portion, a functional substance, and an antibody, or a salt thereof, represented by the following Formula (III):

A-L-B'(—F)—R'-T    (III)

wherein
A is an affinity substance to an antibody,
L is a cleavable linker that is a divalent group comprising a cleavable portion,
B' is a trivalent group comprising a portion formed by a reaction between a functional substance and a bioorthogonal functional group,
F is a functional substance,
R' is a portion formed by a reaction between an antibody and a reactive group, and
T is an antibody, wherein
the affinity substance to an antibody is a polypeptide comprising a glutamine residue (Q) at an N-terminal.

(2) The conjugate or salt thereof according to (1), wherein the antibody is a monoclonal antibody.

(3) The conjugate or salt thereof according to (1) or (2), wherein the antibody is an IgG antibody.

(4) The conjugate or salt thereof according to any one of (1) to (3), wherein the antibody is derived from a human.

(5) The conjugate or salt thereof according to any one of (1) to (4), wherein the antibody comprises any one Fc region protein selected from the group consisting of the following (A) to (C) and has an antigen-binding ability:
  (A) an Fc region protein comprising an amino acid sequence of SEQ ID NO: 1;
  (B) an Fc region protein comprising an amino acid sequence with one or several amino acid residues inserted, added, deleted, or substituted in the amino acid sequence of SEQ ID NO: 1; or
  (C) an Fc region protein comprising an amino acid sequence having 90% or more identity to the amino acid sequence of SEQ ID NO: 1.

(6) The conjugate or salt thereof according to any one of (1) to (5), wherein the antibody comprises one or more specific amino acid residues in a target region consisting of 1 to 50 consecutive amino acid residues and comprises five or more of the specific amino acid residues in a non-target region other than the target region, and
the structural unit represented by A-L-B'(—F)—R' is bound to the one or more specific amino acid residues comprised in the target region with 30% or more regioselectivity.

(7) The conjugate or salt thereof according to (6), wherein the same type of amino acid residue as the specific amino acid residue other than the specific amino acid residue present at the specific position is not comprised in a region up to a remote position of "a" (where "a" is any integer of 1 to 10) amino acid residues to an N-terminal side and a C-terminal side each with respect to the specific amino acid present at the specific position.

(8) The conjugate or salt thereof according to any one of (1) to (7), wherein
the antibody comprises a plurality of heavy chains, and
T has a structural unit represented by A-L-B'(—F)—R' in a plurality of corresponding target regions in the plurality of heavy chains, and as a result, the antibody has a plurality of structural units represented by A-L-B'(—F)—R'.

(9) The conjugate or salt thereof according to any one of (1) to (8), wherein when the functional substance has a functional group easily reacting with a bioorthogonal functional group, or when the functional substance is derivatized so as to have a functional group easily reacting with the bioorthogonal functional group, the functional group easily reacting with the bioorthogonal functional group is selected from the group consisting of an azide residue, an aldehyde residue, a thiol residue, an alkyne residue, an alkene residue, a halogen residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, a thioester residue, an α-halocarbonyl residue, an isonitrile residue, a sydnone residue, and a selenium residue.

(10) The conjugate or salt thereof according to any one of (1) to (9), wherein when the functional substance has a functional group easily reacting with a bioorthogonal functional group, or when the functional substance is derivatized so as to have a functional group easily reacting with the bioorthogonal functional group, the functional group easily reacting with the bioorthogonal functional group is selected from the group consisting of the following:

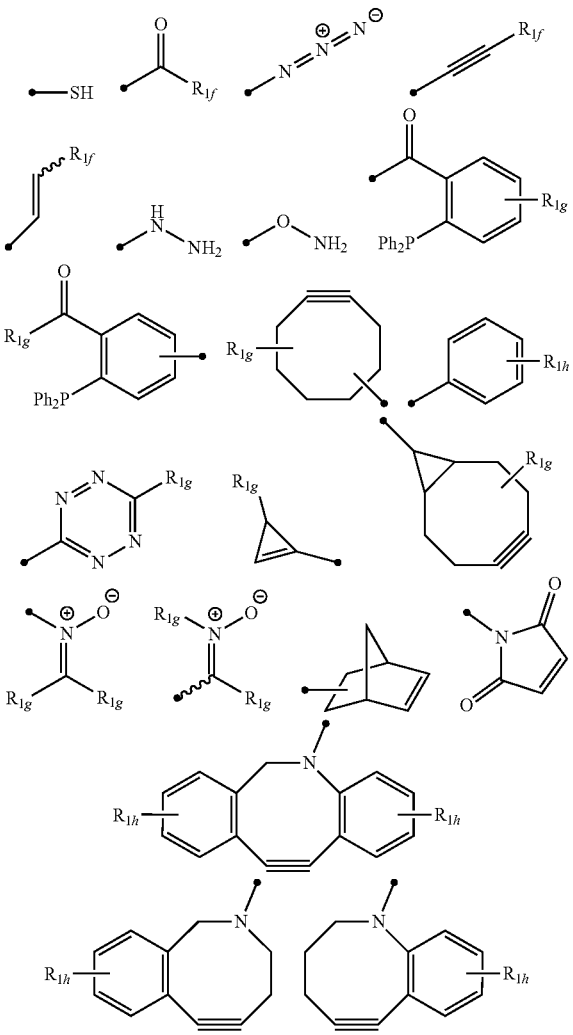

wherein
$R_{1f}$, one or a plurality of $R_{1g}$s, and one or a plurality of $R_{1h}$s are the same as or different from each other, and each an atom or a group selected from the group consisting of the above (i) to (vii) or an electron-withdrawing group, and • is a bond to the functional substance.

(11) The conjugate or salt thereof according to any one of (1) to (10), wherein the portion formed by a reaction between an antibody and a reactive group is formed by a reaction between a lysine residue, a tyrosine residue, or a tryptophan residue and a reactive group specific to a side chain of any one of the lysine residue, the tyrosine residue, and the tryptophan residue.

(12) The conjugate or salt thereof according to any one of (1) to (11), wherein the portion formed by a reaction between an antibody and a reactive group is formed by a reaction between a lysine residue and a reactive group specific to a side chain of the lysine residue.

(13) The conjugate or salt thereof according to any one of (1) to (12), wherein the portion formed by the reaction corresponds to any one chemical structure selected from the group consisting of the following:

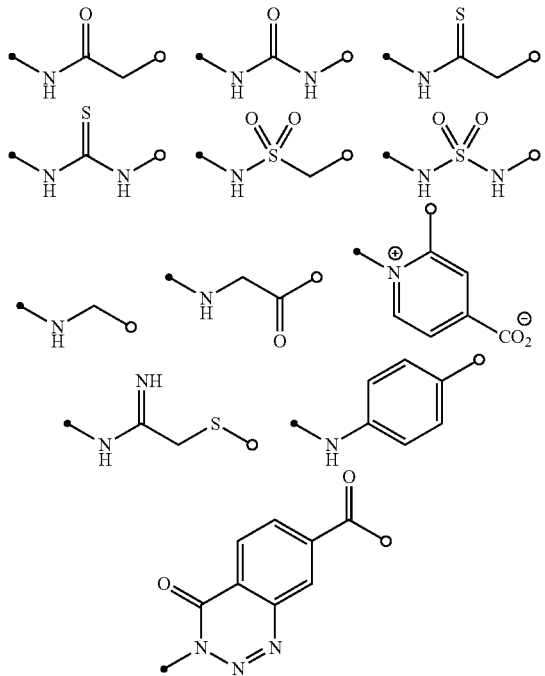

wherein ● (black circle) indicates a bond to a T-side portion, and ○ (white circle) indicates a bond to a B-side portion.

(14) The conjugate or salt thereof according to any one of (1) to (13), wherein the functional substance is a drug or a labelling substance.

(15) The conjugate or salt thereof according to any one of (1) to (13), wherein the functional substance is a small compound.

(16) The conjugate or salt thereof according to (14) or (15), wherein the drug is an anticancer drug.

(17) The conjugate or salt thereof according to any one of (1) to (16), wherein a main chain coupling A with R' has 4 to 20 atoms.

(18) The conjugate or salt thereof according to any one of (1) to (17), wherein a main chain coupling A with R comprises no cyclic structure.

(19) The conjugate or salt thereof according to any one of (1) to (18), wherein the partial structure represented by L-B comprises no peptide portion.

(20) The conjugate or salt thereof according to any one of (1) to (19), wherein the compound represented by the above Formula (III) is represented by the following (III'):

A-B2'(—F2)-L'-B1'(—F1)-R'-T    (III')

wherein

A, R', and T are the same as those in the above Formula (II),

L' is a cleavable linker that is a divalent group comprising a cleavable portion, B1' and B2' are the same as or different from each other and are each a trivalent group comprising a portion formed by a reaction between a functional substance and a bioorthogonal functional group, F1 and F2 are the same as or different from each other and are each a functional substance, and B1'(—F1) and B2'(—F2) may have a symmetrical structure about L'.

(21) The conjugate or salt thereof according to (20), wherein the compound represented by the above Formula (III') is represented by the following (III''):

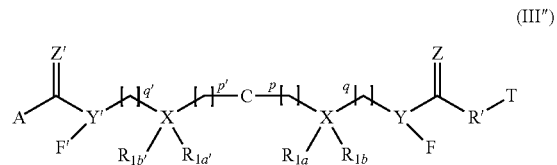

(III'')

wherein

A, R', and T are the same as those in the above Formula (III),

C is a cleavable portion, p and p' are the same as or different from each other and are each any integer of 0 to 10, q and q' are the same as or different from each other and are each any integer of 0 to 10, X and X' are the same as or different from each other and are each a carbon atom, a nitrogen atom, or a single bond (where $R_{1b}$ is absent when X is a nitrogen atom, $R_{1b'}$ is absent when X' is a nitrogen atom, $R_{1a}$ and $R_{1b}$ are absent when X is a single bond, and $R_{1a'}$ and $R_{1b'}$ are absent when X' is a single bond), $R_{1a}$, $R_{1b}$, $R_{1a'}$, and $R_{1b'}$ are the same as or different from each other and are each selected from the group consisting of the above (i) to (vii), Y and Y' are the same as or different from each other and are each a residue obtained by removing one hydrogen atom from Y in the above Formula (B-1), Z and Z' are the same as or different from each other and are the same as Z in the above Formula (B-1), and F and F' are the same as or different from each other and are each a functional substance.

(22) A conjugate having an affinity substance to an antibody, a functional substance, and an antibody, or a salt thereof, represented by the following Formula (III):

A-L-B'(—F)—R'-T    (III)

wherein

A is an affinity substance to an antibody,

L is a cleavable linker that is a divalent group comprising a cleavable portion, B' is a trivalent group comprising a portion formed by a reaction between a functional substance and a bioorthogonal functional group, F is a functional substance, R' is a portion formed by a reaction between an antibody and a reactive group specific to a side chain of a lysine residue, and T is an antibody, wherein the affinity substance to an antibody is a polypeptide comprising a glutamine residue (Q) at an N-terminal.

Method for producing conjugate having affinity substance to antibody, cleavable portion, functional substance, and antibody, or salt thereof.

(23) A method for producing a conjugate having an affinity substance to an antibody, a cleavable portion, a functional substance, and an antibody, or a salt thereof, the method comprising reacting an antibody having an affinity substance to an antibody and a cleavable portion, or a salt thereof, represented by the following Formula (II):

$$A\text{-}L\text{-}B\text{—}R'\text{-}T \qquad (II)$$

wherein

A is an affinity substance to an antibody,

L is a cleavable linker that is a divalent group comprising a cleavable portion, B is (a) a divalent group comprising a bioorthogonal functional group, R' is a portion formed by a reaction between an antibody and a reactive group, and T is an antibody, with a functional substance to form a conjugate having an affinity substance to an antibody, a cleavable portion, a functional substance, and an antibody, or a salt thereof, represented by the following Formula (III):

$$A\text{-}L\text{-}B'(\text{—}F)\text{—}R'\text{-}T \qquad (III)$$

wherein

A, L, R', and T are the same as those in the above Formula (II),

B' is a trivalent group comprising a portion formed by a reaction between a functional substance and a bioorthogonal functional group, and F is a functional substance, wherein the affinity substance to an antibody is a polypeptide comprising a glutamine residue (Q) at an N-terminal.

(24) The method according to (23), wherein the reactive group is specific to a side chain of a lysine residue.

(25) A method for producing a conjugate having an affinity substance to an antibody, a cleavable portion, a functional substance, and an antibody, or a salt thereof, the method comprising:

(A) reacting a compound or a salt thereof, represented by the following Formula (I):

$$A\text{-}L\text{-}B\text{—}R \qquad (I)$$

wherein

A is an affinity substance to an antibody,

L is a cleavable linker that is a divalent group comprising a cleavable portion, B is (a) a divalent group comprising a bioorthogonal functional group, and R is a reactive group to the antibody, with an antibody to form an antibody having an affinity substance to an antibody and a cleavable portion, or a salt thereof, represented by the following Formula (II):

$$A\text{-}L\text{-}B\text{—}R'\text{-}T \qquad (II)$$

wherein

A, L, and B are the same as those in the above formula (I),

R' is a portion formed by a reaction between an antibody and a reactive group, and T is an antibody; and (B) reacting the antibody having an affinity substance to an antibody and a cleavable portion, or a salt thereof with a functional substance to form a conjugate having an affinity substance to an antibody, a cleavable portion, a functional substance, and an antibody, or a salt thereof, represented by the following Formula (III):

$$A\text{-}L\text{-}B'(\text{—}F)\text{—}R'\text{-}T \qquad (III)$$

wherein

A and L are the same as those in the above Formula (I),

R' and T are the same as those in the above Formula (II),

B' is a trivalent group comprising a portion formed by a reaction between a functional substance and a bioorthogonal functional group, and F is a functional substance, wherein the affinity substance to an antibody is a polypeptide comprising a glutamine residue (Q) at an N-terminal.

According to a fourth embodiment, the present invention provides a method for producing an antibody having a bioorthogonal functional group or bioorthogonal functional groups.

(1) A method for producing an antibody having a bioorthogonal functional group or bioorthogonal functional groups, or a salt thereof, the method comprising cleaving a cleavable portion of an antibody having an affinity substance to an antibody and a cleavable portion, or a salt thereof, represented by the following Formula (II):

$$A\text{-}L\text{-}B\text{—}R'\text{-}T \qquad (II)$$

wherein

A is an affinity substance to an antibody,

L is a cleavable linker that is a divalent group comprising a cleavable portion, B is (a) a divalent group comprising a bioorthogonal functional group or (b) a divalent group comprising no bioorthogonal functional group, R' is a portion formed by a reaction between an antibody and a reactive group, and T is an antibody, to form an antibody having a bioorthogonal functional group or bioorthogonal functional groups, or a salt thereof, represented by the following Formula (IV):

$$L1\text{-}B\text{—}R'\text{-}T \qquad (IV)$$

wherein

B, R', and T are the same as those in the above Formula (II), and

L1 is (i') a monovalent group comprising a bioorthogonal functional group or (ii') a monovalent group comprising no bioorthogonal functional group, wherein the affinity substance to an antibody is a polypeptide comprising a glutamine residue (Q) at an N-terminal.

(2) The method according to (1), wherein L is (i) a cleavable linker that is a divalent group comprising a cleavable portion capable of forming a bioorthogonal functional group on a reactive group side by cleavage or (ii) a cleavable linker that is a divalent group comprising a cleavable portion not capable of forming a bioorthogonal functional group on a reactive group side by cleavage.

(3) The method according to (2), wherein
L is the cleavable linker of the above (i),
L1 is (i') the monovalent group comprising a bioorthogonal functional group, and
B is the divalent group of the above (a) or (b).
(4) The method according to (2) or (3), wherein
L is the cleavable linker of the above (i),
L1 is (i') the monovalent group comprising a bioorthogonal functional group, and
B is the divalent group of the above (b).
(5) The method according to (2), wherein
L is the cleavable linker of the above (ii),
L1 is (i') the monovalent group comprising no bioorthogonal functional group, and
B is the divalent group of the above (a).
(6) The method according to any one of (1) to (5), wherein the reactive group is specific to a side chain of a lysine residue.
(7) A method for producing an antibody having a bioorthogonal functional group or bioorthogonal functional groups, or a salt thereof, the method comprising
(A) reacting a compound or a salt thereof, represented by the following Formula (I):

A-L-B—R     (I)

wherein
A is an affinity substance to an antibody,
L is a cleavable linker that is a divalent group comprising a cleavable portion,
B is (a) a divalent group comprising a bioorthogonal functional group or (b) a divalent group comprising a bioorthogonal functional group, and
R is a reactive group to the antibody, with an antibody
to form an antibody having an affinity substance to an antibody and a cleavable portion, or a salt thereof, represented by the following Formula (II):

A-L-B—R'-T     (II)

wherein
A, L, and B are the same as those in the above Formula (I),
R' is a portion formed by a reaction between an antibody and a reactive group, and
T is an antibody; and
(B) cleaving a cleavable portion of the antibody having an affinity substance to an antibody and a cleavable portion, or a salt thereof
to form an antibody having a bioorthogonal functional group or bioorthogonal functional groups, or a salt thereof, represented by the following Formula (IV):

L1-B—R'-T     (IV)

wherein
B, R', and T are the same as those in the above Formula (II), and
L1 is (i') a monovalent group comprising a bioorthogonal functional group or (ii') a monovalent group comprising no bioorthogonal functional group, wherein
the affinity substance to an antibody is a polypeptide comprising a glutamine residue (Q) at an N-terminal.
According to a fifth embodiment, the present invention provides a method for producing an antibody having a functional substance or functional substances, or a salt thereof.
(1) A method for producing an antibody having a functional substance or functional substances, or a salt thereof, the method comprising cleaving a cleavable portion of a conjugate having an affinity substance to an antibody, a cleavable portion, a functional substance, and an antibody, or a salt thereof, represented by the following Formula (III):

A-L-B'(—F)—R'-T     (III)

wherein
A is an affinity substance to an antibody,
L is a cleavable linker that is a divalent group comprising a cleavable portion,
B' is a trivalent group comprising a portion formed by a reaction between a functional substance and a bioorthogonal functional group,
F is a functional substance,
R' is a portion formed by a reaction between an antibody and a reactive group, and
T is an antibody,
to form an antibody having a functional substance or functional substances, or a salt thereof, represented by the following Formula (V1):

L1-B'(—F)—R'-T     (V1)

wherein
L1 is (i') a monovalent group comprising a bioorthogonal functional group or (ii') a monovalent group comprising no bioorthogonal functional group, and
B', F, R', and T are the same as those in the above Formula (III), wherein
the affinity substance to an antibody is a polypeptide comprising a glutamine residue (Q) at an N-terminal.
(2) The method according to (1), wherein the reactive group is specific to a side chain of a lysine residue.
(3) A method for producing an antibody having a functional substance or functional substances, or a salt thereof, the method comprising:
(A) reacting an antibody having an affinity substance to an antibody and a cleavable portion, or a salt thereof, represented by the following Formula (II):

A-L-B—R'-T     (II)

wherein
A is an affinity substance to an antibody,
L is a cleavable linker that is a divalent group comprising a cleavable portion,
B is (a) a divalent group comprising a bioorthogonal functional group,
R' is a portion formed by a reaction between an antibody and a reactive group, and
T is an antibody, with a functional substance
to form a conjugate having an affinity substance to an antibody, a cleavable portion, a functional substance, and an antibody, or a salt thereof, represented by the following Formula (III):

A-L-B'(—F)—R'-T     (III)

wherein
A, L, R', and T are the same as those in the above Formula (II),
B' is a trivalent group comprising a portion formed by a reaction between a functional substance and a bioorthogonal functional group, and
F is a functional substance; and
(B) cleaving a cleavable portion of the conjugate having an affinity substance to an antibody, a cleavable portion, a functional substance, and an antibody, or a salt thereof to form an antibody having a functional substance or functional substances, or a salt thereof, represented by the following Formula (V1):

$$\text{L1-B'(—F)—R'-T} \tag{V1}$$

wherein
L1 is (i') a monovalent group comprising a bioorthogonal functional group or (ii') a monovalent group comprising no bioorthogonal functional group, and
B', F, R', and T are the same as those in the above Formula (III), wherein
the affinity substance to an antibody is a polypeptide comprising a glutamine residue (Q) at an N-terminal.

(4) A method for producing an antibody having a functional substance or functional substances, or a salt thereof, the method comprising:
(A) reacting a compound having an affinity substance to an antibody, a cleavable portion, and a reactive group, or a salt thereof, represented by the following Formula (I):

$$\text{A-L-B—R} \tag{I}$$

wherein
A is an affinity substance to an antibody,
L is a cleavable linker that is a divalent group comprising a cleavable portion,
B is (a) a divalent group comprising a bioorthogonal functional group, and
R is a reactive group to the antibody, with an antibody to form an antibody having an affinity substance to an antibody and a cleavable portion, or a salt thereof, represented by the following Formula (II):

$$\text{A-L-B—R'-T} \tag{II}$$

wherein
A, L, and B are the same as those in the above Formula (I),
R' is a portion formed by a reaction between an antibody and a reactive group, and
T is an antibody;
(B) reacting the antibody having an affinity substance to an antibody and a cleavable portion, or a salt thereof with a functional substance
to form a conjugate having an affinity substance to an antibody, a cleavable portion, a functional substance, and an antibody, or a salt thereof, represented by the following Formula (III):

$$\text{A-L-B'(—F)—R'-T} \tag{III}$$

wherein
A and L are the same as those in the above Formula (I),
R' and T are the same as those in the above Formula (II),
B' is a trivalent group comprising a portion formed by a reaction between a functional substance and a bioorthogonal functional group, and
F is a functional substance; and
(C) cleaving a cleavable portion of the conjugate having an affinity substance to an antibody, a cleavable portion, a functional substance, and an antibody, or a salt thereof
to form an antibody having a functional substance or functional substances, or a salt thereof, represented by the following Formula (V1):

$$\text{L1-B'(—F)—R'-T} \tag{V1}$$

wherein
L1 is (i') a monovalent group comprising a bioorthogonal functional group or (ii') a monovalent group comprising no bioorthogonal functional group, and
B', F, R', and T are the same as those in the above formula (III), wherein
the affinity substance to an antibody is a polypeptide comprising a glutamine residue (Q) at an N-terminal.

(5) A method for producing an antibody having a functional substance or functional substances, or a salt thereof, the method comprising:
(A) cleaving a cleavable portion of an antibody having an affinity substance to an antibody and a cleavable portion, or a salt thereof, represented by the following Formula (II):

$$\text{A-L-B—R'-T} \tag{II}$$

wherein
A is an affinity substance to an antibody,
L is a cleavable linker that is a divalent group comprising a cleavable portion,
B is (a) a divalent group comprising a bioorthogonal functional group or (b) a divalent group comprising no bioorthogonal functional group,
R' is a portion formed by a reaction between an antibody and a reactive group, and
T is an antibody
to form an antibody having a bioorthogonal functional group or bioorthogonal functional groups, or a salt thereof, represented by the following Formula (IV):

$$\text{L1-B—R'-T} \tag{IV}$$

wherein
B, R', and T are the same as those in the above Formula (II), and
L1 is (i') a monovalent group comprising a bioorthogonal functional group or (ii') a monovalent group comprising no bioorthogonal functional group; and
(B) reacting the antibody having a bioorthogonal functional group or bioorthogonal functional groups, or a salt thereof with one or more types of functional substances
to form an antibody having a functional substance or functional substances, or a salt thereof, represented by the following Formula (V2):

$$\text{F-L1'-B—R'-T} \tag{V2}$$

wherein
B, R', and T are the same as those in the above Formula (IV),
L1' is a divalent group comprising a portion formed by a reaction between a functional substance and (i') the monovalent group comprising a bioorthogonal functional group, and
F is a functional substance, or
the following Formula (V3):

$$\text{Fa-L1'-B'(-Fb)-R'-T} \tag{V3}$$

wherein
R' and T are the same as those in the above Formula (IV),
L1' is the same as that in the above Formula (V2),
B' is a divalent group comprising a portion formed by a reaction between a functional substance and a bioorthogonal functional group, and
Fa and Fb are functional substances that are the same as or different from each other, wherein
the affinity substance to an antibody is a polypeptide comprising a glutamine residue (Q) at an N-terminal.

(6) A method for producing an antibody having a functional substance or functional substances, or a salt thereof, the method comprising:

(A) reacting a compound or a salt thereof, represented by the following Formula (I):

A-L-B—R           (I)

wherein

A is an affinity substance to an antibody,
L is a cleavable linker that is a divalent group comprising a cleavable portion,
B is (a) a divalent group comprising a bioorthogonal functional group or (b) a divalent group comprising no bioorthogonal functional group, and
R is a reactive group to the antibody, with an antibody to form an antibody having an affinity substance to an antibody and a cleavable portion, or a salt thereof, represented by the following Formula (II):

A-L-B—R'-T           (II)

wherein

A, L, and B are the same as those in the above Formula (I),
R' is a portion formed by a reaction between an antibody and a reactive group, and
T is an antibody;

(B) cleaving a cleavable portion of the antibody having an affinity substance to an antibody and a cleavable portion, or a salt thereof
to form an antibody having a bioorthogonal functional group or bioorthogonal functional groups, or a salt thereof, represented by the following Formula (IV):

L1-B—R'-T           (IV)

wherein

B, R', and T are the same as those in the above Formula (II), and
L1 is (i') a monovalent group comprising a bioorthogonal functional group or (ii') a monovalent group comprising no bioorthogonal functional group; and (C) reacting the antibody having a bioorthogonal functional group or bioorthogonal functional groups, or a salt thereof with one or more types of functional substances
to form an antibody having a functional substance or functional substances, or a salt thereof, represented by the following Formula (V2):

F-L1'-B—R'-T           (V2)

wherein

B, R', and T are the same as those in the above Formula (IV),
L1' is a divalent group comprising a portion formed by a reaction between a functional substance and (i') the monovalent group comprising a bioorthogonal functional group, and
F is a functional substance, or
the following Formula (V3):

Fa-L1'-B'(-Fb)-R'-T           (V3)

wherein

R' and T are the same as those in the above Formula (IV),
L1' is the same as that in the above Formula (V2),
B' is a trivalent group comprising a portion formed by a reaction between a functional substance and a bioorthogonal functional group, and
Fa and Fb are functional substances that are the same as or different from each other, wherein the affinity substance to an antibody is a polypeptide comprising a glutamine residue (Q) at an N-terminal.

Effect of the Invention (I) A compound having an affinity substance to an antibody, a cleavable portion, and a reactive group, or a salt thereof according to the present invention is useful for regioselective modification of an antibody, for example.

(I) The compound or a salt thereof according to the present invention, (II) an antibody (regioselectively) having an affinity substance to an antibody and a cleavable portion, or a salt thereof according to the present invention, and (III) a conjugate (regioselectively) having an affinity substance to an antibody, a cleavable portion, a functional substance, and an antibody, or a salt thereof according to the present invention are useful, for example, as an intermediate for preparing an antibody (regioselectively) having a bioorthogonal functional group or bioorthogonal functional groups, or a salt thereof, and an antibody (regioselectively) having a functional substance or functional substances, or a salt thereof. The antibody (regioselectively) having a functional substance or functional substances, or a salt thereof is useful, for example, as a pharmaceutical or a reagent (e.g., a diagnostic reagent or a reagent for research). The antibody (regioselectively) having a bioorthogonal functional group or bioorthogonal functional groups, or a salt thereof is useful as an intermediate for preparing an antibody (regioselectively) having a functional substance or functional substances, or a salt thereof. Therefore, (I) the compound or salt thereof according to the present invention, (II) the antibody or salt thereof according to the present invention, and (III) the conjugate or salt thereof according to the present invention are useful, for example, as synthetic intermediates for pharmaceuticals or reagents.

In addition, by using a polypeptide comprising a glutamine residue (Q) at an N-terminal as an affinity substance to an antibody, an amino group (—NH$_2$) in the glutamine residue (Q) at the N-terminal reacts (is pyroglutamylated) with an amide group (e.g., —CONH$_2$ in the glutamine residue (Q) when QET is comprised at the N-terminal) present in a side chain thereof, and therefore the amino group can be protected. Therefore, a linker that mediates a binding of the affinity substance to an antibody can be specifically added to a specific amino acid residue in the affinity substance.

Furthermore, according to a polypeptide secretion production method using a coryneform bacterium as a host (CspB fusion method), by adding N-terminal three residues Gln-Glu-Thr (QET) of a CspB mature protein to an N-terminal of a target polypeptide, an advantage of the polypeptide secretion production method can be enjoyed. Therefore, this method is suitable for preparing a polypeptide comprising a glutamine residue (Q) at an N-terminal (affinity substance to an antibody).

BRIEF DESCRIPTION OF DRAWINGS

A more complete appreciation of the invention and many of the attendant advantages thereof will be readily obtained as the same become better understood by reference to the following detailed description when considered in connection with the accompanying drawings, wherein:

FIG. 1-2 is a schematic diagram (Part 2) illustrating a concept of regioselective modification of an antibody with the compound of the present invention. Cleavage of a cleavable portion in a linker (L) forms an antibody regioselectively modified with a bioorthogonal functional group.

FIG. 1-3 is a schematic diagram (Part 3) illustrating a concept of regioselective modification of an antibody with the compound of the present invention. A reaction between a bioorthogonal functional group and a functional substance (e.g., drug) forms an antibody regioselectively modified with a functional substance.

FIG. 2 is a diagram illustrating a relationship among embodiments of the present invention (a salt is not illustrated). In reaction (1), a compound having an affinity substance to an antibody, a cleavable portion, and a reactive group is reacted with an antibody to form an antibody having an affinity substance to an antibody and a cleavable portion. In reaction (2), the antibody having an affinity substance to an antibody and a cleavable portion is reacted with a functional substance to form a conjugate having an affinity substance to an antibody, a cleavable portion, a functional substance, and an antibody. In reaction (3), a cleavable portion of the conjugate having an affinity substance to an antibody, a cleavable portion, a functional substance, and an antibody is cleaved to form an antibody having a functional substance or functional substances (at this time, a portion comprising the affinity substance is formed as a by-product). In reaction (4), a cleavable portion of the antibody having an affinity substance to an antibody and a cleavable portion is cleaved to form an antibody having a bioorthogonal functional group or bioorthogonal functional groups (at this time, a portion comprising the affinity substance is formed as a by-product). In reaction (5), the antibody having a bioorthogonal functional group or bioorthogonal functional groups is reacted with a functional substance to form an antibody having a functional substance or functional substances. Reactions (2) and (5) can be performed in a similar manner to each other. Reactions (3) and (5) can also be performed in a similar manner to each other.

FIG. 3 is a diagram illustrating a consensus amino acid sequence between an Fc region in a heavy chain of trastuzumab and an IgG1 Fc region (SEQ ID NO: 1).

FIG. 4 is a diagram illustrating (1) an amino acid sequence of a heavy chain of trastuzumab (SEQ ID NO: 2), (2) an amino acid sequence of an IgG1 Fc region obtained by cleaving a sugar chain with PNGase (SEQ ID NO: 3), and (3) an amino acid sequence of a light chain of trastuzumab (SEQ ID NO: 4).

FIG. 11-1 is a diagram illustrating a CID spectrum of a product ion of m/z 764.68 (theoretical value: 764.40) corresponding to divalent y12 indicating modification of a lysine residue at position 246/248 of a human IgG heavy chain in EU numbering (Example 7).

FIG. 11-2 is a diagram illustrating results of searching for a peptide fragment comprising a modification to a lysine residue for a trypsin digestion of trastuzumab (thiol-introduced compound (+145.019 Da) subjected to carbamidomethylation with iodoacetamide) using a Proteome Discoverer (Thermo Fisher Scientific K.K.) (Example 7). The horizontal axis indicates an identified lysine residue, and the vertical axis indicates Peptide Spectrum Matches (PSMs). Note that the residue number of a lysine residue on a heavy chain VH domain and a light chain is described using the number in a sequence (that is, an N-terminal amino acid is the first. Hereinafter the same), and the residue number of a lysine residue on heavy chain CH1, CH2, and CH3 domains is described using EU numbering.

FIG. 13-1 is a diagram illustrating a CID spectrum of a product ion of m/z 838.23 (theoretical value: 837.94) corresponding to divalent y13 indicating modification of a lysine residue at position 246/248 of a human IgG heavy chain in EU numbering (Example 8).

FIG. 13-2 is a diagram illustrating results of searching for a peptide fragment comprising a modification to a lysine residue for a trypsin digestion of trastuzumab (thiol-introduced compound (+145.019 Da) subjected to carbamidomethylation with iodoacetamide) using a Proteome Discoverer (Thermo Fisher Scientific K.K.) (Example 8). The horizontal axis indicates an identified lysine residue, and the vertical axis indicates Peptide Spectrum Matches (PSMs). Note that the residue number of a lysine residue on a heavy chain VH domain and a light chain is described using the number in a sequence, and the residue number of a lysine residue on heavy chain CH1, CH2, and CH3 domains is described using EU numbering.

FIG. 15-1 is a diagram illustrating a CID spectrum of a product ion of m/z 838.29 (theoretical value: 837.94) corresponding to divalent y13 indicating modification of a lysine residue at position 246/248 of a human IgG heavy chain in EU numbering (Example 9).

FIG. 15-2 is a diagram illustrating results of searching for a peptide fragment comprising a modification to a lysine residue for a trypsin digestion of trastuzumab (thiol-introduced compound (+145.019 Da) subjected to carbamidomethylation with iodoacetamide) using a Proteome Discoverer (Thermo Fisher Scientific K.K.) (Example 9). The horizontal axis indicates an identified lysine residue, and the vertical axis indicates Peptide Spectrum Matches (PSMs). Note that the residue number of a lysine residue on a heavy chain VH domain and a light chain is described using the number in a sequence, and the residue number of a lysine residue on heavy chain CH1, CH2, and CH3 domains is described using EU numbering.

FIG. 27-1 is a diagram illustrating a CID spectrum of a product ion of m/z 1022.73 (theoretical value: 1022.51) corresponding to divalent y16 indicating modification of a lysine residue at position 288/290 of a human IgG heavy chain in EU numbering (Example 12).

FIG. 27-2 is a diagram illustrating results of searching for a peptide fragment comprising a modification to a lysine residue for a trypsin digestion of trastuzumab (thiol-introduced compound (+145.019 Da) subjected to carbamidomethylation with iodoacetamide using a BioPharma Finder (Example 12). The horizontal axis indicates an identified lysine residue, and the vertical axis indicates intensity. Note that the residue number of a lysine residue on a heavy chain VH domain and a light chain is described using the number in a sequence (that is, the N-terminal amino acid is the first. Hereinafter the same), and the residue number of a lysine residue on heavy chain CH1, CH2, and CH3 domains is described using EU numbering.

FIG. 32-1 is a diagram illustrating a CID spectrum of a product ion of m/z 1166.99 (theoretical value: 1166.61) corresponding to divalent y20 indicating modification of a lysine residue at position 246/248 of a human IgG heavy chain in EU numbering (Example 14).

FIG. 32-2 is a diagram illustrating results of searching for a peptide fragment comprising a modification to a lysine residue for a trypsin digestion of trastuzumab (thiol-introduced compound (+145.019 Da) subjected to carbamidomethylation with iodoacetamide using a BioPharma Finder (Example 14). The horizontal axis indicates an identified lysine residue, and the vertical axis indicates intensity. Note that the residue number of a lysine residue on a heavy chain VH domain and a light chain is described using the number in a sequence (that is, the N-terminal amino acid is the first. Hereinafter the same), and the residue number of a lysine residue on heavy chain CH1, CH2, and CH3 domains is described using EU numbering.

DETAILED DESCRIPTION OF THE PREFERRED EMBODIMENTS

Figure 1:
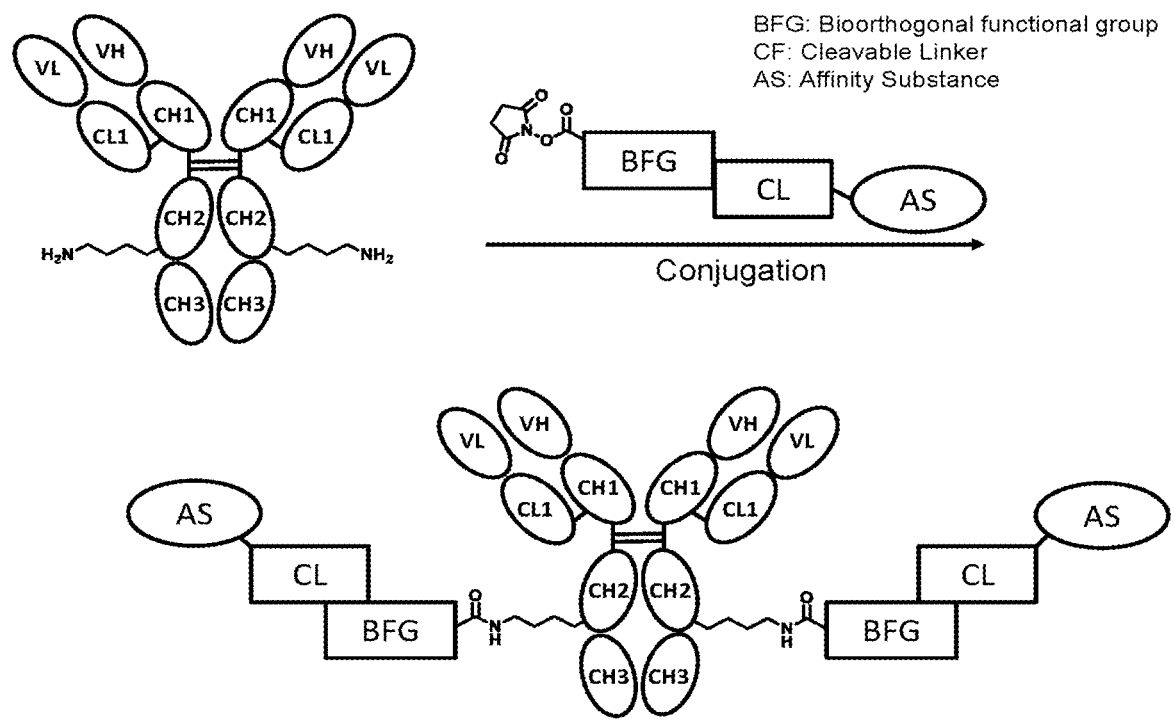
FIG. 1-1 is a schematic diagram (Part 1) illustrating a concept of regioselective modification of an antibody with a compound of the present invention [compound having an affinity substance to an antibody, a cleavable portion, and a reactive group: A-L-B—R(I)]. First, the compound of the present invention associates with an antibody (T) via an affinity substance to an antibody (A). Next, the compound of the present invention reacts with a side chain of a specific amino acid residue (a side chain of a lysine residue in the drawing) in a target region present near a site of association between the affinity substance and the antibody via a reactive group (R) (activated ester in the drawing) to form a conjugate of the compound of the present invention and the antibody [antibody regioselectively having a structural unit comprising an affinity substance to an antibody and a cleavable portion: A-L-B—R'-T(II)].

1. Compound Having Affinity Substance to Antibody, Cleavable Portion, and Reactive Group, or Salt Thereof.

1-1. Outline

The present invention provides a compound having an affinity substance to an antibody, a cleavable portion, and a reactive group, or a salt thereof, represented by Formula (I).

A-L-B—R            (I)

wherein

A is an affinity substance to an antibody,

L is a cleavable linker that is a divalent group comprising a cleavable portion, B is (a) a divalent group comprising a bioorthogonal functional group or (b) a divalent group comprising no bioorthogonal functional group, and R is a reactive group to the antibody.

In Formula (I) and other formulae presented in relation to the present invention, - (hyphen) indicates that two units present on both sides thereof covalently bind to each other. Consequently, in Formula (I), A covalently binds to L, L covalently binds to A and B, B covalently binds to L and R, and R covalently binds to B.

1-2. Affinity Substance to Antibody (A)

In Formula (I), A is an affinity substance to an antibody. The affinity substance is a substance having binding ability through a noncovalent bond to an antibody.

The affinity substance used in the present invention targets an antibody. The antibody may be a protein (e.g., glycoprotein) modified with a biomolecule (e.g., sugar) or a protein unmodified with a biomolecule. As the antibody, any antibody to any component such as a bio-derived component, a virus-derived component, or a component found in an environment can be used, but an antibody to a bio-derived component or a virus-derived component is preferred. Examples of the bio-derived component include components derived from animals such as mammals and birds (e.g., chickens), insects, microorganisms, plants, fungi, and fishes (e.g., protein). The bio-derived component is preferably a component derived from mammals. Examples of the mammals include primates (e.g., humans, monkeys, and chimpanzees), rodents (e.g., mice, rats, guinea pigs, hamsters, and rabbits), pets (e.g., dogs and cats), domestic animals (e.g., cows, pigs, and goats), and work animals (e.g., horses and sheep). The bio-derived component is more preferably a component derived from primates or rodents (e.g., protein), and even more preferably a human-derived component (e.g., protein) from a viewpoint of clinical application of the present invention. Examples of the virus-derived component include components derived from influenza viruses (e.g., avian influenza viruses and swine influenza viruses), AIDS virus, Ebola virus, and phage viruses (e.g., protein).

The antibody is a polyclonal antibody or a monoclonal antibody, and is preferably a monoclonal antibody. Examples of the monoclonal antibody include chimeric antibodies, humanized antibodies, human antibodies, antibodies with a certain sugar chain added (e.g., an antibody modified so as to have a sugar chain-binding consensus sequence such as an N-type sugar chain-binding consensus sequence), bi-specific antibodies, scFv antibodies, Fab antibodies, F(ab')$_2$ antibodies, VHH antibodies, Fc region proteins, and Fc-fusion proteins. The antibody may be a divalent antibody (e.g., IgG, IgD, or IgE) or a tetravalent or higher antibody (e.g., IgA antibody or IgM antibody).

The antibody as a target of the affinity substance may comprise any amino acid residues and preferably comprises 20 types of natural L-α-amino acid residues normally comprised in proteins. Examples of such amino acid residues include L-alanine (A), L-asparagine (N), L-cysteine (C), L-glutamine (Q), L-isoleucine (I), L-leucine (L), L-methionine (M), L-phenylalanine (F), L-proline (P), L-serine (S), L-threonine (T), L-tryptophan (W), L-tyrosine (Y), L-valine (V), L-aspartic acid (D), L-glutamic acid (E), L-arginine (R), L-histidine (H), L-lysine (K), and glycine (G) (hereinafter, description of L is omitted). The antibody may comprise e.g., 100 or more, preferably 120 or more, more preferably 150 or more, even more preferably 180 or more, and particularly preferably 200 or more amino acid residues. The antibody may comprise e.g., 1,000 or less, preferably 900 or less, more preferably 800 or less, even more preferably 700 or less, and particularly preferably 600 or less amino acid residues. More specifically, the antibody may comprise e.g., 100 to 1,000, preferably 120 to 900, more preferably 150 to 800, even more preferably 180 to 700, and particularly preferably 200 to 600 amino acid residues. When the antibody is an antibody (e.g., the monoclonal antibody described above), the above number of amino acid residues may correspond to amino acid residues of a heavy chain of the antibody.

The antibody as the target of the affinity substance is further a protein comprising specific amino acid residues having a side chain or a terminal (an N-terminal and/or a C-terminal), preferably a side chain, with which a reactive group described below is capable of reacting at one position or a plurality of positions (preferably a plurality of positions). Examples of such specific amino acid residues include 14 types of amino acid residues described below; preferred are amino acid residues selected from the group consisting of a lysine residue, a tyrosine residue, a tryptophan residue, and a cysteine residue. More preferred examples of such specific amino acid residues include amino acid residues selected from the group consisting of a lysine residue, a tyrosine residue, and a tryptophan residue. Considering that the compound of the present invention can regioselectively modify an antibody, preferred is an antibody comprising such specific amino acid residues at a plurality of positions. The positions are not limited to particular positions as long as they are two or more positions and may be e.g., three or more positions, preferably five or more positions, more preferably ten or more positions, even more preferably 20 or more positions, and particularly preferably 30 or more positions. The positions may be e.g., 200 or less positions, preferably 180 or less positions, more preferably 150 or less positions, even more preferably 120 or less positions, and particularly preferably 100 or less positions. More specifically, the positions may be e.g., 3 to 200 positions, preferably 5 to 180 positions, more preferably 10 to 150 positions, even more preferably 20 to 120 positions, and particularly preferably 30 to 100 positions. Even for such an antibody comprising the specific amino acid residues at a plurality of positions, the compound of the present invention can regioselectively modify a specific amino acid residue present at one specific position. It is said that the number of lysine residues of human IgG1 is generally about 70 to 90, for example, although it depends on an amino acid composition in a variable region. The present invention has succeeded in regioselectively modifying such a lysine residue present at a specific position of human IgG1.

More specifically, in the present invention, from a viewpoint of, while maintaining the function of an antibody (that is, while maintaining native folding without denaturing the antibody), modifying an amino acid residue present at a specific position in the antibody, preferred is regioselective modification of an amino acid residue exposed to a surface of the antibody. In human IgG such as human IgG1, for example, exposed lysine residues and exposed tyrosine residues are present at the following positions (refer to http://www.imgt.org/IMGTScientificChart/Numbering/Hu_IGHGnber.html by EU numbering). Note that in the present application, for convenience of explanation, the residue number on heavy chain CH1, CH2, and CH3 domains may be described using EU numbering, and the residue number on a heavy chain VH domain and a light chain may be described using the number in a sequence (that is, the N-terminal amino acid is the first).

(1) Exposed Lysine Residues
  CH2 domain (position 246, position 248, position 274, position 288, position 290, position 317, position 320, position 322, and position 338)
  CH3 domain (position 360, position 414, and position 439)
(2) Exposed Tyrosine Residues
  CH2 domain (position 278, position 296, and position 300)
  CH3 domain (position 436)

Consequently, when human IgG such as human IgG1 is modified with a lysine residue or a tyrosine residue, modification at the above positions is preferred.

When human IgG such as human IgG1 is modified with a lysine residue or a tyrosine residue, among the positions of (1) and (2), lysine residues or tyrosine residues present at the following positions, which are high in the degree of exposure to the surface, may be preferably modified.

(1') Exposed Lysine Residues
  CH2 domain (position 246, position 248, position 274, position 288, position 290, position 317, position 320, and position 322)
  CH3 domain (position 360, position 414, and position 439)
(2') Exposed Tyrosine Residues
  CH2 domain (position 278, position 296, and position 300)
  CH3 domain (position 436)

Consequently, when human IgG such as human IgG1 is modified with a lysine residue or a tyrosine residue, modification at the above positions is more preferred.

When human IgG such as human IgG1 is modified with a lysine residue, among the positions of (1), lysine residues present at certain positions (e.g., position 246, position 248, position 288, position 290, and position 317) in the CH2 domain, which can be efficiently modified in the present invention, may be more preferably modified.

In a specific embodiment, the antibody as the target of the affinity substance, when comprising the specific amino acid residues at a plurality of positions as described above, may comprise one or more specific amino acid residues in a target region consisting of 1 to 50 consecutive amino acid residues and comprise five or more of the specific amino acid residues in a non-target region other than the target region. The target region may consist of preferably one to 30, more preferably one to 20, and even more preferably one to ten, one to five, or one to three (that is, one, two, or three) amino acid residues. The target region may be particularly preferably a region consisting of a specific amino acid residue present at a specific position. Such a specific position, which varies depending on the types of the target protein and the affinity substance and the like, may be e.g., a specific position in a specific region of a constant region of an antibody (e.g., CH1, CH2, and CH3) and preferably a position in CH2 of an antibody. The target region may be more specifically the following residues following Eu numbering in human IgG Fc:

(1) a Lys248 residue (hereinafter, also referred to simply as "Lys248" in the present specification and corresponding to the 18th residue in the human IgG CH2 region (SEQ ID NO: 1)) or a Lys246 residue (hereinafter, also referred to simply as "Lys246" in the present specification and corresponding to the 16th residue in the human IgG CH2 region (SEQ ID NO: 1));

(2) a Lys288 residue (hereinafter, also referred to simply as "Lys288" in the present specification and corresponding to the 58th residue in the human IgG CH2 region (SEQ ID NO: 1)) or a Lys290 residue (hereinafter, also referred to simply as "Lys290" in the present specification and corresponding to the 60th residue in the human IgG CH2 region (SEQ ID NO: 1));

and (3) a Lys317 residue (hereinafter, also referred to simply as "Lys317" in the present specification and corresponding to the 87th residue in the human IgG CH2 region (SEQ ID NO: 1)).

The present invention can modify the specific amino acid residue in the target region highly regioselectively. Such regioselectivity may be e.g., 30% or more, preferably 40% or more, more preferably 50% or more, even more preferably 60% or more, and particularly preferably 70% or more, 80% or more, 90% or more, 95% or more, 96% or more, 97% or more, 98% or more, 99% or more, or 100% or more.

The target region does not necessarily comprise the same type of amino acid residue as the specific amino acid residue other than the specific amino acid residue present at the specific position in a region up to a remote position of "a" (where "a" is any integer of 1 to 10) amino acid residues to an N-terminal side and a C-terminal side each with respect to the specific amino acid present at the specific position. The symbol "a" is preferably an integer of 1 to 5, more preferably an integer of 1 to 3, even more preferably 1 or 2, and particularly preferably 1.

In a preferred embodiment, the antibody is a monoclonal antibody. Examples of the isotype of the monoclonal antibody and the like include IgG (e.g., IgG1, IgG2, IgG3, and IgG4), IgM, IgA, IgD, IgE, and IgY. The monoclonal antibody is a full-length antibody or an antibody fragment (e.g., F(ab')₂, Fab', Fab, Fv, and a single-chain antibody); the full-length antibody is preferred.

The antibody is an antibody to any antigen. Such an antigen may be a component found in the organisms and viruses described above, for example. Examples of such an antigen also include a protein [which includes an oligopeptide and a polypeptide, and may be a protein (e.g., glycoprotein) modified with a biomolecule such as sugar], a sugar chain, a nucleic acid, and a small compound.

The antibody may be preferably an antibody with a protein as an antigen. Examples of the protein include cell membrane receptors, cell membrane proteins other than cell membrane receptors (e.g., extracellular matrix proteins), ligands, and soluble receptors.

More specifically, the protein as the antigen of the antibody may be a disease target protein. Examples of the disease target protein include the following.

(1) Cancerous Region

PD-L1, GD2, PDGFRα (a platelet-derived growth factor receptor), CD22, HER2, phosphatidyl serine (PS), EpCAM, fibronectin, PD-1, VEGFR-2, CD33, HGF, gpNMB, CD27, DEC-205, folic acid receptors, CD37, CD19, Trop2, CEACAM5, SiP, HER3, IGF-1R, DLL4, TNT-1/B, CPAAs, PSMA, CD20, CD105 (Endoglin), ICAM-1, CD30, CD16A, CD38, MUC1, EGFR, KIR2DL1, KIR2DL2, NKG2A, tenascin-C, IGF (insulin-like growth factor), CTLA-4, mesothelin, CD138, c-Met, Ang2, VEGF-A, CD79b, ENPD3, folic acid receptor α, TEM-1, GM2, Glypican 3, macrophage inhibitory factor, CD74, Notch1, Notch2, Notch3, CD37, TLR-2, CD3, CSF-1R, FGFR2b, HLA-DR, GM-CSF, EphA3, B7-H3, CD123, gpA33, Frizzled7 receptor, DLL4, VEGF, RSPO, LIV-1, SLITRK6, Nectin-4, CD70, CD40, CD19, SEMA4D (CD100), CD25, MET, Tissue Factor, IL-8, EGFR, cMet, KIR3DL2, Bst1 (CD157), P-Cadherin, CEA, GITR, TAM (tumor associated macrophage), CEA, DLL4, Ang2, CD73, FGFR2, CXCR4, LAG-3, GITR, Fucosyl GM1, IGF-1, Angiopoietin 2, CSF-1R, FGFR3, OX40, BCMA, ErbB3, CD137 (4-1BB), PTK7, EFNA4, FAP, DR5, CEA, Ly6E, CA6, CEACAM5, LAMP1, tissue factor, EPHA2, DR5, B7-H3, FGFR4, FGFR2, α2-PI, A33, GDF15, CAIX, CD166, ROR1, GITR, BCMA, TBA, LAG-3, EphA2, TIM-3, CD-200, EGFRvIII, CD16A, CD32B, PIGF, Ax1, MICA/B, Thomsen-Friedenreich, CD39, CD37, CD73, CLEC12A, Lgr3, transferrin receptors, TGFβ, IL-17, 5T4, RTK, Immune Suppressor Protein, NaPi2b, Lewis blood group B antigen, A34, Lysil-Oxidase, DLK-1, TROP-2, a9 Integrin, TAG-72 (CA72-4), and CD70.

(2) Autoimmune Diseases and Inflammatory Diseases

IL-17, IL-6R, IL-17R, INF-α, IL-5R, IL-13, IL-23, IL-6, ActRIIB, β7-Integrin, IL-4αR, HAS, Eotaxin-1, CD3, CD19, TNF-α, IL-15, CD3e, Fibronectin, IL-1β, IL-1α, IL-17, TSLP (Thymic Stromal Lymphopoietin), LAMP (Alpha4 Beta 7 Integrin), IL-23, GM-CSFR, TSLP, CD28, CD40, TLR-3, BAFF-R, MAdCAM, IL-31R, IL-33, CD74, CD32B, CD79B, IgE (immunoglobulin E), IL-17A, IL-17F, C5, FcRn, CD28, TLR4, MCAM, B7RP1, CXCR1/2 Ligands, IL-21, Cadherin-11, CX3CL1, CCL20, IL-36R, IL-10R, CD86, TNF-α, IL-7R, Kv1.3, a9 Integrin, and LIFHT.

(3) Brain or Nerve Diseases

CGRP, CD20, β amyloid, β amyloid protofibril, Calcitonin Gene-Related Peptide Receptor, LINGO (Ig Domain Containing 1), a Synuclein, extracellular tau, CD52, insulin receptors, tau protein, TDP-43, SOD1, TauC3, and JC virus.

(4) Infectious Diseases

*Clostridium Difficile* toxin B, cytomegalovirus, RS viruses, LPS, *S. Aureus* Alpha-toxin, M2e protein, Psl, PcrV, S. Aureus toxin, influenza A, Alginate, *Staphylococcus aureus*, PD-L1, influenza B, *Acinetobacter*, F-protein, Env, CD3, enteropathogenic *Escherichia coli, Klebsiella*, and *Streptococcus pneumoniae*.

(5) Hereditary Rare Diseases amyloid AL, SEMA4D (CD100), insulin receptors, ANGPTL3, IL4, IL13, FGF23, adrenocorticotropic hormone, transthyretin, and huntingtin.

(6) Eye Diseases

Factor D, IGF-1R, PGDFR, Ang2, VEGF-A, CD-105 (Endoglin), IGF-1R, and β amyloid.

(7) Bone and Orthopedic Region

Sclerostin, Myostatin, Dickkopf-1, GDF8, RNAKL, HAS, Siglec-15

(8) Blood Diseases vWF, Factor IXa, Factor X, IFNγ, C5, BMP-6, Ferroportin, TFPI (9) Other Diseases BAFF (B cell activating factor), IL-1β, PCSK9, NGF, CD45, TLR-2, GLP-1, TNFR1, C5, CD40, LPA, prolactin receptors, VEGFR-1, CB1, Endoglin, PTH1R, CXCL1, CXCL8, IL-1β, AT2-R, and IAPP.

In a more preferred embodiment, the affinity substance to an antibody is an affinity substance to a monoclonal antibody. The isotype of the monoclonal antibody is similar to those described above for the antibody; IgG (e.g., IgG1, IgG2, IgG3, and IgG4) is preferred. The monoclonal antibody is preferably a full-length monoclonal antibody.

In an even more preferred embodiment, the affinity substance to an antibody is an affinity substance to a chimeric antibody, a humanized antibody, or a human antibody (e.g., IgG including IgG1, IgG2, IgG3, and IgG4) as a full-length monoclonal antibody.

In a particularly preferred embodiment, the affinity substance to an antibody is an affinity substance to an antibody, comprising any one Fc region protein selected from the group consisting of the following (A) to (C) and having antigen-binding ability:

(A) an Fc region protein comprising an amino acid sequence of SEQ ID NO: 1;

(B) an Fc region protein comprising an amino acid sequence with one or several amino acid residues inserted, added, deleted, or substituted in the amino acid sequence of SEQ ID NO: 1; or (C) an Fc region protein comprising an amino acid sequence having 90% or more identity to the amino acid sequence of SEQ ID NO: 1.

The amino acid sequence of SEQ ID NO: 1 is an Fc region protein. It is known that such an Fc region protein has secretion ability. Consequently, the Fc region proteins of (A) to (C) can have secretion ability. An antibody comprising such an Fc region protein can have antigen-binding ability. The amino acid residue at position 18 in SEQ ID NO: 1 is any amino acid residue, preferably a neutral amino acid residue, more preferably an amino acid residue having a nonpolar side chain described below, and even more preferably leucine, isoleucine, or alanine, and particularly preferably leucine or alanine. The amino acid residue at position 19 in SEQ ID NO: 1 is any amino acid residue, preferably a neutral amino acid residue or an acidic amino acid residue, more preferably an amino acid residue having a nonpolar side chain or an acidic amino acid residue, and even more preferably leucine or glutamic acid. The amino acid residue at position 21 in SEQ ID NO: 1 is any amino acid residue, preferably a neutral amino acid residue, more preferably an amino acid residue having a nonpolar side chain, and even more preferably glycine or alanine. The amino acid residue at position 140 in SEQ ID NO: 1 is any amino acid residue, preferably an acidic amino acid residue, and more preferably glutamic acid or aspartic acid. The amino acid residue at position 142 in SEQ ID NO: 1 is any amino acid residue, preferably a neutral amino acid residue, more preferably an amino acid residue having a nonpolar side chain, even more preferably methionine, leucine, or isoleucine, and particularly preferably methionine or leucine. The amino acid residue at position 177 in SEQ ID NO: 1 is any amino acid residue, preferably a neutral amino acid residue, more preferably an amino acid residue having an uncharged polar side chain or an amino acid residue having a nonpolar side chain described below, even more preferably threonine, alanine, or glycine, and particularly preferably threonine or alanine.

In a preferred embodiment, the amino acid sequence of SEQ ID NO: 1 may be an amino acid sequence consisting of the amino acid residues at positions 220 to 449 in the amino acid sequence of SEQ ID NO: 2.

In another preferred embodiment, the amino acid sequence of SEQ ID NO: 1 may be an amino acid sequence consisting of the amino acid residues at positions 7 to 236 in the amino acid sequence of SEQ ID NO: 3.

In a specific embodiment, the antibody comprising the Fc region protein comprising the amino acid sequence described above may be an antibody comprising the Fc region protein comprising the amino acid sequence described above and a constant region of an antibody. Such a constant region of an antibody may be a constant region of a chimeric antibody, a humanized antibody, or a human antibody (e.g., IgG including IgG1, IgG2, IgG3, and IgG4).

In (B) the Fc region protein, one or several amino acid residues can be modified by one, two, three, or four variations selected from the group consisting of deletion, substitution, addition, and insertion of amino acid residues. The variations of amino acid residues may be introduced to one region in the amino acid sequence or intruded to a plurality of different regions. The term "one or several" indicates a number that does not significantly impair protein activity. The number indicated by the term "one or several" is e.g., 1 to 100, preferably 1 to 80, more preferably 1 to 50, 1 to 30, 1 to 20, 1 to 10, or 1 to 5 (e.g., 1, 2, 3, 4, or 5).

In (C) the Fc region protein, the percent identity to the amino acid sequence of SEQ ID NO: 1 may be 70% or more, 75% or more, 80% or more, 85% or more, 90% or more, 91% or more, 92% or more, 93% or more, 94% or more, 95% or more, 96% or more, 97% or more, 98% or more, or 99% or more. In the present invention, calculation of the percent identity of peptides or polypeptides (proteins) can be performed by Algorithm blastp. More specifically, calculation of the percent identity of polypeptides can be performed using Scoring Parameters (Matrix: BLOSUM62; Gap Costs: Existence=11 Extension=1; Compositional Adjustments: Conditional compositional score matrix adjustment) as default settings in Algorithm blastp provided in National Center for Biotechnology Information (NCBI). Calculation of the percent identity of polynucleotides (genes) can be performed by Algorithm blastn. More specifically, calculation of the percent identity of polynucleotides can be performed using Scoring Parameters (Match/Mismatch Scores=1, −2; Gap Costs=Linear) as default settings in Algorithm blastn provided in NCBI.

Secretion in secretion ability has the same meaning as secretion (what is called solubility) of a secretory protein. Consequently, "having secretion ability" means functioning as an antibody in a manner similar to normal antibodies.

In the antibody comprising the Fc region protein, a variation may be introduced to a specific site as long as target characteristics (e.g., secretion ability and antigen-binding ability) are maintained. The position of an amino acid residue to which a variation may be introduced that can maintain the target characteristics is obvious to a person skilled in the art. Specifically, a person skilled in the art can 1) compare amino acid sequences of a plurality of proteins having homogeneous characteristics with each other, 2) clarify a relatively preserved region and a relatively non-preserved region, and then 3) predict a region capable of playing an important role for a function and a region incapable of playing an important role for a function from the relatively preserved region and the relatively non-preserved region each and can thus recognize structure-function correlation. Consequently, a person skilled in the art can identify the position of an amino acid residue to which a variation may be introduced in the amino acid sequence of the antibody comprising the Fc region protein.

When an amino acid residue is varied by substitution, the substitution of the amino acid residue may be preservative substitution. The term "preservative substitution" when used in the present specification refers to replacing a certain amino acid residue with an amino acid residue having a similar side chain. Families of amino acid residues having a similar side chain are known in the field concerned. Examples of such families include amino acids having a basic side chain (e.g., lysine, arginine, and histidine), amino acids having an acidic side chain (e.g., aspartic acid, and glutamic acid), amino acids having an uncharged polar side chain (e.g., asparagine, glutamine, serine, threonine, tyrosine, and cysteine), amino acids having a nonpolar side chain (e.g., glycine, alanine, valine, leucine, isoleucine, proline, phenylalanine, methionine, and tryptophan), amino acids having a β-position-branched side chain (e.g., threonine, valine, and isoleucine), amino acids having an aromatic side chain (e.g., tyrosine, phenylalanine, tryptophan, and histidine), amino acids having a hydroxy group (e.g., alcoholic and phenolic)-containing side chain (e.g., serine, threonine, tyrosine), and amino acids having a sulfur-containing side chain (e.g., cysteine and methionine). The preservative substitution of the amino acid may be preferably substitution between aspartic acid and glutamic acid, substitution among arginine, lysine, and histidine, substitution between tryptophan and phenylalanine, substitution between phenylalanine and valine, substitution among leucine, isoleucine, and alanine, or substitution between glycine and alanine.

Examples of the antibody comprising any one Fc region selected from the group consisting of (A) to (C) include chimeric antibodies (e.g., rituximab, basiliximab, infliximab, cetuximab, siltuximab, dinutuximab, and altertoxaximab), humanized antibodies (e.g., daclizumab, palivizumab, trastuzumab, alemtuzumab, omalizumab, efalizumab, bevacizumab, natalizumab (IgG4), tocilizumab, eculizumab (IgG2), mogamulizumab, pertuzumab, obinutuzumab, vedolizumab, pembrolizumab (IgG4), mepolizumab, elotuzumab, daratumumab, ixekizumab (IgG4), reslizumab (IgG4), and atezolizumab), and human antibodies (e.g., adalimumab (IgG1), panitumumab, golimumab, ustekinumab, canakinumab, ofatumumab, denosumab (IgG2), ipilimumab, belimumab, raxibacumab, ramucirumab, nivolumab, dupilumab (IgG4), secukinumab, evolocumab (IgG2), alirocumab, necitumumab, brodalumab (IgG2), and olaratumab) (cases not referring to the IgG subtype indicate that they are IgG1).

In the present invention, the affinity substance to an antibody is a polypeptide comprising a glutamine residue (Q) at an N-terminal. By using a polypeptide comprising a glutamine residue (Q) at an N-terminal as the affinity substance to an antibody, an amino group (—NH$_2$) in the glutamine residue (Q) at the N-terminal reacts (is pyroglutamylated) with an amide group present in a side chain thereof, and therefore the amino group can be protected. Therefore, a linker that mediates binding of the affinity substance to an antibody can be specifically added to a specific amino acid residue (lysine residue having an amino group) in the affinity substance.

Examples of the polypeptide comprising a glutamine residue (Q) at an N-terminal include a polypeptide to which a glutamic acid residue or a peptide comprising a glutamic acid residue at an N-terminal is added to an N-terminal of an antibody-affinity polypeptide. Various antibody-affinity polypeptides have been reported (e.g., WO 2016/186206 A; WO 2013/027796 A; WO 2008/054030 A; WO 2001/045746 A; Fassina G et al., JOURNAL OF MOLECULAR RECOGNITION, 1996, VOL. 6, 564-569; Ehrlich G. K et al., J. Biochem. Biophys. Methods, 2001, VOL. 49, 443-454; Ruvo M et al., ChemBioChem, 2005, VOL. 6, 1242-1253; Krook M et al., Journal of Immunological Methods, 1998, VOL. 221, 151-157; Jacobs J. M. et al., Bio. Techniques, 2003, VOL. 34, 132-141; Carbonell R. G. et al., Journal of Chromatography A, 2009, VOL. 1216, 910-918; Lund L. N. et al., Journal of Chromatography A, 2012, VOL. 1225, 158-167; Warren L. Delano et al., Science, 2000, VOL. 287, 1279-1283; Biochemical Engineering Journal, 2013, VOL. 79, 33-40, all of which are incorporated herein by reference in their entireties).

As the polypeptide comprising a glutamine residue (Q) at an N-terminal, a polypeptide that can be prepared by a polypeptide secretion production method using a coryneform bacterium as a host (WO 2013/062029 A, which is incorporated herein by reference in its entirety) is preferably used. According to this method, N-terminal three residues Gln-Glu-Thr (QET) of a Csp mature protein can be added to an N-terminal of a target polypeptide, and a polypeptide comprising a glutamine residue (Q) at an N-terminal can be prepared easily and in large quantities. Therefore, this method is suitable for preparing an affinity substance to an antibody. Examples of the coryneform bacterium that can be used in this method include a bacterium of the genus *Corynebacterium* (e.g., *Corynebacterium glutamicum* and *Corynebacterium statusonis*), and a bacterium of the genus *Brevibacterium*.

The number of amino acid residues of the polypeptide comprising a glutamine residue (Q) at an N-terminal is not particularly limited, but may be 16 or more and 123 or less from a viewpoint of secretory production efficiency in a polypeptide secretion production method using a coryneform bacterium as a host. The number of such amino acid residues may be preferably 20 or more, 25 or more, 30 or more, 35 or more, 37 or more, or 40 or more. The number of such amino acid residues may also be 73 or less, 68 or less, 64 or less, 61 or less, 58 or less, or 53 or less.

In a specific embodiment, the polypeptide comprising a glutamine residue (Q) at an N-terminal may be selected from the group consisting of the following (1) to (4):

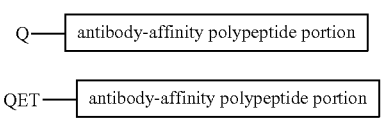

(1)

(2)

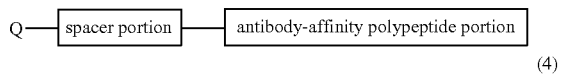

(3)

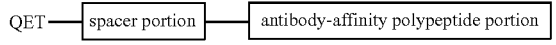

(4)

wherein Q is a glutamine residue at an N-terminal, E is a glutamic acid residue, T is a threonine residue, the solid line is a bond, the spacer portion consists of 1 or more and 50 or less amino acid residues, and the affinity substance to an antibody consists of 15 or more and 70 or less amino acid residues.

In the above polypeptides (1) to (4), the number of amino acid residues in the spacer portion is preferably 1 or more and 40 or less, more preferably 1 or more and 30 or less, even more preferably 1 or more and 20 or less, and particularly preferably 1 or more and 10 or less. As the amino acid residue, any amino acid residue can be used, but 20 types of standard L-α-amino acids forming natural proteins are preferred.

In the above polypeptides (1) to (4), the number of amino acid residues in the antibody-affinity polypeptide portion is 15 or more and 70 or less, and may be preferably 15 or more, 17 or more, 20 or more, 25 or more, 30 or more, 34 or more, 35 or more, or 40 or more, and may be preferably 65 or less, 61 or less, 60 or less, 55 or less, or 50 or less. In the above polypeptides (1) to (4), as the antibody-affinity polypeptide portion, any affinity polypeptide to an antibody (e.g., the above previously reported polypeptide) can be used. However, those selected from the group consisting of protein A, protein G, protein L, protein Z, fragments thereof having affinity to an antibody, and variants thereof having affinity to an antibody are preferred.

Protein A is a non-glycosylated protein (*Staphylococcus aureus* Protein A: SpA) present on a cell wall of *Staphylococcus aureus*. A plurality of domains of protein A (domains A, B, C, D, and E) is each known to have affinity to an antibody (e.g., Moks T et al., Eur J Biochem. 1986 May 2; 156 (3): 637-43, which is incorporated herein by reference in its entirety). Therefore, a polypeptide corresponding to such a domain can be used as a fragment of protein A. More specifically, the polypeptide corresponding to such a domain has the following amino acid sequence (58 to 61 amino acid residues).

(1) Domain A:
(SEQ ID NO: 27)
ADNNENKEQQNAFYEILNMPNLNEEQRNGFIQSLKDDPSQSANLLAEAK
KLNESQAPK (2) Domain B:
(SEQ ID NO: 28)
ADNKENKEQQNAFYEILHLPNLNEEQRNGFIQSLKDDPSQSANLLAEAK
KLNDAQAPK (3) Domain C:
(SEQ ID NO: 29)
ADNKFNKEQQNAFYEILHLPNLTEEQRNGFIQSLKDDPSVSKEILAEAK
KLNDAQAPK (4) Domain D:
(SEQ ID NO: 30)
ADAQQNKENKDQQSAFYEILNMPNLNEEQRNGFIQSLKDDPSQSTNVLG
EAKKLNESQAPK (5) Domain E:
(SEQ ID NO: 31)
AANAAQHDEAQQNAFYQVLNMPNLNADQRNGFIQSLKDDPSQSANVLGE
AQKLNDSQAPK Protein G is a protein present on a cell wall of group G hemolytic *streptococcus* (group G streptococci). A plurality of domains of protein G (domains C2 and C3) is each known to have affinity to an antibody (e.g., Sjobring U J et al., Biol Chem. 1991 Jan. 5; 266 (1): 399-405, which is incorporated herein by reference in its entirety). Therefore, a polypeptide corresponding to such a domain can be used as a fragment of protein G. More specifically, the polypeptide corresponding to such a domain has the following amino acid sequence (60 amino acid residues).

(1) Domain C2:
(SEQ ID NO: 32)
TPAVTTYKLVINGKTLKGETTTEAVDAATAEKVFKQYANDNGVDGEWTY
DDATKTFTVTE (2) Domain C3:
(SEQ ID NO: 33)
TPAVTTYKLVINGKTLKGETTTKAVDAETAEKAFKQYANDNGVDGVWTY
DDATKTFTVTE Protein L is a protein derived from *Peptostreptococcus magnus*. A plurality of domains of protein L (domains C, C1 to C4, and B1 to B5) is each known to have affinity to an antibody (e.g., Graille M el al., Structure. 2001 August; 9 (8):679-87, which is incorporated herein by reference in its entirety). Therefore, a polypeptide corresponding to such a domain can be used as a fragment of protein L. More specifically, the polypeptide corresponding to such a domain has the following amino acid sequence (61 amino acid residues).

(1) Domain C:
(SEQ ID NO: 34)
EVTIKVNLIFADGKIQTAEFKGTFEEATAEAYRYADLLAKVNGEYTADL
EDGGNHMNIKFA (2) Domain C1:
(SEQ ID NO: 35)
EVTIKANLIFADGSTQNAEFKGTFAKAVSDAYAYADALKKDNGEYTVDV
ADKGLTLNIKFA (3) Domain C2:
(SEQ ID NO: 36)
EVTIKVNLIFADGKTQTAEFKGTFEEATAKAYAYADLLAKENGEYTADL
EDGGNTINIKFA (4) Domain C3:
(SEQ ID NO: 37)
EVTIKVNLIFADGKIQTAEFKGTFEEATAKAYAYANLLAKENGEYTADL
EDGGNTINIKFA (5) Domain C4:
(SEQ ID NO: 38)
EVTIKVNLIFADGKTQTAEFKGTFEEATAEAYRYADLLAKVNGEYTADL
EDGGYTINIKFA (6) Domain B1:
(SEQ ID NO: 39)
EVTIKANLIFANGSTQTAEFKGTFEKATSEAYAYADTLKKDNGEYTVDV
ADKGYTLNIKFA (7) Domain B2:
(SEQ ID NO: 40)
EVTIKANLIYADGKTQTAEFKGTFEEATAEAYRYADALKKDNGEYTVDV
ADKGYTLNIKFA (8) Domain B3:
(SEQ ID NO: 41)
EVTIKANLIYADGKTQTAEFKGTFEEATAEAYRYADLLAKENGKYTVDV
ADKGYTLNIKFA (9) Domain B4:
(SEQ ID NO: 42)
EVTIKANLIYADGKTQTAEFKGTFAEATAEAYRYADLLAKENGKYTADL
EDGGYTINIRFA

(10) Domain B5:
(SEQ ID NO: 43)
QVTIKENIYFEDGTVQTATFKGTFAEATAEAYRYADLLSKEHGKYTADL
EDGGYTINIRFA Protein Z is an artificial IgG-binding polypeptide designed based on the above protein A (e.g., Nilsson B et al., Protein Eng. 1987 February-March; 1 (2): 107-13, which is incorporated herein by reference in its entirety). Protein Z has the following amino acid sequence (58 amino acid residues). Like protein Z, Z34C is an artificial IgG-binding polypeptide consisting of full-length 34 amino acid residues designed based on the above protein A (e.g., Starovasnik M A et al., Proc Natl Acad Sci USA. 1997 Sep. 16; 94 (19): 10080-5, which is incorporated herein by reference in its entirety). In contrast to protein Z, Z34C has a plurality of substituted amino acid residues in order to increase its affinity to an antibody, but has a shorter full-length of amino acids than protein Z. Therefore, it can be said that Z34C correspond to a fragment of protein Z. Therefore, a shortened polypeptide of protein Z (e.g., an N-terminal and/or C-terminal shortened polypeptide consisting of at least 34 amino acid residues), and Z34C can be used as fragments of protein Z.

(1) Drotein Z:
(SEQ ID NO: 44)
VDNKFNKEQQNAFYEILHLPNLNEEQRNAFIQSLKDDPSQSANLLAEAK
KLNDAQAPK (2) D34C:
(SEQ ID NO: 45)
ENMQCQRRFYEALHDPNLNEEQRNAKIKSIRDDC The fragment of protein A, protein G, protein L, or protein Z having affinity to an antibody is a shortened polypeptide with N-terminal side and/or C-terminal side amino acid residues of protein A, G, L, or Z deleted. In protein A, G, L, or Z, not all amino acid residues forming protein A, G, L, or Z are required for affinity to an antibody, and it is known that protein A, G, L, or Z has affinity to an antibody even if the N-terminal side and/or C-terminal side amino acid residues are deleted (e.g., those having the above-described domains). Therefore, by preparing a shortened polypeptide with terminal side and/or C-terminal side amino acid residues of protein A, G, L, or Z deleted, and then evaluating whether or not the shortened polypeptide thus prepared has affinity to an antibody, a person skilled in the art can appropriately prepare a fragment of protein A, G, L, or Z having affinity to an antibody.

Examples of the variants of protein A, protein G, protein L, protein Z, or fragments thereof having affinity to an antibody include a homologous polypeptide having 60% or more amino acid sequence identity with protein A, protein G, protein L, protein Z, or fragments thereof and having affinity to an antibody. It is known that even the homologous polypeptide having such a degree of amino acid sequence identity has affinity to an antibody (e.g., Starovasnik M A et al., Proc Natl Acad Sci USA. 1997 Sep. 16; 94 (19): 10080-5, which is incorporated herein by reference in its entirety). The amino acid sequence identity may be preferably 70% or more, more preferably 80% or more, even more preferably 90% or more, and particularly preferably 95% or more (e.g., 96% or more, 97% or more, 98% or more, or 99% or more). The amino acid sequence identity can be calculated in a similar manner to the percent identity of the polypeptide described above.

In a specific embodiment, the antibody-affinity polypeptide portion is a fragment of protein A having affinity to an antibody or a variant thereof. The fragment of protein A having affinity to an antibody or a variant thereof may preferably comprises an amino acid sequence with any one amino acid residue substituted with a lysine residue in an amino acid sequence of FNMQCQRRFYEALHDPNLNEEQRNAXIXSIRDDC (SEQ ID NO: 5) (two Xs are each independently one amino acid residue selected from the group consisting of an arginine residue, a glutamic acid residue, and a glutamine residue) and having 90% or more identity to the amino acid sequence of SEQ ID NO: 5 (it is assumed that substitution with a lysine residue is maintained in the amino acid sequence having 90% or more identity to the amino acid sequence of SEQ ID NO: 5). In other words, it can be said that such a polypeptide portion is either (i) a polypeptide portion in which any one amino acid residue in the amino acid sequence of SEQ ID NO: 5 is substituted with a lysine residue or (ii) a polypeptide portion in which any one amino acid residue in the amino acid sequence of SEQ ID NO: 5 is substituted with a lysine residue, and 1 to 3 amino acid residues other than the lysine residue are substituted with other amino acid residues, or other amino acid residues are inserted or added. The amino acid sequence of SEQ ID NO: 5 may be preferably an amino acid sequence of FNMQCQRRFYEALHDPNLNEEQRNARIRSIRDDC (SEQ ID NO: 6).

In a preferred embodiment, the antibody-affinity polypeptide is a variant of a fragment of protein A having affinity to an antibody with a glutamine residue (Q) or QET added to an N-terminal. Examples of such a variant include the following:

(1)
(SEQ ID NO: 7)
QETNPTENLYFQQKNMQCQRRFYEALHDPNLNEEQRNARIRSIRDDC;

(2)
(SEQ ID NO: 8)
QTADNQKNMQCQRRFYEALHDPNLNEEQRNARIRSIRDDCSQSANLLAE
AQQLNDAQAPQA;

(3)
(SEQ ID NO: 9)
QETKNMQCQRRFYEALHDPNLNEEQRNARIRSIRDDC;

(4)
(SEQ ID NO: 10)
QETFNKQCQRRFYEALHDPNLNEEQRNARIRSIRDDC;

(5)
(SEQ ID NO: 22)
QETENMQCQRRFYEALHDPNLNKEQRNARIRSIRDDC;

(6)
(SEQ ID NO: 23)
QETFNMQCQRRFYEALHDPNLNEEQRNARIRSIKDDC;

(7)
(SEQ ID NO: 51)
QETMQCQRRFYEALHDPNLNEEQRNARIRSIKDDC;

(8)
(SEQ ID NO: 52)
QETQCQRRFYEALHDPNLNEEQRNARIRSIKDDC; and (9)
(SEQ ID NO: 53)
QETCQRRFYEALHDPNLNEEQRNARIRSIKDDC.

In another specific embodiment, the antibody-affinity polypeptide may be a modified peptide (modified Fc-III) of a peptide Fc-III (WO 2001/045746, which is incorporated herein by reference in its entirety) consisting of an amino acid sequence of DCAWHLGELVWCT (SEQ ID NO: 54), which has been reported to have ability to bind to human IgG. Such a modified Fc-III may be, for example as follows:

(10) QETRGNCAYHKGQLVWCTYH (SEQ ID NO: 24); and

(11) QETRGNCAYHKGQIIWCTYH (SEQ ID NO: 25).

At least two cysteine residues separated from each other in each amino acid sequence of the affinity polypeptide can form a cyclic peptide through a disulfide bond. Alternatively, in the peptide, sulfide groups in the two cysteine residues may be coupled with each other through a carbonyl group-containing linker represented by the following.

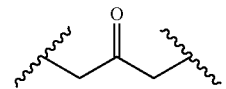 [SMILES: *CC(=O)C*]

The broken line portions of the carbonyl group-containing linker represented by the above mean bond portions with the sulfide groups. The linker is more stable than a normal disulfide bond against a reduction reaction and the like. Such a peptide can be prepared by a method described in WO 2016/186206 A, which is incorporated herein by reference in its entirety, for example.

A novel peptide having such a specific structure is useful for regioselective modification of a Lys248 or Lys246 residue following Eu numbering in human IgG Fc, or amino acid residues other than the Lys248 or Lys246 residue (Examples). An amino acid forming the peptide may be an L-body or a D-body; an L-body is preferred (in Examples, the amino acid residues forming the peptides are all L-bodies).

The peptide may have a specific amino acid residue modified with a cross-linking agent. Examples of such a specific amino acid residue include a lysine residue, an aspartic acid residue, and a glutamic acid residue; preferred is a lysine residue. Examples of the cross-linking agent include cross-linking agents comprising preferably two or more succinimidyl groups such as disuccinimidyl glutarate (DSG) and disuccinimidyl suberate (DSS); cross-linking agents comprising preferably two or more imide acid portions such as dimethyl adipimidate·2HCl (DMA), dimethyl pimelimidate·2HCl (DMP), and dimethyl suberimidate·2HCl (DMS); and cross-linking agents having an SS bond such as dimethyl 3,3'-dithiobispropionimidate·2HCl (DTBP) and dithiobis(succinimidyl propionate) (DSP) (e.g., WO 2016/186206 A, which is incorporated herein by reference in its entirety).

A terminal amino group of the peptide and a terminal carboxy group thereof may be protected. Examples of a protecting group for the N-terminal amino group include an alkylcarbonyl group (an acyl group) (e.g., an acetyl group, a propoxy group, and a butoxycarbonyl group such as a tert-butoxycarbonyl group), an alkyloxycarbonyl group (e.g., a fluorenylmethoxycarbonyl group), an aryloxycarbonyl group, and an arylalkyl(aralkyl) Dxycarbonyl group (e.g., a benzyloxycarbonyl group). The protecting group for the N-terminal amino group is preferably an acetyl group. Examples of a protecting group for the C-terminal carboxy group include a group capable of forming an ester or an amide. Examples of the group capable of forming an ester or an amide include an alkyloxy group (e.g., methyloxy, ethyloxy, propyloxy, butyloxy, pentyloxy, and hexyloxy), an aryloxy group (e.g., phenyloxy and naphthyloxy), an aralkyloxy group (e.g., benzyloxy), and an amino group. The protecting group for the C-terminal carboxy group is preferably an amino group.

1-3. Linker (L)

In formula (I), L is a cleavable linker that is a divalent group comprising a cleavable portion.

The cleavable linker represented by L is a divalent group comprising a cleavable portion. The cleavable portion is a site that can be cleaved by a specific treatment under a condition (a mild condition) incapable of causing denaturation or decomposition of proteins (e.g., cleavage of an amide bond). Therefore, it can be said that the cleavable portion is a site (bond other than an amide bond) that can be cleaved by a specific cleaving treatment under a mild condition. Examples of such a specific treatment include (a) a treatment with one or more substances selected from the group consisting of an acidic substance, a basic substance, a reducing agent, an oxidizing agent, and an enzyme, (b) a treatment with a physical and chemical stimulus selected from the group consisting of light, and (c) leaving a cleavable linker as it is when the cleavable linker comprises a self-degradable cleavable portion. Such a cleavable linker and a cleavage condition therefor are common technical knowledge in the field concerned (e.g., G. Leriche, L. Chisholm, A. Wagner, Bioorganic & Medicinal Chemistry. 20,571 (2012); Feng P. et al., Journal of American Chemical Society. 132,1500 (2010); Bessodes M. et al., Journal of Controlled Release, 99,423 (2004); DeSimone, J. M., Journal of American Chemical Society. 132,17928 (2010); Thompson, D. H., Journal of Controlled Release, 91,187 (2003); and Schoenmarks, R. G., Journal of Controlled Release, 95,291 (2004), all of which are incorporated herein by reference in their entireties). Examples of such a cleavable portion include a disulfide residue, an acetal residue, a ketal residue, an ester residue, a carbamoyl residue, an alkoxyalkyl residue, an imine residue, a tertiary alkyloxycarbamate residue (e.g., a tert-butyloxycarbamate residue), a silane residue, a hydrazone-containing residue (e.g., a hydrazone residue, an acylhydrazone residue, or a bisarylhydrazone residue), a phosphoramidate residue, an aconityl residue, a trityl residue, an azo residue, a vicinaldiol residue, a selenium residue, an aromatic ring-containing residue having an electron-withdrawing group, a coumarin-containing residue, a sulfone-containing residue, an unsaturated bond-containing chain residue, and a glycosyl residue.

The aromatic ring group having an electron-withdrawing group preferably has an aromatic ring group selected from the group consisting of an aryl, an aralkyl, an aromatic heterocyclic group, and an alkyl having an aromatic heterocyclic group, and an aralkyl and an alkyl having an aromatic heterocyclic group are more preferred. The electron-withdrawing group preferably binds to the 2-position of the ring. The aromatic ring-containing residue having an electron-withdrawing group is even more preferably, for example, an aralkyl having an electron-withdrawing group at the 2-position (e.g., benzyl). Examples of the electron-withdrawing group include a halogen atom, an alkyl substituted with a halogen atom (e.g., trifluoromethyl), a boronic acid residue, mesyl, tosyl, triflate, nitro, cyano, a phenyl group, and a keto group (e.g., acyl).

Definitions, examples, and preferred examples of groups such as alkyl, acyl (that is, alkylcarbonyl), alkoxy (that is, alkyloxy), aryl, and aralkyl found as a term such as a prefix or a suffix in relation to the name of a residue as a cleavable portion are similar to those described below.

Examples of the ester residue include an ordinary ester residue comprising a carbon atom and an oxygen atom [e.g. an alkyl ester (e.g., a tertiary alkyloxycarbonyl such as tert-butyloxycarbonyl), an aryl ester (e.g., a phenacyl ester or 2-(diphenylphosphino) benzoate), a glycosyl ester residue, or an orthoester residue], an ester residue comprising a sulfur atom and an oxygen atom (e.g., a thioester residue such as an α-thiophenyl ester residue or an alkyl thioester residue), an ester residue comprising a phosphorus atom and an oxygen atom (e.g., a phosphodiester residue or a phosphotriester residue), and an activated ester residue (e.g., an N-hydroxysuccinimide residue).

Examples of the sulfone-containing residue include a sulfone residue and a quinolinylbenzene sulfonate residue.

The silane residue is preferably a silane residue having a group selected from the group consisting of alkyl, aryl, aralkyl, and alkoxy. Examples of such a silane residue include a dialkyldialkoxysilane residue (e.g., dimethyldialkoxysilane or diethyldialkoxysilane) and a diaryldialkoxysilane residue (e.g., diphenyldialkoxysilane).

The alkoxyalkyl (that is, alkyloxyalkyl) residue is a group obtained by combining alkyloxy and alkyl as described below (definitions, examples, and preferred examples of alkyloxy and alkyl are similar to those described below), and examples thereof include a methoxymethyl residue, an ethoxymethyl residue, a methoxyethyl residue, and an ethoxyethyl residue, but are not limited thereto.

The unsaturated bond-containing chain residue is a residue comprising an unsaturated bond portion comprising only a carbon atom (e.g., vinyl (ethenyl) that is a minimum unit having a carbon-carbon double bond or acetylenyl (ethynyl) that is a minimum unit having a carbon-carbon triple bond), or a residue comprising an unsaturated bond portion (e.g., aldehyde or cyano) comprising a carbon atom and a hetero atom (e.g., a nitrogen atom, a sulfur atom, or an oxygen atom). Examples of the unsaturated bond-containing chain residue include a vinyl ether residue, a cyanoethyl residue, an ethylene residue, and a malondialdehyde residue.

Examples of the acidic substance (also referred to as an electrophilic reagent) include an inorganic acidic substance such as hydrochloric acid, sulfuric acid, or nitric acid, and an organic acidic substance such as formic acid, acetic acid, 4-(2-hydroxyethyl)-1-piperazin propanesulfonic acid, 3-morpholinopropanesulfonic acid, sodium dihydrogen phosphate, citric acid, dodecyl sulfate, N-dodecanoyl sarcosic acid, or trifluoroacetic acid. Examples of a site that can be cleaved by an acidic substance include an alkyloxyarylalkyl residue, a tertiary alkyloxycarbamate residue, an acetal residue, a silane residue, an imine residue, a vinyl ether residue, a Q-thiopropionate residue, a trityl residue, a hydrazone residue, an aconityl residue, an orthoester residue, a carbamoyl residue, and a 2-(diphenylphosphino) benzoate residue.

Examples of the basic substance (also referred to as a nucleophilic reagent) include an inorganic basic substance such as sodium hydroxide, potassium hydroxide, sodium acetate, potassium acetate, or ammonium acetate, and an organic basic substance such as hydroxylamine, triethylamine, or N,N'-diisopropylamine. Examples of a site that can be cleaved by a basic substance include a silane residue, a cyanoethyl residue, a sulfone residue, an ethylene residue, a glycosyl disuccinate residue, an α-thiophenyl ester residue, an unsaturated vinyl sulfide residue, a malondialdehyde residue, an acylhydrazone residue, and alkylthioester residue.

Examples of the reducing agent include cysteine, dithiothreitol, reduced glutathione, and β-mercaptoethanol. Examples of a site that can be cleaved by the reducing agent include a disulfide residue, an alkoxyalkyl residue, and an azo residue.

Examples of the oxidizing agent include sodium periodate and oxidized glutathione. Examples of a site that can be cleaved by the oxidizing agent include a bicinaldiol residue and a selenium residue.

Examples of the enzyme include trypsin, papain, TEV, thrombin, cathepsin B, cathepsin D, cathepsin K, caspase, protease, matrix metalloprotease, lipase, endoglycosidase, and PN gauze F. Examples of a site that can be cleaved by the enzyme include an ester residue, a phosphodiester residue, and a glycosyl residue.

Examples of a site that can be cleaved by light include a 2-nitrobenzyl residue, a phenacyl ester residue, an 8-quinolinebenzene sulfonate residue, a coumarin residue, a phosphotriester residue, a bisarylhydrazone residue, and a bimandithiopropionic acid residue.

Examples of the self-degradable cleavable portion include an activated ester residue (e.g., an N-hydroxysuccinimide residue). More specifically, the cleavable portion may correspond to any one chemical structure selected from the group consisting of the following:

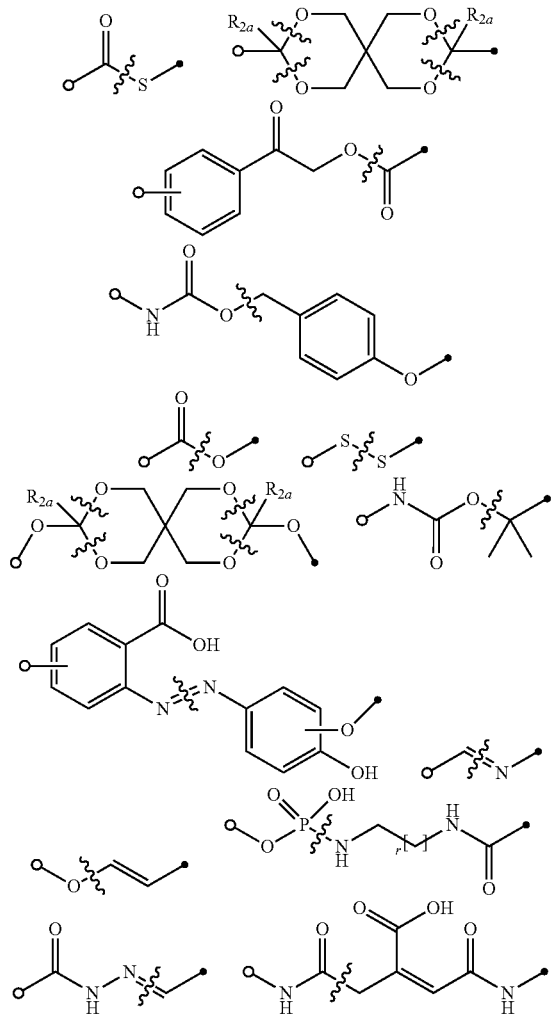

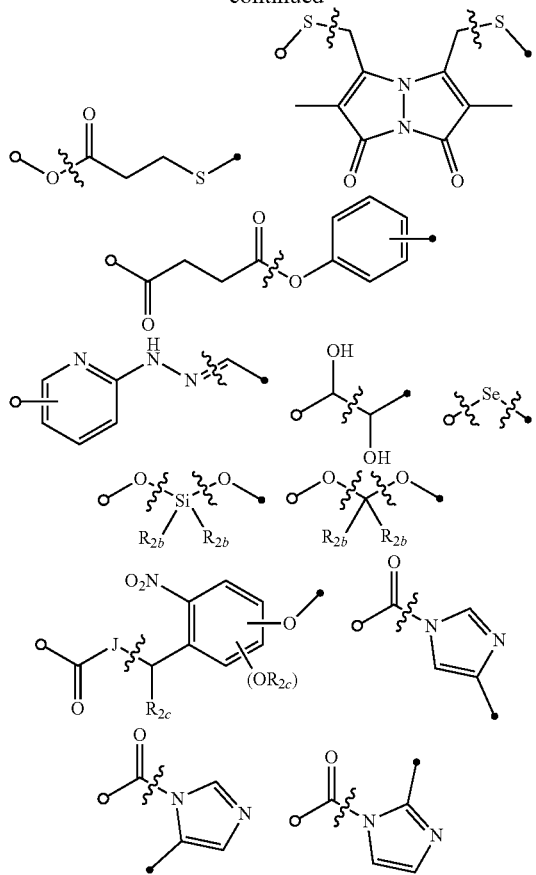

[where the wavy line orthogonal to the bond indicates a cleavage site,
a plurality of $R_{2a}$s, a plurality of $R_{2b}$s, and a plurality of $R_{2c}$s are the same as or different from each other, and are each a hydrogen atom or selected from the group consisting of substituents described below,
J is —CH$_2$—, —O—, or —S—,
r is any integer of 1 to 4,
○ (white circle) indicates a bond to A (or La described below), and ● (black circle) indicates a bond to B (or Lb described below), and
when the chemical structure is asymmetrical about the cleavage site, ● may indicate a bond to A (or La described below), and ○ may indicate a bond to B (or Lb described below)].

J is —CH$_2$—, —O—, or —S—, j is preferably —CH$_2$— or —O—, and more preferably —CH$_2$—.

r is any integer of 1 to 4, preferably any integer of 1 to 3, and more preferably 1 or 2.

In an embodiment, the cleavable linker may be (i) a cleavable linker that is a divalent group comprising a cleavable portion capable of forming a bioorthogonal functional group on a reactive group side by cleavage, or (ii) a cleavable linker that is a divalent group comprising a cleavable portion not capable of forming a bioorthogonal functional group on a reactive group side by cleavage.

Examples of the cleavable portion of (i) include a disulfide residue, an ester residue, an acetal residue, a ketal residue, an imine residue, and a vicinaldiol residue.

More specifically, the cleavable portion of (i) may correspond to, for example, any one chemical structure selected from the group consisting of the following:

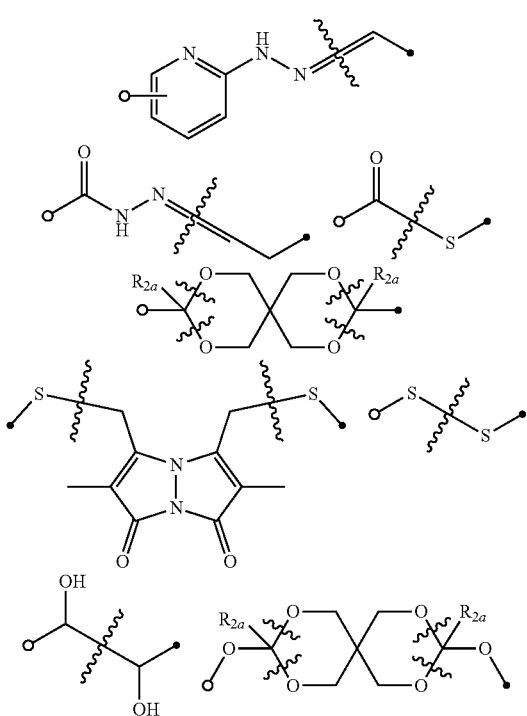
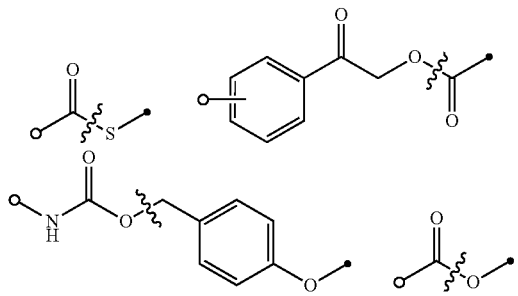

[where the wavy line orthogonal to the bond indicates a cleavage site,
a plurality of $R_{2a}$s are the same as or different from each other, and are each a hydrogen atom or selected from the group consisting of substituents described below,
○ (white circle) indicates a bond to A (or La described below), and ● (black circle) indicates a bond to B (or Lb described below), and
when the chemical structure is asymmetrical about the cleavage site, ● may indicate a bond to A (or La described below), and ○ may indicate a bond to B (or Lb described below)].

Examples of the cleavable portion of (ii) include an ester residue, a carbamoyl residue, an alkoxyalkyl residue, an imine residue, a tertiary alkyloxycarbamate residue, a silane residue, a hydrazone-containing residue, a phosphoramidate residue, an aconityl residue, a trityl residue, an azo residue, a vicinaldiol residue, a selenium residue, an aromatic ring-containing residue with an electron-withdrawing group, a coumarin-containing residue, a sulfone-containing residue, an unsaturated bond-containing chain residue, and a glycosyl residue.

More specifically, the cleavable portion of (ii) may correspond to, for example, any one chemical structure selected from the group consisting of the following:

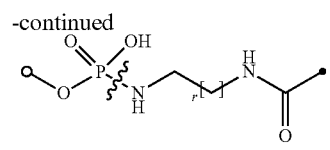
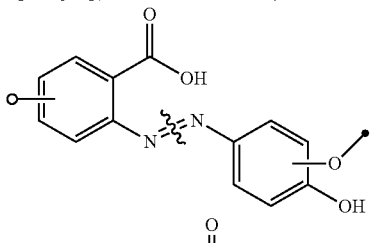
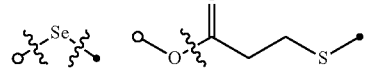
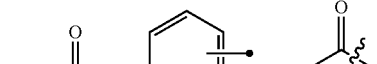
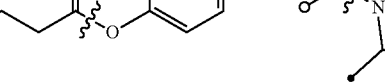
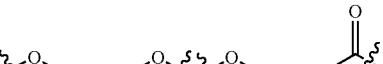
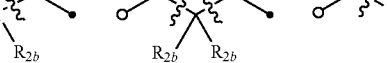
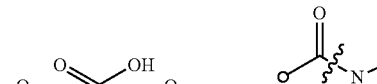
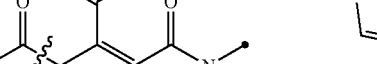
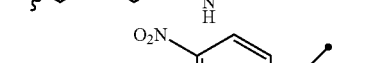
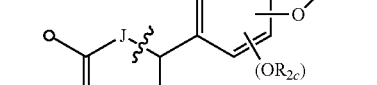
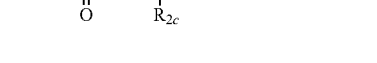
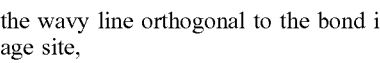
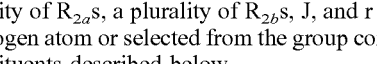
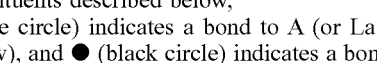
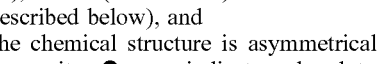
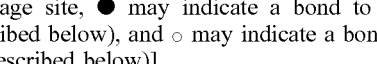
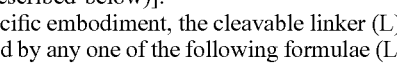
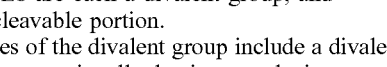

[where the wavy line orthogonal to the bond indicates a cleavage site,
a plurality of $R_{2a}$s, a plurality of $R_{2b}$s, J, and r are each a hydrogen atom or selected from the group consisting of substituents described below,
○ (white circle) indicates a bond to A (or La described below), and ● (black circle) indicates a bond to B (or Lb described below), and
when the chemical structure is asymmetrical about the cleavage site, ● may indicate a bond to A (or La described below), and ○ may indicate a bond to B (or Lb described below)].

In a specific embodiment, the cleavable linker (L) may be represented by any one of the following formulae (L) to (L3)

La—C-Lb (L1)

La—C (L2)

C-Lb (L3)

wherein
La and Lb are each a divalent group, and
C is a cleavable portion.
Examples of the divalent group include a divalent hydrocarbon group optionally having a substituent, a divalent heterocyclic group optionally having a substituent, —C(=O)—, —NR$_a$— (where R$_a$ represents a hydrogen atom or a substituent), —O—, —S—, —C(=S)—, and a group formed by a combination of two or more (e.g., two to eight, preferably two to six, and more preferably two to four) of these.

The divalent hydrocarbon group is a linear, branched, or cyclic divalent hydrocarbon group and preferably a linear or branched divalent hydrocarbon group. Examples of the divalent hydrocarbon group include alkylene, alkenylene, alkynylene, and arylene.

The alkylene is preferably $C_{1-12}$ alkylene, more preferably $C_{1-6}$ alkylene, and particularly preferably $C_{1-4}$ alkylene. The number of carbon atoms does not comprise the number of carbon atoms of a substituent. The alkylene may be linear, branched, or cyclic, and is preferably linear alkylene. Examples of such an alkylene include methylene, ethylene, propylene, butylene, pentylene, and hexylene.

The alkenylene is preferably $C_{2-12}$ alkenylene, more preferably $C_{2-6}$ alkenylene, and particularly preferably $C_{2-4}$ alkenylene. The number of carbon atoms does not comprise the number of carbon atoms of a substituent. The alkenylene may be linear, branched, or cyclic, and is preferably linear alkenylene. Examples of such an alkenylene include ethylenylene, propynylene, butenylene, pentenylene, and hexenylene.

The alkynylene is preferably $C_{2-12}$ alkynylene, more preferably $C_{2-6}$ alkynylene, and particularly preferably $C_{2-4}$ alkynylene. The number of carbon atoms does not comprise the number of carbon atoms of a substituent. The alkynylene may be linear, branched, or cyclic, and is preferably linear alkynylene. Examples of such an alkynylene include ethynylene, propynylene, butynylene, pentynylene, and hexynylene.

The arylene is preferably $C_{6-24}$ arylene, more preferably $C_{6-18}$ arylene, even more preferably $C_{6-14}$ arylene, and still even more preferably $C_{6-10}$ arylene. The number of carbon atoms does not comprise the number of carbon atoms of a substituent. Examples of the arylene include phenylene, naphthylene, and anthracenylene.

The divalent heterocyclic group is a divalent aromatic heterocyclic group or a divalent nonaromatic heterocyclic group. The divalent heterocyclic group preferably comprises, as a hetero atom forming a heterocycle, one or more selected from the group consisting of an oxygen atom, a sulfur atom, a nitrogen atom, a phosphorous atom, a boron atom, and a silicon atom and more preferably comprises one or more selected from the group consisting of an oxygen atom, a sulfur atom, and a nitrogen atom.

The divalent aromatic heterocyclic group is preferably a $C_{1-21}$ divalent aromatic heterocyclic group, more preferably a $C_{1-15}$ divalent aromatic heterocyclic group, even more preferably a $C_{1-9}$ divalent aromatic heterocyclic group, and still even more preferably a $C_{1-6}$ divalent aromatic heterocyclic group. The number of carbon atoms does not comprise the number of carbon atoms of a substituent. More specific examples of the divalent aromatic heterocyclic group include pyrrolediyl, furandiyl, thiophenediyl, pyridinediyl, pyridazinediyl, pyrimidinediyl, pyrazinediyl, triazinediyl, pyrazolediyl, imidazolediyl, thiazolediyl, isothiazolediyl, oxazolediyl, isoxazolediyl, triazolediyl, tetrazolediyl, indolediyl, purinediyl, anthraquinonediyl, carbazolediyl, fluorenediyl, quinolinediyl, isoquinolinediyl, quinazolinediyl, and phthalazinediyl.

The divalent nonaromatic heterocyclic group is preferably a $C_{2-21}$ nonaromatic heterocyclic group, more preferably a $C_{2-15}$ nonaromatic heterocyclic group, even more preferably a $C_{2-9}$ nonaromatic heterocyclic group, and still even more preferably a $C_{2-6}$ nonaromatic heterocyclic group. The number of carbon atoms does not comprise the number of carbon atoms of a substituent. More specific examples of the divalent nonaromatic heterocyclic group include pyrroldionediyl, pyrrolinedionediyl, oxiranediyl, aziridinediyl, azetidinediyl, oxetanediyl, thietanediyl, pyrrolidinediyl, dihydrofurandiyl, tetrahydrofurandiyl, dioxolanediyl, tetrahydrothiophenediyl, pyrrolinediyl, imidazolidinediyl, oxazolidinediyl, piperidinediyl, dihydropyrandiyl, tetrahydropyrandiyl, tetrahydrothiopyrandiyl, morpholinediyl, thiomorpholinediyl, piperazinediyl, dihydrooxazinediyl, tetrahydrooxazinediyl, dihydropyrimidinediyl, and tetrahydropyrimidinediyl.

The divalent group represented by La or Lb may have e.g., one to five, preferably one to three, and more preferably one or two substituents. Such a substituent is similar to the above substituent represented by R$_a$ or R$_b$. Examples of such a substituent include:

(i) a halogen atom;
(ii) a monovalent hydrocarbon group;
(iii) an aralkyl;
(iv) a monovalent heterocyclic group;
(v) R$_c$—O—, R$_c$—C(=O)—, R$_c$—O—C(=O)—, or R$_c$—C(=O)—O—, (where R$_c$ represents a hydrogen atom or a monovalent hydrocarbon group);
(vi) NR$_d$R$_e$—, NR$_d$R$_e$—C(=O)—, NR$_d$R$_e$—C(=O)—O—, or R$_d$—C(=O)—NR$_e$—, (where R$_d$ and R$_e$ are the same as or different from each other, and each represent a hydrogen atom or a monovalent hydrocarbon group); and
(vii) a nitro group, a sulfate group, a sulfonate group, a cyano group, and a carboxyl group.

Examples of the halogen atom include a fluorine atom, a chlorine atom, a bromine atom, and an iodine atom.

Examples of the monovalent hydrocarbon group include a monovalent chain hydrocarbon group, a monovalent alicyclic hydrocarbon group, and a monovalent aromatic hydrocarbon group.

The monovalent chain hydrocarbon group means a hydrocarbon group comprising only a chain structure and does not comprise any cyclic structure in a main chain thereof. Note that the chain structure may be linear or branched. Examples of the monovalent chain hydrocarbon group include alkyl, alkenyl, and alkynyl. The alkyl, alkenyl, and alkynyl may be linear or branched.

The alkyl is preferably $C_{1-12}$ alkyl, more preferably $C_{1-6}$ alkyl, and even more preferably $C_{1-4}$ alkyl. The number of carbon atoms does not comprise the number of carbon atoms of a substituent. Examples of the $C_{1-12}$ alkyl include methyl, ethyl, n-propyl, i-propyl, n-butyl, s-butyl, isobutyl, t-butyl, pentyl, hexyl, heptyl, octyl, nonyl, decyl, and dodecyl.

The alkenyl is preferably $C_{2-12}$ alkenyl, more preferably $C_{2-6}$ alkenyl, and even more preferably $C_{2-4}$ alkenyl. The number of carbon atoms does not comprise the number of carbon atoms of a substituent. Examples of the $C_{2-12}$ alkenyl include vinyl, propenyl, and n-butenyl.

The alkynyl is preferably $C_{2-12}$ alkynyl, more preferably $C_{2-6}$ alkynyl, and even more preferably $C_{2-4}$ alkynyl. The number of carbon atoms does not comprise the number of carbon atoms of a substituent. Examples of the $C_{2-12}$ alkynyl include ethynyl, propynyl, and n-butynyl.

The monovalent chain hydrocarbon group is preferably alkyl.

The monovalent alicyclic hydrocarbon group means a hydrocarbon group comprising only an alicyclic hydrocarbon as a cyclic structure and not comprising any aromatic ring, in which the alicyclic hydrocarbon may be monocyclic or polycyclic. Note that the monovalent alicyclic hydrocarbon group is not necessarily required to comprise only an alicyclic hydrocarbon but may comprise a chain structure in part thereof. Examples of the monovalent alicyclic hydrocarbon group include cycloalkyl, cycloalkenyl, and cycloalkynyl, which may be monocyclic or polycyclic.

The cycloalkyl is preferably $C_{3-12}$ cycloalkyl, more preferably $C_{3-6}$ cycloalkyl, and even more preferably $C_{5-6}$ cycloalkyl. The number of carbon atoms does not comprise the number of carbon atoms of a substituent. Examples of the $C_{3-12}$ cycloalkyl include cyclopropyl, cyclobutyl, cyclopentyl, and cyclohexyl.

The cycloalkenyl is preferably $C_{3-12}$ cycloalkenyl, more preferably $C_{3-6}$ cycloalkenyl, and even more preferably $C_{5-6}$ cycloalkenyl. The number of carbon atoms does not comprise the number of carbon atoms of a substituent. Examples of the $C_{3-12}$ cycloalkenyl include cyclopropenyl, cyclobutenyl, cyclopentenyl, and cyclohexenyl.

The cycloalkynyl is preferably $C_{3-12}$ cycloalkynyl, more preferably $C_{3-6}$ cycloalkynyl, and even more preferably $C_{5-6}$ cycloalkynyl. The number of carbon atoms does not comprise the number of carbon atoms of a substituent. Examples of the $C_{3-12}$ cycloalkynyl include cyclopropynyl, cyclobutynyl, cyclopentynyl, and cyclohexynyl.

The monovalent alicyclic hydrocarbon group is preferably cycloalkyl.

The monovalent aromatic hydrocarbon group means a hydrocarbon group comprising an aromatic cyclic structure. Note that the monovalent aromatic hydrocarbon group is not necessarily required to comprise only an aromatic ring and may comprise a chain structure or alicyclic hydrocarbon in part thereof, in which the aromatic ring may be monocyclic or polycyclic. The monovalent aromatic hydrocarbon group is preferably $C_{6-12}$ aryl, more preferably $C_{6-10}$ aryl, and even more preferably $C_6$ aryl. The number of carbon atoms does not comprise the number of carbon atoms of a substituent. Examples of the $C_{6-12}$ aryl include phenyl and naphthyl.

The monovalent aromatic hydrocarbon group is preferably phenyl.

Among these groups, the monovalent hydrocarbon group is preferably alkyl, cycloalkyl, and aryl and more preferably alkyl.

The aralkyl refers to arylalkyl. Definitions, examples, and preferred examples of the aryl and the alkyl in the arylalkyl are as described above. The aralkyl is preferably $C_{3-15}$ aralkyl. Examples of such an aralkyl include benzoyl, phenethyl, naphthylmethyl, and naphthylethyl.

The monovalent heterocyclic group refers to a group obtained by removing one hydrogen atom from a heterocycle of a heterocyclic compound. The monovalent heterocyclic group is a monovalent aromatic heterocyclic group or a monovalent nonaromatic heterocyclic group. The monovalent heterocyclic group preferably comprises one or more selected from the group consisting of an oxygen atom, a sulfur atom, a nitrogen atom, a phosphorus atom, a boron atom, and a silicon atom and more preferably comprises one or more selected from the group consisting of an oxygen atom, a sulfur atom, and a nitrogen atom as a hetero atom comprised in the heterocyclic group.

The monovalent aromatic heterocyclic group is preferably a $C_{1-15}$ aromatic heterocyclic group, more preferably a $C_{1-9}$ aromatic heterocyclic group, and even more preferably a $C_{1-6}$ aromatic heterocyclic group. The number of carbon atoms does not comprise the number of carbon atoms of a substituent. Examples of the monovalent aromatic heterocyclic group include pyrrolyl, furanyl, thiophenyl, pyridinyl, pyridazinyl, pyrimidinyl, pyrazinyl, triazinyl, pyrazolyl, imidazolyl, thiazolyl, isothiazolyl, oxazolyl, isoxazolyl, triazolyl, tetrazolyl, indolyl, purinyl, anthraquinolyl, carbazonyl, fluorenyl, quinolinyl, isoquinolinyl, quinazolinyl, and phthalazinyl.

The monovalent nonaromatic heterocyclic group is preferably a $C_{2-15}$ nonaromatic heterocyclic group, more preferably a $C_{2-9}$ nonaromatic heterocyclic group, and even more preferably a $C_{2-6}$ nonaromatic heterocyclic group. The number of carbon atoms does not comprise the number of carbon atoms of a substituent. Examples of the monovalent nonaromatic heterocyclic group include oxiranyl, aziridinyl, azetidinyl, oxetanyl, thietanyl, pyrrolidinyl, dihydrofuranyl, tetrahydrofuranyl, dioxolanyl, tetrahydrothiophenyl, pyrolinyl, imidazolidinyl, oxazolidinyl, piperidinyl, dihydropyranyl, tetrahydropyranyl, tetrahydrothiopyranyl, morpholinyl, thiomorpholinyl, piperazinyl, dihydrooxazinyl, tetrahydrooxazinyl, dihydropyrimidinyl, and tetrahydropyrimidinyl.

Among these groups, the monovalent heterocyclic group is preferably a five-membered or six-membered heterocyclic group.

The substituent may be preferably the following:
(i') a halogen atom;
(ii') $C_{1-12}$ alkyl, $C_{1-12}$ phenyl, or $C_{1-12}$ naphthyl;
(iii') $C_{3-15}$ aralkyl;
(iv') a five-membered or six-membered heterocycle;
(v') $R_c$—O—, $R_c$—C(=O)—, $R_c$—O—C(=O)—, or $R_c$—C(=O)—O— (where $R_c$ represents a hydrogen atom or $C_{1-12}$ alkyl);
(vi') $NR_dR_e$—, $NR_dR_e$—C(=O)—, $NR_dR_e$—C(=O)—O—, or $R_d$—C(=O)—$NR_c$—, (where $R_d$ and $R_c$ are the same as or different from each other, and each represent a hydrogen atom or $C_{1-12}$ alkyl); and
(vii') the same groups as those enumerated in (vii).

The substituent may be more preferably the following:
(i'') a halogen atom;
(ii'') $C_{1-12}$ alkyl;
(iii'') $R_c$—O—, $R_c$—C(=O)—, $R_c$—O—C(=O)—, or $R_c$—C(=O)—O—, (where $R_c$ represents a hydrogen atom or $C_{1-12}$ alkyl);
(iv'') $NR_dR_e$—, $NR_dR_e$—C(=O)—, $NR_dR_e$—C(=O)—O—, or $R_d$—C(=O)—$NR_e$—, (where $R_d$ and $R_e$ are the same as or different from each other, and each represent a hydrogen atom or $C_{1-12}$ alkyl); and
(v'') the same groups as those enumerated in (vii).

The substituent may be even more preferably the following:
(i''') a halogen atom;
(ii''') $C_{1-6}$ alkyl;
(iii''') $R_c$—O—, $R_c$—C(=O)—, $R_c$—O—C(=O)—, or $R_c$—C(=O)—O—, (where $R_c$ represents a hydrogen atom or $C_{1-6}$ alkyl);
(iv''') $NR_dR_e$—, $NR_dR_e$—C(=O)—, $NR_dR_e$—C(=O)—O—, or $R_d$—C(=O)—$NR_e$—, (where $R_d$ and $R_e$ are the same as or different from each other, and each represent a hydrogen atom or $C_{1-6}$ alkyl); and
(v''') the same groups as those enumerated in (vii).

The substituent may be particularly preferably the following:
(i'''') a halogen atom;
(ii'''') $C_{1-4}$ alkyl;
(iii'''') $R_c$—O—, $R_c$—C(=O)—, $R_c$—O—C(=O)—, or $R_c$—C(=O)—O—, (where $R_c$ represents a hydrogen atom or $C_{1-4}$ alkyl);

(iv'''') NR$_d$R$_e$—, NR$_d$R$_e$—C(═O)—, NR$_d$R$_e$—C(═O)—O—, or R$_d$—C(═O)—NR$_e$— (where R$_d$ and R$_e$ are the same or different, and each represent a hydrogen atom or C$_{1-4}$ alkyl); or (v'''') the same groups as those enumerated in (vii).

In a specific embodiment, La and Lb may be represented by the following (La') and (Lb'), respectively:

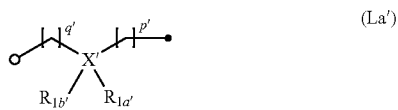

(La')

and

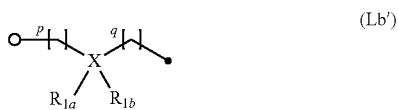

(Lb')

wherein p and p' are the same as or different from each other and are each any integer of 0 to 10, q and q' are the same as or different from each other and are each any integer of 0 to 10, X and X' are the same as or different from each other and are each a carbon atom, a nitrogen atom, or a single bond (where R$_{1b}$ is absent when X is a nitrogen atom, R$_{1b'}$ is absent when X' is a nitrogen atom, R$_{1a}$ and R$_{1b}$ are absent when X is a single bond, and R$_{1a'}$ and R$_{1b'}$ are absent when X' is a single bond), and R$_{1a}$, R$_{1b}$, R$_{1a'}$, and R$_{1b'}$ are the same as or different from each other and are each a hydrogen atom or selected from the group consisting of the above substituents.

p and p' are the same as or different from each other and are each any integer of 0 to 10, preferably an integer of 0 to 8, more preferably an integer of 0 to 6, even more preferably an integer of 0 to 4, and particularly preferably 0, 1, or 2. p and p' are preferably the same as each other.

q and q' are the same as or different from each other and are each any integer of 0 to 10, preferably an integer of 0 to 8, more preferably an integer of 0 to 6, even more preferably an integer of 0 to 4, and particularly preferably 0, 1, or 2. q and q' are preferably the same as each other.

X and X' are the same as or different from each other and are each a carbon atom, a nitrogen atom, or a single bond, and preferably a carbon atom or a single bond. X and X' are preferably the same as each other.

R$_{1a}$, R$_{1b}$, R$_{1a'}$, and R$_{1b'}$ are the same as or different from each other and are each a hydrogen atom or selected from the group consisting of substituents described below. Definitions, examples, and preferred examples of the substituents are as described above. R$_{1a}$, R$_{1b}$, R$_{1a'}$, and R$_{1b'}$ are each preferably a hydrogen atom.

1-4. (a) Divalent Group Comprising Bioorthogonal Functional Group or (b) Divalent Group Comprising No Bioorthogonal Functional Group (B)

In formula (I), B is (a) a divalent group comprising a bioorthogonal functional group or (b) a divalent group comprising no bioorthogonal functional group.

The bioorthogonal functional group refers to a group that does not react with biological components (e.g., amino acids, nucleic acids, lipids, sugars, and phosphoric acids) or has a low reaction rate to the biological components but selectively reacts with components other than the biological components. The bioorthogonal functional group is well known in the technical field concerned (e.g., refer to Sharpless K. B. et al., Angew. Chem. Int. Ed. 40,2004 (2015); Bertozzi C. R. et al., Science 291,2357 (2001); Bertozzi C. R. et al., Nature Chemical Biology 1,13 (2005), all of which are incorporated herein by reference in their entireties).

When the target of the affinity substance is an antibody, the bioorthogonal functional group is a bioorthogonal functional group to a protein. The bioorthogonal functional group to a protein is a group that does not react with side chains of 20 types of natural amino acid residues forming proteins and reacts with certain functional groups. The 20 types of natural amino acids forming proteins are alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), valine (V), aspartic acid (D), glutamic acid (E), arginine (R), histidine (H), and lysine (L). Among these 20 types of natural amino acids, glycine, which has no side chain (that is, which has a hydrogen atom as a side chain), and alanine, isoleucine, leucine, phenylalanine, and valine, which each have a hydrocarbon group as a side chain (that is, which each comprise no hetero atom selected from the group consisting of a sulfur atom, a nitrogen atom, and an oxygen atom in a side chain thereof) are inactive to normal reactions. Consequently, the bioorthogonal functional group to a protein is a functional group incapable of reacting with, in addition to the side chains of these amino acids having side chains inactive to normal reactions, side chains of asparagine, glutamine, methionine, proline, serine, threonine, tryptophan, tyrosine, aspartic acid, glutamic acid, arginine, histidine, and lysin.

Examples of such a bioorthogonal functional group that cannot react with proteins include an azide residue, an aldehyde residue, a thiol residue, an alkene residue (in other words, it is only required to have a vinylene (ethenylene) portion, which is a minimum unit having a carbon-carbon double bond. Hereinafter the same), an alkyne residue (in other words, it is only required to have an ethynylene portion, which is a minimum unit having a carbon-carbon triple bond. Hereinafter the same), a halogen residue, a tetrazine residue, a nitrone residue, a hydroxylamine residue, a nitrile residue, a hydrazine residue, a ketone residue, a boronic acid residue, a cyanobenzothiazole residue, an allyl residue, a phosphine residue, a maleimide residue, a disulfide residue, a thioester residue, an α-halocarbonyl residue (e.g., a carbonyl residue having a fluorine atom, a chlorine atom, a bromine atom, or an iodine atom at an α-position. Hereinafter the same), an isonitrile residue, a sydnone residue, and a selenium residue. Examples of the proteins include a protein that can comprise a free thiol (cysteine) (e.g., a protein other than an antibody) and a protein that cannot comprise a free thiol (e.g., an antibody). In the protein that cannot comprise a free thiol, a thiol functions as the bioorthogonal functional group. Consequently, a target of the affinity substance is an antibody that cannot comprise a free thiol, and therefore the bioorthogonal functional group comprises a thiol. The divalent group may comprise one or more types (e.g., two, three, or four types) of bioorthogonal functional groups; the divalent group may preferably comprise one type of bioorthogonal functional group.

In an embodiment, the divalent group comprising a bioorthogonal functional group may be a divalent group comprising, in a main chain thereof, a bioorthogonal functional group selected from the group consisting of an azide residue, an aldehyde group, a thiol residue, an alkyne residue, an alkene residue, a tetrazine residue, a nitron residue, a hydroxylamine residue, a nitrile residue, a hydrazine residue, a ketone residue, a boronic acid residue, a cyanobenzothiazole residue, an allyl residue, a phosphine residue, a maleimide residue, a disulfide residue, a thioester residue, an α-halocarbonyl residue, an isonitrile residue, a sydnone residue, and a selenium residue.

In another embodiment, the divalent group comprising a bioorthogonal functional group may be a divalent group comprising, in a side chain thereof, a bioorthogonal functional group selected from the group consisting of an azide residue, an aldehyde residue, a thiol residue, an alkyne residue, an alkene residue, a halogen residue, a tetrazine residue, a nitron residue, a hydroxylamine residue, a nitrile residue, a hydrazine residue, a ketone residue, a boronic acid residue, a cyanobenzothiazole residue, an allyl residue, a phosphine residue, a maleimide residue, a disulfide residue, an α-halocarbonyl residue, an isonitrile residue, a sydnone residue, and a selenium residue.

More specifically, the bioorthogonal functional group may correspond to any one chemical structure selected from the group consisting of the following:

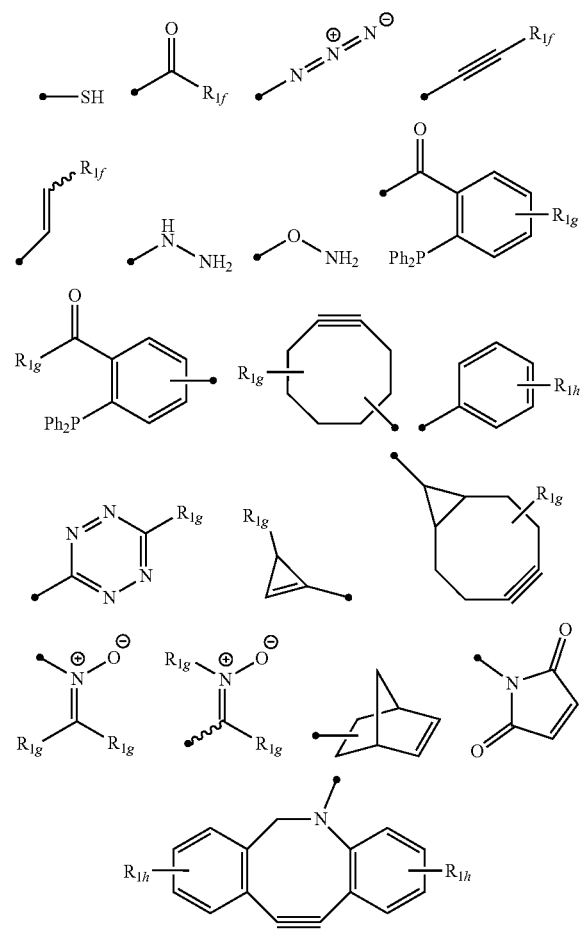

wherein
$R_{1f}$, one or a plurality of $R_{1g}$s, and one or a plurality of $R_{1h}$s are the same as or different from each other, and are each an atom or a group selected from the group consisting of the above (i) to (vii) or an electron-withdrawing group, and
• is a bond.

Examples of the electron-withdrawing group include those described above; preferred are a halogen atom, a boronic acid residue, mesyl, tosyl, and triflate.

In an embodiment, B may be (a) a divalent group comprising a bioorthogonal functional group. The number of bioorthogonal functional groups comprised in the divalent group is one or more, for example 1 to 5, preferably 1 to 3, more preferably 1 or 2, and even more preferably 1. When a plurality of bioorthogonal functional groups is comprised in the divalent group, the plurality of bioorthogonal functional groups may be of the same type or different types, but is preferably of the same type from a viewpoint of adopting a simple structure and the like.

In a specific embodiment, B may be (a1) a divalent group comprising a bioorthogonal functional group in a main chain thereof. The divalent group comprising a bioorthogonal functional group in a main chain thereof is a group in which a bioorthogonal functional group itself selected from the group consisting of an azide residue, an aldehyde group, a thiol residue, an alkyne residue, an alkene residue, a tetrazine residue, a nitron residue, a hydroxylamine residue, a nitrile residue, a hydrazine residue, a ketone residue, a boronic acid residue, a cyanobenzothiazole residue, an allyl residue, a phosphine residue, a maleimide residue, a disulfide residue, a thioester residue, an α-halocarbonyl residue, an isonitrile residue, a sydnone residue, and a selenium residue is a divalent group, or a group in which the above-described divalent group is coupled with one terminal or both terminals of such a divalent bioorthogonal functional group. A definition, examples, and preferred examples of the divalent group to be coupled are similar to the divalent group described above.

In another specific embodiment, B may be (a2) a divalent group comprising a bioorthogonal functional group in a side chain thereof. The divalent group comprising a bioorthogonal functional group in a side chain thereof is a divalent group substituted with a bioorthogonal functional group selected from the group consisting of an azide residue, an aldehyde residue, a thiol residue, an alkyne residue, an alkene residue, a halogen residue, a tetrazine residue, a nitron residue, a hydroxylamine residue, a nitrile residue, a hydrazine residue, a ketone residue, a boronic acid residue, a cyanobenzothiazole residue, an allyl residue, a phosphine residue, a maleimide residue, a disulfide residue, an α-halocarbonyl residue, an isonitrile residue, a sydnone residue, and a selenium residue, or a group comprising the bioorthogonal functional group. A definition, examples, and preferred examples of the divalent group to be substituted are similar to the divalent group described above.

In another embodiment, B may be (b) a divalent group comprising no bioorthogonal functional group. Such a divalent group may be an alkylene optionally having a substituent, a cycloalkylene optionally having a substituent, an aryl optionally having a substituent, a divalent heterocyclic group optionally having a substituent, —NR$_a$— (where R$_a$ represents a hydrogen atom or a substituent), —O—, and a combination of two or more (e.g., two to eight, preferably two to six, and more preferably two to four) of these. The substituent to be optionally comprised and the substituent for R$_a$ are substituents other than the bioorthogonal functional group. Examples of such a substituent include alkyl, cycloalkyl, aralkyl, a monovalent heterocyclic group, hydroxyl, amino, alkyloxy (alkoxy), cycloalkyloxy, and aralkyloxy. The number of such substituents is, for example, 1 to 5, preferably 1 to 3, more preferably 1 or 2, and even more preferably 1.

Definitions, examples, and preferred examples of alkyl, cycloalkyl, aralkyl, and a monovalent heterocyclic group for the substituent other than the bioorthogonal functional group are as described above.

Definitions, examples, and preferred examples of alkyl in alkyloxy (alkoxy), cycloalkyl in cycloalkyloxy, and aralkyl in aralkyloxy for the substituent other than the bioorthogonal functional group are as described above. More specific examples of alkyloxy include methyloxy, ethyloxy, propyloxy (e.g., n-propyloxy or iso-propyloxy), butyloxy (e.g., n-butyloxy, iso-butyloxy, sec-butyloxy, or tert-butyloxy), pentyloxy (e.g., n-pentyloxy), and hexyloxy (e.g., n-hexyloxy). Examples of cycloalkyloxy include cyclopropyloxy, cyclobutyloxy, cyclopentyloxy, and cyclohexyloxy. Examples of aralkyloxy include benzoyloxy, phenethyloxy, naphthylmethyloxy, and naphthylethyloxy.

The divalent group comprising no bioorthogonal functional group may also be a group that is highly inactive to a reaction. Therefore, such a divalent group may comprise only a carbon atom and a hydrogen atom. Such a divalent group is alkylene, cycloalkylene, aryl, or a combination of two or more (e.g., two or three) of these. When the divalent group comprising no bioorthogonal functional group is highly inactive to a reaction, such a divalent group may have a substituent selected from the group consisting of alkylene, cycloalkylene, and aryl as a highly inactive substituent to a reaction. The number of substituents that are highly inactive to a reaction is, for example, 1 to 5, preferably 1 to 3, and more preferably 1 or 2.

In a specific embodiment, B may be represented by the following Formula (B-1):

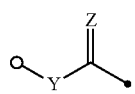

(B-1)

wherein
Y is —NH—, —O—, —CH$_2$—, or a group represented by the following Formula (B-2):

(B-2)

wherein
V and V' are the same as or different from each other and are each —NH—, —O—, —CH$_2$—, or a single bond, V1 is (a) a divalent group comprising a bioorthogonal functional group or (b) a divalent group comprising no bioorthogonal functional group, s is any integer of 0 to 10, and ○ and ● in Formula (B-2) have the same orientation as
○ and ● in Formula (B-1), respectively, Z is an oxygen atom, a sulfur atom, or a hydrogen atom (—C(═Z)— represents —CH$_2$—when Z is a hydrogen atom), and in Formula (B-1), ○ (white circle) indicates a bond to an L-side portion, and ● (black circle) indicates a bond to an R-side portion.

Y is —NH—, —O—, —CH$_2$—, or a group represented by the above formula (B-2). Y may be —NH—, —O—, or —CH$_2$— from a viewpoint of simplification of the structure or the like. Alternatively, Y may be —CH$_2$— or a group represented by the above formula (B-2) from a viewpoint of designing a structure based on a carbon atom or the like.

Z is an oxygen atom, a sulfur atom, or a hydrogen atom, but is preferably an oxygen atom or a sulfur atom.

V and V' are each —NH—, —O—, —CH$_2$—, or a single bond, and preferably —CH$_2$— or a single bond.

V1 is (a) a divalent group comprising a bioorthogonal functional group or (b) a divalent group comprising no bioorthogonal functional group. Such a divalent group is similar to that described above.

The divalent group in V1 is preferably a divalent hydrocarbon group optionally having a substituent or a divalent heterocyclic group optionally having a substituent. A definition, examples, and preferred examples of the divalent hydrocarbon group are similar to those described above, but for V1, alkylene, alkenylene, alkynylene, cycloalkylene, cycloalkenylene, cycloalkynylene, and arylene are preferred. For example, when the divalent group is not substituted at a portion comprising a bioorthogonal functional group, alkenylene, alkynylene, cycloalkenylene, and cycloalkynylene are preferred. On the other hand, when the divalent group is substituted at a portion comprising a bioorthogonal functional group, alkylene, cycloalkylene, and arylene are preferred. Examples and preferred examples of these groups are as described above. A definition, examples, and preferred examples of the divalent heterocyclic group are similar to those described above, but for V1, a five-membered or six-membered heterocyclic group is preferred. Examples and preferred examples of the five-membered or six-membered heterocyclic group are similar to those described above. A definition, examples, and preferred examples of the substituent are as described above. The number of (a) bioorthogonal functional groups that may be comprised in V1 is, for example, 1 to 5, preferably 1 to 3, more preferably 1 or 2, and even more preferably 1. When a plurality of bioorthogonal functional groups is comprised in the divalent group, the plurality of bioorthogonal functional groups may be of the same type or different types. The plurality of bioorthogonal functional groups is preferably of the same type from viewpoints of adopting a simple structure, improving reactivity, and the like. The plurality of bioorthogonal functional groups is preferably of different types from viewpoints of ensuring a differentiated reaction and the like. The number of (b) substituents that may be comprised in V1 is 1 to 5, preferably 1 to 3, and more preferably 1 or 2.

s is any integer of 0 to 10, preferably an integer of 0 to 8, more preferably an integer of 0 to 6, even more preferably an integer of 0 to 4, and particularly preferably 0, 1, or 2.

In a more specific embodiment, V1 may be a divalent group comprising, as a side chain, a group represented by the following Formula (B-3):

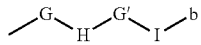
(B-3)

wherein

G and G' are the same as or different from each other and are each —NH—, —O—, —CH$_2$—, a single bond, or a group represented by the following Formula (B-4):

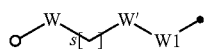
(B-4)

wherein

W and W' are the same as or different from each other and are each —NH—, —C—, —CH$_2$—, or a single bond, W1 is (a) a divalent group comprising a bioorthogonal functional group or (b) a divalent group comprising no bioorthogonal functional group, t is any integer of 0 to 10, ○ (white circle) in Formula (B-4) indicates a bond in a direction of the bond (•) in Formula (B-3), and ● (black circle) in Formula (B-4) indicates a bond in a direction of the b side in Formula (B-3), H is —CH$_2$, —C=O—, —C=S—, —NH—, or a single bond, I is a divalent hydrocarbon group, a divalent heterocycle, or a single bond, and b is any one group represented by the following:

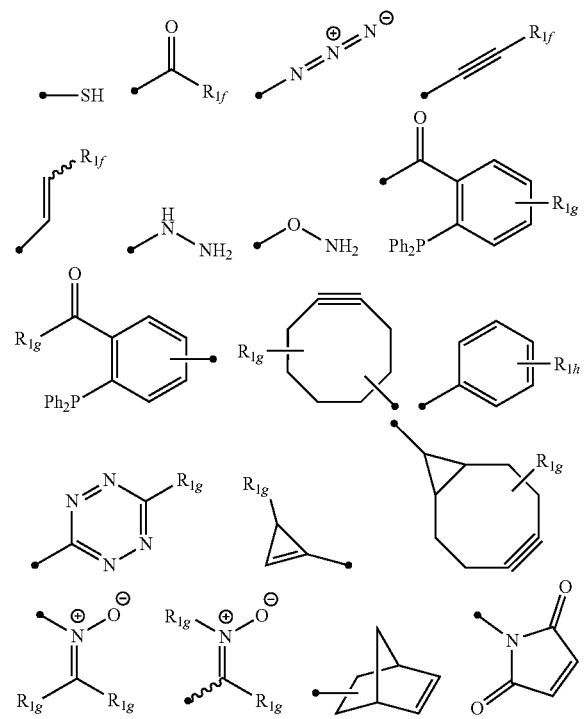

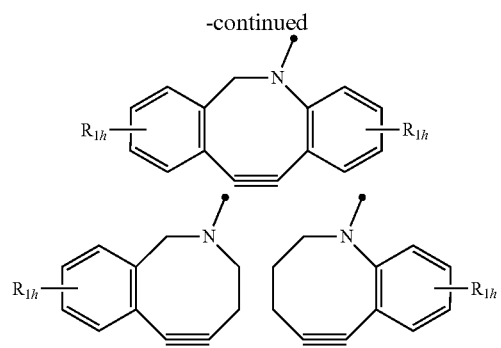

wherein $R_{1f}$, one or a plurality of $R_{1g}$s, and one or a plurality of $R_{1h}$s are the same as or different from each other, and are each an atom or a group selected from the group consisting of the above (i) to (vii) or an electron-withdrawing group, and

• is a bond. Such a divalent group is a divalent hydrocarbon group or a divalent heterocyclic group, preferably a divalent hydrocarbon group optionally having a substituent, more preferably alkylene, alkenylene, alkynylene, cycloalkylene, cycloalkenylene, cycloalkynylene, or arylene, even more preferably alkylene, cycloalkylene, or arylene, and particularly preferably alkylene. Examples and preferred examples of these groups are as described above. These groups may be each substituted with a substituent other than the above side chain. The number of such substituents is 1 to 5, preferably 1 to 3, and more preferably 1 or 2. Examples and preferred examples of the substituents are as described above.

G and G' are the same as or different from each other and are each —NH—, —O—, —CH$_2$—, a single bond, or a group represented by the above Formula (B-4). G and G' may be each —NH—, —O—, —CH$_2$—, or a single bond from a viewpoint of simplification of the structure or the like.

Alternatively, G and G' may be each —CH$_2$—, a single bond, or a group represented by the above formula (B-4) from a viewpoint of designing a structure based on a carbon atom or the like.

H is —CH$_2$—, —C=O—, —C=S—, —NH—, or a single bond. H is preferably —CH$_2$— or a single bond.

I is a divalent hydrocarbon group, a divalent heterocycle, or a single bond. The divalent hydrocarbon group and the divalent heterocycle may be each substituted or is not necessarily substituted with a substituent Definitions, examples, and preferred examples of the divalent hydrocarbon group, the divalent heterocycle, and the substituent are similar to those described above in V1.

W and W' are the same as or different from each other and are each —NH—, —O—, —CH$_2$—, or a single bond, and preferably —CH$_2$— or a single bond.

W1 is (a) a divalent group comprising a bioorthogonal functional group or (b) a divalent group comprising no bioorthogonal functional group. Such a divalent group is similar to that described above.

t is any integer of 0 to 10, preferably an integer of 0 to 8, more preferably an integer of 0 to 6, even more preferably an integer of 0 to 4, and particularly preferably 0, 1, or 2.

1-5. Reactive Group (R)

In Formula (I), R is a reactive group to an antibody. Such a reactive group is common technical knowledge in the technical field concerned.

The reactive group is a group the type of which is the same as or different from that of the bioorthogonal functional group.

For example, when B is (a) a divalent group comprising a bioorthogonal functional group, the type of the reactive group may be different from that of the bioorthogonal functional group. This is because when the type of the reactive group is the same as that of the bioorthogonal functional group, reaction specificity of the reactive group to an antibody is not ensured. In addition, this is because the bioorthogonal functional group cannot react with side chains of 20 types of natural amino acid residues forming antibodies.

More specifically, among the above-described 20 types of natural amino acids forming proteins, glycine, which has no side chain, and alanine, isoleucine, leucine, phenylalanine, and valine, which each have a hydrocarbon group as a side chain, are inactive to normal reactions. Consequently, the reactive group to a protein is a group capable of reacting with side chains of one or more types of (e.g., two, three, or four types of) amino acids out of 14 types of amino acids consisting of asparagine, glutamine, methionine, proline, serine, threonine, tryptophan, tyrosine, aspartic acid, glutamic acid, arginine, histidine, and lysin. Depending on a condition such as an amino acid composition of a protein, one or more types of (e.g., two, three, or four types of) of reactive groups may be comprised in the compound represented by Formula (I). However, one type of reactive group may be preferably comprised in the compound represented by Formula (I).

The reactive group is preferably a group capable of reacting with a side chain of any one type of amino acid out of the above-described 14 amino acids forming proteins.

The reactive group may be more preferably a reactive group specific to a side chain of any one type of amino acid out of lysine, tyrosine, tryptophan, and cysteine.

The reactive group may be even more preferably a reactive group specific to a side chain of any one type of amino acid out of lysine, tyrosine, and tryptophan.

When the protein is human IgG such as human IgG1, the reactive group is preferably a reactive group specific to a side chain of lysine or tyrosine.

The reactive group specific to a side chain of a lysine residue is a group capable of specifically reacting with an amino group (NHJ) present in the side chain of the lysine residue, and examples thereof include an activated ester residue (e.g., N-hydroxysuccinimide residue), a vinyl sulfone residue, a sulfonyl chloride residue, an isocyanate residue, an isothiocyanate residue, an aldehyde residue, a 1,4,7,10-tetraazacyclododecane-1,4,7,10-tetraacetic acid residue, a 2-imino-2-methoxyethyl residue, and a diazonium terephthalic acid residue.

Examples of a coupling portion formed by a reaction between the above-described reactive group specific to a side chain of a lysine residue and an amino group ($NH_2$) present in the side chain of the lysine residue include an amide residue, a urea residue, a pyridine residue, a carbamate residue, and a sulfonamide residue.

More specifically, the reactive group specific to a side chain of a lysine residue may correspond to any one chemical structure selected from the group consisting of the following:

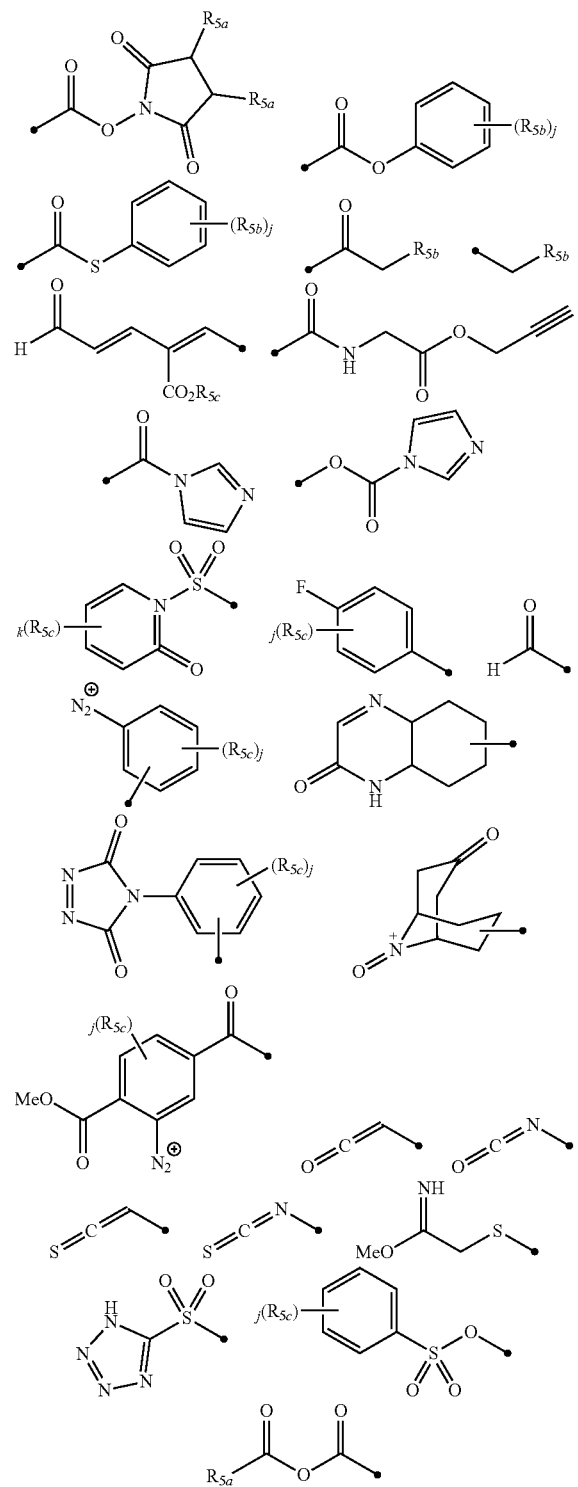

wherein $R_{5a}$ and $R_{5c}$ are each a hydrogen atom or the substituent described above, $R_{5b}$ is an electron-withdrawing group, j is any integer of 1 to 5, and k is any integer of 1 to 4.

$R_{5a}$ and $R_{5c}$ are each a hydrogen atom or the substituent described above. Definitions, examples, and preferred examples of the substituent are as described above.

$R_{5b}$ is an electron-withdrawing group. Examples of such an electron-withdrawing group include those described above; preferred are a halogen atom, a boronic acid residue, mesyl, tosyl, and triflate.

j is any integer of 1 to 5, preferably an integer of 1 to 3, and more preferably 1 or 2.

k is any integer of 1 to 4, preferably an integer of 1 to 3, and more preferably 1 or 2.

The coupling portion formed by a reaction between the above chemical structure, which is a reactive group specific to a side chain of a lysine residue, and an amino group ($NH_2$) present in the side chain of the lysine residue may correspond to any one chemical structure selected from the group consisting of the following.

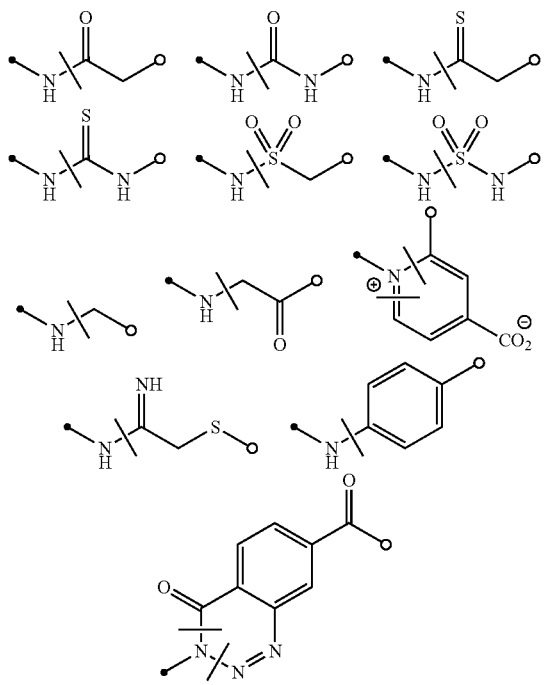

wherein ● (black circle) indicates a bond to a T-side portion, and ○ (white circle) indicates a bond to a B-side portion, and the straight line orthogonal to the bond indicates a bond formed by a reaction.

A reactive group specific to a side chain of a tyrosine residue is a group capable of specifically reacting with an atom at the ortho position of a phenolic hydroxyl group (OH) present in the side chain of the tyrosine residue, and examples thereof include a diazonium residue, a diazodicarbochelate residue, and a 2,3-dihydro-1H-pyrazin-6-one residue.

More specifically, the reactive group specific to a side chain of a tyrosine residue may correspond to any one chemical structure selected from the group consisting of the following:

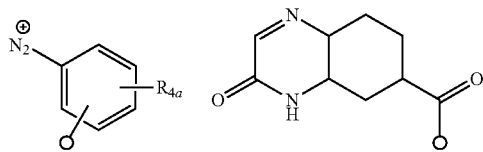

-continued

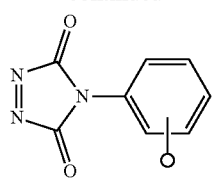

wherein $R_{4a}$ is a hydrogen atom or the substituent described above, and ○ indicates a bond to B.

$R_{4a}$ is a hydrogen atom or the substituent described above. Definitions, examples, and preferred examples of the substituent are as described above.

A coupling portion formed by a reaction between the above chemical structure, which is a reactive group specific to a side chain of a tyrosine residue, and an atom at the ortho position of a phenolic hydroxyl group (OH) present in the side chain of the tyrosine residue may correspond to any one chemical structure selected from the group consisting of the following.

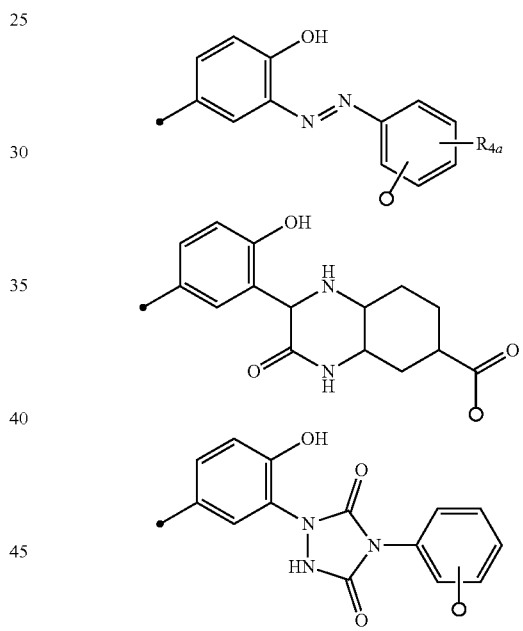

wherein $R_{4a}$ is a hydrogen atom or the substituent described above, ● indicates a bond to T, and ○ indicates a bond to B.

$R_{4a}$ is a hydrogen atom or the substituent described above. Definitions, examples, and preferred examples of the substituent are as described above.

The reactive group specific to a side chain of a tryptophan residue is a group capable of specifically reacting with a ring-constituting atom at the 3-position of an indol group present in the side chain of the tryptophan residue, and examples thereof include a 9-azabicyclo [3.3.1]nonan-3-one-N-oxyl residue.

More specifically, the reactive group specific to a side chain of a tryptophan residue may correspond to any one chemical structure selected from the group consisting of the following:

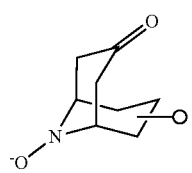

wherein ○ indicates a bond to B.

A coupling portion formed by a reaction between the above chemical structure, which is a reactive group specific to a side chain of a tryptophan residue, and a ring-constituting atom at the 3-position of an indol group present in the side chain of the tryptophan residue may correspond to any one chemical structure selected from the group consisting of the following.

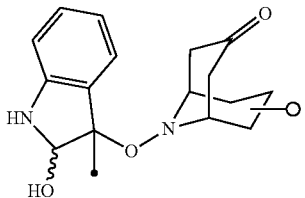

wherein ● indicates a bond to T, and ○ indicates a bond to B.

The reactive group may be particularly preferably a reactive group specific to a side chain of lysine.

1-6. Partial Structure "L-B"

1-6-1. Length of Main Chain in Partial Structure "L-B" Coupling A with R

In Formula (I), the length of the main chain (linear portion in L-B) coupling A (affinity substance) with R (reactive group) can be appropriately designed depending on various factors such as the types of antibody and affinity substance, and a relationship between an affinity substance target site in the antibody and the positions and number of specific amino acid residues in the target region (e.g., specific position) described above, with which R should react and to which R should bind. In the compound represented by Formula (I), the affinity substance is associated with an antibody, and then the reactive group covalently binding to the affinity substance via L-B reacts with a group in a side chain of a specific amino acid residue (e.g., an amino group in a side chain of a lysine residue) present near the target site. Consequently, the compound represented by Formula (I) can covalently bind to the antibody. At this time, when a specific amino acid residue with which R should react and to which R should bind is not present at any other position in a region near the specific amino acid residue, in a region near the target site, and in a region between the specific amino acid residue and the target site, the reactive group can regioselectively bind to the specific amino acid residue without strictly controlling the length of the main chain. Of course, even when the specific amino acid residue is present at any other position in such a region, the reactive group can regioselectively bind to the specific amino acid residue by controlling the length of the main chain.

The length of the main chain coupling A with R can vary depending on factors such as the types of antibody and affinity substance to the antibody, and a relationship regarding the positions and number of specific amino acid residues in the target site in the antibody, but may be about 5 Å or more, preferably about 7.5 Å or more, and more preferably about 10.5 Å or more. The length of such a main chain may also be, for example, about 30 Å or less, preferably about 23 Å or less, and more preferably about 16.5 Å or less. More specifically, the length of such a main chain may be, for example, about 5.0 to 30 Å, preferably about 7.5 to 23 Å, and more preferably about 10.5 to 16.5 Å.

By the way, it is common technical knowledge in the technical field concerned that a relationship regarding a length (distance) between atoms is as illustrated in the table below. Therefore, a person skilled in the art can appropriately design a main chain having a number of atoms corresponding to the above-described length (A) of the main chain with reference to the length between atoms in the table below.

TABLE 1

Relationship of length (distance) between carbon atoms present at both end in straight-chain alkylenes

| straight-chain alkylenes | Length (Angstrom) |
|---|---|
| $CH_2$—$CH_2$ (C2) | about 1.5 |
| $CH_2$—$CH_2$—$CH_2$ (C3) | about 3.0 |
| C4 | about 4.5 |
| C5 | about 6.0 |
| C6 | about 7.5 |
| C7 | about 9.0 |
| C8 | about 10.5 |
| C9 | about 12.0 |
| C10 | about 13.5 |
| straight-chain alkenylene | |
| CH=CH | about 1.5 |

More specifically, the length of the main chain coupling A with R can also be defined as the number of atoms constituting the main chain (excluding hydrogen atoms and substituents). The number of atoms constituting the main chain may be, for example, 4 (about 5.0 Å) or more, preferably 6 (about 7.5 Å), and more preferably 8 (about 10.5 Å) or more. The number of atoms of the main chain may also be, for example, 20 (about 30 Å) or less, preferably 16 (about 23 Å) or less, and more preferably 12 (about 16.5 Å) or less. More specifically, the number of atoms of the main chain may be, for example, 4 to 20, preferably 6 to 16, and more preferably 8 to 12.

When the main chain has a structure comprising no cyclic structure, the number of atoms of the main chain can be determined by counting the number of atoms in a chain structure.

On the other hand, when the main chain has a structure comprising a cyclic structure, the number of atoms of the main chain does not necessarily correspond to the above-described length, and the length that can be defined by the number of atoms of the main chain tends to be shorter than the above-described length. Even in such a case, the number of atoms of the main chain can be conveniently counted from a viewpoint of defining the length of the main chain. Specifically, the number of atoms of the main chain in such a case can be determined by counting the number of atoms of the shortest route connecting two bonds in the cyclic structure in addition to the number of atoms in a chain structure comprising no divalent cyclic structure in the main chain (e.g., refer to the (a) to (d) thick routes below).

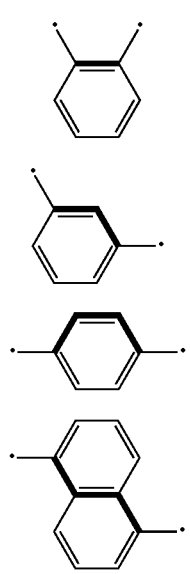

• is a bond.

In the case of (a), the shortest route is the thick route, and thus the number of atoms in the divalent cyclic structure counted as the number of atoms of the main chain is two.

In the case of (b), the shortest route is the thick route, and thus the number of atoms in the divalent cyclic structure counted as the number of atoms of the main chain is three.

In the case of (c), any route is the shortest route (the same distance), and thus the number of atoms in the divalent cyclic structure counted as the number of atoms of the main chain is four.

In the case of (d), the route of the condensed site is the shortest route, and thus the number of atoms in the divalent cyclic structure counted as the number of atoms of the main chain is four.

The portion coupling A with R (excluding a side chain) represented by L-B may preferably have a chain structure comprising no divalent cyclic structure. In this case, L and B can be appropriately designed such that the chain portion coupling A with R represented by L-B comprises no divalent cyclic group.

1-6-2. Specific Structure of Partial Structure "L-B"

In the above Formula (I), L and B have structures that can be related to each other. Therefore, in the above Formula (I), L and B can be defined as a partial structure represented by "L-B".

In an embodiment, the cleavable linker may be (i) a cleavable linker that is a divalent group comprising a cleavable portion capable of forming a bioorthogonal functional group on a reactive group side by cleavage, or (ii) a cleavable linker that is a divalent group comprising a cleavable portion not capable of forming a bioorthogonal functional group on a reactive group side by cleavage.

In a specific embodiment, when L is the cleavable linker of (i) above, B is (a) a divalent group comprising a bioorthogonal functional group or (b) a divalent group comprising no bioorthogonal functional group.

When L is the cleavable linker of (i) above, B is preferably (a) a divalent group comprising a bioorthogonal functional group. In this case, the type of the bioorthogonal functional group formed in (i) may be the same as or different from the type of the bioorthogonal functional group in (a). The type of the bioorthogonal functional group formed in (i) may be the same as the type of the bioorthogonal functional group in (a) from viewpoints of adopting a simpler structure and/or improving reactivity to a single functional substance, and the like. On the other hand, the type of the bioorthogonal functional group formed in (i) may be different from the type of the bioorthogonal functional group in (a) from viewpoints of ensuring differentiated reactivity to two or more types of functional substances, not using some bioorthogonal functional groups in the reaction, and the like.

Alternatively, when L is the cleavable linker of (i) above, B may be (b) a divalent group comprising no bioorthogonal functional group. In this case, the compound or salt thereof represented by Formula (I) has a simpler structure and is therefore easily synthesized.

In another specific embodiment, where L is the cleavable linker of (ii) above, B is (a) a divalent group comprising a bioorthogonal functional group.

In a specific embodiment, the partial structure represented by L-B preferably comprises no peptide portion. In this case, the antibody having a functional substance or functional substances according to the present invention obtained by using the compound of the present invention (e.g., an antibody drug conjugate) has an advantage that a peptide portion capable of having immunogenicity cannot be comprised as a linker.

In a specific embodiment, the partial structure represented by "L-B" may have a symmetric structure [e.g., cis type (that is, Z) or trans type (that is, E)] about an atom present at the central position of the main chain (linear portion in L-B) coupling A with R (e.g., when the number of atoms constituting the main chain is odd) or a binding site present at the central position of the main chain (e.g., when the number of atoms constituting the main chain is even). For example, the binding site present at the central position can be designed as the above-described cleavable portion in the cleavable linker. When the partial structure represented by "L-B" has a symmetrical structure, the partial structure represented by "L-B" can be easily synthesized. For example, by reacting the same divalent groups each having a functional group capable of reacting to form a cleavable portion at one terminal (e.g., chain-like divalent groups each having an SH group at one terminal) with each other, a symmetric structure comprising a cleavable portion at the central position of the main chain (chain-like divalent group-S—S-chain-like divalent group) can be achieved.

Therefore, the partial structure represented by "L-B" may be a partial structure represented by "B2-L'-B1" (that is, L is a divalent group represented by B2-L' and B is B1.). In this case, the compound represented by the above Formula (I) can be defined as a compound represented by the following Formula (I').

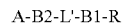 A-B2-L'-B1-R   (I')

wherein

A and R are the same as those in the above Formula (I),

L' is a cleavable linker that is a divalent group comprising a cleavable portion, B1 and B2 are the same as or different from each other and are each (a) a divalent group comprising a bioorthogonal functional group or (b) a divalent group comprising no bioorthogonal functional group, and B1 and B2 may have a symmetrical structure about L'.

B1 and B2 are the same as or different from each other, and definitions, examples, and preferred examples of B1 and B2 are similar to those of B.

In a specific embodiment, L' may be represented by any one of the following formulae (L1) to (L3):

(L1')

(L2')

(L3')

wherein
La' and Lb' are each a divalent group, and
C' is a cleavable portion.

Definitions, examples, and preferred examples of the divalent groups represented by La' and Lb' are similar to those of the divalent groups represented by La' and Lb', respectively.

A definition, examples, and preferred examples of the cleavable portion represented by C' are similar to those of the cleavable portion represented by C.

In another specific embodiment, the structural unit represented by L-B may be represented by the following Formula (LB').

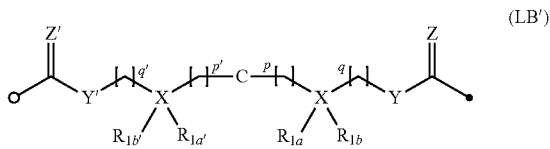

(LB')

wherein
definitions, examples, and preferred examples of C, p, p', q, q', X, X', $R_{1a}$, $R_{1a'}$, $R_{1b}$, $R_{1b'}$, Y, Y', Z, and Z' are the same as those described above, and
○ (white circle) indicates a bond to A, and ■ (black circle) indicates a bond to R.

Therefore, the above Formula (I) can be defined as the following Formula (I''),

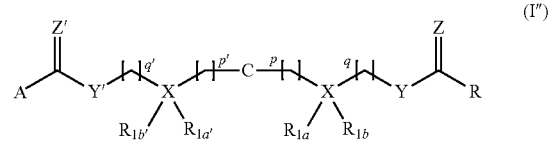

(I'')

wherein
definitions, examples, and preferred examples of A, R, C, p, p', q, q', X, X', $R_{1a}$, $R_{1a'}$, $R_{1b}$, $R_{1b'}$, Y, Y', Z, and Z' are the same as those described above.

In the above Formulae (LB') and (I''), the length from C (carbon atom) at C=Z to C (carbon atom; at C=Z' is similar to the length of the main chain coupling A with R. In these Formulae, the length from C at C=Z to C at C=Z' can also be defined as the number of atoms constituting the coupling chain of the partial structure coupling from C at C=Z to C at C=Z' (excluding hydrogen atoms and substituents) with each other. The number of atoms described above is similar to the number of atoms constituting the main chain coupling A with R. The coupling chain of the partial structure coupling from C at C=Z to C at C=Z' (excluding hydrogen atoms and substituents) with each other may comprise a cyclic structure or is not necessarily comprise a cyclic structure, but preferably comprises no cyclic structure. The coupling chain (excluding hydrogen atoms and substituents) may preferably comprise no peptide portion.

1-7. Production Method

The compound having an affinity substance to an antibody, a cleavable portion, and a reactive group, or a salt thereof can be prepared appropriately. The compound having an affinity substance to an antibody, a cleavable portion, and a reactive group is represented by Formula (I), preferably Formula (I'), more preferably Formula (I'').

For the affinity substance, one having any functional group can be selected appropriately. Consequently, by using a reactive group capable of reacting with the functional group, the affinity substance is reacted with a structural unit represented by L-B—R or a structural unit represented by R-L-B—R (the two reactive groups are the same as or different from each other), whereby a structural unit represented by A-L-B—R can be prepared. Such a reaction can be performed in an appropriate reaction system such as an organic solvent system or an aqueous solution system at an appropriate temperature (e.g., about 15° C. to 200° C.), for example. The reaction system may comprise an appropriate catalyst. The reaction time is e.g., 1 minute to 20 hours, preferably 10 minutes to 15 hours, more preferably 20 minutes to 10 hours, and even more preferably 30 minutes to 8 hours.

In the reaction system, a molar ratio (Y/X) of a structural unit represented by L-B—R or a structural unit represented by R-L-B—R (Y) to an affinity substance (X) is not limited to a particular ratio because it varies depending on the types of the structural unit and the affinity substance, the number of sites in the affinity substance to be modified with the structural unit, and the like. However, the molar ratio (Y/X) is e.g., 0.1 to 50, preferably 0.5 to 40, more preferably 1 to 35, even more preferably 2 to 25, and particularly preferably 3 to 15.

Determination of formation of the antibody having an affinity substance to an antibody and a cleavable portion, or a salt thereof, which depends on its specific raw materials and the molecular weight of a product, can be performed by electrophoresis, chromatography (e.g., gel permutation chromatography, ion-exchange chromatography, reversed phase column chromatography, and HPLC), or mass spectrometry, for example, and preferably mass spectrometry. The antibody having an affinity substance to an antibody and a cleavable portion, or a salt thereof can be purified appropriately by any method such as chromatography (e.g., the pieces of chromatography described above and affinity chromatography).

1-8. Others

In the inventions described below [e.g., inventions represented by Formulae (II) to (v), formulae having subordinate concepts thereof, and partial structural formulae (e.g., inventions represented by (L1) to (L3), (La'), (Lb'), and (B-1) to (B-4))], any symbols (e.g., A, L, B, and R), terms expressed by the symbols, and the details thereof (e.g., definitions, examples, and preferred examples) are common to those of the invention of the compound or salt thereof represented by the above Formula (I). In addition, a specific portion (e.g., a cleavable portion or a portion capable of forming a bioorthogonal functional group on a reactive group side by cleavage) that can define the invention described below, a specific group (e.g., a bioorthogonal functional group, a divalent group, an alkyl group, a substituent, or an electron-withdrawing group), a specific numerical value, and any technical element (e.g., definitions, examples, and preferred examples) of a salt or the like can also be common to those described above. Consequently, these matters can be quoted appropriately in the inventions described below without any special reference. Similarly, the technical elements of a specific invention described in the inventions described below can be quoted appropriately as the technical elements of the present invention and other inventions.

2. Antibody Having Affinity Substance to Antibody and Cleavable Portion, or Salt Thereof 2-1. Outline The present invention provides an antibody having an affinity substance to an antibody and a cleavable portion, or a salt thereof, represented by Formula (II).

A-L-B—R'-T    (II)

wherein
A is an affinity substance to an antibody,
L is a cleavable linker that is a divalent group comprising a cleavable portion,
B is (a) a divalent group comprising a bioorthogonal functional group or (b) a divalent group comprising no bioorthogonal functional group,
R' is a portion formed by a reaction between an antibody and a reactive group, and
T is an antibody.

2-2. Portion Formed by Reaction Between Antibody and Reactive Group (R')

Definitions, examples, and preferred examples of an antibody and a reactive group in a portion formed by a reaction between the antibody and the reactive group are as described above. The portion formed by a reaction between an antibody and a reactive group is common technical knowledge in the technical field concerned and can be appropriately determined depending on the types of the antibody and the reactive group.

The portion formed by a reaction between an antibody and a reactive group is preferably a portion formed by a reaction between a side chain of any one type of amino acid out of 14 types of amino acids (asparagine, glutamine, methionine, proline, serine, threonine, tryptophan, tyrosine, aspartic acid, glutamic acid, arginine, histidine, and lysin) that can be comprised in the antibody, and a reactive group to the side chain.

The portion formed by a reaction between an antibody and a reactive group may be more preferably a portion formed by a reaction between a side chain of any one type of amino acid out of lysine, tyrosine, tryptophan, and cysteine, and a reactive group specific to the side chain.

The portion formed by a reaction between an antibody and a reactive group may be even more preferably a portion formed by a reaction between a side chain of any one type of amino acid out of lysine, tyrosine, and tryptophan, and a reactive group specific to the side chain. Examples of the portion formed by a reaction between a side chain of any one type of amino acid out of lysine, tyrosine, and tryptophan, and a reactive group specific to the side chain include the coupling portion and/or chemical structure described in the above "1-5. Reactive group (R)".

The portion formed by a reaction between an antibody and a reactive group may be still even more preferably a portion formed by a reaction between a side chain of lysine or tyrosine, and a reactive group specific to the side chain (particularly when the antibody is human IgG such as human IgG1). Examples of the portion formed by a reaction between a side chain of lysine or tyrosine, and a reactive group specific to the side chain include the coupling portion and/or chemical structure described in the above "1-5. Reactive group (R)".

The portion formed by a reaction between an antibody and a reactive group may be particularly preferably a portion formed by a reaction between a side chain of lysine and a reactive group specific to the side chain.

2-3. Partial Structure "L-B"

The details of the partial structure "L-B" are as described in the above "1-6. Partial structure "L-B"".

In a specific embodiment, the partial structure represented by "L-B" may be a partial structure represented by "B2-L'-B1" (that is, IL is a divalent group represented by B2-L' and B is B1.). In this case, the antibody having an affinity substance to an antibody and a cleavable portion, or a salt thereof, represented by Formula (II) can be represented by the following Formula (II').

A-B2-L'-B1-R'-T    (II')

wherein
A, R', and T are the same as those in the above Formula (II),
L' is a cleavable linker that is a divalent group comprising a cleavable portion,
B1 and B2 are the same as or different from each other and are each (a) a divalent group comprising a bioorthogonal functional group or (b) a divalent group comprising no bioorthogonal functional group, and
B1 and B2 may have a symmetrical structure about L'.

In the above formula (II'), L' may be represented by any one of the above Formulae (L1') to (L3').

In another specific embodiment, the structural unit; represented by L-B may be represented by the following Formula (LB').

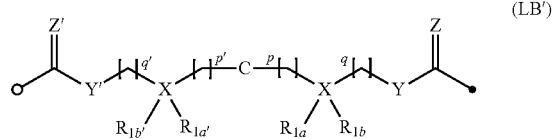

(LB')

wherein
definitions, examples, and preferred examples of C, p, p', q, q', X, X', $R_{1a}$, $R_{1a'}$, $R_{1b}$, $R_{1b'}$, Y, Y', Z, and Z' are the same as those described above, and
○ (white circle) indicates a bond to A, and ● (black circle) indicates a bond to R'.

Therefore, the above Formula (II) can be defined as the following Formula (II").

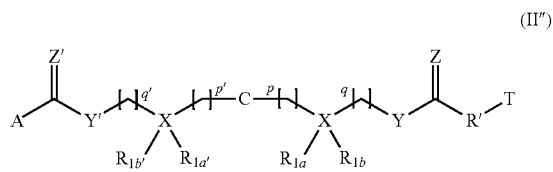

(II")

wherein
definitions, examples, and preferred examples of A, R', T, C, p, p', q, q', X, X', $R_{1a}$, $R_{1a'}$, $R_{1b}$, $R_{1b'}$, Y, Y', Z, and Z' are the same as those described above.

In the above Formulae (LB') and (II"), the length from C (carbon atom) at C=Z to C (carbon atom) at C=Z' is similar to the above-described length of the main chain coupling A with P. In these Formulae, the length from C at C=Z to C at C=Z' can also be defined as the number of atoms constituting the coupling chain of the partial structure coupling from C at C=Z to C at C=Z' (excluding hydrogen atoms and substituents) with each other. The number of atoms described above is similar to the number of atoms constituting the main chain coupling A with R. The coupling chain of the partial structure coupling from C at C=Z to C at C=Z' (excluding hydrogen atoms and substituents) with each other may comprise a cyclic structure or is not necessarily comprise a cyclic structure, but preferably comprises no cyclic structure. The coupling chain (excluding hydrogen atoms and substituents) may preferably comprise no peptide portion.

2-4. Binding Site of Partial Structure Other than Antibody, Possessed by Antibody (Regioselectivity)

A partial structure other than an antibody (e.g., A-L-B—R') can be regioselectively bound to the above-described target region in the antibody (T).

In the present specification, "regioselective" or "regioselectivity" refers to a state in which even though a specific amino acid residue is not present locally in a specific region in the antibody, a certain structural unit capable of binding to the specific amino acid residue in the antibody is present locally in a specific region in the antibody. Consequently, expressions related to regioselectivity such as "regioselectively having," "regioselective binding," and "binding with regioselectivity" mean that the possession rate or the binding rate of a certain structural unit in the target region comprising one or more specific amino acid residues is higher at a significant level than the possession rate or the binding rate of the structural unit in the non-target region comprising a plurality of amino acid residues of the same type as the specific amino acid residues in the target region. Such regioselective binding or possession can be achieved by the present invention, which enables the certain structural unit to preferentially react with the specific amino acid residues in the target region in the antibody, not by randomly reacting the certain structural unit with the specific amino acid residues in the antibody.

Specifically, when T comprises one or more specific amino acid residues in a target region consisting of 1 to 50 consecutive amino acid residues and comprises five or more of the specific amino acid residues in a non-target region other than the target region, a partial structure other than the antibody can be bound to the one or more specific amino acid residues comprised in the target region with 30% or more regioselectivity. Definitions, examples, and preferred examples of the target regions and regioselectivity are as described above.

2-5. Number of Partial Structures Other than Antibody, Possessed by Antibody

The number of partial structures (e.g., A-L-B—R') other than the antibody (T), possessed by the antibody can vary. For example, when T is a multimeric protein comprising a plurality of monomeric proteins, T can have a partial structure other than T in a plurality of corresponding target regions in the plurality of monomeric proteins. As a result, T can have a plurality of partial structures other than T. Therefore, the structure represented by Formula (II), (II'), or (II") indicates that T may have one or more partial structures other than T. The number of partial structures other than T, possessed by T can be adjusted by appropriately setting conditions such as the type of antibody and a reaction ratio between the antibody and a structural unit introduced thereinto. Such a number varies depending on the type of antibody, but may be, for example, 1 to 8, preferably 1 to 4, and more preferably 1 or 2.

In a specific embodiment, the antibody may have a plurality of partial structures other than the antibody when the antibody is a multimeric protein comprising a plurality of monomeric proteins. According to the present invention, a plurality of partial structures other than the antibody can be introduced into the same target region of a plurality of monomeric proteins.

In a preferred embodiment, the antibody may comprise a plurality of heavy chains. Definitions, examples, and preferred examples of the antibody are as described above. The number of heavy chains depends on the type of antibody. For example, IgG, IgE, and IgD can each have two heavy chains. IgA can have two or four heavy chains. IgM can have eight heavy chains. The number of partial structures other than the antibody, possessed by the antibody (antibody) can be considered as synonymous with DAR. In the present invention, the number of partial structures other than the antibody, possessed by the antibody may be 1 or 2 (preferably 2) for IgG, IgE, and IgD, 1 to 4 (preferably 4) for IgA, and 1 to 8 (preferably 8) for IgM.

2-6. Production Method

The present invention provides a method for producing an antibody having an affinity substance to an antibody and a cleavable portion, or a salt thereof, the method comprising the following:

(A1) reacting a compound having an affinity substance to an antibody, a cleavable portion, and a reactive group, or a salt thereof with an antibody to form an antibody having an affinity substance to an antibody and a cleavable portion, or a salt thereof.

The compound having an affinity substance to an antibody, a cleavable portion, and a reactive group is represented by Formula (I), preferably Formula (I'), more preferably Formula (I"). The compound having an affinity substance to an antibody and a cleavable portion is represented by Formula (II), preferably Formula (II'), more preferably Formula (II").

The compound having an affinity substance to an antibody, a cleavable portion, and a reactive group, or a salt thereof has the reactive group, and therefore can react with an antibody. Such a reaction can be appropriately performed under a condition incapable of causing denaturation or decomposition (e.g., cleavage of an amide bond) of proteins (a mild condition). Such a reaction can be performed in an appropriate reaction system such as a buffer at room temperature (e.g., about 15° C. to 30° C.), for example. The pH of the buffer is e.g., 5 to 9, preferably 5.5 to 8.5, and more preferably 6.0 to 8.0. The buffer may comprise an appropriate catalyst. The reaction time is e.g., 1 minute to 20 hours, preferably 10 minutes to 15 hours, more preferably 20 minutes to 10 hours, and even more preferably 30 minutes to 8 hours. For the details of such a reaction, refer to G. J. L. Bernardes et al., Chem. Rev., 115,2174 (2015); G. J. L. Bernardes et al., Chem. Asian. J., 4,630 (2009); B. G. Davies et al., Nat. Commun., 5,4740 (2014); A. Wagner et al., Bioconjugate. Chem., 25,825 (2014), all of which are incorporated herein by reference in their entireties, for example.

In the reaction system, a molar ratio (Y/X) of a compound having an affinity substance to an antibody, a cleavable portion, and a reactive group, or a salt thereof (Y) to an antibody (X) is not limited to a particular ratio because it varies depending on the types of the compound having an affinity substance to an antibody, a cleavable portion, and a reactive group, and the antibody, the number of sites in the antibody to be modified by the compound having an affinity substance to an antibody, a cleavable portion, and a reactive group (e.g., DAR), and the like. However, the molar ratio (Y/X) is e.g., 0.1 to 100, preferably 0.5 to 80, more preferably 1 to 70, even more preferably 2 to 50, and particularly preferably 3 to 30.

Determination of formation of the antibody having an affinity substance to an antibody and a cleavable portion, or a salt thereof, which depends on its specific raw materials and the molecular weight of a product, can be performed by electrophoresis, chromatography (e.g., gel permutation chromatography, ion-exchange chromatography, reversed phase column chromatography, and HPLC), or mass spectrometry, for example, and preferably mass spectrometry. Determination of regioselectivity can be performed by peptide mapping, for example. Peptide mapping can be performed by protease (e.g., trypsin or chymotrypsin) treatment and mass spectrometry, for example. For the protease, an endoprotease is preferred. Examples of such an endoprotease include trypsin, chymotrypsin, Glu-C, Lys-N, Lys-C, and Asp-N. Determination of the number of partial structures other than the antibody, possessed by the antibody can be performed by electrophoresis, chromatography, or mass spectrometry, for example, and preferably mass spectrometry. The antibody having an affinity substance to an antibody and a cleavable portion, or a salt thereof can be purified appropriately by any method such as chromatography (e.g., the pieces of chromatography described above and affinity chromatography).

3. Conjugate Having Affinity Substance to Antibody, Cleavable Portion, Functional Substance, and Antibody, or Salt Thereof 3-1. Outline The present invention provides a conjugate having an affinity substance to an antibody, a cleavable portion, a functional substance, and an antibody, or a salt thereof, represented by Formula (III).

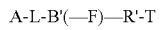  (III)

wherein

A is an affinity substance to an antibody,

L is a cleavable linker that is a divalent group comprising a cleavable portion, B' is a trivalent group comprising a portion formed by a reaction between a functional substance and a bioorthogonal functional group, F is a functional substance, R' is a portion formed by a reaction between an antibody and a reactive group, and T is an antibody.

In Formula (III) or another formula, R' covalently binds to B' instead of F.

3-2. Functional Substance (F)

The functional substance is not limited to a particular substance as long as it is a substance imparting any function to the antibody; examples thereof include drugs, labelling substances, and stabilizers; preferred are drugs and labelling substances. The functional substance may be a single functional substance or a substance in which two or more functional substances are coupled with each other.

The drug may be a drug to any disease. Examples of such a disease include cancer (e.g., lung cancer, stomach cancer, colon cancer, pancreatic cancer, renal cancer, liver cancer, thyroid cancer, prostatic cancer, bladder cancer, ovarian cancer, uterine cancer, bone cancer, skin cancer, a brain tumor, and melanoma), autoimmune diseases and inflammatory diseases (e.g., allergic diseases, articular rheumatism, and systemic lupus erythematosus), brain or nerve diseases (e.g., cerebral infarction, Alzheimer's disease, Parkinson disease, and amyotrophic lateral sclerosis), infectious diseases (e.g., microbial infectious diseases and viral infectious diseases), hereditary rare diseases (e.g., hereditary spherocytosis and nondystrophic myotonia), eye diseases (e.g., age-related macular degeneration, diabetic retinopathy, and retinitis pigmentosa), diseases in the bone and orthopedic field (e.g., osteoarthritis), blood diseases (e.g., leukosis and purpura), and other diseases (e.g., diabetes, metabolic diseases such as hyperlipidemia, liver diseases, renal diseases, lung diseases, circulatory system diseases, and digestive system diseases). When the antibody is an antibody to a target protein of a certain disease, the drug may be a drug related to the certain disease (e.g., a drug that treats the certain disease or a drug that relieves side effects caused by use of the antibody to the target protein of the certain disease).

More specifically, the drug is an anti-cancer agent. Examples of the anti-cancer agent include chemotherapeutic agents, toxins, and radioisotopes or substances comprising them. Examples of chemotherapeutic agents include DNA injuring agents, antimetabolites, enzyme inhibitors, DNA intercalating agents, DNA cleaving agents, topoisomerase inhibitors, DNA binding inhibitors, tubulin binding inhibitors, cytotoxic nucleosides, and platinum compounds. Examples of toxins include bacteriotoxins (e.g., diphtheria toxin) and phytotoxins (e.g., ricin). Examples of radioisotopes include radioisotopes of a hydrogen atom (e.g., $^{3}$H), radioisotopes of a carbon atom (e.g., $^{14}$C), radioisotopes of a phosphorous atom (e.g., $^{32}$P), radioisotopes of a sulfur atom (e.g., $^{35}$S), radioisotopes of yttrium (e.g., $^{90}$Y), radioisotopes of technetium (e.g., $^{99m}$Tc), radioisotopes of indium (e.g., $^{111}$In), radioisotopes of an iodide atom (e.g., $^{123}$I, $^{125}$I, $^{129}$I, and $^{131}$I), radioisotopes of samarium (e.g., $^{153}$Sm), radioisotopes of rhenium (e.g., $^{186}$Re), radioisotopes of astatine (e.g., $^{211}$At), and radioisotopes of bismuth (e.g., $^{212}$Bi). More specific examples of the drug include auristatin (MMAE, MMAF), maytansine (DM1, DM4), PBD (pyrrolobenzodiazepine), IGN, camptothecin analogs, calicheamicin, duocarmycin, eribulin, anthracycline, dmDNA31, and tubricin.

Examples of labelling substances include enzymes (e.g., peroxidase, alkaline phosphatase, luciferase, and Q3-galactosidase), affinity substances (e.g., streptavidin, biotin, digoxigenin, and aptamer), fluorescent substances (e.g., fluorescein, fluorescein isothiocyanate, rhodamine, green-fluorescent protein, and red-fluorescent protein), luminescent substances (e.g., luciferin, aequorin, acridinium ester, tris(2,2'-bipyridyl) Duthenium, and luminol), and radioisotopes (e.g., those described above) or substances comprising them.

The functional substance is a large compound, a middle compound, or a small compound and is preferably a small compound. The small compound refers to compounds with a molecular weight of 1,500 or lower. The small compound is a natural compound or a synthesized compound. The molecular weight of the small compound may be 1,200 or lower, 1,000 or lower, 900 or lower, 800 or lower, 700 or lower, 600 or lower, 500 or lower, 400 or lower, or 300 or lower. The molecular weight of the small compound may be 30 or higher, 40 or higher, or 50 or higher. The small compound may be any of the drugs or labelling substances described above. Examples of the small compound include amino acids, oligopeptides, vitamins, nucleosides, nucleotides, oligonucleotides, monosaccharides, oligosaccharides, lipids, fatty acids, and salts thereof.

3-3. Trivalent Group Comprising Portion Formed by Reaction Between Functional Substance and Bioorthogonal Functional Group (B')

B' is similar to (a) the divalent group comprising a bioorthogonal functional group in B described above except that the bioorthogonal functional group in (a) reacts with a functional substance. Therefore, definitions, examples, and preferred examples of the trivalent group and the orthogonal functional group in B' are similar to those in B except that the bioorthogonal functional group in (a) reacts with a functional substance.

The functional substance has various functional groups corresponding to its structure. When the functional substance has a functional group easily reacting with the bioorthogonal functional group, the functional group of the functional substance and the bioorthogonal functional group can be reacted with each other appropriately. The function group easily reacting with the bioorthogonal functional group can vary depending on a specific type of the bioorthogonal functional group. A person skilled in the art can select an appropriate functional group as the functional group easily reacting with the bioorthogonal functional group appropriately (e.g., Boutureira et al., Chem. Rev., 2015, 115, 2174-2195, which is incorporated herein by reference in its entirety). Examples of the functional group easily reacting with the bioorthogonal functional group include, but are not limited to, a maleimide residue and a disulfide residue when the bioorthogonal functional group is a thiol residue, an azide residue when the bioorthogonal functional group is an alkyne residue, and a hydrazine residue when the bioorthogonal functional group is an aldehyde residue or a ketone residue. For example, when the bioorthogonal functional group is a thiol residue and the functional group easily reacting with the bioorthogonal functional group is a maleimide residue or a disulfide residue (or vice versa), the trivalent group comprising a portion formed by a reaction between the functional substance and the bioorthogonal functional group may be a trivalent group comprising a thiosuccinimide residue or a trivalent group comprising a disulfide residue; when the bioorthogonal functional group is an alkyne residue and the functional group easily reacting with the bioorthogonal functional group is an azide residue (or vice versa), the trivalent group comprising a portion formed by a reaction between the functional substance and the bioorthogonal functional group may be a trivalent group comprising a triazole residue (which may be condensed with another ring or is not necessarily condensed therewith); and when the bioorthogonal functional group is an aldehyde residue or a ketone residue and the functional group easily reacting with the bioorthogonal functional group is a hydrazine residue (or vice versa), the trivalent group comprising a portion formed by a reaction between the functional substance and the bioorthogonal functional group may be a trivalent group comprising a hydrazone residue (e.g., Boutureira et al., Chem. Rev., 2015, 115, 2174-2195, which is incorporated herein by reference in its entirety). The trivalent group comprising a thiosuccinimide residue, the trivalent group comprising a disulfide residue, the trivalent group comprising a triazole residue (which may be condensed with another ring or is not necessarily condensed therewith), or the trivalent group comprising a hydrazone residue is a preferred example of the trivalent group comprising a portion formed by a reaction between the functional substance and the bioorthogonal functional group.

On the other hand, when the functional substance has no functional group easily reacting with the bioorthogonal functional group, a substance derivatized so as to have a desired functional group can be used as the functional substance. For example, when the functional substance is an antibody, an antibody derivatized so as to have a functional group not naturally possessed by the antibody can be used. In this case, the derivatization of the antibody may be performed by the method of the present invention. In this case, an antibody derivatized so as to have a desired bioorthogonal functional group regioselectively can be used as the functional substance.

Derivatization is common technical knowledge in the field concerned (e.g., WO 2004/010957 A, United States Patent Application Publication No. 2006/0074008, and United States Patent Application Publication No. 2005/0238649, all of which are incorporated herein by reference in their entireties). Derivatization may be performed using the cross-linking agent described above, for example. Alternatively, derivatization may be performed using a specific linker having a desired functional group. Such a linker may be able to separate the functional substance and the antibody from each other through cleavage of the linker under an appropriate condition (e.g., intracellular or extracellular), for example. Examples of such a linker include peptidyl linkers decomposed by specific proteases [e.g., intracellular proteases (e.g., proteases present in lysosome or endosome) and extracellular proteases (e.g., secretory proteases)](e.g., U.S. Pat. No. 6,214,345; Dubowchik et al., Pharm. Therapeutics 83: 67-123 (1999), both which are incorporated herein by reference in their entireties) and linkers capable of being cleaved at local acidic sites present in living bodies (e.g., U.S. Pat. Nos. 5,622,929, 5,122,368, and 5,824,805, all of which are incorporated herein by reference in their entireties). The linker may be self-immolative (e.g., WO 02/083180 A, WO 04/043493 A, and WO 05/112919 A, all of which are incorporated herein by reference in their entireties). In the present invention, the derivatized functional substance can also be referred to simply as the "functional substance."

Definitions, examples, and preferred examples of the functional substance and the bioorthogonal functional group in the trivalent group comprising a portion formed by a reaction between the functional substance and the bioorthogonal functional group are as described above. The portion formed by a reaction between the functional substance and the bioorthogonal functional group is common technical knowledge in the technical field concerned, and can be appropriately determined depending on the types of the functional substance (a derivatized portion when the functional substance is derivatized) and the bioorthogonal functional group.

The trivalent group comprising a portion formed by a reaction between the functional substance and the bioorthogonal functional group (1) may be a trivalent group comprising a thiosuccinimide residue, a triazole residue, or a hydrazone residue referred to in the above-described preferred examples, or (2) which is not limited to a particular group, may be a trivalent group comprising a residue selected from the group consisting of a disulfide residue (this residue has been referred to in the above-described preferred examples), an acetal residue, a ketal residue, an ester residue, a carbamoyl residue, an alkoxyalkyl residue, an imine residue, a tertiary alkyloxy carbamate residue, a silane residue, a hydrazone-containing residue, a phosphoramidate residue, an aconityl residue, a trityl residue, an azo residue, a vicinal diol residue, a selenium residue, an aromatic ring-containing residue having an electron-withdrawing group, a coumarin-containing residue, a sulfone-containing residue, an unsaturated bond-containing chain residue, and a glycosyl residue, for example.

The trivalent group comprising a portion formed by a reaction between the functional substance and the bioorthogonal functional group, which is not limited to a particular group, may be a trivalent group comprising a residue corresponding to any one chemical structure selected from the group consisting of the following:

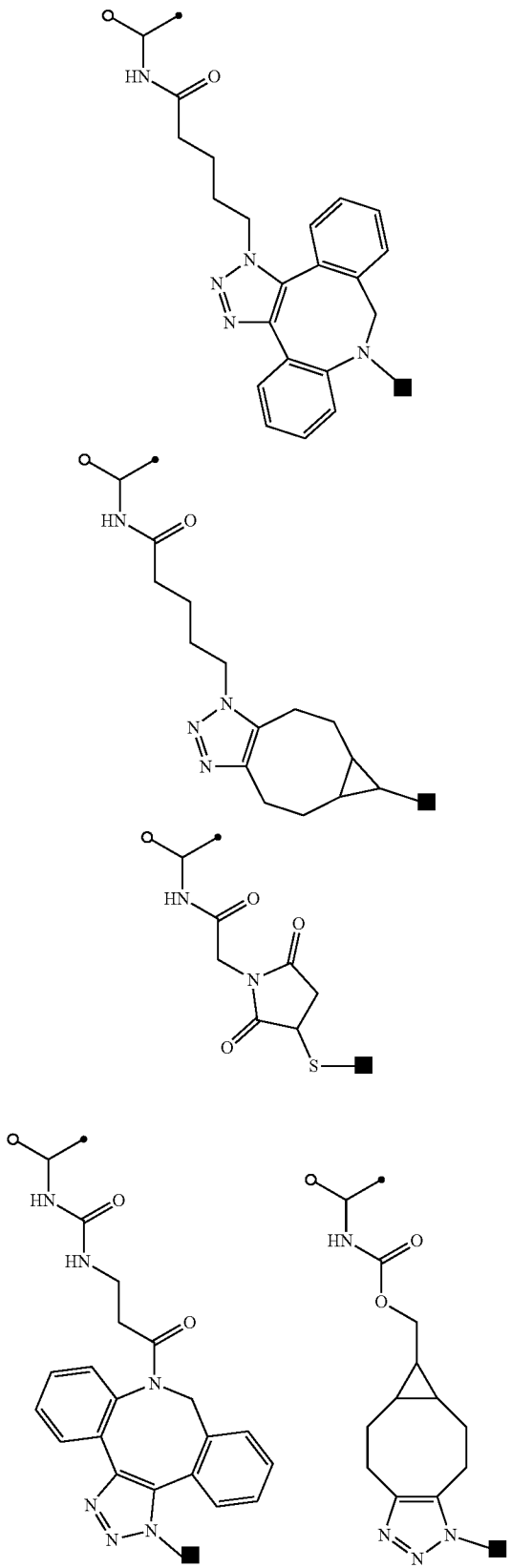

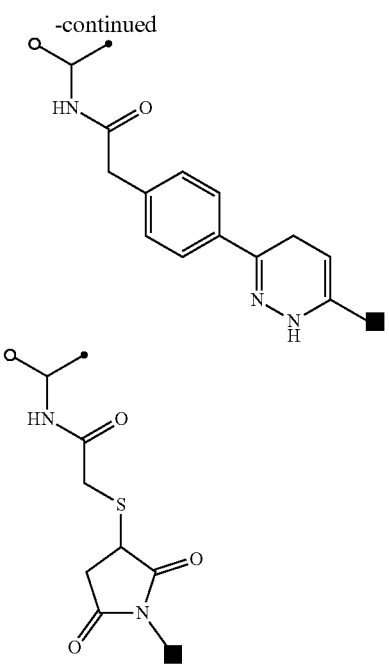

wherein
the black square indicates a bond to a functional substance-side portion,
○ (white circle) indicates a bond to an L-side portion, and
● (black circle) indicates a bond to an R'-side portion,
when the chemical structure is asymmetrical about a cleavable portion, ● may indicate a bond to an L-side portion, and ○ may indicate a bond to an R'-side portion.

3-4. Partial Structure "L-B'(—F)"

The details of the partial structure "L-B'(—F)" are as described in the above "1-6. Partial structure "L-B"" except that B has been changed to B'(—F).

In an embodiment, the cleavable linker may be (i) a cleavable linker that is a divalent group comprising a cleavable portion capable of forming a bioorthogonal functional group on a reactive group side by cleavage, or (ii) a cleavable linker that is a divalent group comprising a cleavable portion not capable of forming a bioorthogonal functional group on a reactive group side by cleavage.

In a specific embodiment, the cleavable linker may be the cleavable linker of (ii) above. This is because B' already binds to the functional substance (F), and therefore it is not necessary to form a bioorthogonal functional group on a reactive group side.

In another specific embodiment, the partial structure represented by L-B'(—F) may be a partial structure represented by B2' (—F2)-L'-B1' (—F1) (that is, L is B2'(—F2)-L', and B' is B1'). In this case, the conjugate having an affinity substance to an antibody, a cleavable portion, a functional substance, and an antibody, or a salt thereof, represented by the above Formula (III) can be represented by the following Formula (III').

A-B2'(—F2)-L'-B1'(—F1)-R'-T        (III')

wherein
A, R', and T are the same as those in the above Formula (III),
L' is a cleavable linker that is a divalent group comprising a cleavable portion, B1' and B2' are the same as or different from each other and are each a trivalent group comprising a portion formed by a reaction between a functional substance and a bioorthogonal functional group, F1 and F2 are the same as or different from each other and are each a functional substance, and B1'(—F1) and B2'(—F2) may have a symmetrical structure about L'.

B1' and B2' are the same as or different from each other, and definitions, examples, and preferred examples of B1' and B2' are similar to those of B'.

In the above formula (III'), L' may be represented by any one of the above Formulae (L1') to (L3').

In another specific embodiment, the structural unit represented by L-B'(—F) may be represented by the following Formula (LB'(F)').

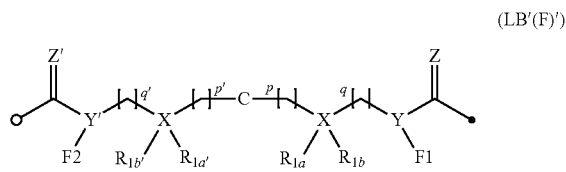

(LB'(F)')

wherein definitions, examples, and preferred examples of C, F1, F2, p, p', q, q', X, X', $R_{1a}$, $R_{1a'}$, $R_{1b}$, $R_{1b'}$, Z, and Z' are the same as those described above, Y and Y' are the same as or different from each other and are each a residue obtained by removing one hydrogen atom from Y in the above Formula (B-1), and ○ (white circle) indicates a bond to A, and ● (black circle) indicates a bond to R'.

More specifically, in Y and Y', the residue obtained by removing one hydrogen atom from Y in the above formula (B-1) is —N(—)-, —CH(—)-, or a group obtained by removing one hydrogen atom from the above Formula (B-2). Y may be —N(—)- or —CH(—)- from a viewpoint of simplification of the structure or the like. Alternatively, Y may be —CH(—)- or a group obtained by removing one hydrogen atom from the above Formula (B-2) from a viewpoint of designing a structure based on a carbon atom or the like.

The group obtained by removing one hydrogen atom from the above Formula (B-2) is a group obtained by removing one hydrogen atom from the following Formula (B-2'):

(B-2')

wherein

V and V' are the same as or different from each other and are each —NH—, —O—, —CH$_2$—, or a single bond, V1 is (a) a divalent group comprising a bioorthogonal functional group or (b) a divalent group comprising no bioorthogonal functional group, s is any integer of 0 to 10, and ○ and ● in Formula (B-2') have the same orientation as ○ and ═ in Formula (B-1), respectively. A definition, examples, and preferred examples of s in Formula (B-2') are similar to those in Formula (B-2). Therefore, in formula (B-2'), one of V and V' may be —N(—)- or —CH(—)-. Alternatively, in Formula (B-2'), V1 may be a trivalent group obtained by removing one hydrogen atom from the divalent group of (a) or (b) above. Alternatively, in Formula (B-2'), one of the s —CH$_2$-s may be —CH(—)-.

In this case, the above Formula (III) can be defined as the following Formula (II").

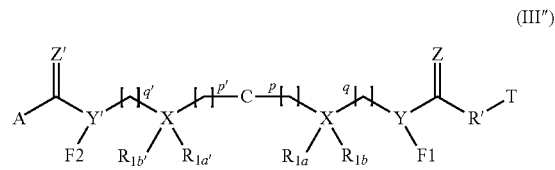

(III")

wherein definitions, examples, and preferred examples of A, R, C, F1, F2, p, p', q, q', X, X', $R_{1a}$, $R_{1a'}$, $R_{1b}$, $R_{1b'}$, Y, Y', Z, and Z' are the same as those described above.

In the above Formulae (LB'(F)') and (III"), the length from C (carbon atom) at C═Z to C (carbon atom) at C═Z' is similar to the above-described length of the main chain coupling A with R. In these Formulae, the length from C at C═Z to C at C═Z' can also be defined as the number of atoms constituting the coupling chain of the partial structure coupling from C at C═Z to C at C═Z' (excluding hydrogen atoms and substituents) with each other. The number of atoms described above is similar to the number of atoms constituting the main chain coupling A with R. The coupling chain of the partial structure coupling from C at C═Z to C at C═Z' (excluding hydrogen atoms and substituents) with each other may comprise a cyclic structure or is not necessarily comprise a cyclic structure, but preferably comprises no cyclic structure. The coupling chain (excluding hydrogen atoms and substituents) may preferably comprise no peptide portion.

3-5. Binding Site of Partial Structure Other than Antibody, Possessed by Antibody (Regioselectivity)

A partial structure other than an antibody (e.g., A-L-B'(—F)—R') can be regioselectively bound to the above-described target region in the antibody (T). Specifically, when T comprises one or more specific amino acid residues in a target region consisting of 1 to 50 consecutive amino acid residues and comprises five or more of the specific amino acid residues in a non-target region other than the target region, a partial structure other than the antibody can be bound to the one or more specific amino acid residues comprised in the target region with 30% or more regioselectivity. Definitions, examples, and preferred examples of the target regions and regioselectivity are as described above.

3-6. Number of Partial Structures Other than Antibody, Possessed by Antibody

The number of partial structures (e.g., A-L-B'(—F)—R') other than the antibody (T), possessed by the antibody can vary. For example, when T is a multimeric protein comprising a plurality of monomeric proteins, T can have a partial structure other than T in a plurality of corresponding target regions in the plurality of monomeric proteins. As a result, T can have a plurality of partial structures other than T. Therefore, the structure represented by Formula (III), (III'), or (III") indicates that T may have one or more partial structures other than T. The number of partial structures other than T, possessed by T can be adjusted by appropriately setting conditions such as the type of antibody and a reaction ratio between the antibody and a structural unit introduced thereinto. Such a number varies depending on the type of antibody, but may be, for example, 1 to 8, preferably 1 to 4, and more preferably 1 or 2.

In a specific embodiment, the antibody may have a plurality of partial structures other than the antibody when the antibody is a multimeric protein comprising a plurality of monomeric proteins. According to the present invention, a plurality of partial structures other than the antibody can be introduced into the same target region of a plurality of monomeric proteins.

In a preferred embodiment, the antibody may comprise a plurality of heavy chains. Definitions, examples, and preferred examples of the antibody are as described above. In the present invention, the number of partial structures other than the antibody, possessed by the antibody may be 1 or 2 (preferably 2) for IgG, IgE, and IgD, 1 to 4 (preferably 4) for IgA, and 1 to 8 (preferably 8) for IgM.

3-7. Production Method

The present invention provides a method for producing a conjugate having an affinity substance to an antibody, a cleavable portion, a functional substance, and an antibody, or a salt thereof, the method comprising the following:

(B1) reacting an antibody having an affinity substance to an antibody and a cleavable portion, or a salt thereof with a functional substance to form a conjugate having an affinity substance to an antibody, a cleavable portion, a functional substance, and an antibody, or a salt thereof.

The compound having an affinity substance to an antibody and a cleavable portion is represented by Formula (II), preferably Formula (II'), more preferably Formula (II"). The conjugate having an affinity substance to an antibody, a cleavable portion, a functional substance, and an antibody is represented by Formula (III), preferably Formula (III'), more preferably Formula (III").

The antibody having an affinity substance to an antibody and a cleavable portion, or a salt thereof has a bioorthogonal functional group capable of reacting with a functional substance, and therefore can react with the functional substance. Such a reaction can be appropriately performed under a condition incapable of causing denaturation or decomposition (e.g., cleavage of an amide bond) of proteins (a mild condition) as described in "2-6. Production Method" above.

In the reaction system, a molar ratio (Y/X) of a functional substance (Y) to an antibody having an affinity substance to an antibody and a cleavable portion, or a salt thereof (X) is not limited to a particular ratio because it varies depending on the types of the antibody and the functional substance, the number of sites in the antibody to be modified with the functional substance (e.g., DAR), and the like. However, the molar ratio (Y/X) is e.g., 0.1 to 100, preferably 0.5 to 80, more preferably 1 to 70, even more preferably 2 to 50, and particularly preferably 3 to 30.

Determination of formation of the conjugate having an affinity substance to an antibody, a cleavable portion, a functional substance, and an antibody, or a salt thereof, which depends on its specific raw materials and the molecular weight of a product, can be performed by electrophoresis, chromatography (e.g., gel permutation chromatography, ion-exchange chromatography, reversed phase column chromatography, and HPLC), or mass spectrometry, for example, and preferably mass spectrometry. Determination of regioselectivity, determination of the number of partial structures other than an antibody, and purification can be appropriately performed by the method described in "2-6. Production Method" above.

The present invention also provides a method for producing a conjugate having an affinity substance to an antibody, a cleavable portion, a functional substance, and an antibody, or a salt thereof, the method comprising the following:

(B2) reacting a compound having an affinity substance to an antibody, a cleavable portion, and a reactive group, or a salt thereof with an antibody to form an antibody having an affinity substance to an antibody and a cleavable portion, or a salt thereof; and (B3) reacting the antibody having an affinity substance to an antibody and a cleavable portion, or a salt thereof with a functional substance to form a conjugate having an affinity substance to an antibody, a cleavable portion, a functional substance, and an antibody, or a salt thereof.

The step (B2) can be performed in a similar manner to the step (A1) described in "2-6. Production Method" above. The step (B3) can be performed in a similar manner to the step (B1). The steps (B2) and (B3) can be performed separately. Alternatively, the steps (B2) and (B3) can be performed at the same time depending on a combination such as a reaction pair of a specific amino acid residue that is a reaction target in an antibody and a reactive group, or a reaction pair of a functional group in a functional substance and a bioorthogonal functional group. That is, when the steps (B2) and (B3) are performed at the same time, a product-containing reaction solution obtained in the step (B2) may be subjected to the step (B3) without isolating a product obtained in the step (B2).

4. Antibody Having Bioorthogonal Functional Group, or Salt Thereof 4-1. Outline of Production Method The present invention provides a method for producing an antibody having a bioorthogonal functional group or bioorthogonal functional groups, or a salt thereof, represented by Formula (IV).

$$L1\text{-}B\text{—}R'\text{-}T \quad (IV)$$

wherein

L1 is (i') a monovalent group comprising a bioorthogonal functional group or (ii') a monovalent group comprising no bioorthogonal functional group, B is (a) a divalent group comprising a bioorthogonal functional group or (b) a divalent group comprising no bioorthogonal functional group, R' is a portion formed by a reaction between an antibody and a reactive group, and T is an antibody.

4-2. (I') Monovalent Group Comprising Bioorthogonal Functional Group, or (ii') Monovalent Group Comprising No Bioorthogonal Functional Group (L1)

In Formula (IV), L1 is (i') a monovalent group comprising a bioorthogonal functional group or (ii') a monovalent group comprising no bioorthogonal functional group. Such a monovalent group can be formed by cleavage of the above-described cleavable linker that is a divalent group comprising a cleavable portion. Therefore, L1 may be a monovalent group that can be formed by cleavage of a residue or a chemical structure of the above-described cleavable portion. More specifically, (i') the monovalent group comprising a bioorthogonal functional group may be a monovalent group that can be formed by cleavage of (i) the above-described cleavable linker that is a divalent group comprising a cleavable portion capable of forming a bioorthogonal functional group on a reactive group side by cleavage, and (ii') the monovalent group comprising no bioorthogonal functional group may be a monovalent group that can be formed by cleavage of (ii) the cleavable linker that is a divalent group comprising a cleavable portion not capable of forming a bioorthogonal functional group on a reactive group side by cleavage.

In a specific embodiment, L1 may be represented by any one of the following Formula (L1-1) or (L1-2):

C1-Lb           (L1-1)

C1           (L1-2)

wherein,
Lb is a divalent group, and
C1 is a bioorthogonal functional group, or a group other than the bioorthogonal functional group.

Examples of the divalent group include a divalent hydrocarbon group optionally having a substituent, a divalent heterocyclic group optionally having a substituent, —C(=O)—, —NR$_a$— (where R$_a$ represents a hydrogen atom or a substituent), —O—, —S—, —C(=S)—, and a group formed by a combination of two or more (e.g., two to eight, preferably two to six, and more preferably two to four) of these. Definitions, examples, and preferred examples of the divalent hydrocarbon group, the divalent heterocyclic group, and the substituent are as described above.

A definition, examples, and preferred examples of the bioorthogonal functional group are as described above.

Examples of the group other than the bioorthogonal functional group include those other than the bioorthogonal functional group out of the above-described substituents. Examples of such a group other than the bioorthogonal functional group include alkyl, cycloalkyl, aralkyl, a monovalent heterocyclic group, hydroxyl, amino, alkyloxy (alkoxy), cycloalkyloxy, and aralkyloxy. Definitions, examples, and preferred examples of these groups and components of these groups (e.g., alkyl in alkyloxy (alkoxy), cycloalkyl in cycloalkyloxy, and aralkyl in aralkyloxy) are similar to those described above.

In a specific embodiment, Lb may be represented by the following (Lb'):

(Lb')

wherein
p is any integer of 0 to 10,
q is any integer of 0 to 10,
X is a carbon atom, a nitrogen atom, or a single bond (where R$_{1b}$ is absent when X is a nitrogen atom, R$_{1a}$ and R$_{1b}$ are absent when X is a single bond),
R$_{1a}$ and R$_{1b}$ are the same as or different from each other and are each a hydrogen atom or selected from the group consisting of the above substituents, and
○ (white circle) indicates a bond to C1, and ● (black circle) indicates a bond to B.

Definitions, examples, and preferred examples of p, q, X, R$_{1a}$, and R$_{1b}$ (substituents) are as described above.

4-3. Partial Structure "L1-B"

4-3-1. Length of Partial Structure "L1-B" Coupling L1 Terminal Portion with R'

In Formula (IV), the length of a partial structure (linear portion in "L1-B") coupling the L1 terminal portion (or C1 terminal portion) formed by cleavage with R' (or the number of atoms of a main chain coupling a bioorthogonal functional group with a side chain of a specific amino acid residue in an antibody regioselectively having a bioorthogonal functional group or bioorthogonal functional groups, or a salt thereof, not limited to a specific formula such as Formula (IV). Hereinafter the same) can be appropriately designed depending on various factors as described in "1-6-1. Length of main chain in partial structure "L-B" coupling A with R" above.

The length of the partial structure coupling the L1 terminal portion (or C1 terminal portion) formed by cleavage with R' may be, for example, about 2.5 Å or more, preferably about 4 Å or more, and more preferably about 5 Å or more. The length of the partial structure may also be, for example, about 15 Å or less, preferably about 12 Å or less, and more preferably about 8 Å or less. More specifically, the length of the partial structure may be, for example, about 2.5 to 15 Å, preferably about 4 to 12 Å, and more preferably about 5 to 8 Å.

More specifically, the length of the partial structure coupling the L1 terminal portion (or C1 terminal portion) formed by cleavage with R' can be defined as the number of atoms constituting the coupling chain (excluding hydrogen atom and substituent) of the partial structure. The number of atoms constituting the coupling chain may be, for example, 2 (about 2.5 Å) or more, preferably 3 (about 4 Å) or more, and more preferably 4 (about 5 Å) or more. The number of atoms constituting the coupling chain may also be, for example, 10 (about 15 Å) or less, preferably 8 (about 12 Å) or less, and more preferably 6 (about 8 Å) or less. More specifically, the number of atoms constituting the coupling chain may be, for example, 2 to 10, preferably 3 to 8, and more preferably 4 to 6.

When the coupling chain of the partial structure coupling the L1 terminal portion (or C1 terminal portion) formed by cleavage with R' has a chain structure comprising no divalent cyclic structure, the number of atoms in the coupling chain can be determined by counting the number of atoms in the coupling chain.

On the other hand, when the coupling chain of the partial structure coupling the L1 terminal portion (or C1 terminal portion) formed by cleavage with R' has a structure comprising a divalent cyclic structure, the number of atoms of the coupling chain does not necessarily correspond to the length described above, and the length that can be defined by the number of atoms in the coupling chain tends to be shorter than the length described above. Even in such a case, the number of atoms in the coupling chain can be conveniently counted from a viewpoint of defining the length of the coupling chain with the number of atoms. Specifically, the number of atoms of the coupling chain in such a case may be determined by counting the number of atoms of the shortest route connecting two bonds in the divalent cyclic structure in addition to the number of atoms in a chain structure comprising no divalent cyclic structure in the coupling chain.

The coupling chain of the partial structure coupling the L1 terminal portion (or C1 terminal portion) formed by cleavage with R' may preferably have a chain structure comprising no divalent cyclic structure. In this case, L1-B can be appropriately designed such that the coupling chain having the partial structure coupling the terminal portion formed by cleavage with R' comprises no divalent cyclic group.

In a specific embodiment, the partial structure represented by L1-B preferably comprises no a peptide portion. In this case, the antibody having a functional substance or functional substances according to the present invention, obtained by using the antibody having a bioorthogonal functional group or bioorthogonal functional groups according to the present invention (e.g., an antibody drug conjugate) has an advantage that a peptide portion capable of having immunogenicity cannot be comprised as a linker.

4-3-2. Specific Structure of Partial Structure "L1-B"

In the above Formula (IV), L1 and B have structures that can be related to each other. Therefore, in the above Formula (IV), L1 and B can be defined as a partial structure represented by "L1-B".

In a specific embodiment, when L1 is (i') a monovalent group comprising a bioorthogonal functional group, B is (a) a divalent group comprising a bioorthogonal functional group or (b) a divalent group comprising no bioorthogonal functional group.

When L1 is (i') the monovalent group comprising a bioorthogonal functional group, B is preferably (a) the divalent group comprising a bioorthogonal functional group. In this case, the type of the bioorthogonal functional group in (i') may be the same as or different from the type of the bioorthogonal functional group in (a). The type of the bioorthogonal functional group formed in (i) may be the same as the type of the bioorthogonal functional group in (a) from viewpoints of adopting a simpler structure and/or improving reactivity to a single functional substance, and the like. On the other hand, the type of the bioorthogonal functional group in (i') may be different from the type of the bioorthogonal functional group in (a) from viewpoints of ensuring differentiated reactivity to two or more types of functional substances, not using some bioorthogonal functional groups in the reaction, and the like.

Alternatively, when L1 is (i') the monovalent group comprising a bioorthogonal functional group, B may be (b) the divalent group comprising no bioorthogonal functional group. In this case, the antibody having a bioorthogonal functional group or bioorthogonal functional groups, or a salt thereof, represented by Formula (IV) has a simpler structure and is therefore easily synthesized.

In another specific embodiment, when L1 is (ii') the monovalent group comprising no bioorthogonal functional group, B may be (a) the divalent group comprising a bioorthogonal functional group.

In a specific embodiment, the structural unit represented by L1-B may be represented by the following Formula (LAB').

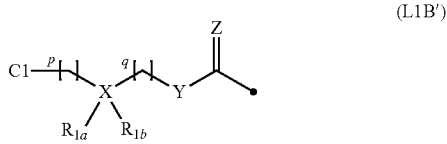

(L1B')

wherein
definitions, examples, and preferred examples of C1, p, q, X, $R_{1a}$, $R_{1b}$, Y, and Z are the same as those described above, and
● (black circle) indicates a bond to R'.

Therefore, the above Formula (IV) can be defined as the following Formula (IV').

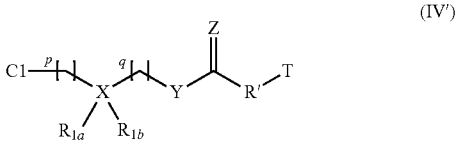

(IV')

wherein
definitions, examples, and preferred examples of C1, p, q, X, $R_{1a}$, $R_{1b}$, Y, Z, R', and T are the same as those described above.

In the above Formulae (L1B') and (IV'), the length from C at C=Z to C1 is similar to the length of the partial structure coupling the L1 terminal portion (or C1 terminal portion) formed by cleavage with R'. In these Formulae, the length from C at C=Z to C1 can also be defined as the number of atoms constituting the coupling chain of the partial structure from C at C=Z to C1 (excluding hydrogen atoms and substituents). The number of atoms described above is similar to the number of atoms constituting the partial structure coupling the L1 terminal portion (or C1 terminal portion) formed by cleavage with R' (excluding hydrogen atom and substituent). The coupling chain of the partial structure coupling from C at C=Z to C1 (excluding hydrogen atoms and substituents) may comprise a cyclic structure or is not necessarily comprise a cyclic structure, but preferably comprises no cyclic structure. The coupling chain (excluding hydrogen atoms and substituents) may preferably comprise no peptide portion.

4-4. Binding Site of Partial Structure Other than Antibody, Possessed by Antibody (Regioselectivity)

A partial structure other than an antibody (e.g., L1-B—R') can be regioselectively bound to the above-described target region in the antibody (T). Specifically, when T comprises one or more specific amino acid residues in a target region consisting of 1 to 50 consecutive amino acid residues and comprises five or more of the specific amino acid residues in a non-target region other than the target region, a partial structure other than the antibody can be bound to the one or more specific amino acid residues comprised in the target region with 30% or more regioselectivity. Definitions, examples, and preferred examples of the target regions and regioselectivity are as described above.

4-5. Number of Partial Structures Other than Antibody, Possessed by Antibody

The number of partial structures (e.g., L1-B—R') other than the antibody (T), possessed by the antibody can vary. For example, when T is a multimeric protein comprising a plurality of monomeric proteins, T can have a partial structure other than T in a plurality of corresponding target regions in the plurality of monomeric proteins. As a result, T can have a plurality of partial structures other than T. Therefore, the structure represented by Formula (IVI), (IV'), or (IV") indicates that T may have one or more partial structures other than T. The number of partial structures other than T, possessed by T can be adjusted by appropriately setting conditions such as the type of antibody and a reaction ratio between the antibody and a structural unit introduced thereinto. Such a number varies depending on the type of antibody, but may be, for example, 1 to 8, preferably 1 to 4, and more preferably 1 or 2.

In a specific embodiment, the antibody may have a plurality of partial structures other than the antibody when the antibody is a multimeric protein comprising a plurality of monomeric proteins. According to the present invention, a plurality of partial structures other than the antibody can be introduced into the same target region of a plurality of monomeric proteins.

In a preferred embodiment, the antibody may comprise a plurality of heavy chains. Definitions, examples, and preferred examples of the antibody are as described above. In the present invention, the number of partial structures other than the antibody, possessed by the antibody may be 1 or 2 (preferably 2) for IgG, IgE, and IgD, 1 to 4 (preferably 4) for IgA, and 1 to 8 (preferably 8) for IgM.

4-6. Production Method The present invention provides a method for producing an antibody having a bioorthogonal functional group or bioorthogonal functional groups or a salt thereof, the method comprising the following:

(C1) cleaving a cleavable portion of an antibody having an affinity substance to an antibody and a cleavable portion, or a salt thereof to form an antibody having a bioorthogonal functional group or bioorthogonal functional groups, or a salt thereof.

The compound having an affinity substance to an antibody and a cleavable portion is represented by Formula (II), preferably Formula (II'), more preferably Formula (II"). The antibody having a bioorthogonal functional group or bioorthogonal functional groups is represented by Formula (IV), preferably Formula (IV'), more preferably Formula (IV").

The antibody having an affinity substance to an antibody and a cleavable portion, or a salt thereof has the above-described cleavable portion that can be cleaved by a cleaving treatment, and therefore can be cleaved. Such a cleaving reaction can be appropriately performed under a condition incapable of causing denaturation or decomposition (e.g., cleavage of an amide bond) of proteins (a mild condition) as described in "2-6. Production Method" above.

Examples of the cleaving treatment include (a) a treatment with one or more substances selected from the group consisting of an acidic substance, a basic substance, a reducing agent, an oxidizing agent, and an enzyme, (b) a treatment with a physical and chemical stimulus selected from the group consisting of light, and (c) leaving a cleavable linker as it is when the cleavable linker comprises a self-degradable cleavable portion. Conditions for such a cleaving treatment are common technical knowledge in the field concerned (e.g., G. Leriche, L. Chisholm, A. Wagner, Bioorganic & Medicinal Chemistry. 20,571 (2012); Feng P. et al., Journal of American Chemical Society. 132,1500 (2010-); Bessodes M. et al., Journal of Controlled Release, 99,423 (2004); DeSimone, J. M., Journal of American Chemical Society. 132,17928 (2010); Thompson, D. H., Journal of Controlled Release, 91,187 (2003); and Schoenmarks, R. G., Journal of Controlled Release, 95,291 (2004), all of which are incorporated herein by reference in their entireties).

Determination of formation of the antibody having a bioorthogonal functional group or bioorthogonal functional groups, or a salt thereof, which depends on its specific raw materials and the molecular weight of a product, can be performed by electrophoresis, chromatography (e.g., gel permutation chromatography, ion-exchange chromatography, reversed phase column chromatography, and HPLC), or mass spectrometry, for example, and preferably mass spectrometry. Determination of regioselectivity, determination of the number of partial structures other than an antibody, and purification can be appropriately performed by the method described in "2-6. Production Method" above.

The present invention also provides a method for producing an antibody having a bioorthogonal functional group or bioorthogonal functional groups, or a salt thereof, the method comprising the following:

(C2) reacting a compound having an affinity substance to an antibody, a cleavable portion, and a reactive group, or a salt thereof with an antibody to form an antibody having an affinity substance to an antibody and a cleavable portion, or a salt thereof; and (C3) cleaving a cleavable portion of the antibody having an affinity substance to an antibody and a cleavable portion, or a salt thereof to form an antibody having a bioorthogonal functional group or bioorthogonal functional groups, or a salt thereof.

The step (C2) can be performed in a similar manner to the step (A1) described in "2-6. Production Method" above. The step (C3) can be performed in a similar manner to the step (C1). The steps (C2) and (C3) can be performed separately. Alternatively, the steps (C2) and (C3) can be performed at the same time depending on a factor such as a combination of a reactive group and a bioorthogonal functional group that can be formed by cleavage (non-reactivity). That is, when the steps (C2) and (C3) are performed at the same time, a product-containing reaction solution obtained in the step (C2) may be subjected to the step (C3) without isolating a product obtained in the step (C2).

5. Method for Producing Antibody Having Functional Substance, or Salt Thereof 5-1. Outline The present invention provides a method for producing an antibody having a functional substance or functional substances, or a salt thereof, represented by Formula (V), the method comprising the following.

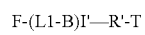

$$F\text{-}(L1\text{-}B)I'\text{---}R'\text{-}T \qquad (V)$$

wherein

L1 is (i') a monovalent group comprising a bioorthogonal functional group or (ii') a monovalent group comprising no bioorthogonal functional group, B is (a) a divalent group comprising a bioorthogonal functional group or (b) a divalent group comprising no bioorthogonal functional group, the structural unit represented by (L1-B)' is a divalent structural unit comprising a portion formed by a reaction between a functional substance and one or both of the bioorthogonal functional groups in (i') and (a), F is a functional substance, R' is a portion formed by a reaction between an antibody and a reactive group, and T is an antibody.

5-2. Partial Structure "F-(L1-B)'"

5-2-1. Length of Partial Structure "L1-B" Coupling F with R'

In Formula (V), the length of the partial structure "L1-B" (linear portion in "L1-B") coupling F with R' (or the number of atoms of a main chain coupling a functional substance with a side chain of a specific amino acid residue in an antibody regioselectively having a functional substance or functional substances, or a salt thereof, not limited to a specific formula such as Formula (V), or the number of atoms of a main chain coupling a bioorthogonal functional group with a side chain of a specific amino acid residue when a functional substance is coupled with an antibody via the bioorthogonal functional group. Hereinafter the same) can be appropriately designed depending on various factors as described in "1-6-1. Length of main chain in partial structure "L-B" coupling A with R" above.

The length of the partial structure coupling F with R' may be, for example, about 2.5 Å or more, preferably about 4 Å or more, and more preferably about 5 Å or more. The length of the partial structure may also be, for example, about 15 Å or less, preferably about 12 Å or less, and more preferably about 8 Å or less. More specifically, the length of the partial structure may be, for example, about 2.5 to 15 Å, preferably about 4 to 12 Å, and more preferably about 5 to 8 Å.

More specifically, the length of the partial structure coupling F with R' can also be defined as the number of atoms constituting the coupling chain (excluding hydrogen atoms and substituents) of the partial structure. The number of atoms constituting the coupling chain may be, for example, 2 (about 2.5 Å) or more, preferably 3 (about 4 Å) or more, and more preferably 4 (about 5 Å) or more. The number of atoms constituting the coupling chain may also be, for example, 10 (about 15 Å) or less, preferably 8 (about 12 Å) or less, and more preferably 6 (about 8 Å) or less. More specifically, the number of atoms constituting the coupling chain may be, for example, 2 to 10, preferably 3 to 8, and more preferably 4 to 6.

When the coupling chain of the partial structure coupling F with R' has a chain structure comprising no divalent cyclic structure, the number of atoms in the coupling chain can be determined by counting the number of atoms in the coupling chain.

On the other hand, when the coupling chain of the partial structure coupling F with R' has a structure comprising a divalent cyclic structure, the number of atoms of the coupling chain does not necessarily correspond to the length described above, and the length that can be defined by the number of atoms in the coupling chain tends to be shorter than the length described above. Even in such a case, the number of atoms in the coupling chain can be conveniently counted from a viewpoint of defining the length of the coupling chain with the number of atoms. Specifically, the number of atoms of the coupling chain in such a case may be determined by counting the number of atoms of the shortest route connecting two bonds in the divalent cyclic structure in addition to the number of atoms in a chain structure comprising no divalent cyclic structure in the coupling chain.

The coupling chain of the partial structure coupling F with R' may preferably have a chain structure comprising no divalent cyclic structure. L1-B can be appropriately designed such that the coupling chain having the partial structure coupling F with R' comprises no divalent cyclic group.

In a specific embodiment, the partial structure represented by L1-B preferably comprises no a peptide portion. In this case, the antibody having a functional substance or functional substances according to the present invention (e.g., an antibody drug conjugate) has an advantage that a peptide portion capable of having immunogenicity is not comprised as a linker.

5-2-2. Specific Structure of Partial Structure "F-(L1-B)'"

In Formula (V), L1 and B in F-(L1-B)' have structures that can be related to each other. Therefore, in the above Formula (V), L1 and B can be defined as a partial structure represented by "L1-B".

The structural unit represented by F-(L1-B)' is a portion formed by a reaction between a functional substance and one or both of the bioorthogonal functional groups in (i') and (a). The bioorthogonal functional group that has been subjected to the reaction is absent in Formula (V).

Therefore, in Formula (V), one or both of the bioorthogonal functional groups in (i') and (a) are absent. The portion formed by a reaction between a functional substance and one or both of the bioorthogonal functional groups in (i') and (a) is the same as the portion formed by a reaction between a functional substance and a bioorthogonal functional group. Therefore, in the present specification, an example (name of residue) and a specific example (chemical structural formula) of the portion formed by a reaction between a functional substance and one or both of the bioorthogonal functional groups in (i') and (a) are the same as those described above for the portion formed by a reaction between a functional substance and a bioorthogonal functional group.

In an embodiment, when L1 is (i') a monovalent group comprising a bioorthogonal functional group, B is (a) a divalent group comprising a bioorthogonal functional group or (b) a divalent group comprising no bioorthogonal functional group.

In a preferred embodiment, when L1 is (i') the monovalent group comprising a bioorthogonal functional group, B is preferably (a) the divalent group comprising a bioorthogonal functional group. In this case, the type of the bioorthogonal functional group in (i') may be the same as or different from the type of the bioorthogonal functional group in (a). The type of the bioorthogonal functional group formed in (i) may be the same as the type of the bioorthogonal functional group in (a) from viewpoints of adopting a simpler structure and/or improving reactivity to a single functional substance, and the like. On the other hand, the type of the bioorthogonal functional group in (i') may be different from the type of the bioorthogonal functional group in (a) from viewpoints of ensuring differentiated reactivity to two or more types of functional substances, not using some bioorthogonal functional groups in the reaction, and the like.

In another preferred embodiment, when L1 is (i') the monovalent group comprising a bioorthogonal functional group, B may be (b) the divalent group comprising no bioorthogonal functional group. In this case, the antibody having a functional substance or functional substances, or a salt thereof, represented by Formula (V) has a simpler structure and is therefore easily synthesized.

In another embodiment, when L1 is (ii') the monovalent group comprising no bioorthogonal functional group, B may be (a) the divalent group comprising a bioorthogonal functional group.

In a specific embodiment, when the bioorthogonal functional groups in (i') and (a) are of different types, the antibody having a functional substance or functional substances, or a salt thereof represented by formula (V) may be represented by Formula (V1) or (V2).

L1-B'(—F)—R'-T     (V1)

wherein
L1 is (i') a monovalent group comprising a bioorthogonal functional group or (ii') a monovalent group comprising no bioorthogonal functional group,
B' is a trivalent group comprising a portion formed by a reaction between a functional substance and a bioorthogonal functional group,
F is a functional substance,
R' is a portion formed by a reaction between an antibody and a reactive group, and
T is an antibody.

F-L1'-B—R'-T     (V2)

wherein
L1' is a divalent group comprising a portion formed by a reaction between a functional substance and (i') a monovalent group comprising a bioorthogonal functional group,
B is (a) a divalent group comprising a bioorthogonal functional group or (b) a divalent group comprising no bioorthogonal functional group,
F is a functional substance,
R' is a portion formed by a reaction between an antibody and a reactive group, and
T is an antibody.

L1' is a divalent group comprising a portion formed by a reaction between a functional substance and (i') the monovalent group comprising a bioorthogonal functional group. The portion formed by a reaction between a functional substance and (i') the monovalent group comprising a bioorthogonal functional group is the same as the portion formed by a reaction between a functional substance and a bioorthogonal functional group. Therefore, in the present specification, an example (name of residue) and a specific example (chemical structural formula) of the portion formed by a reaction between a functional substance and (i') the monovalent group comprising a bioorthogonal functional group are the same as those described above for the portion formed by a reaction between a functional substance and a bioorthogonal functional group. Therefore, since the functional substance reacts with the bioorthogonal functional group, the divalent group (L1') comprising a portion formed by a reaction between a functional substance and (i') the monovalent group comprising a bioorthogonal functional group can also be expressed as a divalent group comprising a portion formed by a reaction between a functional substance and a bioorthogonal functional group (hereinafter the same). More specifically, the divalent group comprising a portion formed by a reaction between a functional substance and a bioorthogonal functional group (1) may be a divalent group comprising a thiosuccinimide residue, a triazole residue, or a hydrazone residue referred to in the above-described preferred examples, or (2) which is not limited to a particular group, may be a divalent group comprising a residue selected from the group consisting of a disulfide residue (this residue has been referred to in the above-described preferred examples), an acetal residue, a ketal residue, an ester residue, a carbamoyl residue, an alkoxyalkyl residue, an imine residue, a tertiary alkyloxy carbamate residue, a silane residue, a hydrazone-containing residue, a phosphoramidate residue, an aconityl residue, a trityl residue, an azo residue, a vicinal diol residue, a selenium residue, an aromatic ring-containing residue having an electron-withdrawing group, a coumarin-containing residue, a sulfone-containing residue, an unsaturated bond-containing chain residue, and a glycosyl residue, for example. However, (1) the divalent group comprising a thiosuccinimide residue, a triazole residue, or a hydrazone residue is preferred.

In another specific embodiment, when the bioorthogonal functional groups in (i') and (a) are of the same type or different types, the antibody having a functional substance or functional substances, or a salt thereof, represented by formula (V) may be represented by Formula (V3).

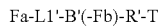
(V3)

wherein
L1' is a divalent group comprising a portion formed by a reaction between a functional substance and (i') a monovalent group comprising a bioorthogonal functional group,
B' is a trivalent group comprising a portion formed by a reaction between a functional substance and a bioorthogonal functional group,
Fa and Eb are functional substances that are the same as or different from each other,
R' is a portion formed by a reaction between an antibody and a reactive group, and
T is an antibody.

In a specific embodiment, the structural unit represented by L1-B'(—F) in the above Formula (VL) may be represented by the following Formula (L1B'(F)).

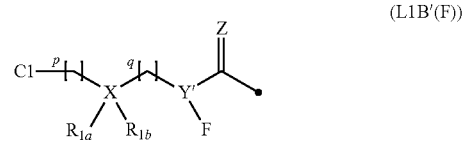
(L1B'(F))

wherein
definitions, examples, and preferred examples of F, C1, p, q, X, $R_{1a}$, $R_{1b}$, and Z are the same as those described above,
Y' is a residue obtained by removing one hydrogen atom from Y in the above Formula (B-1), and
● (black circle) indicates a bond to R'.
Definitions, examples, and preferred examples of the residue obtained by removing one hydrogen atom from Y in the above Formula (3-1) are similar to those described above.

Therefore, the above Formula (V1) can be defined as the following Formula (V1').

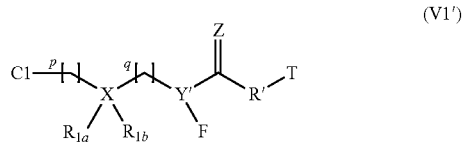
(V1')

wherein
definitions, examples, and preferred examples of F, C1, p, q, X, $R_{1a}$, $R_{1b}$, Z, R', and T are the same as those described above, and
Y' is a residue obtained by removing one hydrogen atom from Y in the above Formula (B-1).

In a specific embodiment, the structural unit represented by F-L1'-B in the above Formula (V2) may be represented by the following Formula (FL1'B).

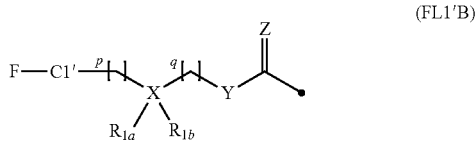
(FL1'B)

wherein
definitions, examples, and preferred examples of F, p, q, X, $R_{1a}$, $R_{1b}$, Y, and Z are the same as those described above,
C1' is a portion formed by a reaction between a functional substance and a bioorthogonal functional group, and
● (black circle) indicates a bond to R'.
C1' is a portion formed by a reaction between a functional substance and a bioorthogonal functional group.

Definitions, examples, and preferred examples of the portion formed by a reaction between a functional substance and a bioorthogonal functional group in C1' are similar to those described for the above "divalent group comprising a portion formed by a reaction between a functional substance and a bioorthogonal functional group" (hereinafter the same).

Therefore, the above Formula (V2) can be defined as the following Formula (V2').

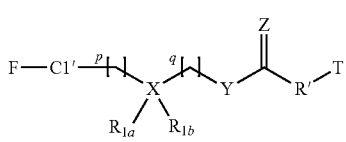
(V2')

wherein
definitions, examples, and preferred examples of F, p, q, X, $R_{1a}$, $R_{1b}$, Y, Z, R', and T are the same as those described above, and
C1' is a portion formed by a reaction between a functional substance and a bioorthogonal functional group.

In a specific embodiment, the structural unit represented by Fa-L1'-B'(-Fb) in the above Formula (V3) may be represented by the following Formula (FaL1'B'(Fb)).

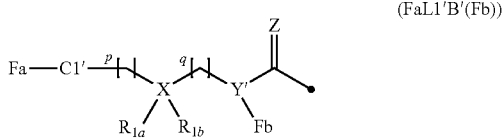
(FaL1'B'(Fb))

wherein
definitions, examples, and preferred examples of Fa, Fb, p, q, X, $R_{1a}$, $R_{1b}$, and Z are the same as those described above,
C1' is a portion formed by a reaction between a functional substance and a bioorthogonal functional group,
Y' is a residue obtained by removing one hydrogen atom from Y in the above Formula (B-1), and
● (black circle) indicates a bond to R'.

Therefore, the above Formula (V3) can be defined as the following Formula (V3').

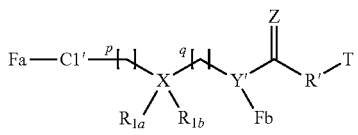
(V3')

wherein
definitions, examples, and preferred examples of Fa, Fb, p, q, X, $R_{1a}$, $R_{1b}$, Z, R', and T are the same as those described above,
C1' is a portion formed by a reaction between a functional substance and a bioorthogonal functional group, and
Y' is a residue obtained by removing one hydrogen atom from Y in the above Formula (B-1).

In the above Formulae (L1B'(F)), (FL1'B), (-FaL1'B' (F2)), (V1'), (V2'), and (V3'), the length from C at C=Z to C1 is similar to the length of the partial structure coupling the L1 terminal portion (or C1 terminal portion) formed by cleavage with R'. In these Formulae, the length from C at C=Z to C1 can also be defined as the number of atoms constituting the coupling chain of the partial structure from C at C=Z to C1 (excluding hydrogen atoms and substituents). The number of atoms described above is similar to the number of atoms constituting the partial structure coupling the L1 terminal portion (or C1 terminal portion) formed by cleavage with R' (excluding hydrogen atom and substituent). The coupling chain of the partial structure coupling from C at C=Z to C1 (excluding hydrogen atoms and substituents) may comprise a cyclic structure or is not necessarily comprise a cyclic structure, but preferably comprises no cyclic structure.

The coupling chain (excluding hydrogen atoms and substituents) may preferably comprise no peptide portion.

5-3. Binding Site of Partial Structure Other than Antibody, Possessed by Antibody (Regioselectivity)

A partial structure other than an antibody (e.g., F-(L1-B) '—R') can be regioselectively bound to the above-described target region in the antibody (T). Specifically, when T comprises one or more specific amino acid residues in a target region consisting of 1 to 50 consecutive amino acid residues and comprises five or more of the specific amino acid residues in a non-target region other than the target region, a partial structure other than the antibody can be bound to the one or more specific amino acid residues comprised in the target region with 30% or more regioselectivity. Definitions, examples, and preferred examples of the target regions and regioselectivity are as described above.

5-4. Number of Partial Structures Other than Antibody, Possessed by Antibody

The number of partial structures (e.g., F-(L1-B)'—R') other than the antibody (T), possessed by the antibody can vary. For example, when T is a multimeric protein comprising a plurality of monomeric proteins, T can have a partial structure other than T in a plurality of corresponding target regions in the plurality of monomeric proteins. As a result, T can have a plurality of partial structures other than T. Therefore, the structure represented by Formula (V), (V1), (V2), (V3), (V1'), (V2'), or (V3') indicates that T may have one or more partial structures other than T. The number of partial structures other than T, possessed by T can be adjusted by appropriately setting conditions such as the type of antibody and a reaction ratio between the antibody and a structural unit introduced thereinto. Such a number varies depending on the type of antibody, but may be, for example, 1 to 8, preferably 1 to 4, and more preferably 1 or 2.

In a specific embodiment, the antibody may have a plurality of partial structures other than the antibody when the antibody is a multimeric protein comprising a plurality of monomeric proteins. According to the present invention, a plurality of partial structures other than the antibody can be introduced into the same target region of a plurality of monomeric proteins.

In a preferred embodiment, the antibody may comprise a plurality of heavy chains. Definitions, examples, and preferred examples of the antibody are as described above. In the present invention, the number of partial structures other than the antibody, possessed by the antibody may be 1 or 2 (preferably 2) for IgG, IgE, and IgD, 1 to 4 (preferably 4) for IgA, and 1 to 8 (preferably 8) for IgM.

5-5. Production Method

The present invention provides a method for producing an antibody having a functional substance or functional substances, or a salt thereof. This production method can be classified into (D) a method using a conjugate having an affinity substance to an antibody, a cleavable portion, a functional substance, and an antibody, or a salt thereof as a raw material (refer to reaction (3) in FIG. 2), and (E) a method using an antibody having a bioorthogonal functional group or bioorthogonal functional groups, or a salt thereof as a raw material (refer to reaction (5) in FIG. 2).

(D) The method using a conjugate having an affinity substance to an antibody, a cleavable portion, a functional substance, and an antibody, or a salt thereof as a raw material comprises the following:

(D1) cleaving a cleavable portion of a conjugate having an affinity substance to an antibody, a cleavable portion, a functional substance, and an antibody, or a salt thereof to form an antibody having a functional substance or functional substances, or a salt thereof.

The conjugate having an affinity substance to an antibody, a cleavable portion, a functional substance, and an antibody is represented by Formula (III), preferably Formula (III'), more preferably Formula (III''). The antibody having a functional substance or functional substances is represented by Formula (V), preferably Formula (V1), (V2), or (V3), more preferably Formula (V1'), (V2'), or (V3').

The conjugate having an affinity substance to an antibody, a cleavable portion, a functional substance, and an antibody, or a salt thereof has the above-described cleavable portion that can be cleaved by a cleaving treatment, and therefore can be cleaved. Such a cleaving reaction can be performed in such a manner as described in "4-6. Production Method" above.

Determination of formation of the antibody having a functional substance or functional substances, or a salt thereof, which depends on its specific raw materials and the molecular weight of a product, can be performed by electrophoresis, chromatography (e.g., gel permutation chromatography, ion-exchange chromatography, reversed phase column chromatography, and HPLC), or mass spectrometry, for example, and preferably mass spectrometry. Determination of regioselectivity, determination of the number of partial structures other than an antibody, and purification can be appropriately performed by the method described in "2-6. Production Method" above.

The present invention also provides a method for producing an antibody having a functional substance or functional substances, or a salt thereof, the method comprising the following:

(D2) reacting an antibody having an affinity substance to an antibody and a cleavable portion, or a salt thereof with a functional substance to form a conjugate having an affinity substance to an antibody, a cleavable portion, a functional substance, and an antibody, or a salt thereof; and (D3) cleaving a cleavable portion of the conjugate having an affinity substance to an antibody, a cleavable portion, a functional substance, and an antibody, or a salt thereof to form an antibody having a functional substance or functional substances, or a salt thereof.

The step (D2) can be performed in a similar manner to the step (B1) described in "3-7. Production Method" above. The step (D3) can be performed in a similar manner to the step (D1). The steps (D2) and (D3) can be performed separately. Alternatively, the steps (D2) and (D3) can be performed at the same time depending on a factor such as a combination of a cleavable portion, a functional substance, and a bioorthogonal functional group. That is, when the steps (D2) and (D3) are performed at the same time, a product-containing reaction solution obtained in the step (D2) may be subjected to the step (D3) without isolating a product obtained in the step (D2).

The present invention further provides a method for producing an antibody having a functional substance or functional substances, or a salt thereof, the method comprising the following:

(D4) reacting a compound having an affinity substance to an antibody, a cleavable portion, and a reactive group, or a salt thereof with an antibody to form an antibody having an affinity substance to an antibody and a cleavable portion, or a salt thereof;

(D5) reacting the antibody having an affinity substance to an antibody and a cleavable portion, or a salt thereof with a functional substance to form a conjugate having an affinity substance to an antibody, a cleavable portion, a functional substance, and an antibody, or a salt thereof; and (D6) cleaving a cleavable portion of the conjugate having an affinity substance to an antibody, a cleavable portion, a functional substance, and an antibody, or a salt thereof to form an antibody having a functional substance or functional substances, or a salt thereof.

The step (D4) can be performed in a similar manner to the step (A1) described in "2-6. Production Method" above. The steps (D5) and (D6) can be performed in a similar manner to the steps (D2) and (D3). The step (D5) can be performed in a similar manner to the step (B1) described in "3-7. Production Method" above. The step (D6) can be performed in a similar manner to the step (D1). The steps (D4) to (D6) can be performed separately. Alternatively, at least some steps in the steps (D4) to (D6) can be performed at the same time depending on a factor such as a combination of a reactive group, a cleavable portion, a functional substance, and a bioorthogonal functional group. That is, when two or more steps in the steps (D4) to (D6) are performed at the same time, a product-containing reaction solution obtained in a previous step may be subjected to a subsequent step without isolating a product obtained in the previous step.

(E) The method using an antibody having a bioorthogonal functional group or bioorthogonal functional groups, or a salt thereof as a raw material comprises the following:

(E1) reacting an antibody having a bioorthogonal functional group or bioorthogonal functional groups, or a salt thereof with a functional substance to form an antibody having a functional substance or functional substances, or a salt thereof.

The antibody having a bioorthogonal functional group or bioorthogonal functional groups is represented by Formula (IV), preferably Formula (IV'). The antibody having a functional substance or functional substances is represented by Formula (V), preferably Formula (V1), (V2), or (V3), more preferably Formula (V1'), (V2'), or (V3').

The antibody having a bioorthogonal functional group or bioorthogonal functional groups, or a salt thereof has the bioorthogonal functional group, and therefore can react with a functional substance. Such a reaction can be performed in such a manner as described in "3-7. Production Method" above.

Determination of formation of the antibody having a functional substance or functional substances, or a salt thereof can be performed by the method described above. Determination of regioselectivity, determination of the number of partial structures other than an antibody, and purification can be appropriately performed by the method described in "2-6. Production Method" above.

The present invention also provides a method for producing an antibody having a functional substance or functional substances, or a salt thereof, the method comprising the following:

(E2) cleaving a cleavable portion of an antibody having an affinity substance to an antibody and a cleavable portion, or a salt thereof to form an antibody having a bioorthogonal functional group or bioorthogonal functional groups, or a salt thereof; and (E3) reacting the antibody having a bioorthogonal functional group or bioorthogonal functional groups, or a salt thereof with a functional substance to form an antibody having a functional substance or functional substances, or a salt thereof.

The step (E2) can be performed in a similar manner to the step (C1) described in "4-6. Production Method" above. The step (E3) can be performed in a similar manner to the step (E1). The steps (E2) and (E3) can be performed separately. Alternatively, the steps (E2) and (E3) can be performed at the same time depending on a factor such as a combination of a cleavable portion, a functional substance, and a bioorthogonal functional group. That is, when the steps (E2) and (E3) are performed at the same time, a product-containing reaction solution obtained in the step (E2) may be subjected to the step (E3) without isolating a product obtained in the step (E2).

The present invention further provides a method for producing an antibody having a functional substance or functional substances, or a salt thereof, the method comprising the following:

(E4) reacting a compound having an affinity substance to an antibody, a cleavable portion, and a reactive group, or a salt thereof with an antibody to form an antibody having an affinity substance to an antibody and a cleavable portion, or a salt thereof;

(E5) cleaving a cleavable portion of the antibody having an affinity substance to an antibody and a cleavable portion, or a salt thereof to form an antibody having a bioorthogonal functional group or bioorthogonal functional groups, or a salt thereof; and (E6) reacting the antibody having a bioorthogonal functional group or bioorthogonal functional groups, or a salt thereof with a functional substance to form an antibody having a functional substance or functional substances, or a salt thereof.

The step (E4) can be performed in a similar manner to the step (A1) described in "2-6. Production Method" above. The steps (E5) and (E6) can be performed in a similar manner to the steps (E2) and (E3). The steps (E4) to (E6) can be performed separately. Alternatively, at least some steps in the steps (E4) to (E6) can be performed at the same time depending on a factor such as a combination of a reactive group, a cleavable portion, a functional substance, and a bioorthogonal functional group. That is, when two or more steps in the steps (E4) to (E6) are performed at the same time, a product-containing reaction solution obtained in a previous step may be subjected to a subsequent step without isolating a product obtained in the previous step.

6. Salt

In the present invention, examples of the salt include salts with inorganic acids, salts with organic acids, salts with inorganic bases, salts with organic bases, and salts with amino acids. Examples of salts with inorganic acids include salts with hydrogen chloride, hydrogen bromide, phosphoric acid, sulfuric acid, and nitric acid. Examples of salts with organic acids include salts with formic acid, acetic acid, trifluoroacetic acid, lactic acid, tartaric acid, fumaric acid, oxalic acid, maleic acid, citric acid, succinic acid, malic acid, benzenesulfonic acid, and p-toluenesulfonic acid. Examples of salts with inorganic bases include salts with alkali metals (e.g., sodium and potassium), alkaline-earth metals (e.g., calcium and magnesium), other metals such as zinc and aluminum, and ammonium. Examples of salts with organic bases include salts with trimethylamine, triethylamine, propylenediamine, ethylenediamine, pyridine, ethanolamine, monoalkyl ethanolamine, dialkyl ethanolamine, diethanolamine, and triethanolamine. Examples of salts with amino acids include salts with basic amino acids (e.g., arginine, histidine, lysine, and ornithine) and acidic amino acids (e.g., aspartic acid and glutamic acid). The salt is preferably a salt with an inorganic acid (e.g., hydrogen chloride) or a salt with an organic acid (e.g., trifluoroacetic acid).

7. Uses

The compound having an affinity substance to an antibody, a cleavable portion, and a reactive group, or a salt thereof according to the present invention is useful for regioselective modification of an antibody, for example. Consequently, the present invention provides a reagent of regioselectively modifying an antibody, the reagent comprising a compound having an affinity substance affinity substance to an antibody, a cleavable portion, and a reactive group, or a salt thereof.

The regioselective modifying reagent of the present invention may be provided in a form of a composition further comprising other components. Examples of such other compounds include solutions and stabilizers (e.g., antioxidants and preservatives). Among solutions, aqueous solutions are preferred. Examples of aqueous solutions include water (e.g., distilled water, sterilized distilled water, purified water, and a physiological saline solution) and buffers (e.g., an aqueous phosphoric acid solution, a Tris-hydrochloric acid buffer, a carbonic acid-bicarbonic acid buffer, an aqueous boric acid solution, a glycine-sodium hydroxide buffer, and a citric acid buffer); buffers are preferred. The pH of solutions is e.g., 5.0 to 9.0 and preferably 5.5 to 8.5. The regioselective modifying reagent of the present invention can be provided in a liquid form or a powder form (e.g., freeze-dried powder).

The antibody (regioselectively) having an affinity substance to an antibody and a cleavable portion, or a salt thereof according to the present invention, the conjugate (regioselectively) having an affinity substance to an antibody, a cleavable portion, a functional substance, and an antibody, or a salt thereof according to the present invention, and the antibody (regioselectively) having a bioorthogonal functional group or bioorthogonal functional groups, or a salt thereof according to the present invention are useful, for example, as an intermediate for preparing an antibody (regioselectively) having a functional substance or functional substances, or a salt thereof.

The antibody (regioselectively) having a functional substance or functional substances, or a salt thereof according to the present invention is useful as pharmaceuticals or reagents (e.g., diagnostic reagents and reagents for research), for example.

In particular, the antibody (regioselectively) having a functional substance or functional substances, or a salt thereof according to the present invention is useful as pharmaceuticals. It is reported as described that when the number of bonds and the bond positions of a drug of an antibody drug conjugate (ADC) are changed, pharmacokinetics, a releasing rate of the drug, and effects change. Under these circumstances, next-generation ADCs are required to control the number and positions of a drug to be conjugated. It is believed that when the number and positions are constant, the problems of expected efficacy, variations in conjugate medicines, and lot difference, or what is called regulation, will be solved. The antibody having a functional substance or functional substances, or a salt thereof according to the present invention can solve such a problem of regulation. Consequently, the antibody having a functional substance or functional substances, or a salt thereof according to the present invention may be provided in the form of a pharmaceutical composition. Such a pharmaceutical composition may comprise a pharmaceutically allowable carrier in addition to the antibody having a functional substance or functional substances, or a salt thereof. Examples of the pharmaceutically allowable carrier include, but are not limited to, excipients such as sucrose, starch, mannitol, sorbitol, lactose, glucose, cellulose, talc, calcium phosphate, and calcium carbonate; binders such as cellulose, methylcellulose, hydroxypropylcellulose, polypropylpyrrolidone, gelatin, gum arabic, polyethylene glycol, sucrose, and starch; disintegrators such as starch, carboxymethylcellulose, hydroxypropyl starch, sodium hydrogencarbonate, calcium phosphate, and calcium citrate; lubricants such as magnesium stearate, Aerosil, talc, sodium lauryl sulfate; aromatics such as citric acid, menthol, glycyl lysine ammonium salts, glycine, and orange powder; preservatives such as sodium benzoate, sodium hydrogen sulfite, methylparaben, and propylparaben; stabilizers such as citric acid, sodium citrate, and acetic acid, suspensions such as methylcellulose, polyvinylpyrrolidone, and aluminum stearate; dispersants such as surfactants; diluents such as water, a physiological saline solution, and orange juice; and base waxes such as cacao butter, polyethylene glycol, and refined kerosene. The antibody having a functional substance or functional substances, or a salt thereof according to the present invention may also have any modification (e.g., PEGylation) achieving stability.

Examples of preparations suitable for oral administration include liquid medicines dissolving an effective amount of a ligand in a diluted solution such as water, a physiological saline solution, or orange juice; capsules, sachets, and tablets comprising an effective amount of a ligand as a solid or granules; suspension medicines suspending an effective amount of an active ingredient in an appropriate dispersion medium; and emulsions dispersing a solution dissolving an effective amount of an active ingredient in an appropriate dispersion medium to be emulsified.

The pharmaceutical composition is suitable for nonoral administration (e.g., intravenous injection, hypodermic injection, intramuscular injection, local injection, and intraperitoneal administration). Examples of the pharmaceutical composition suitable for such nonoral administration include aqueous or nonaqueous, isotonic, aseptic injection medicines, which may comprise an antioxidant, a buffer, a bacteriostat, a tonicity agent, or the like. Examples thereof also include aqueous or nonaqueous, aseptic suspension medicines, which may comprise a suspension, a solubilizing agent, a thickener, a stabilizer, an antiseptic, or the like.

The dose of the pharmaceutical composition, which varies by the type and activity of an active ingredient, the severity of diseases, an animal type as a subject to be dosed, the drug receptivity, body weight, and age of a subject to be dosed, or the like, can be set appropriately.

Other features of the invention will become apparent in the course of the following descriptions of exemplary embodiments which are given for illustration of the invention and are not intended to be limiting thereof.

EXAMPLES

Example 1. Design of Modified Protein a and Secretory Expression Thereof in *C. glutamicum*

(1-1) Outline of Design of Modified Protein A

In the present invention, it is necessary to bind a linker to a protein. That is, in order to achieve a specific binding of a linker to a specific amino acid residue in a protein, it is necessary to design the protein such that the protein has only one amino group capable of reacting with the linker. Based on this, the following variation was performed.

A) All Ks (lysines) in protein are varied to Rs (arginines)

B) By comprising Q (glutamine) as an N-terminal amino acid, Q (glutamine) is pyroglutamylated, and the N-terminal amino group is converted into an amide.

An actual modified protein A was designed as follows according to the rules of A) and B) above.

(1-2) Preparation of Modified Protein A

The following modified proteins A were prepared.

(a) CspB6Tev-QZ34C
(SEQ ID NO: 7)
QETNPTENLYFQQKNMQCQRRFYEALHDPNLNEEQRNARIRSIRDDC (b) QZ34C-60
(SEQ ID NO: 8)
QTADNQKNMQCQRRFYEALHDPNLNEEQRNARIRSIRDDCSQSANLLAE
AQQLNDAQAPQA (c) QET-Z34C1
(SEQ ID NO: 9)
QETKNMQCQRRFYEALHDPNLNEEQRNARIRSIRDDC (d) QET-Z34C2
(SEQ ID NO: 10)
QETENKQCQRRFYEALHDPNLNEEQRNARIRSIRDDC (e) QET-Z34C3
(SEQ ID NO: 22)
QETENMQCQRRFYEALHDPNLNKEQRNARIRSIRDDC (f) QET-Z34C4
(SEQ ID NO: 23)
QETENMQCQRRFYEALHDPNLNEEQRNARIRSIKDDC (1-3) Expression of Modified Protein A Expression of these modified proteins A was examined using Corynex (registered trademark). In expression using Corynex (registered trademark), a CspB fusion method (WO 2013/062029, which is incorporated herein by reference in its entirety), that is, a technique capable of improving the secretory production amount of a target protein by inserting a base sequence encoding an amino acid sequence comprising N-terminal three residues Gln-Glu-Thr (QET) of a CspB mature protein between a base sequence encoding a signal peptide and a base sequence encoding a target protein was utilized. In addition, since an N-terminal of a CspB tag is Q, there is an advantage that Q at the first residue can be pyroglutamylated to protect the N-terminal amino group after cleavage of the signal sequence. In particular, for QET-Z34C1 and QET-Z34C2, by using these findings, highly secreted expression of modified proteins A has succeeded while additional sequences are minimized. That is, in addition to the rules A) and B) above, it is effective to consider the rule C) below in expression of an affinity protein using Corynex (registered trademark).

C) Three residues of QET are added to an N-terminal to improve secretory efficiency using Corynex (registered trademark).

Hereinafter, Examples of expression studies using Corynex (registered trademark) will be described.

(1-4) Construction of Secretory Expression Plasmids of CspB6Tev-QZ34C, QZ34C-60, QET-Z34C1, and QET-Z34C2

As modified proteins A (modified Z34C), the above four types of amino acid sequences of CspB6Tev-QZ34C, QZ34C-60, QET-Z34C1, and QET-Z34C2 were designed, and base sequences encoding these proteins were designed in consideration of codon usage frequency of *C. glutamicum*. Furthermore, the following expression cassettes were designed so as to make secretory expression by *C. glutamicum* possible.

CspB6Tev-QZ34C is a fusion protein of a signal peptide 30 amino acid residue of CspB derived from *C. glutamicum* ATCC13869 strain, an N-terminal 6 amino acid residue QETNPT (SEQ ID NO: 11) of CspB mature protein derived from *C. glutamicum* ATCC13869 strain, a recognition sequence ENLYFQ (SEQ ID NO: 12) of proTev protease, and QZ34C (hereinafter referred to as "CspBss-CspB6Tev-QZ34C"). The designed base sequence encoding CspBss-CspB6Tev-QZ34C and the amino acid sequence thereof are illustrated in SEQ ID NOs: 13 and 14, respectively. Since CspB6Tev-QZ34C is cleaved with proTev protease after secretory expression to remove a CspB6Tev sequence QETNPTENLYFQ (SEQ ID NO: 15), it is possible to obtain a protein of QZ34C.

Base sequence encoding CspBss-CspB6Tev-QZ34C
(SEQ ID NO: 13)
atgtttaacaaccgtatccgcactgcagctctcgctggtgcaatcgcaa
tctccaccgcagcttccggcgtagctatcccagcattcgctcaggagac
caacccaaccgagaacctgtacttccagcagaagaacatgcagtgtcag
cgtcgcttctacgaggccctccacgaccctaacctcaacgaggaacagc
gtaacgcgcgtattcgctccatccgcgatgactgctaa Amino acid sequence of CspBss-CspB6Tev-QZ34C
(SEQ ID NO: 14)
MENNRIRTAALAGAIAISTAASGVAIPAFAQETNPTENLYFQQKNMQCQ
RRFYEALHDPNLNEEQRNARIRSIRDDC QZ34C-60 is a fusion protein of a signal peptide 25 amino acid residue of CspA derived from *C. ammoniagenes* ATCC6872 strain and QZ34C-60 (hereinafter referred to as "CspAss-QZ34C-60"). The designed base sequence encoding CspAss-QZ34C-60 and the amino acid sequence thereof are illustrated in SEQ ID NOs: 16 and 17, respectively.

Base sequence encoding CspAss-QZ34C-60
(SEQ ID NO: 16)
atgaaacgcatgaaatcgctggctgcggcgctcaccgtcgctggggcca
tgctggccgcacctgtggcaacggcacagaccgcagacaaccagaagaa
catgcagtgtcagcgtcgcttctacgaggccctccacgaccctaacctc
aacgaggaacagcgtaacgcgcgtattcgctccatccgcgatgactgct
cccagtccgcaaacctcctcgcagaggcacagcagctcaacgacgcaca
ggcaccacaggcataa Amino acid sequence of CspAss-QZ34C-60
(SEQ ID NO: 17)
MKRMKSLAAALTVAGAMLAAPVATAQTADNQKNMQCQRRFYEALHDPNL
NEEQRNARIRSIRDDCSQSANLLAEAQQLNDAQAPQA QET-Z34C1 is a fusion protein of a signal peptide 30 amino acid residue of CspB derived from *C. glutamicum* ATCC13869 strain, an N-terminal 3 amino acid residue QET of CspB mature protein derived from *C. glutamicum* ATCC13869 strain, and Z34C1 (hereinafter referred to as "CspBss-QET-Z34C1"). The designed base sequence encoding CspBss-QET-Z34C1 and the amino acid sequence thereof are illustrated in SEQ ID NOs: 18 and 19, respectively.

Base sequence encoding CspBss-QET-Z34C1
(SEQ ID NO: 18)
atgtttaacaaccgtatccgcactgcagctctcgctggtgcaatcgcaa
tctccaccgcagcttccggcgtagctatcccagcattcgctcaggagac
caagaacatgcagtgtcagcgtcgcttctacgaggccctccacgaccct
aacctcaacgaggaacagcgtaacgcgcgtattcgctccatccgcgatg
actgctaa Amino acid sequence of CspBss-QET-Z34C1
(SEQ ID NO: 19)
MFNNRIRTAALAGAIAISTAASGVAIPAFAQETKNMQCQRRFYEALHDP
NLNEEQRNARIRSIRDDC QET-Z34C2 is a fusion protein of a signal peptide 30 amino acid residue of CspB derived from *C. glutamicum* ATCC13869 strain, an N-terminal 3 amino acid residue QET of CspB mature protein derived from *C. glutamicum* ATCC13869 strain, and Z34C2 (hereinafter referred to as "CspBss-QET-Z34C2"), and a base sequence encoding the fusion protein was designed. The designed base sequence encoding CspBss-QET-Z34C2 and the amino acid sequence thereof are illustrated in SEQ ID NOs: 20 and 21, respectively.

Base sequence encoding CspBss-QET-Z34C2
(SEQ ID NO: 20)
atgtttaacaaccgtatccgcactgcagctctcgctggtgcaatcgcaa
tctccaccgcagcttccggcgtagctatcccagcattcgctcaggagac
cttcaacaagcagtgtcagcgtcgcttctacgaggccctccacgaccct
aacctcaacgaggaacagcgtaacgcgcgtattcgctccatccgcgatg
actgctaa Amino acid sequence of CspBss-QET-Z34C2
(SEQ ID NO: 21)
MENNRIRTAALAGAIAISTAASGVAIPAFAQETENKQCQRRFYEALHDP
NLNEEQRNARIRSIRDDC Expression cassettes of four types of protein A variants were designed in each of which a promoter of a cspB gene derived from *C. glutamicum* ATCC13869 strain was coupled with each of upstream sides of the base sequences described in CspBss-CspB6Tev-QZ34C, CspAss-QZ34C-60, CspBss-QET-Z34C1, and CspBss-QET-Z34C2, and a KpnI site was added to the 5'-side and a BamHI site was added to the 3'-side, and total synthesis was performed. By inserting the totally synthesized DNA fragments (expression cassettes of modified proteins A) into the KpnI-BamHI site of pPK4 described in JP 9-322774 A, pPK4_CspBss-CspB6Tev-QZ34C, pPK4 CspAss-QZ34C-60, pPK4 CspBss-QET-Z34C1, and pPK4_CspBss-QET-Z34C2, which are secretory expression plasmids of modified proteins A, were constructed, respectively. As a result of determining the base sequences of the inserted fragments, it was determined that the expression cassettes of modified proteins A as designed were constructed, respectively. The base sequence was determined using BigDye® Terminator v3.1 Cycle Sequencing Kit (Applied Biosystems) and 3130 Genetic Analyzer (Applied Biosystems).

(1-5) Secretory Expression of Each Modified Protein a in *C. glutamicum*

Using pPK4 CspBss-CspB6Tev-QZ34C, pPK4 CspAss-QZ34C-60, pPK4_CspBss-QET-Z34C1, and pPK4_CspBss-QET-Z34C2 constructed above, *C. glutamicum* YDK010::phoS (W302C) strain described in WO2016/171224 was transformed to obtain YDK010::phoS (W302C)/pPK4_CspBss-CspB6Tev-QZ34C strain, YDK010::phoS (W302C)/pPK4_CspAss-QZ34C-60 strain, YDK010::phoS (W302C)/pPK4_CspBss-QET-Z34C1 strain, and YDK010::phoS (W302C)/pPK4_CspBss-QET-Z34C2 strain. *C. glutamicum* YDK010::phoS (W302C) strain was obtained by substituting a wild-type phoS gene of *C. glutamicum* YDK010 described in WO2002/081694 with a variant type phoS (W302C) gene. The variant type phoS (W302C) gene encodes a PhoS protein (W302C) in which a tryptophan residue at position 302 is substituted with a cysteine residue. YDK010 strain is lacking a cell surface protein PS2 (CspB) of *C. glutamicum* AJ12036 strain (FERM BP-734). AJ12036 strain was originally deposited as an international deposit on Mar. 26, 1984 at the Institute of Microbial Industry Technology, Institute of Industrial Technology (currently, Patent Organism Depositary Center, National Institute of Technology and Evaluation, Postal Code: 292-0818, Address: Room 120, Kazusakamatari 2-5-8, Kisarazu City, Chiba Prefecture, Japan), and has been given the deposit number FERM BP-734.

Each of the obtained transformants was cultured at 30° C. for 72 hours in an MMTG liquid medium comprising 25 mg/L canamycin (120 g of glucose, 3 g of magnesium sulfate heptahydrate, 30 g of ammonium sulfate, 1.5 g of potassium dihydrogen phosphate, 0.03 g of iron sulfate heptahydrate, 0.03 g of manganese sulfate pentahydrate, 0.45 mg of thiamine hydrochloride, 0.45 mg of biotin, 0.15 g of DL-methionine, soybean hydrochloric acid hydrolyzate (total nitrogen amount 0.2 g), and 50 g of calcium carbonate, the total volume of which was set to 1 L with water, and the pH of which was adjusted to pH 7.0).

Figure 5:
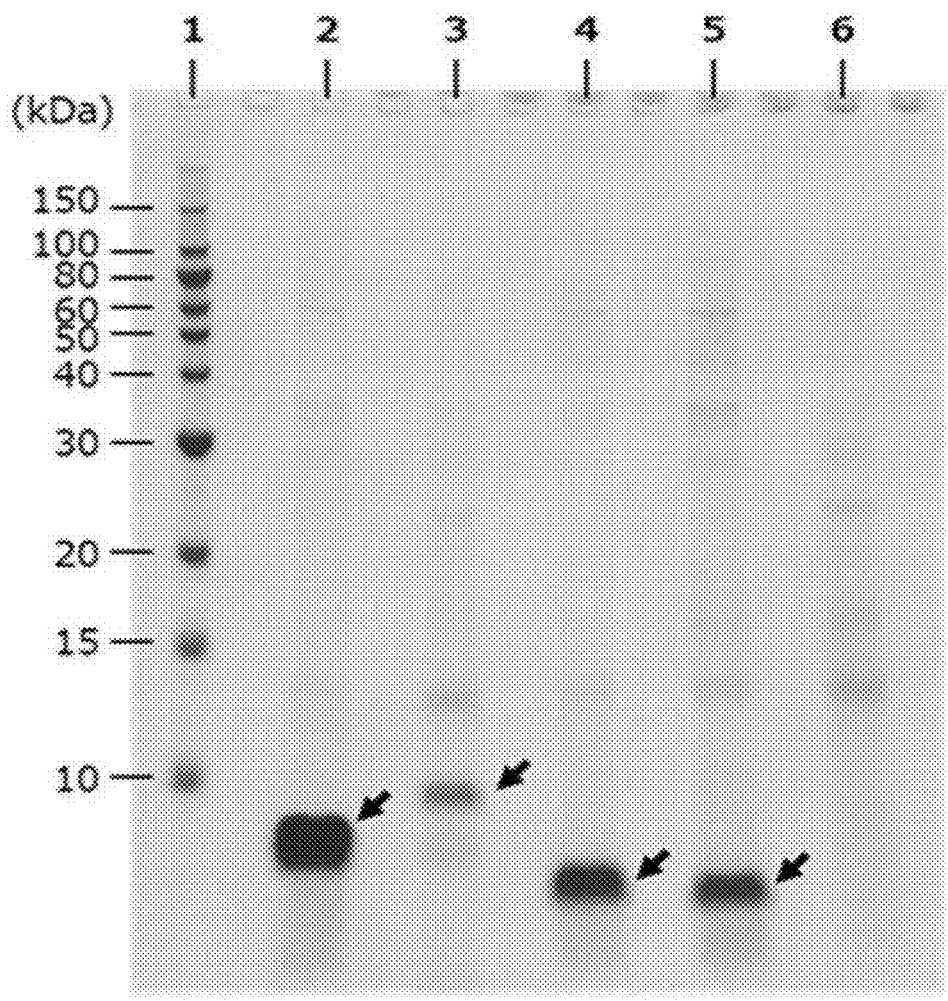
FIG. 5 is a diagram illustrating secretory expression of each modified protein A in *C. glutamicum*. Lane 1: Molecular weight marker; Lane 2: Protein band estimated to be CspB6Tev-QZ34C; Lane 3: Protein band estimated to be QZ34C-60; Lane 4: Protein band estimated to be QET-Z34C1; Lane 5: Protein band estimated to be QET-Z34C2

After completion of the culture, 6.5 µL of the culture supernatant obtained by centrifuging each of the culture solutions was subjected to reducing SDS-PAGE, and then stained with Quick-CBB (Wako). As a result, a protein band estimated to be CspB6Tev-QZ34C (FIG. 5, Lane 2) was detected in the culture supernatant of YDK010::phoS (W302C)/pPK4_CspBss-CspB6Tev-QZ34C strain, a protein band estimated to be QZ34C-60 (FIG. 5, Lane 3) was detected in the culture supernatant of YDK010::phoS (W302C)/pPK4_CspAss-QZ34C-60 strain, a protein band estimated to be QET-Z34C1 (FIG. 5, Lane 4) was detected in the culture supernatant of YDK010::phoS(W302C)/pPK4_CspBss-QET-Z34C1 strain, and a protein band estimated to be QET-Z34C2 (FIG. 5, Lane 5) was detected in the culture supernatant of YDK010::phoS(W302C)/pPK4_CspBss-QET-Z34C2 strain.

(1-6) Construction of Secretory Expression Plasmids of QET-Z34C3 and QET-Z34C4 As modified proteins A (modified Z34C), the above two types of amino acid sequences of QET-Z34C3 and QET-Z34C4 were designed, and base sequences encoding these proteins were designated in consideration of codon usage frequency of *C. glutamicum*. Furthermore, the following expression cassettes were designed so as to make secretory expression by *C. glutamicum* possible.

QET-Z34C3 is a fusion protein of a signal peptide 30 amino acid residue of CspB derived from *C. glutamicum* ATCC13869 strain, an N-terminal 3 amino acid residue QET of CspB mature protein derived from *C. glutamicum* ATCC13869 strain, and Z34C3 (hereinafter referred to as "CspBss-QET-Z34C3"). The designed base sequence encoding CspBss-QET-Z34C3 and the amino acid sequence thereof are illustrated in SEQ ID NOs: 55 and 56, respectively.

Base sequence encoding CspBss-QET-Z34C3
(SEQ ID NO: 55)
atgtttaacaaccgtatccgcactgcagctctcgctggtgcaatcgcaa
tctccaccgcagcttccggcgtagctatcccagcattcgctcaggagac
cttcaacatgcagtgtcagcgtcgcttctacgaggccctccacgaccct
aacctcaacaaggaacagcgtaacgcgcgtattcgctccatccgcgatg
actgctaa Amino acid sequence of CspBss-QET-Z34C3
(SEQ ID NO: 56)
MENNRIRTAALAGAIAISTAASGVAIPAFAQETENMQCQRRFYEALHDP
NLNKEQRNARIRSIRDDC QET-Z34C4 is a fusion protein of a signal peptide 30 amino acid residue of CspB derived from *C. glutamicum* ATCC13869 strain, an N-terminal 3 amino acid residue QET of CspB mature protein derived from *C. glutamicum* ATCC13869 strain, and Z34C4 (hereinafter referred to as "CspBss-QET-Z34C4"). The designed base sequence encoding CspBss-QET-Z34C4 and the amino acid sequence thereof are illustrated in SEQ ID NOs: 57 and 58, respectively.

Base sequence encoding CspBss-QET-Z34C4
(SEQ ID NO: 57)
atgtttaacaaccgtatccgcactgcagctctcgctggtgcaatcgcaa
tctccaccgcagcttccggcgtagctatcccagcattcgctcaggagac
cttcaacatgcagtgtcagcgtcgcttctacgaggccctccacgaccct
aacctcaacgaggaacagcgtaacgcgcgtattcgctccatcaaggatg
actgctaa Amino acid sequence of CspBss-QET-Z34C4
(SEQ ID NO: 58)
MENNRIRTAALAGAIAISTAASGVAIPAFAQETENMQCQRRFYEALHDP
NLNEEQRNARIRSIKDDC Expression cassettes of protein A variants were designed in each of which a promoter of a cspB gene derived from *C. glutamicum* ATCC13869 strain was coupled with each of upstream sides of the base sequences described in CspBss-QET-Z34C3 and CspBss-QET-Z34C4, and a KpnI site was added to the 5'-side and a BamHI site was added to the 3'-side, and total synthesis was performed. By inserting the totally synthesized DNA fragments (expression cassettes of modified proteins A) into the KpnI-BamHI site of pPK4 described in JP 9-322774 A, pPK4_CspBss-QET-Z34C3 and pPK4_CspBss-QET-Z34C4, which are secretory expression plasmids of modified proteins A, were constructed, respectively. As a result of determining the base sequences of the inserted fragments, it was determined that the expression cassettes of modified proteins A as designed were constructed, respectively. The base sequence was determined using BigDye® Terminator v3.1 Cycle Sequencing Kit (Applied Biosystems) and 3130 Genetic Analyzer (Applied Biosystems).

(1-7) Secretory Expression of Each Modified Protein a in *C. glutamicum*

Using pPK4_CspBss-QET-Z34C3 and pPK4_CspBss-QET-Z34C4 constructed above, *C. glutamicum* YDK010:: phoS (W302C) strain described in WO 2016/171224 was transformed to obtain YDK010::phoS(W302C)/pPK4_CspBss-QET-Z34C3 strain and YDK010::phoS (W302C)/pPK4_CspBss-QET-Z34C4 strain.

Each of the obtained transformants was cultured at 30° C. for 72 hours in an MMTG liquid medium comprising 25 mg/L kanamycin.

Figure 24:
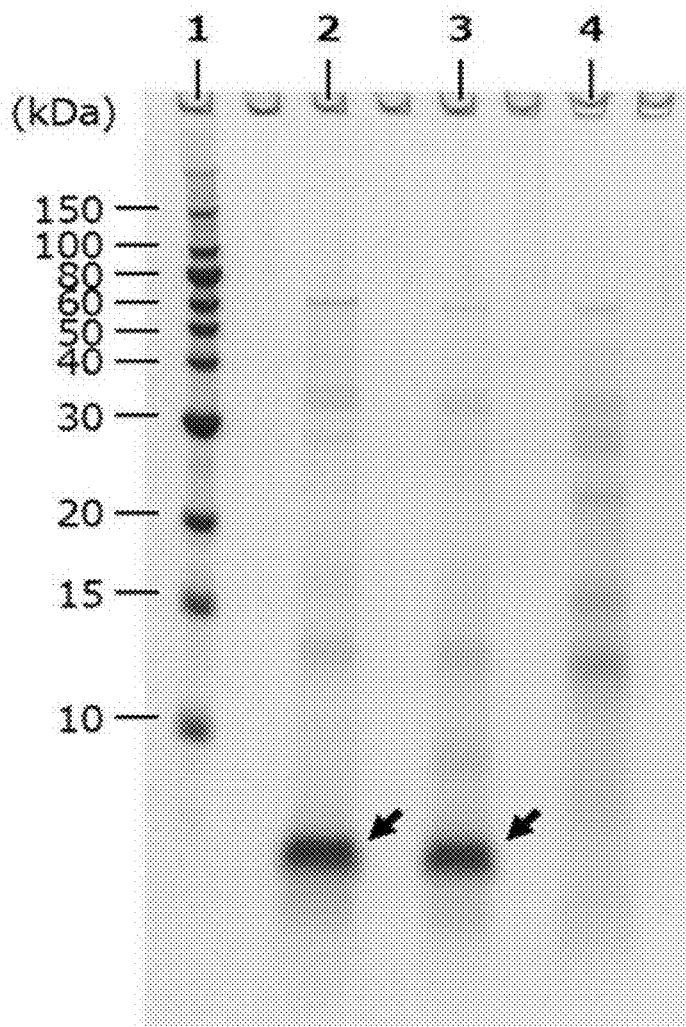
FIG. 24 is a diagram illustrating SDS-PAGE of secretory expression of each modified protein A (QET-Z34C3 and QET-Z34C4) in C. glutamicum.

After completion of the culture, 6.5 µL of the culture supernatant obtained by centrifuging each of the culture solutions was subjected to reducing SDS-PAGE, and then stained with Quick-CBB (Wako). As a result, a protein band estimated to be QET-Z34C3 (FIG. 24, Lane 2) was detected in the culture supernatant of YDK010::phoS(W302C)/pPK4_CspBss-QET-Z34C3 strain, and a protein band estimated to be QET-Z34C4 (FIG. 24, Lane 3) was detected in the culture supernatant of YDK010::phoS(W302C)/pPK4_CspBss-QET-Z34C4 strain.

Example 2. Design of Modified Fc-III and Secretory Expression Thereof in *C. glutamicum*

(2-1) Outline of Design of Modified Fc-III

As a peptide having ability to bind to human IgG, Fc-III consisting of an amino acid sequence of DCAWHLGELVWCT (SEQ ID NO: 54) has been reported (WO 2001/045746). The following modified Fc-III was designed by modifying Fc-III according to the rules A) and B) described in Example (1-1) and the rule C) described in Example (1-3).

(2-2) Preparation of Modified Fc-III

The following modified Fc-IIIs were prepared.

```
(g) QET-LV
                                      (SEQ ID NO: 24)
    QETRGNCAYHKGQLVWCTYH (h) QET-II
                                      (SEQ ID NO: 25)
    QETRGNCAYHKGQIIWCTYH
```

(2-3) Construction of Secretory Expression Plasmids of QET-LV and QET-II

As modified Fc-IIIs, the above two types of amino acid sequences of QET-LV and QET-II were designed, and base sequences encoding these proteins were designated in consideration of codon usage frequency of *C. glutamicum*. Furthermore, the following expression cassettes were designed so as to make secretory expression by *C. glutamicum* possible.

QET-LV is a fusion protein of a signal peptide 30 amino acid residue of CspB derived from *C. glutamicum* ATCC13869 strain, an N-terminal 3 amino acid residue QET of CspB mature protein derived from *C. glutamicum* ATCC13869 strain, and LV (hereinafter referred to as "CspBss-QET-LV"). The designed base sequence encoding CspBss-QET-LV and the amino acid sequence thereof are illustrated in SEQ ID NOs: 59 and 60, respectively.

```
Base sequence encoding CspBss-QET-LV
                                      (SEQ ID NO: 59)
atgtttaacaaccgtatccgcactgcagctctcgctggtgcaatcgcaa
tctccaccgcagcttccggcgtagctatcccagcattcgctcaggagac
ccgcggcaactgcgcataccacaagggccagctggtgtggtgcacctac
cactaa Amino acid sequence of CspBss-QET-LV
                                      (SEQ ID NO: 60)
MFNNRIRTAALAGAIAISTAASGVAIPAFAQETRGNCAYHKGQLVWCTY
H
```

QET-II is a fusion protein of a signal peptide 30 amino acid residue of CspB derived from *C. glutamicum* ATCC13869 strain, an N-terminal 3 amino acid residue QET of CspB mature protein derived from *C. glutamicum* ATCC13869 strain, and II (hereinafter referred to as "CspBss-QET-II"). The designed base sequence encoding CspBss-QET-II and the amino acid sequence thereof are illustrated in SEQ ID NOs: 61 and 62, respectively.

Base sequence encoding CspBss-QET-II atgtttaacaa ccgtatccgcactgcagctctcgctggtgcaatcgcaatcc accgcagcttc cggcgtagctatcccagcattcgctcaggagacccgcggcaactgcgc atac cacaagggccagatcatctggtgcacctaccactaa (SEQ ID NO: 61)

Amino acid sequence of CspBss-QET-II MFNNRIR-TAALAGAIAISTAASGVAIPAFAQETRGNCAYHKG QIIWCTYH (SEQ ID NO: 62)

Expression cassettes of modified Fc-IIIs were designed in each of which a promoter of a cspB gene derived from *C. glutamicum* ATCC13869 strain was coupled with each of upstream sides of the base sequences described in CspBss-QET-LV and CspBss-QET-II, and a KpnI site was added to the 5'-side and a BamHI site was added to the 3'-side, and total synthesis was performed. By inserting the totally synthesized DNA fragments (expression cassettes of modified Fc-IIIs) into the KpnI-BamHI site of pPK4 described in JP 9-322774 A, pPK4 CspBss-QET-LV and pPK4 CspBss-QET-II, which are secretory expression plasmids of modified Fc-IIIs, were constructed, respectively. As a result of determining the base sequences of the inserted fragments, it was determined that the expression cassettes of modified Fc-IIIs as designed were constructed, respectively. The base sequence was determined using BigDye® Terminator v3.1 Cycle Sequencing Kit (Applied Biosystems) and 3130 Genetic Analyzer (Applied Biosystems).

(2-4) Secretory Expression of Each Modified Fc-III in *C. glutamicum*

Using pPK4 CspBss-QET-LV and pPK4 CspBss-QET-II constructed above, *C. glutamicum* YDK010::phoS (W302C) strain described in WO 2016/171224 was transformed to obtain YDK010::phoS(W302C)/pPK4 CspBss-QET-LV strain and YDK010::phoS(W302C)/pPK4 CspBss-QET-II strain.

Each of the obtained transformants was cultured at 30° C. for 72 hours in an MMTG liquid medium comprising 25 mg/L kanamycin.

After completion of the culture, 6.5 µL of the culture supernatant obtained by centrifuging each of the culture solutions, or 6.5 µL of the culture solution uniformly comprising the bacterial cells and the culture supernatant without centrifugation was subjected to reducing SDS-PAGE, and then stained with Quick-CBB (Wako). As a result, a band of a peptide estimated to be QET-LV was detected in the culture supernatant of YDK010::phoS (W302C)/pPK4 CspBss-QET-LV strain (FIG. 25, Lanes 2 and 3), and a band of a peptide estimated to be QET-LV was also detected similarly in the culture solution sample comprising the bacterial cells (FIG. 25, Lanes 7 and 8).

Figure 25:
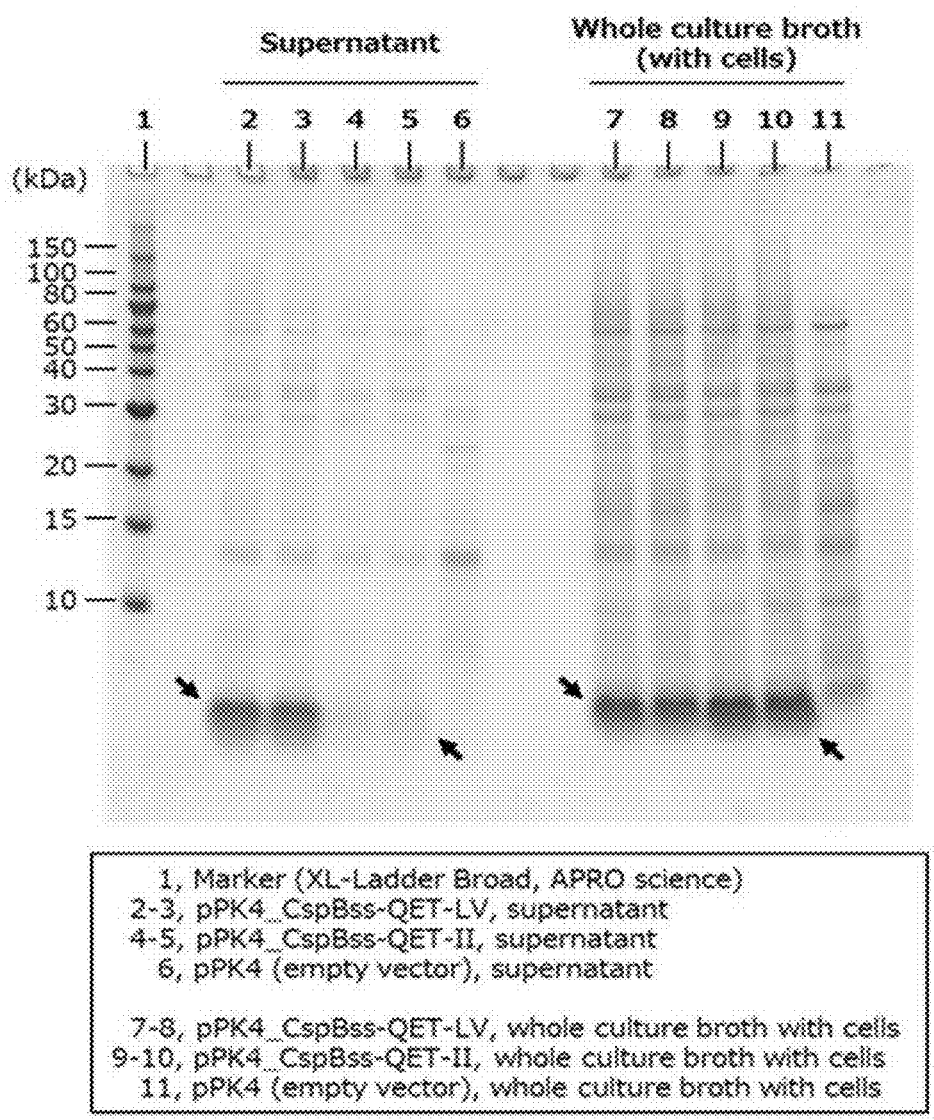
FIG. 25 is a diagram illustrating SDS-PAGE of secretory expression of each modified Fc-III (CspBss-QET-LV and CspBss-QET-II) in C. glutamicum.

In the culture supernatant of the YDK010::phoS (W302C)/pPK4_CspBss-QET-II strain, almost no band of peptide estimated to be QET-II was detected (FIG. 25, Lanes 4-5), while a band of peptides estimated to be QET-II was detected in the culture solution sample comprising the bacterial cells (FIG. 25, Lanes 9 and 10).

From the above results, it is considered that QET-LV is dissolved and present mainly in the culture supernatant after secretion, while QET-II is aggregated and present in the culture solution, or is adsorbed and present in a cell surface layer of the cultured bacterial cells after secretion.

Example 3. Preparation of Compound Having Affinity Substance to Antibody, Cleavable Portion, and Reactive Group The expressed protein was once purified by reverse phase preparative HPLC in order to remove contaminants in the culture solution. A disulfide linker was bound to the purified protein. Specifically, the above was performed as follows.

(3-1) Preparation of Compound Having Affinity Substance to Antibody (CspB6Tev-QZ34C), Cleavable Portion, and Reactive Group As the affinity substance to an antibody, CspB6Tev-QZ34C was used.

QETNPTENLYFQQKNMQCQRRFYEALHDPNLNE-EQRNARIRSIRDDC (SEQ ID NO: 7) (13.0 mg, 2.24 µmol, where the 18th and 47th cysteines form disulfide bonds in the molecule, respectively) was dissolved in N,N-dimethylformamide (0.40 mL). To the resulting solution, a solution obtained by dissolving 3,3'-dithiodipropionic acid di(N-succinimidyl) (18.0 mg, 44.8 µmol) in N,N-dimethylformamide (0.40 mL) was added, and the resulting mixture was stirred at room temperature for 24 hours. The resulting solution was concentrated under reduced pressure to remove acetonitrile. Thereafter, the resulting residue was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05% trifluoroacetic acid. Each fraction was determined by LC-MS. A fraction comprising a product was collected and concentrated under reduced pressure to remove acetonitrile. Thereafter, the resulting residue was freeze-dried to obtain the above expressed protein- and disulfide linker-coupled NHS-activation compound (0.50 mg, 0.08 mol).

(3-2) Preparation of Compound Having Affinity Substance to Antibody (QZ34C-60), Cleavable Portion, and Reactive Group As the affinity substance to an antibody, QZ34C-60 was used. QTADNQKNMQCQRRFYEALHDPNLNEEQRNARI-RSIRDDCSQSANLLAEAQQLNDAQAP QA (SEQ ID NO: 8) (15.8 mg, 2.16 μmol, where the 11th and 40th cysteines form disulfide bonds in the molecule, respectively) was dissolved in N,N-dimethylformamide (0.40 mL). To the resulting solution, a solution obtained by dissolving 3,3'-dithiodipropionic acid di(N-succinimidyl) (17.5 mg, 43.2 μmol) in N,N-dimethylformamide (0.40 mL) was added, and the resulting mixture was stirred at room temperature for 24 hours. The resulting solution was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05% trifluoroacetic acid. Each fraction was determined by LC-MS. A fraction comprising a product was collected and concentrated under reduced pressure to remove acetonitrile. Thereafter, the resulting residue was freeze-dried to obtain the above expressed protein- and disulfide linker-coupled NHS-activation compound (5.20 mg, 0.71 gmol).

(3-3) Preparation of Compound Having Affinity Substance to Antibody (QET-Z34C1), Cleavable Portion, and Reactive Group As the affinity substance to an antibody, QET-Z34C1 was used. QETKNMQCQRRFYEALHDPNLNEEQRNARIR-SIRDDC (SEQ ID NO: 9) (6.70 mg, 1.46 mol, where the 8th and 37th cysteines form disulfide bonds in the molecule, respectively) was dissolved in N,N-dimethylformamide (0.40 mL). To the resulting solution, a solution obtained by dissolving 3,3'-dithiodipropionic acid di(N-succinimidyl) (11.8 mg, 29.2 μmol) in N,N-dimethylformamide (0.20 mL) was added, and the resulting mixture was stirred at room temperature for 24 hours. The resulting solution was concentrated under reduced pressure to remove acetonitrile. Thereafter, the resulting residue was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05% trifluoroacetic acid. Each fraction was determined by LC-MS. A fraction comprising a product was collected and concentrated under reduced pressure to remove acetonitrile. Thereafter, the resulting residue was freeze-dried to obtain the above expressed protein- and disulfide linker-coupled NHS-activation compound (1.00 mg, 0.21 μmol).

(3-4) Preparation of Compound Having Affinity Substance to Antibody (QET-Z34C2), Cleavable Portion, and Reactive Group As the affinity substance to an antibody, QET-Z34C2 was used. QETFNKQCQRRFYEALHDPNLNEEQRNARIR-SIRDDC (SEQ ID NO: 10) (9.50 mg, 2.07 gmol, where the 8th and 37th cysteines form disulfide bonds in the molecule, respectively) was dissolved in N,N-dimethylformamide (0.20 mL). To the resulting solution, a solution obtained by dissolving 3,3'-dithiodipropionic acid di(N-succinimidyl) (33.0 mg, 82.8 μmol) in N,N-dimethylformamide (0.40 mL) was added, and the resulting mixture was stirred at room temperature for 24 hours. The resulting solution was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05% trifluoroacetic acid. Each fraction was determined by LC-MS. A fraction comprising a product was collected and concentrated under reduced pressure to remove acetonitrile. Thereafter, the resulting residue was freeze-dried to obtain the above expressed protein- and disulfide linker-coupled NHS-activation compound (0.90 mg, 0.18 μmol).

Example 4. Preparation of Antibody Having Affinity Substance to Antibody (CspB6Tev-QZ34C) and Cleavable Portion The anti-HER2 antibody trastuzumab was specifically modified by a conjugation reaction with the compound prepared in (3-1) above to prepare an antibody having an affinity substance to an antibody (CspB6Tev-QZ34C) and a cleavable portion. Then, the prepared antibody was analyzed.

(4-1) Specific Modification of Anti-HER2 IgG Antibody Trastuzumab and Analysis Thereof by ESI-TOFMS The peptide- and disulfide linker-coupled NHS-activation compound synthesized in (3-1) above was dissolved in N,N'-dimethylformamide to adjust the concentration to 21.6 mM. 500 μg of anti-HER2 IgG antibody trastuzumab (Chugai Pharmaceutical Co., Ltd.) was dissolved in 171 μL of 50 mM sodium acetate buffer (pH 5.5), 8.5 μL (10 equivalents to the antibody) of 4 mM peptide reagent was added thereto, and the resulting mixture was stirred at room temperature for one hour. The reaction solution was substituted with 100 mM sodium citrate buffer (pH 2.9) to stop the reaction, and further substituted with 20 mM PBS buffer. The mass was measured by ESI-TOFMS; for the raw material trastuzumab, a peak was observed at 148059, for a product with one binding peptide introduced, a peak was observed at 154033, and for a product with two binding peptides introduced, a peak was observed at 160000.

(4-2) Determination of Heavy Chain Selectivity of Specific Modified Compound of Trastuzumab Under Reduction Conditions by ESI-TOFMS Analysis To the antibody-peptide conjugate formed in (4-1) above, 5 μL of a 7 mM tris(2-carboxyethyl) phosphine hydrochloride solution (equivalent to the antibody) was added, and the resulting mixture was stirred at room temperature for 20 minutes. The mass was measured by ESI-TOFMS; for the raw material trastuzumab synthesized, heavy chain peaks were observed at 50594 and 50756, and a light chain peak was observed at 23439, whereas for the product, heavy chain peaks were observed at 50683 and 50845 with a thiopropionyl group introduced into the heavy chain, and a light chain peak was observed at 23439, the same as that of the raw material.

(4-3) HIC-UPLC Analysis of Specific Modification of Anti-HER2 IgG Antibody Trastuzumab The antibody-peptide conjugate formed in (4-1) above and the raw material antibody were analyzed by HIC. As the column, Protein-Pak Hi Res HIC Column (Waters) 4.6×100 mm 2.5 µm was used. Detection was performed by using A_Buffer: 0.1 M PiNa, 2.3 M $(NH_4)SO_4$, pH 7.0 and B_Buffer: 0.1 M PiNa at pH 7.0 at a flow rate of 0.6 ml/min at gradient A60% B40%→A0% B100% for 16 min (data collection 20 min) at a column temperature of 40° C. at a thermostat temperature of 40° C. at a detector wavelength of 280 nm.

Figure 6:
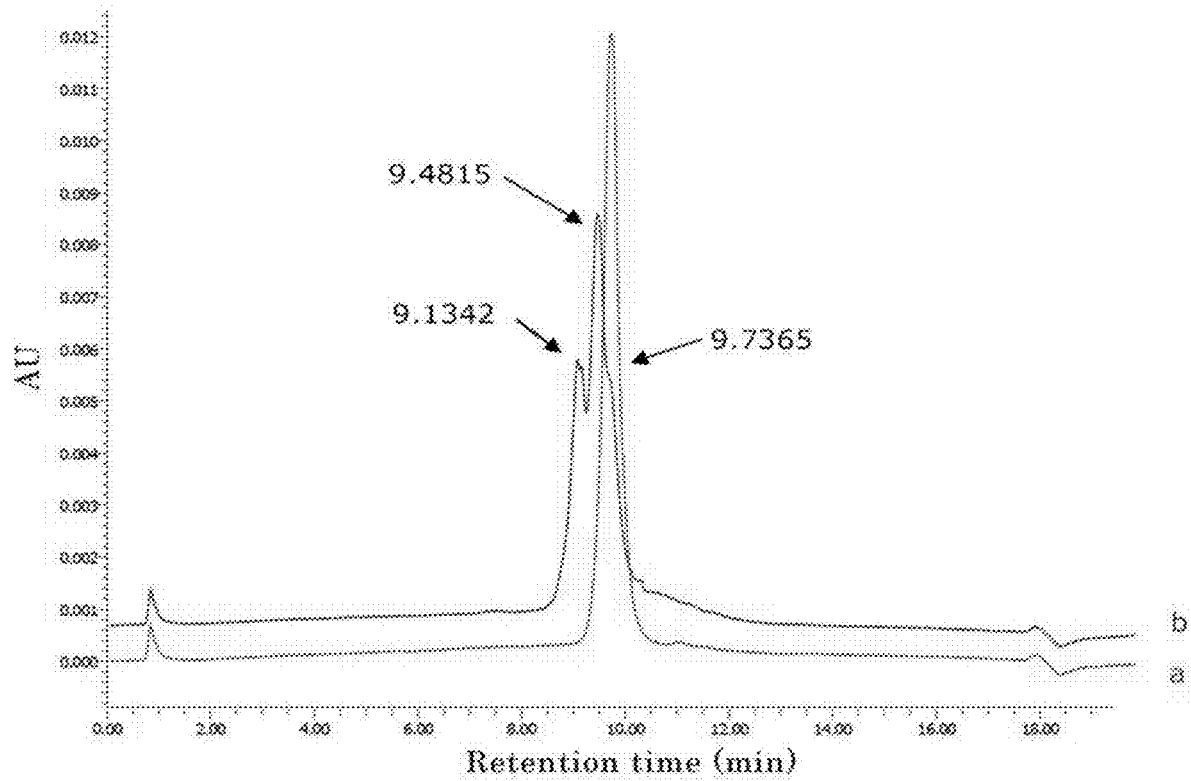
FIG. 6 is a diagram illustrating results of hydrophobic interaction chromatography (HIC)-UPLC analysis of specific modification of trastuzumab (detection wavelength: UV 280 nm) (Example 3). AU on the vertical axis indicates absorbance (the same applies in the following drawings).

A sample was reacted under the following conditions.
a: Trastuzumab raw material
b: Trastuzumab+10 equivalents of peptide- and disulfide linker-coupled NHS-activation compound As a result, the chromatogram of FIG. 6 was obtained. A compound having Retension Time of 9.7365 minutes is considered to be the trastuzumab raw material, a compound having Retension Time of 9.4815 minutes is considered to be a compound with one peptide introduced, and a compound having Retension Time of 9.1342 minutes is considered to be a compound with two peptides introduced (FIG. 6).

Example 5. Preparation of Antibody Having Affinity Substance to Antibody (QZ34C-60) and Cleavable Portion The anti-HER2 antibody trastuzumab was specifically modified by a conjugation reaction with the compound prepared in (3-2) above to prepare an antibody having an affinity substance to an antibody (QZ34C-60) and a cleavable portion. Then, the prepared antibody was analyzed.

(5-1) Specific Modification of Anti-HER2 IgG Antibody Trastuzumab and Analysis Thereof by ESI-TOFMS The peptide- and disulfide linker-coupled NHS-activation compound synthesized in (3-2) above was dissolved in N,N'-dimethylformamide to adjust the concentration to 1.8 mM. 500 µg of anti-HER2 IgG antibody trastuzumab (Chugai Pharmaceutical Co., Ltd.) was dissolved in 171 µL of 50 mM sodium acetate buffer (pH 5.5), 9.4 µL (10 equivalents to the antibody) of 1.8 mM peptide reagent was added thereto, and the resulting mixture was stirred at room temperature for one hour. The reaction solution was substituted with 100 mM sodium citrate buffer (pH 2.9) to stop the reaction, and further substituted with 20 mM PBS buffer. The mass was measured by ESI-TOFMS; for the raw material trastuzumab, a peak was observed at 148228, for a product with one binding peptide introduced, a peak was observed at 155416, and for a product with two binding peptides introduced, a peak was observed at 162595.

(5-2) Determination of Heavy Chain Selectivity of Specific Modified Compound of Trastuzumab Under Reduction Conditions by ESI-TOFMS Analysis To the antibody-peptide conjugate formed in (5-1) above, 5 µL of a 7 mM tris(2-carboxyethyl) phosphine hydrochloride solution (equivalent to the antibody) was added, and the resulting mixture was stirred at room temperature for 20 minutes. The mass was measured by ESI-TOFMS; for the raw material trastuzumab synthesized, heavy chain peaks were observed at 50596 and 50757, and a light chain peak was observed at 23440, whereas for the product, heavy chain peaks were observed at 50679 and 50844 with a thiopropionyl group introduced into the heavy chain, and a light chain peak was observed at 23440, the same as that of the raw material.

(5-3) HIC-UPLC Analysis of Specific Modification of Anti-HER2 IgG Antibody Trastuzumab The antibody-peptide conjugate formed in (5-1) above and the raw material antibody were analyzed by HIC. As the column, Protein-Pak Hi Res HIC Column (Waters) 4.6×100 mm 2.5 µm was used. Detection was performed by using A_Buffer: 0.1 M PiNa, 2.3 M $(NH_4)_2SO_4$, pH 7.0 and B_Buffer: 0.1 M PiNa at pH 7.0 at a flow rate of 0.6 ml/min at gradient A60% B40%→A0% B100% for 16 min (data collection 20 min) at a column temperature of 40° C. at a thermostat temperature of 40° C. at a detector wavelength of 280 nm.

Figure 7:
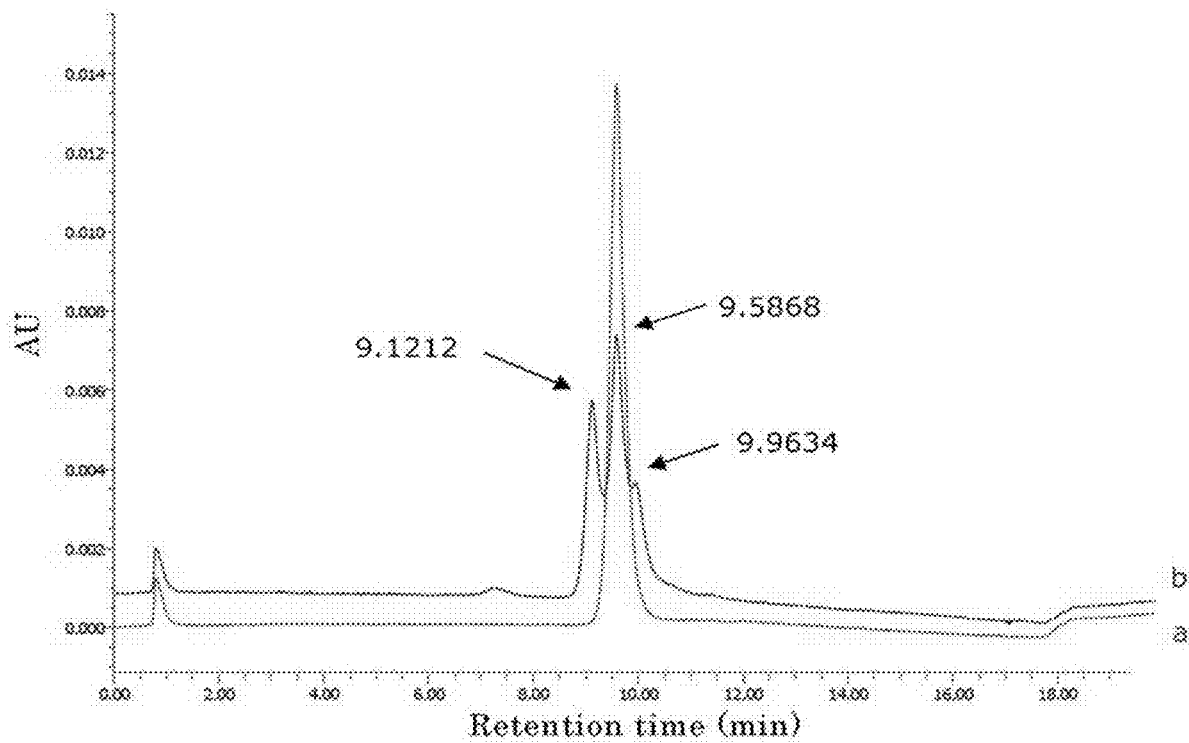
FIG. 7 is a diagram illustrating results of HIC-UPLC analysis of specific modification of trastuzumab (detection wavelength: UV 280 nm) (Example 4).

A sample was reacted under the following conditions.
a: Trastuzumab raw material
b: Trastuzumab+10 equivalents of peptide- and disulfide linker-coupled NHS-activation compound As a result, the chromatogram of FIG. 7 was obtained. A compound having Retension Time of 9.9634 minutes is considered to be the trastuzumab raw material, a compound having Retension Time of 9.5868 minutes is considered to be a compound with one peptide introduced, and a compound having Retension Time of 9.1212 minutes is considered to be a compound with two peptides introduced (FIG. 7).

Example 6. Preparation of Antibody Having Affinity Substance to Antibody (QET-Z34C1) and Cleavable Portion The anti-HER2 antibody trastuzumab was specifically modified by a conjugation reaction with the compound prepared in (3-3) above to prepare an antibody having an affinity substance to an antibody (QET-Z34C1) and a cleavable portion. Then, the prepared antibody was analyzed.

(6-1) Specific Modification of Anti-HER2 IgG Antibody Trastuzumab and Analysis Thereof by ESI-TOFMS The peptide- and disulfide linker-coupled NHS-activation compound synthesized in (3-3) above was dissolved in N,N'-dimethylformamide to adjust the concentration to 3.6 mM. 250 µg of anti-HER2 IgG antibody trastuzumab (Chugai Pharmaceutical Co., Ltd.) was dissolved in 84.4 µL of 50 mM sodium acetate buffer (pH 5.5), 4.7 µL (10 equivalents to the antibody) of 3.6 mM peptide reagent was added thereto, and the resulting mixture was stirred at room temperature for one hour. The reaction solution was substituted with 100 mM sodium citrate buffer (pH 2.9) to stop the reaction, and further substituted with 20 mM PBS buffer. The mass was measured by ESI-TOFMS; for the raw material trastuzumab, a peak was observed at 148226, for a product with one binding peptide introduced, a peak was observed at 151027, and for a product with two binding peptides introduced, a peak was observed at 153022.

(6-2) Determination of Heavy Chain Selectivity of Specific Modified Compound of Trastuzumab Under Reduction Conditions by ESI-TOFMS Analysis To the antibody-peptide conjugate formed in (6-1) above, 5 µL of a 7 mM tris(2-carboxyethyl) phosphine hydrochloride solution (equivalent to the antibody) was added, and the resulting mixture was stirred at room temperature for 20 minutes. The mass was measured by ESI-TOFMS; for the raw material trastuzumab synthesized, heavy chain peaks were observed at 50594 and 50756, and a light chain peak was observed at 23439, whereas for the product, heavy chain peaks were observed at 50681 and 50845 with a thiopropionyl group introduced into the heavy chain, and a light chain peak was observed at 23439, the same as that of the raw material.

(6-3) HIC-UPLC Analysis of Specific Modification of Anti-HER2 IgG Antibody Trastuzumab The antibody-peptide conjugate formed in (6-1) above and the raw material antibody were analyzed by HIC. As the column, Protein-Pak Hi Res HIC Column (Waters) 4.6×100 mm 2.5 m was used. Detection was performed by using A_Buffer: 0.1 M PiNa, 2.3 M $(NH_4)_2SO_4$, pH 7.0 and B_Buffer: 0.1 M PiNa at pH 7.0 at a flow rate of 0.6 ml/min at gradient A60% B40%→A0% B100% for 16 min (data collection 20 min) at a column temperature of 40° C. at a thermostat temperature of 40° C. at a detector wavelength of 280 nm.

Figure 8:
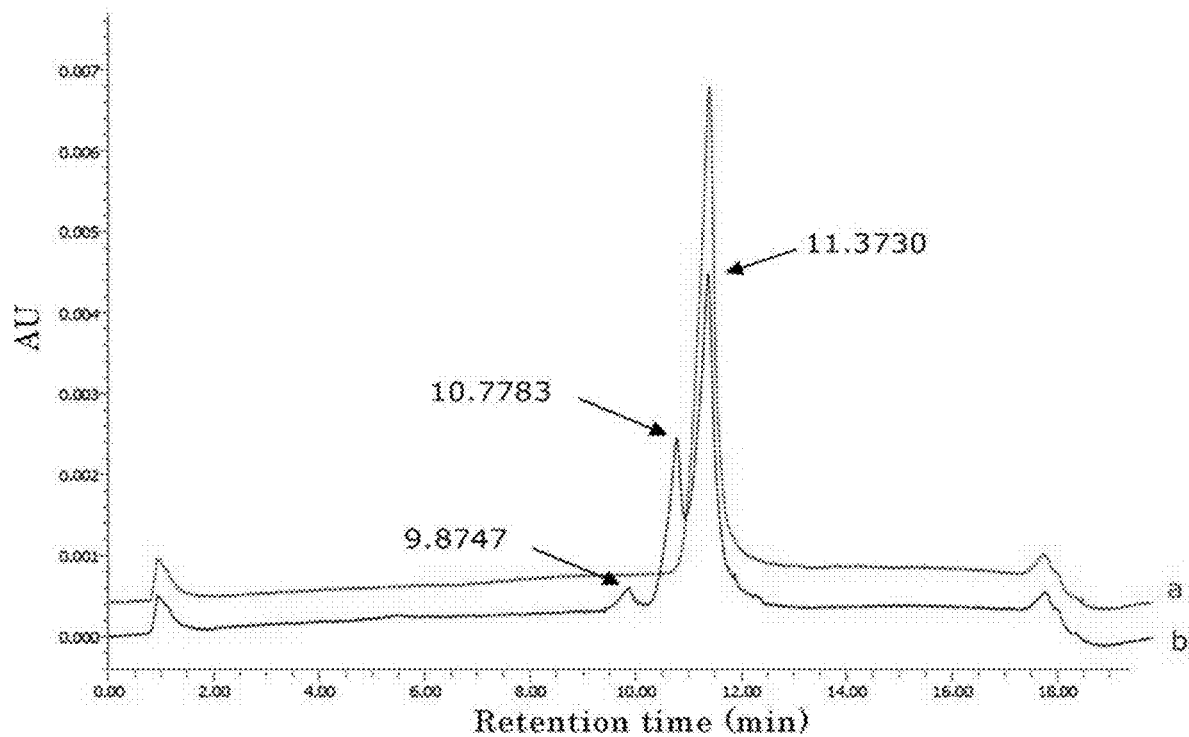
FIG. 8 is a diagram illustrating results of HIC-UPLC analysis of specific modification of trastuzumab (detection wavelength: UV 280 nm) (Example 5).

A sample was reacted under the following conditions.

a: Trastuzumab raw material b: Trastuzumab+10 equivalents of peptide- and disulfide linker-coupled NHS-activation compound As a result, the chromatogram of FIG. 8 was obtained. A compound having Retension Time of 11.3730 minutes is considered to be the trastuzumab raw material, a compound having Retension Time of 10.7783 minutes is considered to be a compound with one peptide introduced, and a compound having Retension Time of 9.8747 minutes is considered to be a compound with two peptides introduced (FIG. 8).

(6-4) Linker Cleavage and Reoxidation of Trastuzumab-Peptide Conjugate

By linker cleavage and reoxidation of the antibody-peptide conjugate obtained in (6-1) above, an antibody in which thiopropionyl groups are regioselectively introduced into Lys246 and Lys248 in EU numbering (that is, an antibody regioselectively having a bioorthogonal functional group or bioorthogonal functional groups) can be obtained.

Linker Cleavage

400 μg of the antibody-peptide conjugate was dissolved in 60 mM phosphate buffer (pH 8.0) to adjust the concentration to 72 μM. Then, 10.0 μL of 20 mM D,L-dithiothreitol (60 equivalents to the trastuzumab-peptide conjugate) was added thereto. The resulting mixture was stirred at room temperature for 16 hours to cleave a disulfide bond in the linker.

Reoxidation

Next, a reoxidation step is performed in order to re-bond the disulfide bond in the cleaved antibody along with the disulfide bond in the linker (Jagath R Junutula et al., NATURE BIOTECHNOLOGY, 26 (8), 925-932 (2008), which is incorporated herein by reference in its entirety). Specifically, the reaction solution is solvent-substituted with 9.57 mM PBS buffer (pH 7.0) using Amicon 10K to adjust the concentration of the trastuzumab-peptide conjugate to 18 μM. Then, 6.4 μL of 10 mM dehydroascorbic acid (20 equivalents to the trastuzumab-peptide conjugate) was added thereto. The resulting mixture was stirred at room temperature for three hours to perform reoxidation.

Example 7. Preparation of Antibody Having Affinity Substance to Antibody (QET-Z34C2) and Cleavable Portion The anti-HER2 antibody trastuzumab was specifically modified by a conjugation reaction with the compound prepared in (3-4) above to prepare an antibody having an affinity substance to an antibody (QET-Z34C2) and a cleavable portion. Then, the prepared antibody was analyzed.

(7-1) Specific Modification of Anti-HER2 IgG Antibody Trastuzumab and Analysis Thereof by ESI-TOFMS The peptide- and disulfide linker-coupled NHS-activation compound synthesized in (3-4) above was dissolved in N,N'-dimethylformamide to adjust the concentration to 9.2 mM. 1000 μg of anti-HER2 IgG antibody trastuzumab (Chugai Pharmaceutical Co., Ltd.) was dissolved in 200 μL of 20 mM sodium acetate buffer (pH 6.5), 20 μL (27 equivalents to the antibody) of 9.2 mM peptide reagent was added thereto, and the resulting mixture was stirred at room temperature for one hour. The reaction solution was substituted with 100 mM sodium citrate buffer (pH 2.9) to stop the reaction, and further substituted with 20 mM PBS buffer. The mass was measured by ESI-TOFMS; for the raw material trastuzumab, a peak was observed at 148234, for a product with one binding peptide introduced, a peak was observed at 152978, and for a product with two binding peptides introduced, a peak was observed at 157721.

(7-2) HIC-UPLC Analysis of Specific Modification of Anti-HER2 IgG Antibody Trastuzumab The antibody-peptide conjugate formed in (7-1) above and the raw material antibody were analyzed by HIC. As the column, Protein-Pak Hi Res HIC Column (Waters) 4.6×100 mm 2.5 μm was used. Detection was performed by using A_Buffer: 0.1 M PiNa, 2.3 M $(NH_4)_2SO_4$, pH 7.0 and B_Buffer: 0.1 M PiNa at pH 7.0 at a flow rate of 0.6 ml/min at gradient A60% B40%→A0% B100% for 16 min (data collection 20 min) at a column temperature of 40° C. at a thermostat temperature of 40° C. at a detector wavelength of 280 nm.

Figure 9:
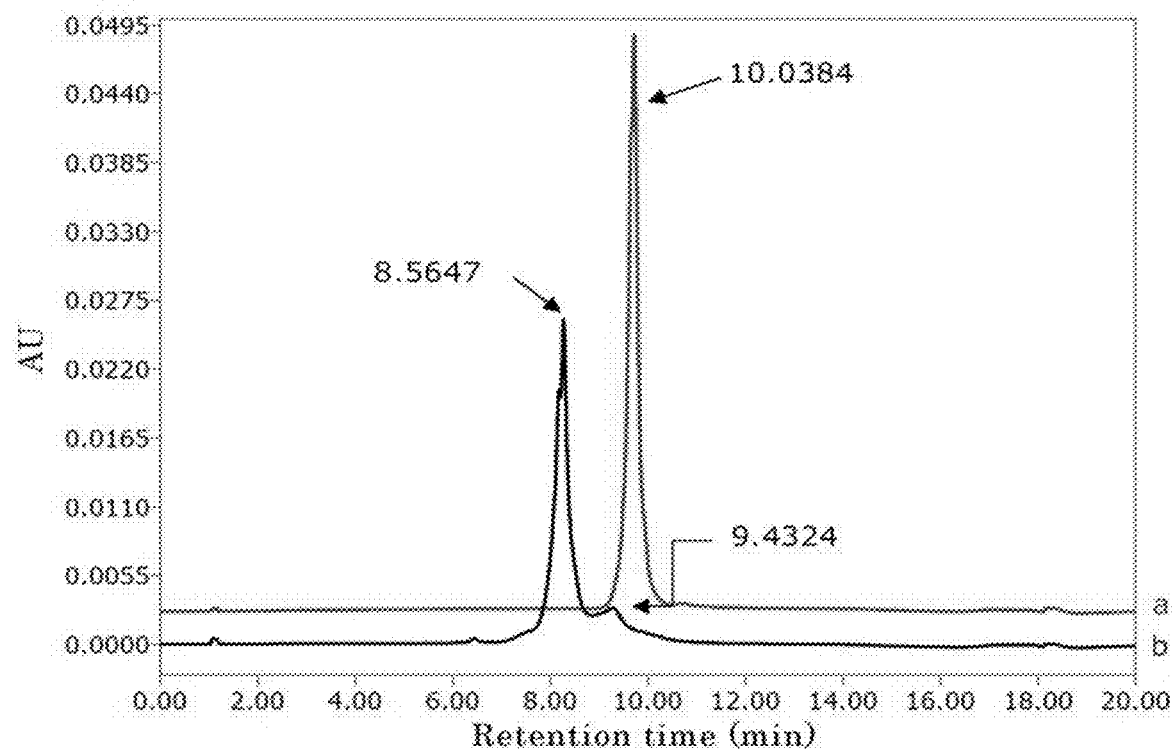
FIG. 9 is a diagram illustrating results of HIC-UPLC analysis of specific modification of trastuzumab (detection wavelength: UV 280 nm) (Example 6).

A sample was reacted under the following conditions.

a: Trastuzumab raw material b: Trastuzumab+27 equivalents of peptide- and disulfide linker-coupled NHS-activation compound As a result, the chromatogram of FIG. 9 was obtained. A compound having Retension Time of 10.0384 minutes is considered to be the trastuzumab raw material, a compound having Retension Time of 9.4324 minutes is considered to be a compound with one peptide introduced, and a compound having Retension Time of 8.5647 minutes is considered to be a compound with two peptides introduced (FIG. 9).

Example 8. Peptide Mapping by Trypsin Treatment of Thiol-Introduced Trastuzumab Prepared by Using Affinity Substance to Antibody (CspB6Tev-QZ34C)

(8-1) Trypsin Treatment of Thiol-Introduced Trastuzumab

The thiol-introduced trastuzumab obtained in (4-1) above was subjected to sugar chain cleavage with PNGaseF (manufactured by New England BioLabs), and then peptide mapping was performed. To a 1.5 mL low-adsorption micro test tube, 10 μL of a sample solution, a 50 mM ammonium hydrogencarbonate buffer, and 10 μL of a 20 mM aqueous dithiothreitol solution dissolved in 40% trifluoroethanol were added. The resulting mixture was heated at 65° C. for one hour, then 10 μL of a 50 mM aqueous iodoacetamide solution was added thereto, and the resulting mixture was reacted in a dark place at room temperature for 30 minutes. After the reaction, 40 μL of a 50 mM ammonium hydrogencarbonate buffer was added thereto, the resulting mixture was stirred, 10 μL of a 20 ng/μL aqueous trypsin solution was added thereto, and the resulting mixture was subjected to enzyme digestion at 37° C. for 16 hours. After the digestion, 2 μL of a 20% aqueous trifluoroacetic acid solution was added thereto to stop the reaction, and LC-MS/MS measurement was performed.

(8-2) LC-MS/MS Measurement Conditions for Trastuzumab Analyzer
  Nano HPLC: EASY-nLC 1000 (Thermo Fisher Scientific)
  Mass Spectrometer: Tribrid Mass Spectrometer Orbitrap Fusion (Thermo Fisher Scientific)
  HPLC Analysis Conditions
  Trap column: Acclaim PepMap (registered trademark) 100, 75 µm×2 cm, (Thermo Fisher Scientific)
  Analysis column: ESI-column (NTCC-360/75-3-125, 75 µm×12.5 cm, 3 µm (Nikkyo Technos Co., Ltd.))
  Mobile Phase A: a 0.1% aqueous formate solution
  Mobile Phase B: a 0.1% formate acetonitrile solution
  Loading solution: a 0.1% aqueous trifluoroacetic acid solution
  Flow rate: 300 nL/min
  Sample injection amount: 1 µL
  Gradient condition (B %): 2% (0.0 minute to 0.5 minute), 2%→30% (0.5 minute to 23.5 minutes), 30%→75% (23.5 minutes to 25.5 minutes), and 75% (25.5 minutes to 35.0 minutes).
  Mass Spectrometer Analysis Conditions
  Ionization: ESI, Positive mode
  Scan type: Data Dependent Acquisition
  Activation Type: Collision Induced Dissociation (CID)
  Data acquisition was performed using Xcalibur 3.0 (Thermo Fisher Scientific) and Thermo Orbitrap Fusion Tune Application 2.0 (Thermo Fisher Scientific) as accompanying software.

(8-3) Analysis Conditions for Modified Site of Trastuzumab
  Modified site analysis of an LC-MS/MS measurement result was performed using Proteome Discoverer version 1.4 (Thermo Fisher Scientific).
  For analysis with Proteome Discoverer, Sequest HT was used as a search engine, and a precursor ion range was set to 350 to 5000 Da, and Total Intensity Threshold was set to 0.01% of peak top intensity. Trypsin was set as a digestive enzyme, and Maximum Missed Cleavage Sites was set to 3. Values of Mass Tolerance of precursor and fragment ions were 5 ppm and 0.5 Da, respectively. For Static Modification, Carbamidomethyl (+57.021 Da) was set as modification of a cysteine residue with iodoacetamide. For Dynamic Modifications, oxidation of a methionine residue (+15.995 Da) and a modified compound to a lysine residue (thiol-introduced compound subjected to carbamidomethylation with iodoacetamide (+145.019 Da)) were set. Furthermore, a filter was set such that only those with High Peptide Confidence were observed.
  In addition, (1) and (3) illustrated in FIG. 4 were used as data of an amino acid sequence to be searched for a modification site.

Figures 1, 2:
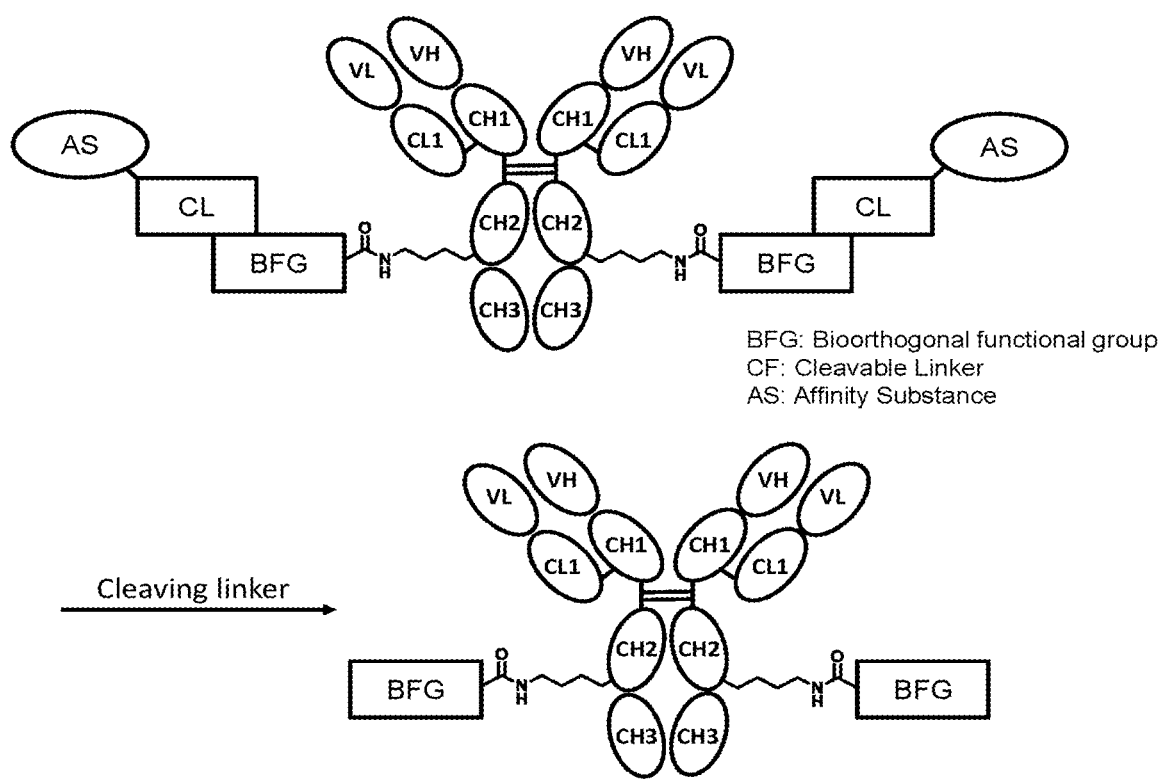
Figures 1, 2, 3:
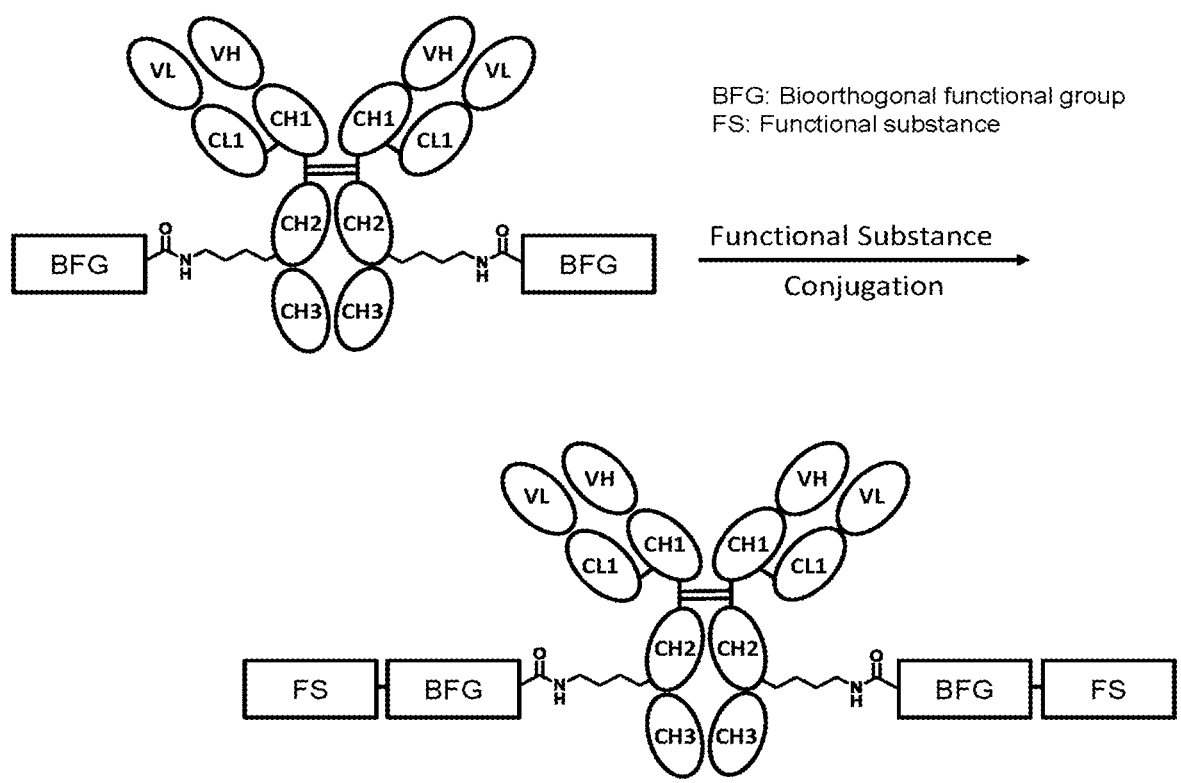
Figure 2:
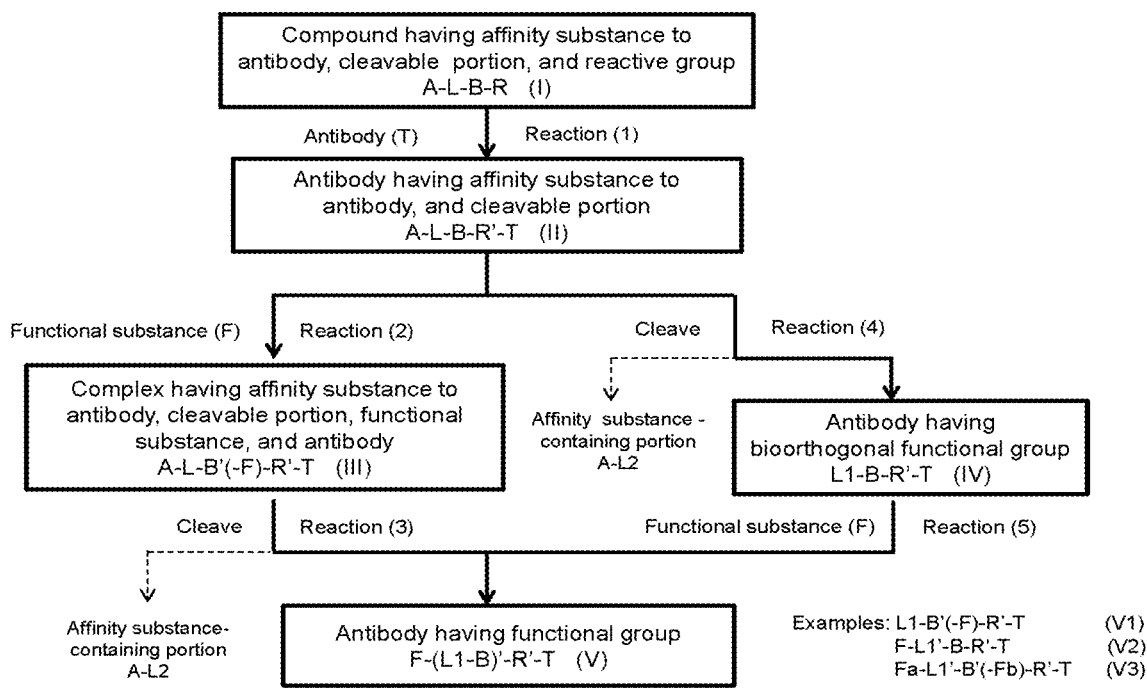
Figure 10:
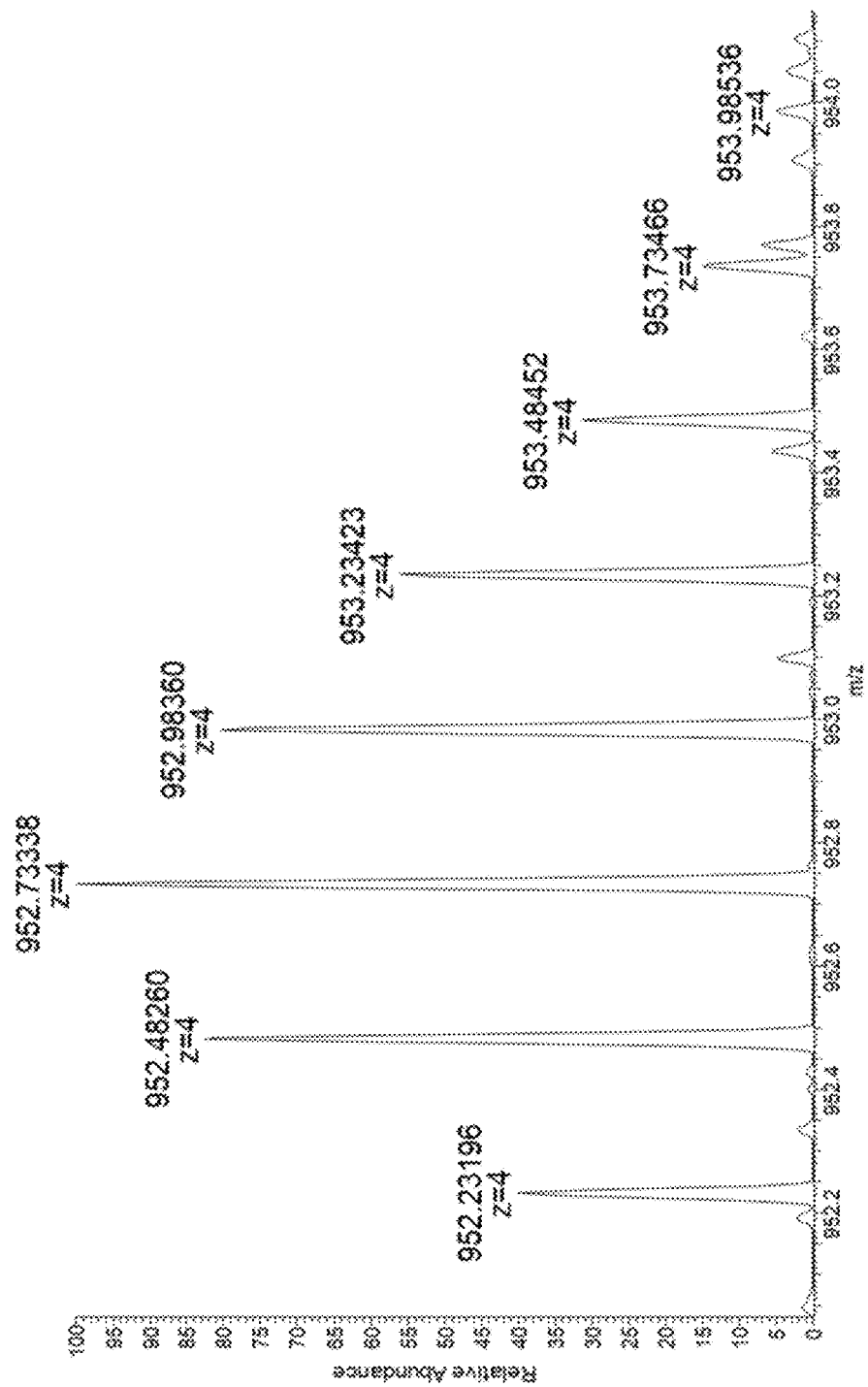
FIG. 10 is a diagram illustrating an MS spectrum of a peptide fragment of THTCPPCPAPELLGGPSV FLFPP KPKDTLMISR (SEQ ID NO: 26), which is a peptide consisting of 33 amino acid residues comprising a modified site to a lysine residue by trypsin digestion of trastuzumab (thiol-introduced compound (+145.019 Da) subjected to carbamidomethylation with iodoacetamide) (measured value: m/z 952.23196, theoretical value: 952.22900, tetravalent) (Example 7).
Figures 1, 11:
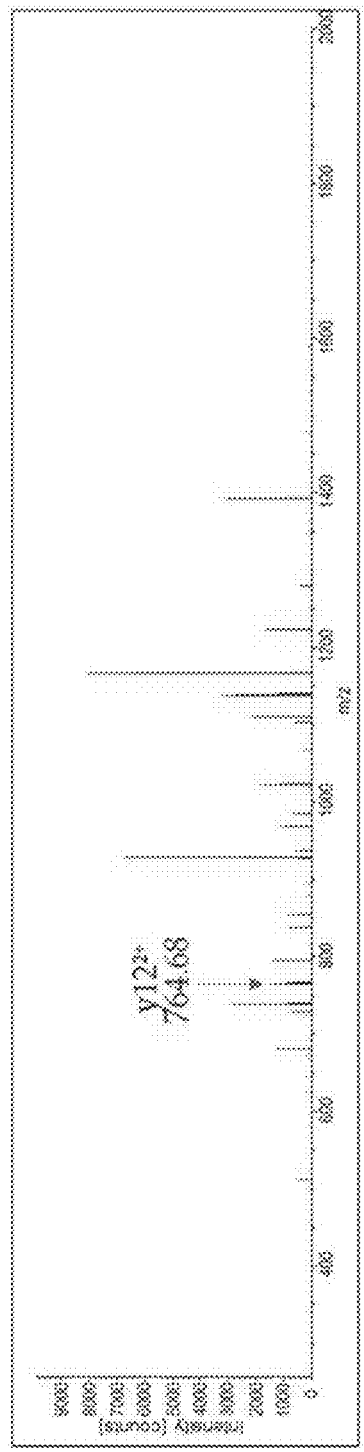
Figures 2, 11:
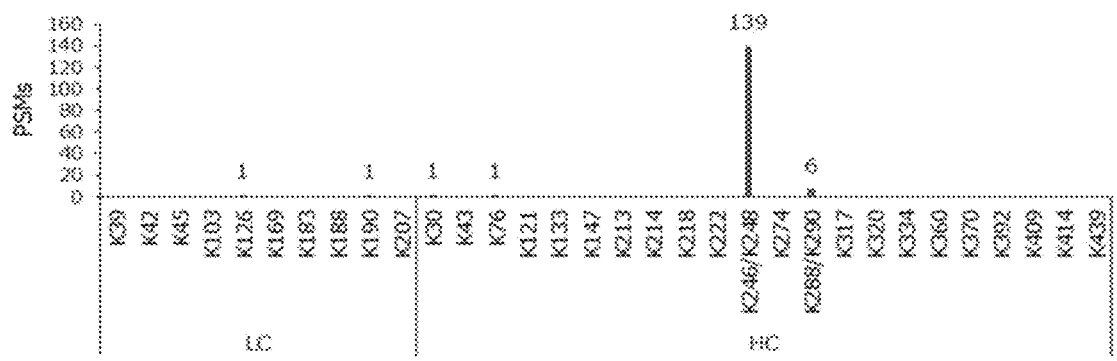

(8-4) Analysis Result of Modified Site of Trastuzumab by LC-MS/MS
  As a result of analysis using LC-MS/MS, an MS spectrum of a peptide fragment of THTCPPCPAPELLGGPSV FLFPPKPKDTLMISR (SEQ ID NO: 26), which is a peptide consisting of 33 amino acid residues comprising a modified site to a lysine residue by trypsin digestion of trastuzumab (thiol-introduced compound (+145.019 Da)) subjected to carbamidomethylation with iodoacetamide) (measured value: m/z 952.23196; theoretical value: 952.22900; tetravalent) was observed (FIG. 10); and from a CID spectrum, a product ion of m/z 764.68 (theoretical value: 764.40) corresponding to divalent y12 indicating modification of a lysine residue at position 246 or 248 of a heavy chain in EU numbering was determined (FIG. 11-1). In addition, analysis with Proteome Discoverer indicated that modification to a lysine residue at position 246 or 248 occurred highly selectively (FIG. 11-2).
  From this result, it was found that in (4-1) above, conjugation progressed regioselectively at Lys246 and Lys248 in EU numbering on the heavy chain of the antibody.

Example 9. Peptide Mapping by Trypsin Treatment of Thiol-Introduced Trastuzumab Prepared by Using Affinity Substance to Antibody (QZ34C-60)

Figure 12:
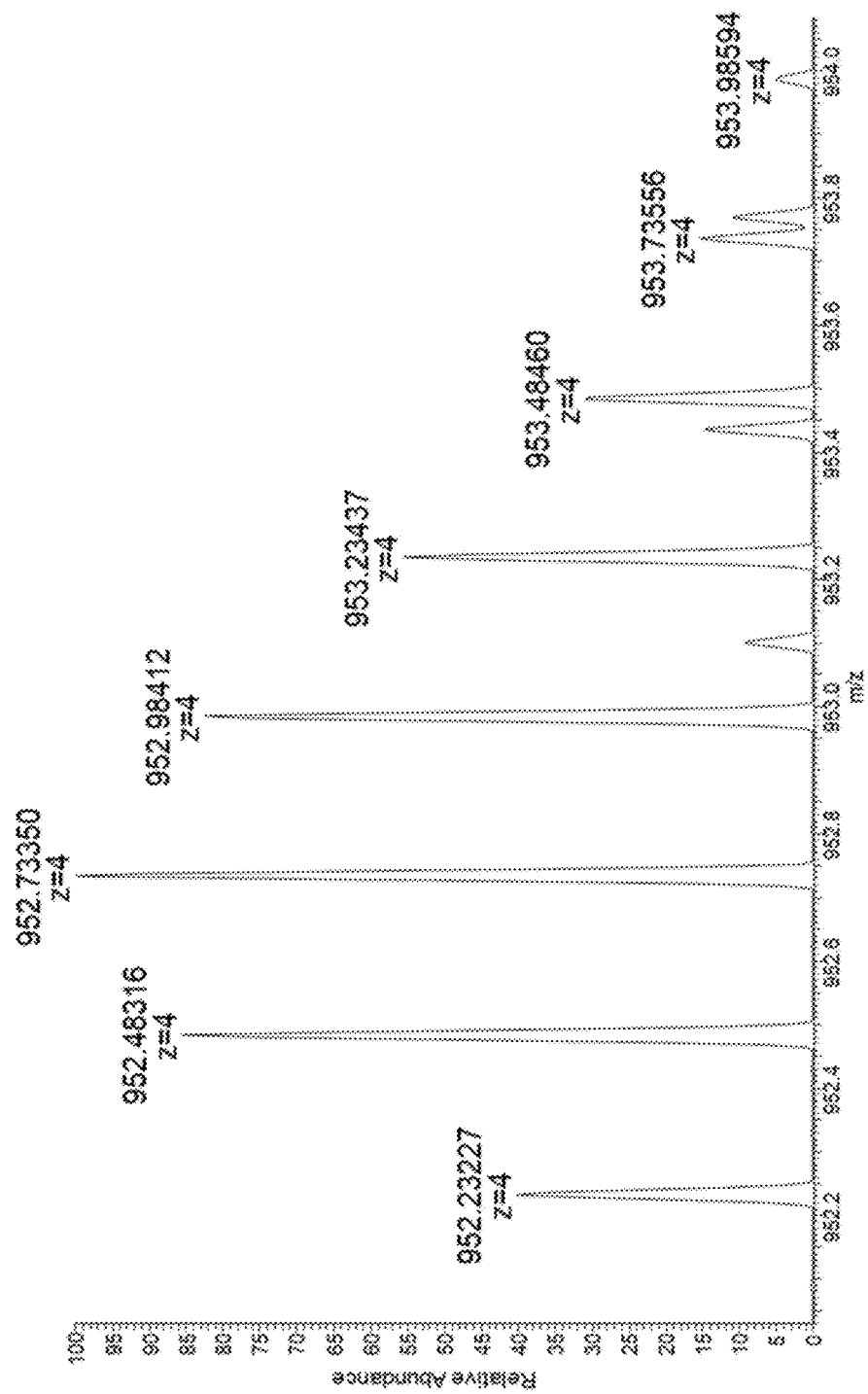
FIG. 12 is a diagram illustrating an MS spectrum of a peptide fragment of THTCPPCPAPELLGGPSVFL FPPKPKDTLMISR (SEQ ID NO: 26), which is a peptide consisting of 33 amino acid residues comprising a modified site to a lysine residue by trypsin digestion of trastuzumab (thiol-introduced compound (+145.019 Da) subjected to carbamidomethylation with iodoacetamide) (measured value: m/z 952.23227, theoretical value: 952.22900, tetravalent) (Example 8).
Figures 1, 13:
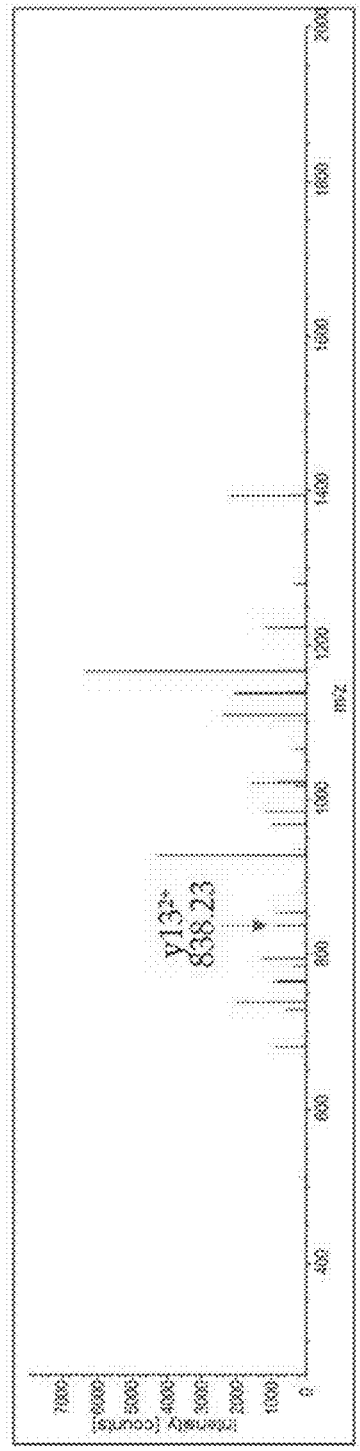
Figures 2, 13:
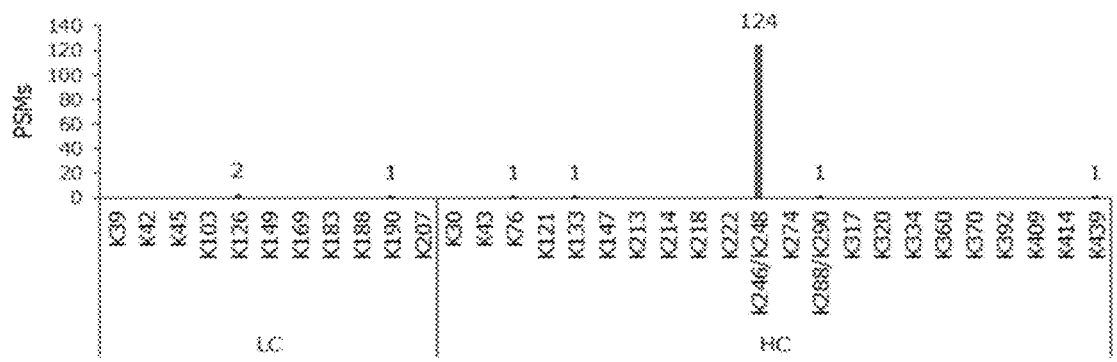

(9-1) Trypsin Treatment of Thiol-Introduced Trastuzumab
  The thiol-introduced trastuzumab obtained in (5-1) above was subjected to the same treatment as in (8-1) above, and then LC-MS/MS measurement was performed.
(9-2) LC-MS/MS Measurement Conditions for Trastuzumab
  Measuring device and measuring conditions for HPLC and mass spectrometry are the same as those in (8-2) above.
(9-3) Analysis Conditions for Modified Site of Trastuzumab
  Conditions for modification site analysis for an LC-MS/MS measurement result are the same as those in (8-3) above.
(9-4) Analysis Result of Modified Site of Trastuzumab by LC-MS/MS
  As a result of analysis using LC-MS/MS, an MS spectrum of a peptide fragment of THTCPPCPAPELLGG PSVFLFPPKPKDTLMISR (SEQ ID NO: 26), which is a peptide consisting of 33 amino acid residues comprising a modified site to a lysine residue by trypsin digestion of trastuzumab (thiol-introduced compound (+145.019 Da) subjected to carbamidomethylation with iodoacetamide) (measured value: m/z 952.23227; theoretical value: 952.22900; tetravalent) was observed (FIG. 12); and from a CID spectrum, a product ion of m/z 838.23 (theoretical value: 837.94) corresponding to divalent y13 indicating modification of a lysine residue at position 246 or 248 of a heavy chain in EU numbering was determined (FIG. 13-1). In addition, analysis with Proteome Discoverer indicated that modification to a lysine residue at position 246 or 248 occurred highly selectively (FIG. 13-2).
  From this result, it was found that in (5-1) above, conjugation progressed regioselectively at Lys246 and Lys248 in EU numbering on the heavy chain of the antibody.

Example 10. Peptide Mapping by Trypsin Treatment of Thiol-Introduced Trastuzumab Prepared by Using Affinity Substance to Antibody (QET-Z34C2)

Figure 14:
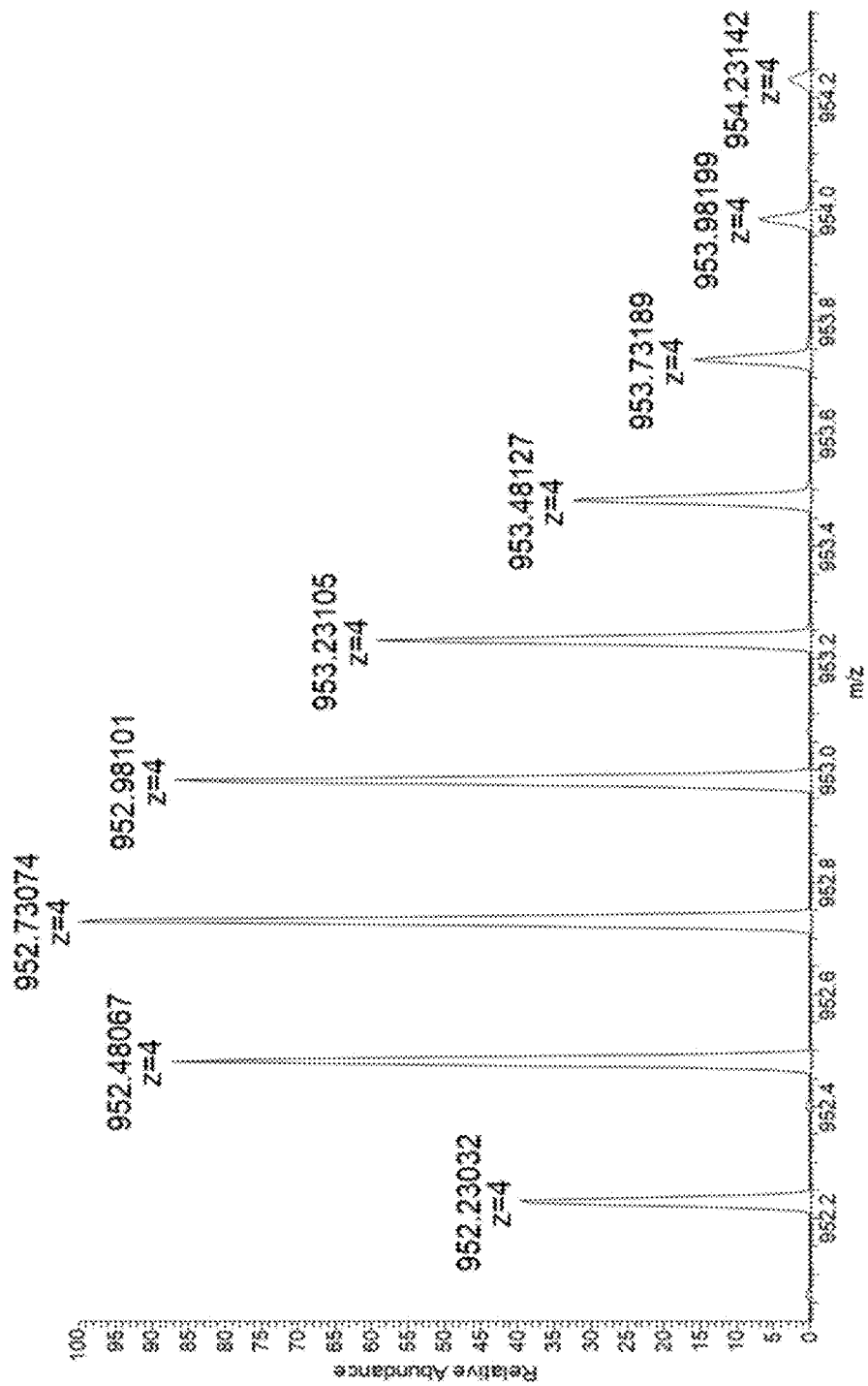
FIG. 14 is a diagram illustrating an MS spectrum of a peptide fragment of THTCPPCPAPELLGGPSVFLFPPKPKDTLMISR (SEQ ID NO: 26), which is a peptide consisting of 33 amino acid residues comprising a modified site to a lysine residue by trypsin digestion of trastuzumab (thiol-introduced compound (+145.019 Da) subjected to carbamidomethylation with iodoacetamide) (measured value: m/z 952.23032, theoretical value: 952.22900, tetravalent) (Example 9).
Figures 1, 15:
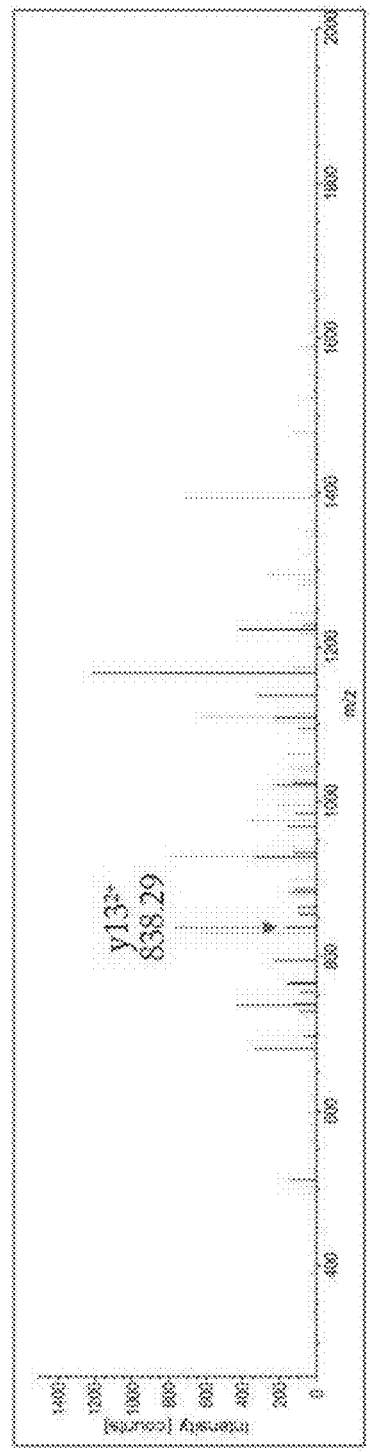
Figures 2, 15:
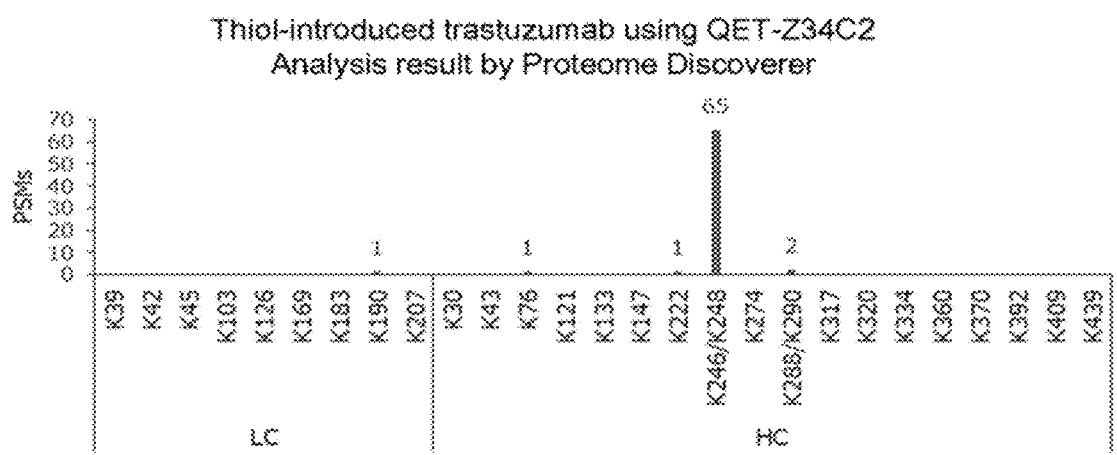

(10-1) Trypsin Treatment of Thiol-Introduced Trastuzumab
  The thiol-introduced trastuzumab obtained in (7-1) above was subjected to the same treatment as in (8-1) above, and then LC-MS/MS measurement was performed.
(10-2) LC-MS/MS Measurement Conditions for Trastuzumab
  Measuring device and measuring conditions for HPLC and mass spectrometry are the same as those in (8-2) above.
(10-3) Analysis Conditions for Modified Site of Trastuzumab
  Conditions for modification site analysis for an LC-MS/MS measurement result are the same as those in (8-3) above.
(10-4) Analysis Result of Modified Site of Trastuzumab by LC-MS/MS
  As a result of analysis using LC-MS/MS, an MS spectrum of a peptide fragment of THTCPPCPAPELLGGPS VFLFPPKPKDTLMISR (SEQ ID NO: 26), which is a peptide consisting of 33 amino acid residues comprising a modified site to a lysine residue by trypsin digestion of trastuzumab (thiol-introduced compound (+145.019 Da) subjected to carbamidomethylation with iodoacetamide) (measured value: m/z 952.23032; theoretical value: 952.22900; tetravalent) was observed (FIG. 14); and from a CID spectrum, a product ion of m/z 838.29 (theoretical value: 837.94) corresponding to divalent y13 indicating modification of a lysine residue at position 246 or 248 of a heavy chain in EU numbering was determined (FIG. 15-1). In addition, analysis with Proteome Discoverer indicated that modification to a lysine residue at position 246 or 248 occurred highly selectively (FIG. 15-2).

From this result, it was found that in (7-1) above, conjugation progressed regioselectively at Lys246 and Lys248 in EU numbering on the heavy chain of the antibody.

Example 11. Preparation and Analysis of Antibody Having Affinity Substance to Antibody (QET-Z34C4) and Cleavable Portion (11-1) Preparation of Compound Having Affinity Substance to Antibody (QET-Z34C4), Cleavable Portion, and Reactive Group QETFNMQCQRRFYEALHDPNLNEEQRNARIR-SIKDDC (SEQ ID NO: 23) (44.0 mg, 9.70 µmol) was dissolved in N,N-dimethylformamide (0.60 mL). To the resulting solution, a solution obtained by dissolving 3,3'-dithiodipropionic acid di(N-succinimidyl) (78.0 mg, 194 mol) in N,N-dimethylformamide (0.40 mL) was added, and the resulting mixture was stirred at room temperature for 24 hours. The resulting solution was concentrated under reduced pressure to remove acetonitrile. Thereafter, the resulting residue was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05% trifluoroacetic acid. Each fraction was determined by LC-MS. A fraction comprising a product was collected and concentrated under reduced pressure to remove acetonitrile. Thereafter, the resulting residue was freeze-dried to obtain the above expressed protein- and disulfide linker-coupled NHS-activation compound (15 mg, 3.10 µmol).

MS(ESI) D/z:z=4 1210.1[M+4H]$^{4+}$ (11-2) Specific Modification of Anti-HER2 IgG Antibody Trastuzumab and Analysis Thereof by ESI-TOFMS The peptide- and disulfide linker-coupled NHS-activation compound synthesized in (11-1) was dissolved in dimethyl sulfoxide to adjust the concentration to 10 mM. 500 µg of anti-HER2 IgG antibody trastuzumab (Chugai Pharmaceutical Co., Ltd.) was dissolved in 188 µL of 20 mM sodium acetate buffer (pH 5.5), 3.88 µL (10 equivalents to the antibody) of 10 mM peptide reagent was added thereto, and the resulting mixture was stirred at room temperature for one hour. The reaction solution was substituted with 9.56 mM PBS buffer. To 200 µL of the specific modified compound of trastuzumab substituted with PBS buffer (200 µg of antibody), 20 µL of GlycoBuffer and 8 µL of PNGaseF (50,000 units/mL) were added, and the resulting mixture was stirred at 37° C. for 24 hours. The reaction solution was substituted with a 20 mM aqueous ammonium acetate solution and the mass was measured by ESI-TOFMS; for the raw material trastuzumab, a peak was observed at 145170, for a product with one binding peptide introduced, a peak was observed at 149901, and for a product with two binding peptides introduced, a peak was observed at 154628.

Example 12. Peptide Mapping by Trypsin Treatment of Thiol-Introduced Trastuzumab Prepared by Using Affinity Substance to Antibody (QET-Z34C4)

(12-1) Trypsin Treatment of Thiol-Introduced Trastuzumab

Peptide mapping was performed on the thiol-introduced trastuzumab obtained in (11-2) above. To a 1.5 mL low-adsorption micro test tube, 10 µL of a sample solution, a 50 mM ammonium hydrogencarbonate buffer, and 10 µL of a 20 mM aqueous dithiothreitol solution dissolved in 40% trifluoroethanol were added. The resulting mixture was heated at 65° C. for one hour, then 10 µL of a 50 mM aqueous iodoacetamide solution was added thereto, and the resulting mixture was reacted in a dark place at room temperature for 30 minutes. After the reaction, 40 µL of a 50 mM ammonium hydrogencarbonate buffer was added thereto, the resulting mixture was stirred, 10 µL of a 20 ng/µL aqueous trypsin solution was added thereto, and the resulting mixture was subjected to enzyme digestion at 37° C. for 16 hours. After the digestion, 2 µL of a 20% aqueous trifluoroacetic acid solution was added thereto to stop the reaction, and LC-MS/MS measurement was performed.

(12-2) LC-MS/MS Measurement Conditions for Trastuzumab Analyzer

Nano HPLC: EASY-nLC 1000 (Thermo Fisher Scientific)
Mass Spectrometer: Tribrid Mass Spectrometer Orbitrap Fusion (Thermo Fisher Scientific)

HPLC Analysis Conditions
Trap column: Acclaim PepMap (registered trademark) 100, 75 µm×2 cm, (Thermo Fisher Scientific)
Analysis column: ESI-column (NTCC-360/75-3-125, 75 µm×12.5 cm, 3 µm (Nikkyo Technos Co., Ltd.))
Mobile Phase A: a 0.1% aqueous formate solution
Mobile Phase B: a 0.1% formate acetonitrile solution
Loading solution: a 0.1% aqueous trifluoroacetic acid solution
Flow rate: 300 nL/min
Sample injection amount: 1 µL
Gradient condition (B %): 2% (0.0 minute to 0.5 minute), 2%→30% (0.5 minute to 23.5 minutes), 30%→75% (23.5 minutes to 25.5 minutes), and 75% (25.5 minutes to 35.0 minutes).

Mass Spectrometer Analysis Conditions
Ionization: ESI, Positive mode
Scan type: Data Dependent Acquisition
Activation Type: Collision Induced Dissociation (CID)
Data acquisition was performed using Xcalibur 3.0 (Thermo Fisher Scientific) and Thermo Orbitrap Fusion Tune Application 2.0 (Thermo Fisher Scientific) as accompanying software.

(12-3) Analysis Conditions for Modified Site of Trastuzumab

Modified site analysis of an LC-MS/MS measurement result was performed using BioPharma Finder 3.0 (Thermo Fisher Scientific).

The analysis with BioPharma Finder was performed by setting S/N threshold to 1 and setting MS Noise Level to 0.01% of a peak top intensity. A digestive enzyme was set to Trypsin, and e Specificity was set to High. Furthermore, Mass Tolerance at the time of peak detection was set to 4 ppm, and Mass Accuracy at the time of peptide identification was set to 5 ppm. For Static Modification, Carbamidomethyl (+57.021 Da) was set as modification of a cysteine residue with iodoacetamide. For Dynamic Modifications, oxidation of a methionine residue (+15.995 Da) and a modified compound to a lysine residue (thiol-introduced compound subjected to carbamidomethylation with iodoacetamide (+145.019 Da)) were set. In addition, a filter was set such that only those with a Confidence Score of 80 or higher and with observed MS/MS were obtained.

In addition, (1) and (3) illustrated in FIG. 4 were used as data of an amino acid sequence to be searched for a modification site.

(12-4) Analysis Result of Modified Site of Trastuzumab by LC-MS/MS

Figure 26:
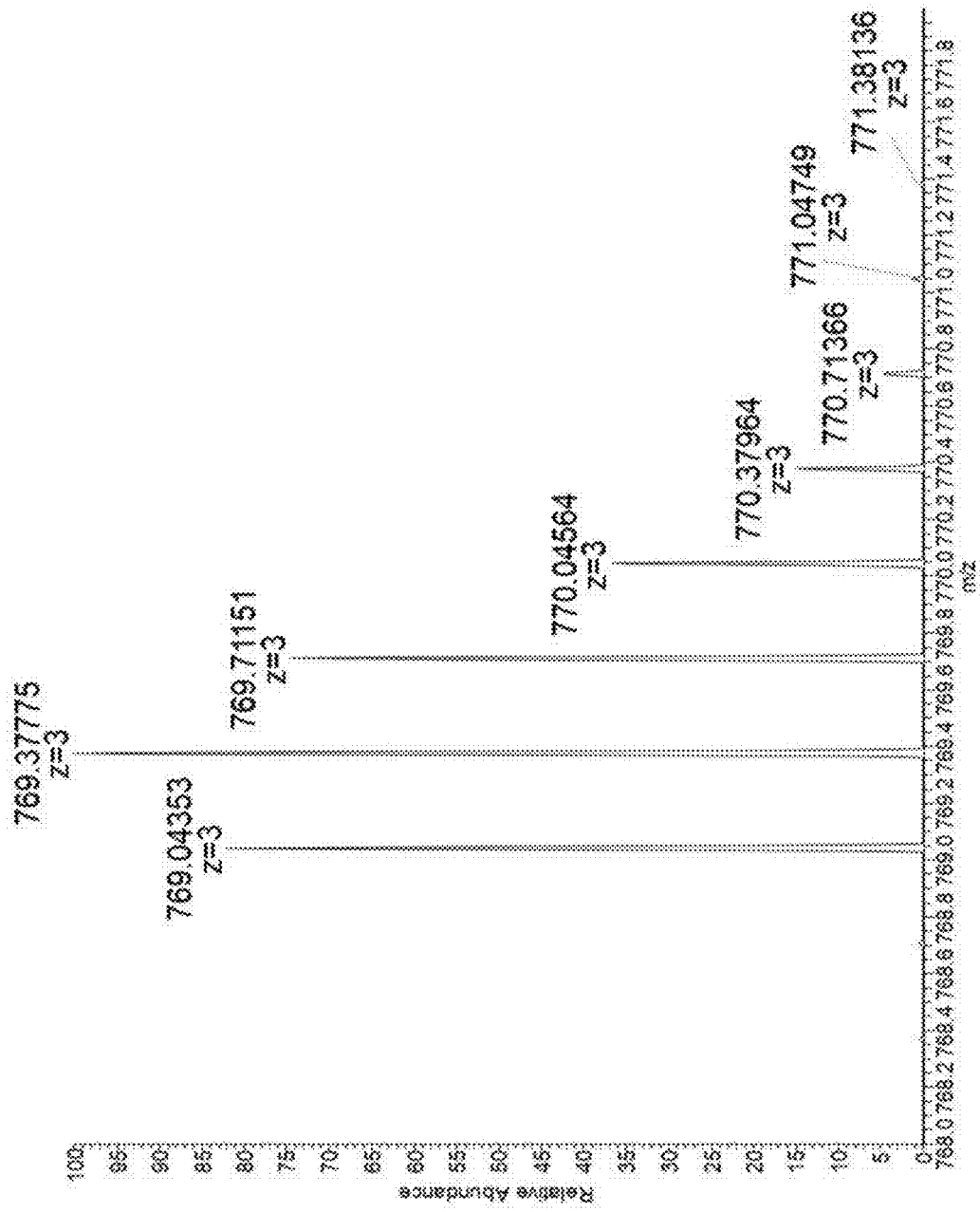
FIG. 26 is a diagram illustrating an MS spectrum of a peptide fragment of FNWYVDGVEVHNAKTKPR (SEQ ID NO: 50), which is a peptide consisting of 18 amino acid residues comprising a modified site to a lysine residue by trypsin digestion of trastuzumab (thiol-introduced compound (+145.019 Da) subjected to carbamidomethylation with iodoacetamide) (measured value: m/z 769.04353, theoretical value: 769.04482, trivalent).
Figures 1, 27:
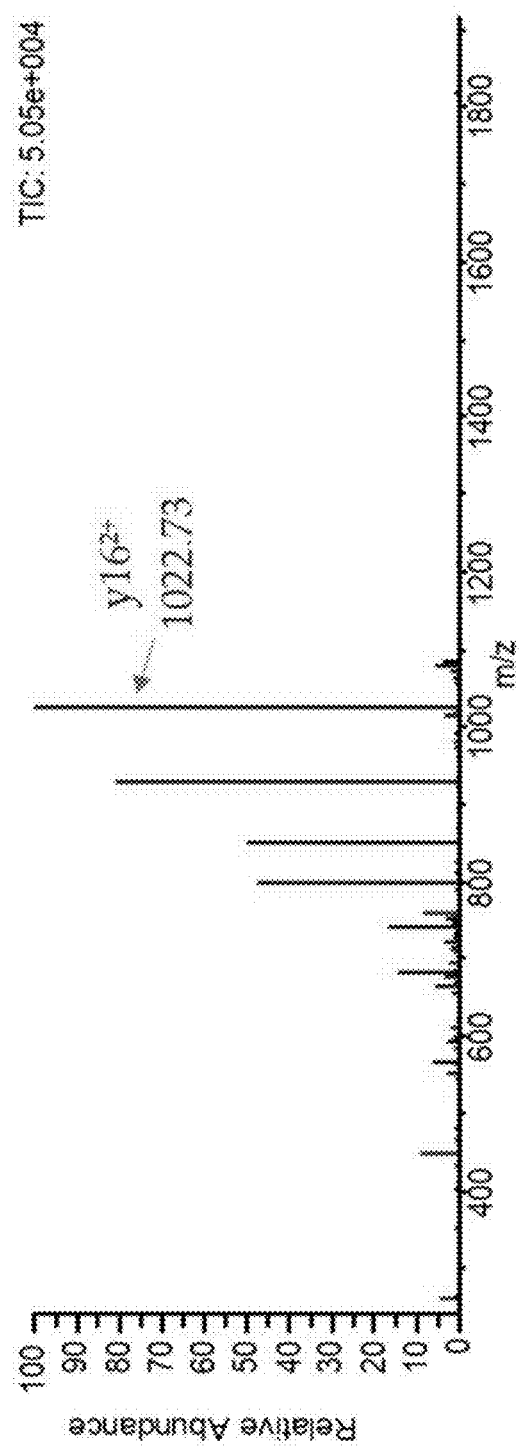
Figures 2, 27:
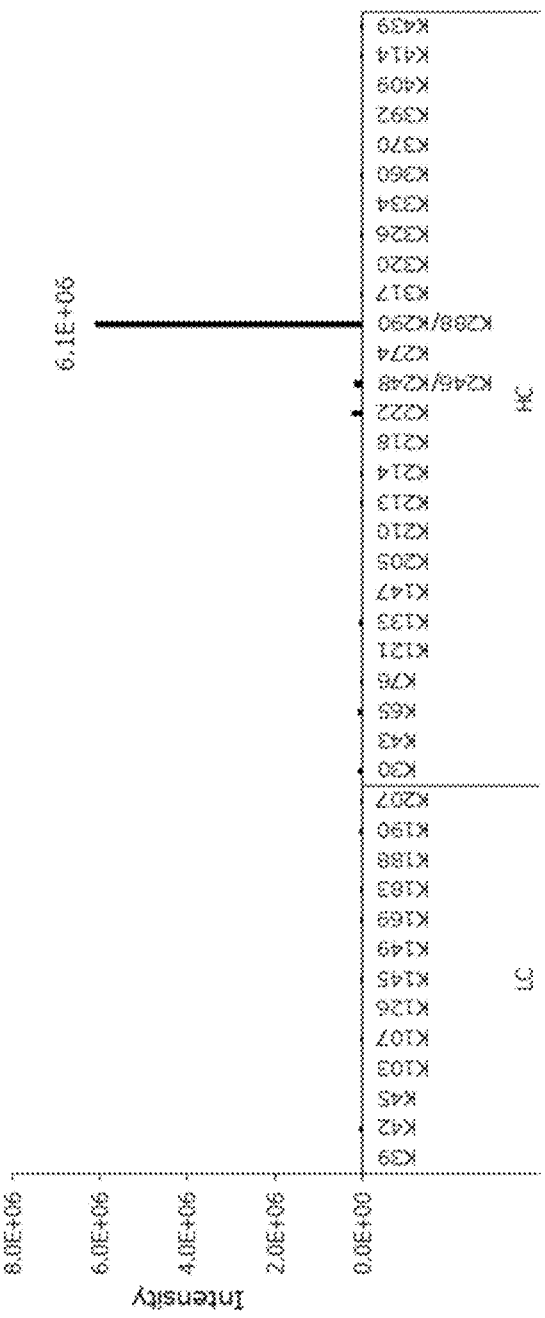

As a result of analysis using LC-MS/MS, an MS spectrum of a peptide fragment of FNWYVDGVEVHNAKTKPR (SEQ ID NO: 50), which is a peptide consisting of 18 amino acid residues comprising a modified site to a lysine residue by trypsin digestion of trastuzumab (thiol-introduced compound (+145.019 Da) subjected to carbamidomethylation with iodoacetamide) (measured value: m/z 769.04353; theoretical value: 769.04482; trivalent) was observed (FIG. 26); and from a CID spectrum, a product ion of m/z 1022.73 (theoretical value: 1022.51) corresponding to divalent y16 indicating modification of a lysine residue at position 288 or 290 of a heavy chain in EU numbering was determined (FIG. 27-1). In addition, analysis with BioPharma Finder indicated that modification to a lysine residue at position 288 or 290 occurred highly selectively (FIG. 27-2).

From this result, it was found that in (11-2) above, conjugation progressed regioselectively at Lys288 and Lys290 in EU numbering on the heavy chain of the antibody.

Example 13 Preparation and Analysis of Antibody Having Affinity Substance to Antibody (Modified Fc-III (QET-LV)) and Cleavable Portion (13-1) Preparation of Compound Having Affinity Substance to Antibody (Modified Fc-III (QET-LV)), Cleavable Portion, and Reactive Group QETRGNCAYHKGQLVWCTYH (SEQ ID NO: 24) (50.0 mg, 21.0 μmol, where the 7th and 17th cysteines form disulfide bonds in the molecule, respectively) was dissolved in N,N-dimethylformamide (1.00 mL). To the resulting solution, di-(N-succinimidyl) 3,3'-dithiodipropionate (255 mg, 630 μmol) was added, and the resulting mixture was stirred at room temperature for 24 hours. After determination of the reaction by LC-MS, the resulting solution was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05% trifluoroacetic acid. Each fraction was determined by LC-MS. A fraction comprising a product was collected and concentrated under reduced pressure to remove acetonitrile. Thereafter, the resulting residue was freeze-dried to obtain the above peptide- and disulfide linker-coupled compound (1.2 mg, 0.45 μmol).

Figure 28:
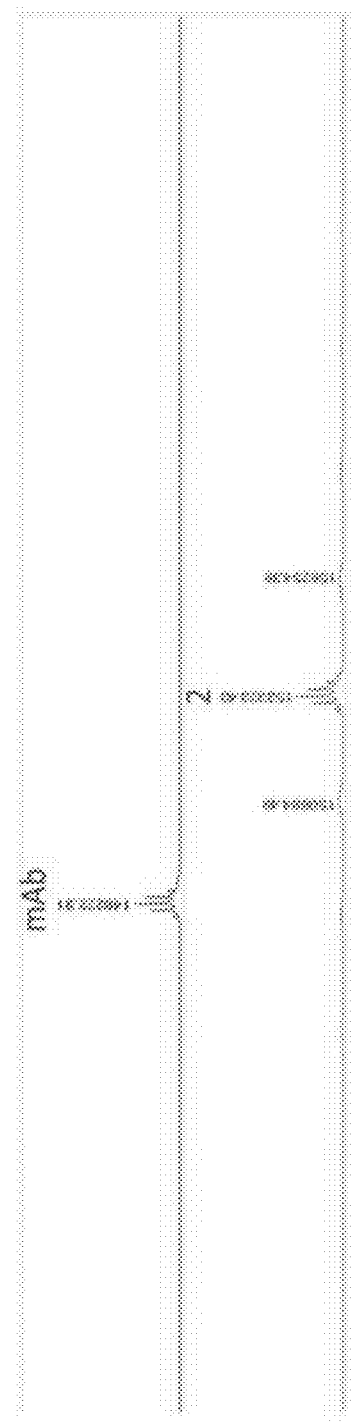
FIG. 28 is a diagram illustrating determination of a specific modified compound of trastuzumab by ESI-TOFMS analysis (Example 13).

(13-2) Specific Modification of Anti-HER2 IgG Antibody Trastuzumab and Analysis Thereof by ESI-TOFMS The peptide- and linker-coupled compound synthesized in (13-1) was dissolved in dimethyl sulfoxide to adjust the concentration to 20 mM. 500 μg of anti-HER2 IgG antibody trastuzumab (Chugai Pharmaceutical Co., Ltd.) was dissolved in 100 μL (500 μg/100 μL) of 50 mM sodium acetate buffer (pH4.7 or pH5.5), 1.69 μL (10 equivalents to the antibody) of 20 mM peptide reagent was added thereto, and the resulting mixture was stirred at room temperature for one hour. The reaction solution was substituted with 20 mM ammonium acetate buffer. The mass was measured by ESI-TOFMS; for the raw material trastuzumab, a peak was observed at 148222. For the pH 4.7, a peak was observed at 153323 indicating a compound having two binding peptides introduced. For the pH 5.5, a peak was observed at 153511 indicating a compound having two binding peptides introduced (FIG. 28).

Figure 29:
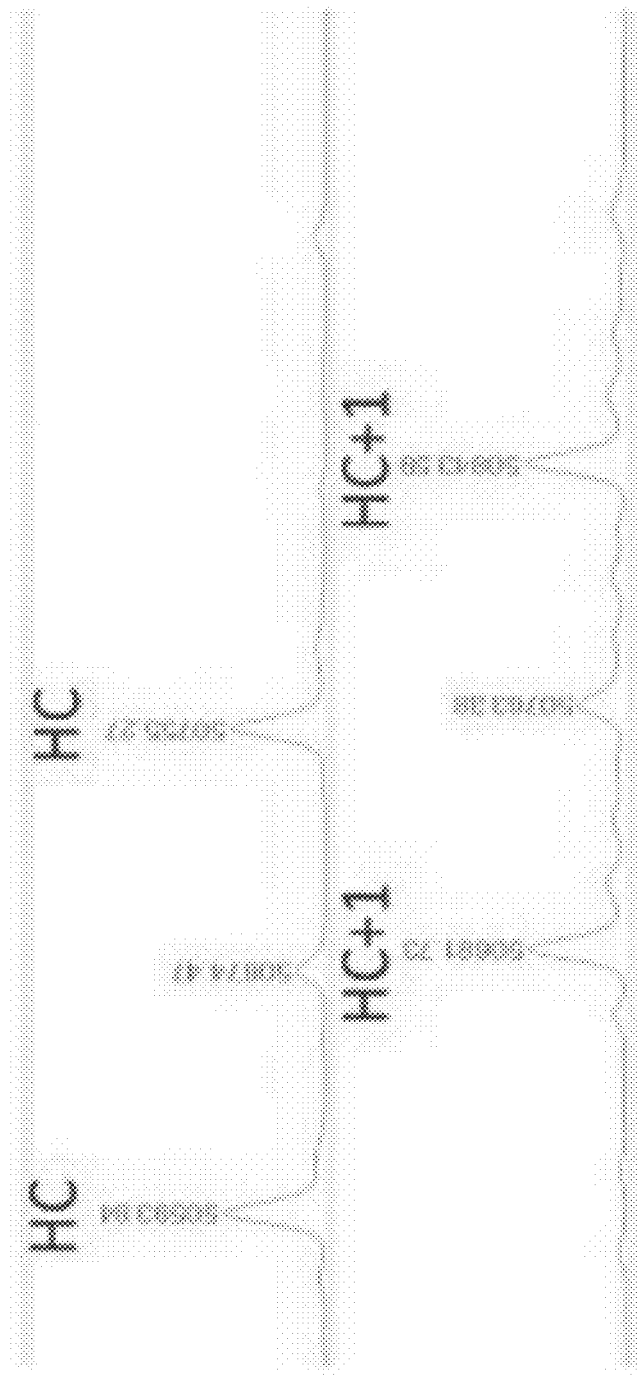
FIG. 29 is a diagram illustrating results of HIC-UPLC analysis of specific modification of trastuzumab (detection wavelength: UV 280 nm) (Example 13).

(13-3) Determination of Heavy Chain Selectivity of Specific Modified Compound of Trastuzumab Under Reduction Conditions by ESI-TOFMS Analysis To the antibody-peptide conjugate formed in (13-2), 2 μL of a 100 mM tris(2-carboxyethyl) phosphine hydrochloride solution (equivalent to the antibody) was added, and the resulting mixture was stirred at room temperature for 15 minutes. The mass was measured by ESI-TOFMS; for the raw material trastuzumab synthesized, heavy chain peaks were observed at 50594 and 50755, and a light chain peak was observed at 23439, and for the pH 4.7, heavy chain peaks were observed at 50681 and 50843 with a linker introduced, a light chain peak was observed at 23439, the same as that of the raw material, and a peak was observed at 23526 with a linker introduced. For the pH 5.5, heavy chain peaks were observed at 50681 and 50843 with a linker introduced, a light chain peak was observed at 23439, the same as that of the raw material, and a peak was observed at 23526 with a linker introduced. For the pH 6.4, heavy chain peaks were observed at 50681 and 50843 with a linker introduced, a light chain peak was observed at 23439, the same as that of the raw material, and a peak was observed at 23526 with a linker introduced. For the pH 7.4, heavy chain peaks were observed at 50681 and 50843 with a linker introduced, a light chain peak was observed at 23439, the same as that of the raw material, and a peak was observed at 23527 with a linker introduced. For the pH 8.0, heavy chain peaks were observed at 50681 and 50844 with a linker introduced, a light chain peak was observed at 23439, the same as that of the raw material, and a peak was observed at 23527 with a linker introduced (FIG. 29).

(13-4) HIC-UPLC Analysis of Specific Modification of Anti-HER2 IgG Antibody Trastuzumab The antibody-peptide conjugate formed in (13-2) and the raw material antibody were analyzed by HIC. As the column, Protein-Pak Hi Res HIC Column (Waters) 4.6×100 mm 2.5 μm was used. Detection was performed by using A_Buffer: 0.1 M PiNa, 2.3 M $(NH_4)_2SO_4$, pH 7.0 and B_Buffer: 0.1 M PiNa at pH 7.0 at a flow rate of 0.6 ml/min at gradient A60% B40%→A0% B100% for 16 min (data collection 20 min) at a column temperature of 40° C. at a thermostat temperature of 40° C. at a detector wavelength of 280 nm.

Figure 30:
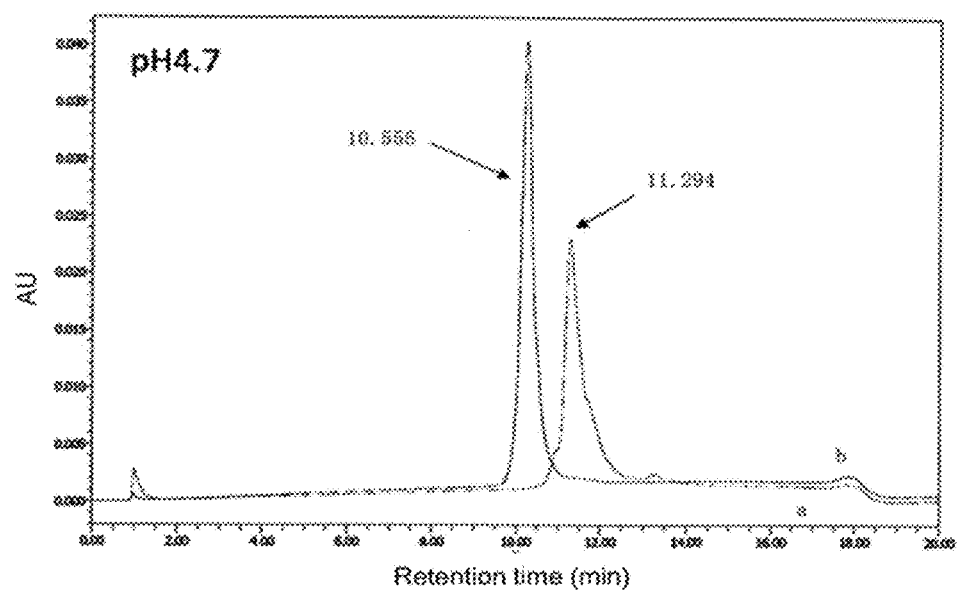
FIG. 30 is a diagram illustrating an MS spectrum of a peptide fragment of THTCPPCPAPELLGGPSVFLFPPKPKDTLMISR (SEQ ID NO: 26), which is a peptide consisting of 33 amino acid residues comprising a modified site to a lysine residue by trypsin digestion of trastuzumab (thiol-introduced compound (+145.019 Da) subjected to carbamidomethylation with iodoacetamide) (measured value: m/z 952.23425, theoretical value: 952.22942, tetravalent) (Example 14).

A sample was reacted under the following conditions.
a: Trastuzumab raw material
b: Trastuzumab+10 equivalents of peptide- and disulfide linker-coupled NHS-activation compound As a result, the chromatogram of FIG. 30 was obtained. A compound having Retension Time of 10.255 minutes is considered to be the trastuzumab raw material, and a compound having Retension Time of 11.294 minutes is considered to be a compound with two peptides introduced (FIG. 30).

Example 14. Peptide Mapping by Trypsin Treatment of Thiol-Introduced Trastuzumab Prepared by Using Affinity Substance to Antibody (Modified Fc-III (QET-LV))

(14-1) Trypsin Treatment of Thiol-Introduced Trastuzumab

The thiol-introduced trastuzumab obtained in (13-2) above was subjected to sugar chain cleavage with PNGaseF (manufactured by New England BioLabs), and then peptide mapping was performed. To a 1.5 mL low-adsorption micro test tube, 10 μL of a sample solution, a 50 mM ammonium hydrogencarbonate buffer, and 10 μL of a 20 mM aqueous dithiothreitol solution dissolved in 40% trifluoroethanol were added. The resulting mixture was heated at 65° C. for one hour, then 10 μL of a 50 mM aqueous iodoacetamide solution was added thereto, and the resulting mixture was reacted in a dark place at room temperature for 30 minutes. After the reaction, 40 μL of a 50 mM ammonium hydrogencarbonate buffer was added thereto, the resulting mixture was stirred, 10 μL of a 20 ng/μL aqueous trypsin solution was added thereto, and the resulting mixture was subjected to enzyme digestion at 37° C. for 16 hours. After the digestion, 2 μL of a 20% aqueous trifluoroacetic acid solution was added thereto to stop the reaction, and LC-MS/MS measurement was performed.

(14-2) LC-MS/MS Measurement Conditions for Trastuzumab Analyzer

Nano HPLC: EASY-nLC 1000 (Thermo Fisher Scientific)
Mass Spectrometer: Tribrid Mass Spectrometer Orbitrap Fusion (Thermo Fisher Scientific)
HPLC Analysis Conditions
Trap column: Acclaim PepMap (registered trademark) 100, 75 μm×2 cm, (Thermo Fisher Scientific)
Analysis column: ESI-column (NTCC-360/75-3-125, 75 μm×12.5 cm, 3 μm (Nikkyo Technos Co., Ltd.))
Mobile Phase A: a 0.1% aqueous formate solution
Mobile Phase B: a 0.1% formate acetonitrile solution
Loading solution: a 0.1% aqueous trifluoroacetic acid solution
Flow rate: 300 nL/min
Sample injection amount: 1 μL
Gradient condition (B %): 2% (0.0 minute to 0.5 minute), 2%→30% (0.5 minute to 23.5 minutes), 30%→75% (23.5 minutes to 25.5 minutes), and 75% (25.5 minutes to 35.0 minutes).
Mass Spectrometer Analysis Conditions
Ionization: ESI, Positive mode
Scan type: Data Dependent Acquisition
Activation Type: Collision Induced Dissociation (CID)
Data acquisition was performed using Xcalibur 3.0 (Thermo Fisher Scientific) and Thermo Orbitrap Fusion Tune Application 2.0 (Thermo Fisher Scientific) as accompanying software.

(14-3) Analysis Conditions for Modified Site of Trastuzumab

Modified site analysis of an LC-MS/MS measurement result was performed using BioPharma Finder 3.0 (Thermo Fisher Scientific).

The analysis with BioPharma Finder was performed by setting S/N threshold to 1 and setting MS Noise Level to 0.01% of a peak top intensity. A digestive enzyme was set to Trypsin, and e Specificity was set to High. Furthermore, Mass Tolerance at the time of peak detection was set to 4 ppm, and Mass Accuracy at the time of peptide identification was set to 5 ppm. For Static Modification, Carbamidomethyl (+57.021 Da) was set as modification of a cysteine residue with iodoacetamide. For Dynamic Modifications, oxidation of a methionine residue (+15.995 Da) and a modified compound to a lysine residue (thiol-introduced compound subjected to carbamidomethylation with iodoacetamide (+145.019 Da)) were set. In addition, a filter was set such that only those with a Confidence Score of 80 or higher and with observed MS/MS were obtained.

In addition, (1) and (3) illustrated in FIG. 4 were used as data of an amino acid sequence to be searched for a modification site.

(14-4) Analysis Result of Modified Site of Trastuzumab by LC-MS/MS

Figure 31:
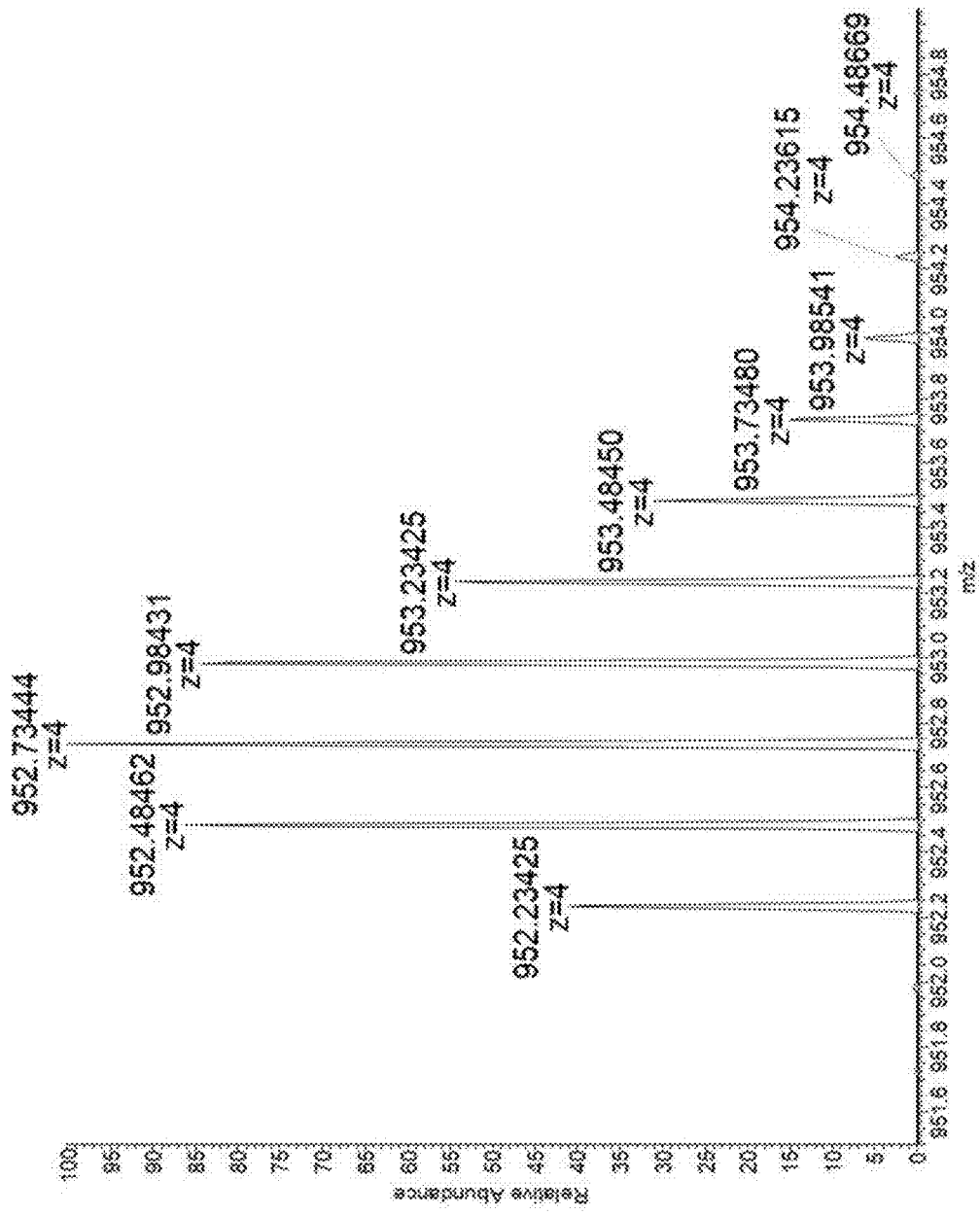
FIG. 31 is a diagram illustrating an MS spectrum of a peptide fragment of THTCPPCPAPELLGGPSVFLFPPKPKDTLMISR (SEQ ID NO: 26), which is a peptide consisting of 33 amino acid residues comprising a modified site to a lysine residue by trypsin digestion of trastuzumab (thiol-introduced compound (+145.019 Da) subjected to carbamidomethylation with iodoacetamide) (measured value: m/z 952.23425, theoretical value: 952.22942, tetravalent) (Example 14).
Figures 1, 32:
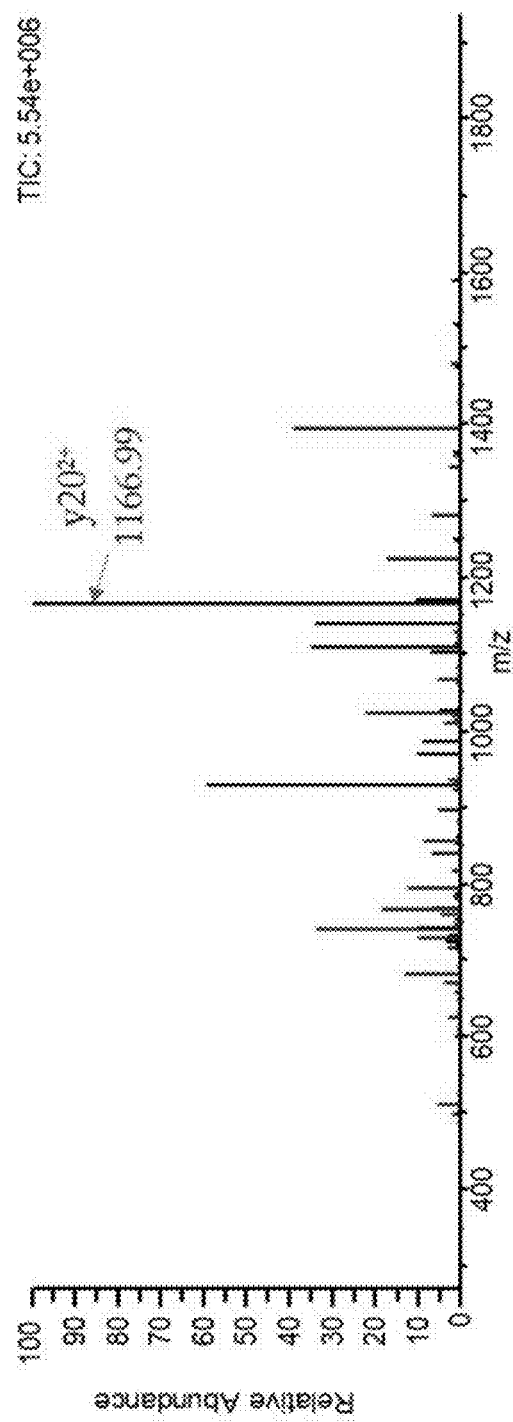
Figures 2, 32:
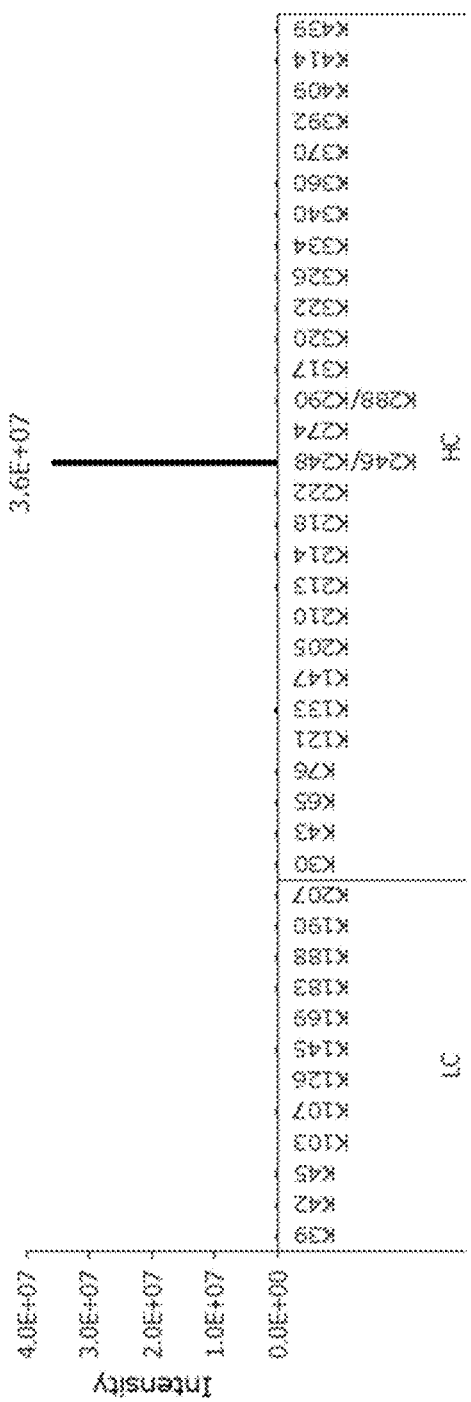

As a result of analysis using LC-MS/MS, an MS spectrum of a peptide fragment of THTCPPCPAPELLGGPS VFLFPPKPKDTLMISR (SEQ ID NO: 26), which is a peptide consisting of 33 amino acid residues comprising a modified site to a lysine residue by trypsin digestion of trastuzumab (thiol-introduced compound (+145.019 Da) subjected to carbamidomethylation with iodoacetamide) (measured value: m/z 952.23425; theoretical value: 952.22942; tetravalent) was observed (FIG. 31); and from a CID spectrum, a product ion of m/z 1166.99 (theoretical value: 1166.61) corresponding to divalent y20 indicating modification of a lysine residue at position 246 or 248 of a heavy chain in EU numbering was determined (FIG. 32-1). In addition, analysis with BioPharma Finder indicated that modification to a lysine residue at position 246 or 248 occurred highly selectively (FIG. 32-2).

From this result, it was found that in (13-2) above, conjugation progressed regioselectively at Lys246 and Lys248 in EU numbering on the heavy chain of the antibody.

Example 15. Preparation and Analysis of Antibody Having Affinity Substance to Antibody (Modified Fc-III (QET-II)) and Cleavable Portion (15-1) Preparation of Compound Having Affinity Substance to Antibody (Modified Fc-III (QET-II)), Cleavable Portion, and Reactive Group QETRGNCAYHKGQIIWCTYH (SEQ ID NO: 25) (46.0 mg, 20.0 μmol, where the 7th and 17th cysteines form disulfide bonds in the molecule, respectively) was dissolved in N,N-dimethylformamide (1.00 mL). To the resulting solution, di-(N-succinimidyl) 3,3'-dithiodipropionate (255 mg, 630 μmol) was added, and the resulting mixture was stirred at room temperature for 24 hours. After determination of the reaction by LC-MS, the resulting solution was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05% trifluoroacetic acid. Each fraction was determined by LC-MS. A fraction comprising a product was collected and concentrated under reduced pressure to remove acetonitrile. Thereafter, the resulting residue was freeze-dried to obtain the above peptide- and disulfide linker-coupled compound (2.5 mg, 1.10 μmol).

(15-2) Specific Modification of Anti-HER2 IgG Antibody Trastuzumab and Analysis Thereof by ESI-TOFMS The peptide- and linker-coupled compound synthesized in (15-1) was dissolved in dimethyl sulfoxide to adjust the concentration to 20 mM. 500 μg of anti-HER2 IgG antibody trastuzumab (Chugai Pharmaceutical Co., Ltd.) was dissolved in 100 μL (500 μg/100 μL) of 50 mM sodium acetate buffer (pH4.7 or pH5.5), 1.69 μL (10 equivalents to the antibody) of 20 mM peptide reagent was added thereto, and the resulting mixture was stirred at room temperature for one hour. The reaction solution was substituted with 20 mM ammonium acetate buffer. The mass was measured by ESI-TOFMS; for the raw material trastuzumab, a peak was observed at 148222. A peak was observed at 153524 indicating a compound having two binding peptides introduced.

SUMMARY

The above results can be summarized as follows.

TABLE 2

Summary of affinity peptide

| Amino acid sequence | SEQ ID NO | Example |
|---|---|---|
| QETNPTENLYFQQKNMQCQRRFYEALHDPNLNEEQRNARIRSIRDDC | 7 | 2-1, 3 |
| QTADNQKNMQCQRRFYEALHDPNLNEEQRNARIRSIRDDCSQSANLLAEAQQLNDAQAPQA | 8 | 2-2, 4 |
| QETKNMQCQRRFYEALHDPNLNEEQRNARIRSIRDDC | 9 | 2-3, 5 |
| QETFNKQCQRRFYEALHDPNLNEEQRNARIRSIRDDC | 10 | 2-4, 6 |
| QETFNMQCQRRFYEALHDPNLNKEQRNARIRSIRDDC | 22 | 1 |
| QETFNMQCQRRFYEALHDPNLNEEQRNARIRSIKDDC | 23 | 1, 11, 12 |
| QETRGNCAYHKGQLVWCTYH | 24 | 2, 13, 14 |
| QETRGNCAYHKGQIIWCTYH | 25 | 2, 15 |

For the antibody, it has been indicated that a specific amino acid residue including the lysine residues at positions 246 and/or 248 (e.g., Examples 7, 8, and 9) can be regioselectively modified.

Furthermore, the following compound having an affinity substance to an antibody (a polypeptide comprising a glutamine residue (Q) at an N-terminal), a cleavable portion, and a reactive group, represented by the following Formula (I), is described with reference to part of Examples as Table 3 below:

A-L-B—R   (I)

wherein

A is an affinity substance to an antibody (a polypeptide comprising a glutamine residue (Q) at an N-terminal), L is a cleavable linker that is a divalent group comprising a cleavable portion, B is (a) a divalent group comprising a bioorthogonal functional group or (b) a divalent group comprising no bioorthogonal functional group, and R is a reactive group to the antibody.

L is (i) a cleavable linker that is a divalent group comprising a cleavable portion capable of forming a bioorthogonal functional group on a reactive group side by cleavage, or (ii) a cleavable linker that is a divalent group comprising a cleavable portion not capable of forming a bioorthogonal functional group on a reactive group side by cleavage.

Specific Structure of Compound

☐: Affinity substance (A)

⬚: Cleavable portion (in L)

◯: Bioorthogonal functional group B(a) or L(ii)

◌: Reactive group

| Example | |
|---|---|
| 3, 7 | 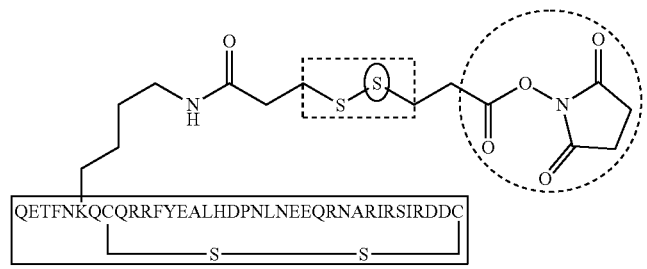 |

The above-amino acid sequence: SEQ ID NO: 10

Antibody having bioorthogonal functional groups which can be produced by using the compound*

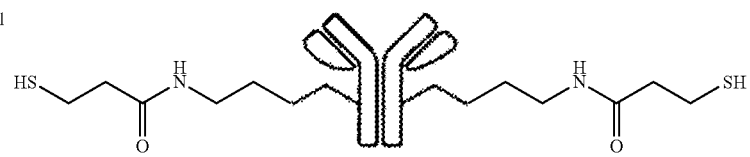

-continued

Specific Structure of Compound
☐: Affinity substance (A)
⬚: Cleavable portion (in L)
○: Bioorthogonal functional group B(a) or L(ii)
◌: Reactive group

| Example | |
|---|---|
| 3, 4 | 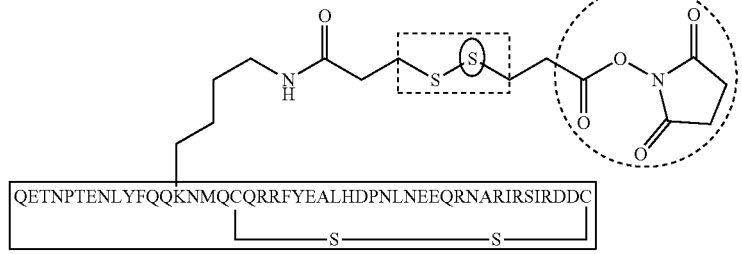 |
| | The above-amino acid sequence: SEQ ID NO: 7 |
| Antibody having bioorthogonal functional groups which can be produced by using the compound* | 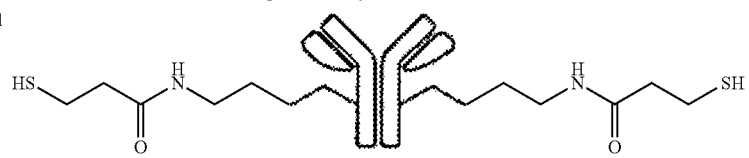 |
| 3, 5 | 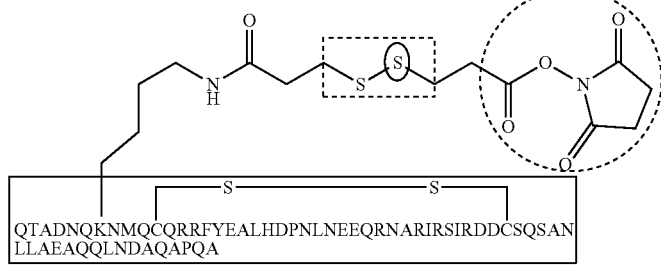 |
| | The above-amino acid sequence: SEQ ID NO: 8 |
| Antibody having bioorthogonal functional groups which can be produced by using the compound* | 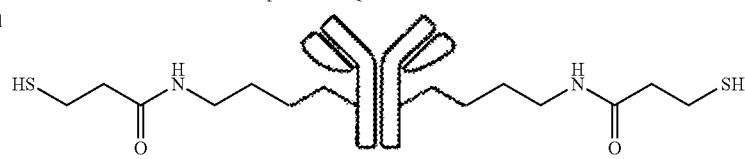 |
| 3, 6 | 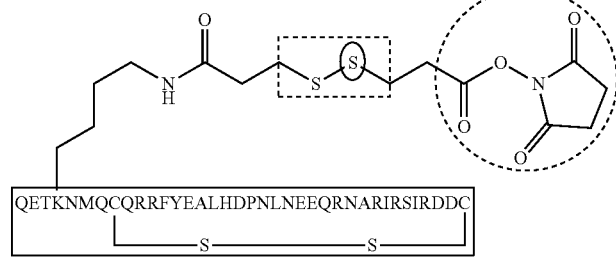 |
| | The above-amino acid sequence: SEQ ID NO: 9 |
| Antibody having bioorthogonal functional groups which can be produced by using the compound* |  |

*The NH—C4 alkyl portion extending from the antibody is derived from a lysine residue side chain of the antibody (hereinafter the same).

Specific Structure of Compound
☐: Affinity substance (A)
⬚: Cleavable portion (in L)
○: Bioorthogonal functional group B(a) or L(ii)
◌: Reactive group (R)

| Example | |
|---|---|
| 1, 11, 12 | 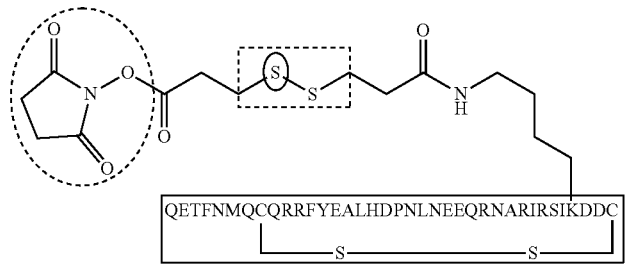 |
| | The above-amino acid sequence: SEQ ID NO: 23 |
| Antibody having bioorthogonal functional groups which can be produced by using the compound* | 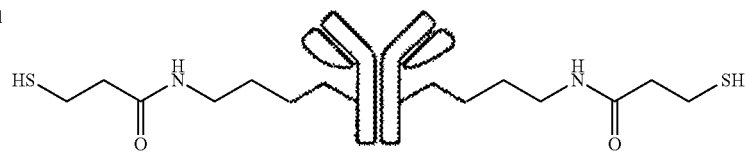 |
| 13, 14 | 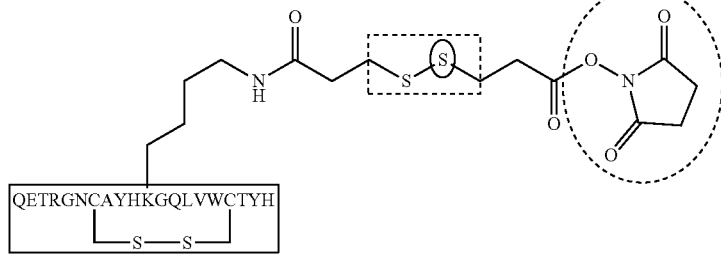 |
| | The above-amino acid sequence: SEQ ID NO: 24 |
| Antibody having bioorthogonal functional groups which can be produced by using the compound* | 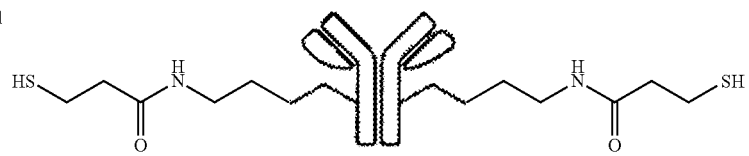 |
| 15 | 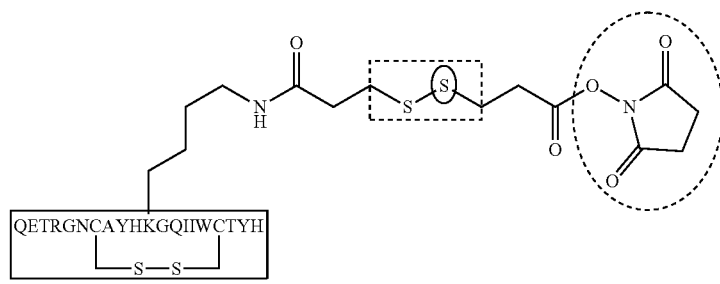 |
| | The above-amino acid sequence: SEQ ID NO: 25 |
| Antibody having bioorthogonal functional groups which can be produced by using the compound* | 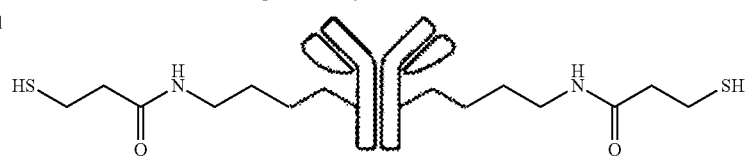 |

As described above, various compounds each having an affinity Substance to an antibody (a polypeptide comprising a glutamine residue (Q) at an N-terminal), a cleavable portion, and a reactive group can be prepared according to a well-known organic synthesis method by appropriately changing the types of the affinity substance to an antibody (A), the cleavable linker that is a divalent group comprising a cleavable portion (L), (a) a divalent group comprising a bioorthogonal functional group or (b) a divalent group comprising no bioorthogonal functional group (B), and the reactive group to an antibody (R). A relationship between an additional example of the compound having an affinity substance to an antibody (a polypeptide comprising a glutamine residue (Q) at an N-terminal), a cleavable portion, and a reactive group, and an antibody having a bioorthogonal functional group or bioorthogonal functional groups, which can be produced using the compound is as follows.

Specific Structure of Compound

☐: Affinity substance (A)

⌐ ¬: Cleavable portion (in L)

○: Bioorthogonal functional group B(a) or L(ii)

Example     ⋯: Reactive group (R)

15

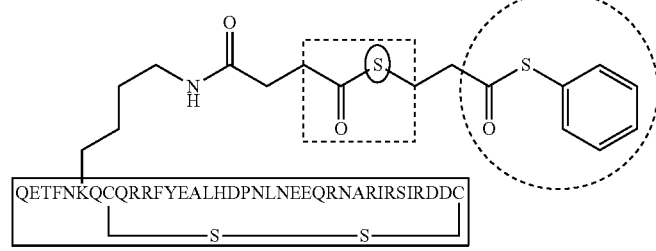

The above-amino acid sequence: SEQ ID NO: 10

Antibody having bioorthogonal functional groups which can be produced by using the compound*

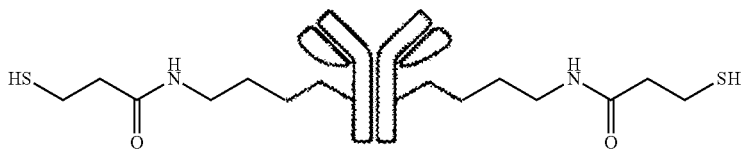

16

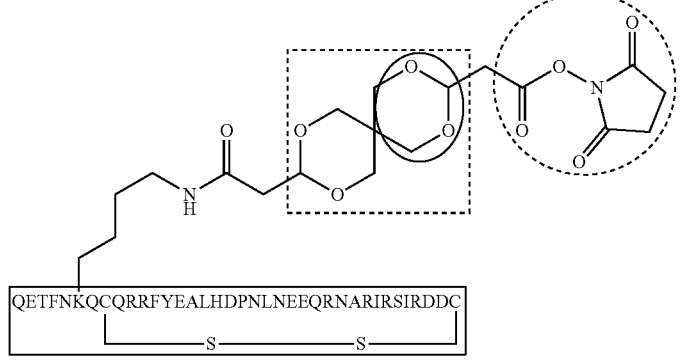

The above-amino acid sequence: SEQ ID NO: 10

Antibody having bioorthogonal functional groups which can be produced by using the compound*

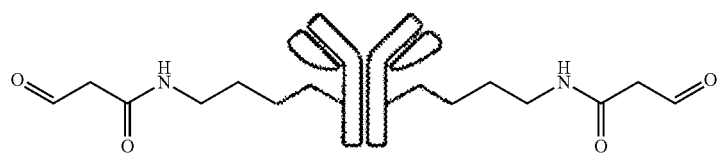

-continued

Specific Structure of Compound
□: Affinity substance (A)
⬚: Cleavable portion (in L)
○: Bioorthogonal functional group B(a) or L(ii)
◌: Reactive group (R)

| Example | |
|---|---|
| 17 | 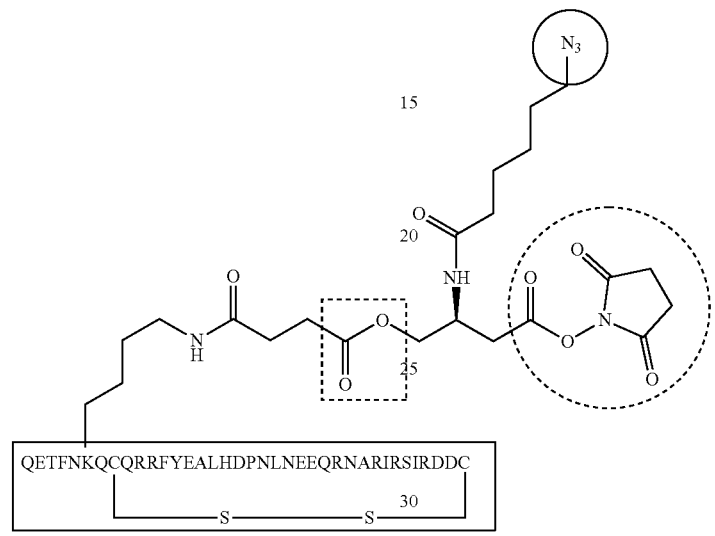<br>The above-amino acid sequence: SEQ ID NO: 10 |
| Antibody having bioorthogonal functional groups which can be produced by using the compound* | 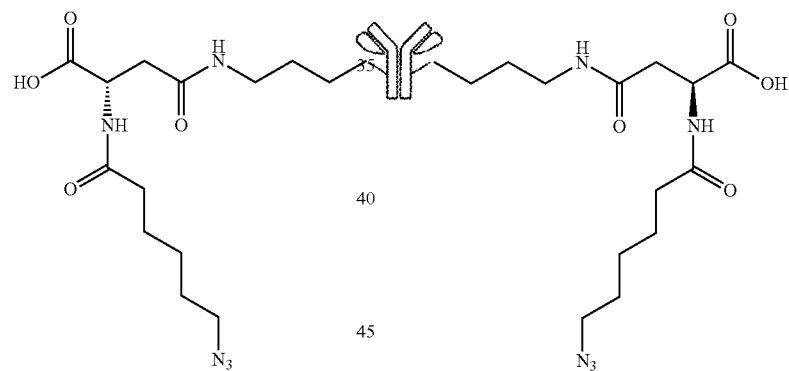 [SMILES: CCCCNC(=O)C[C@H](NC(=O)CCCCCN=[N+]=[N-])C(=O)O ; CCCCNC(=O)C[C@H](NC(=O)CCCCCN=[N+]=[N-])C(=O)O] |
| 18 | 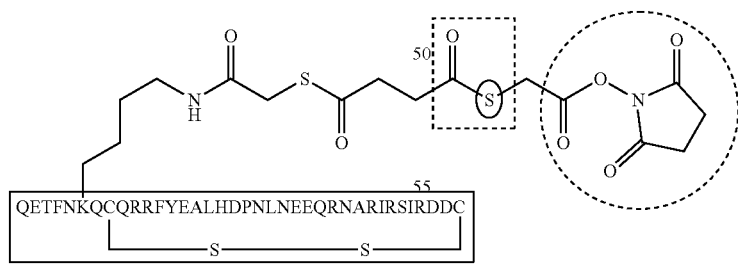<br>The above-amino acid sequence: SEQ ID NO: 10 |
| Antibody having bioorthogonal functional groups which can be produced by using the compound* | 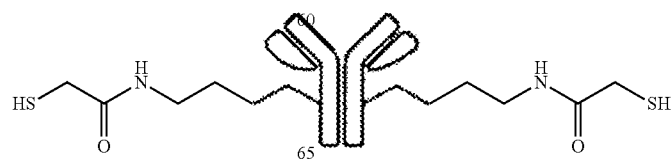 |

|  | Specific Structure of Compound |
|---|---|
|  | □: Affinity substance (A) |
|  | ⬚: Cleavable portion (in L) |
|  | ○: Bioorthogonal functional group B(a) or L(ii) |
| Example | ◌: Reactive group (R) |

19

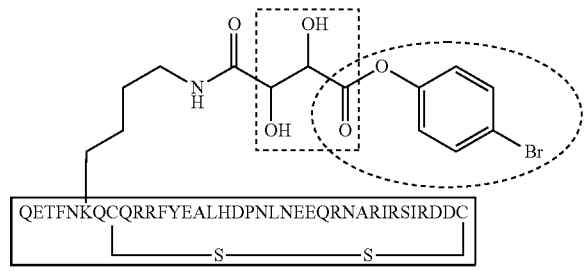

The above-amino acid sequence: SEQ ID NO: 10

Antibody having bioorthogonal functional groups which can be produced by using the compound*

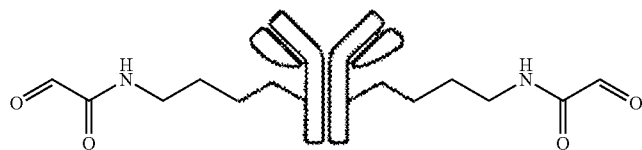

20

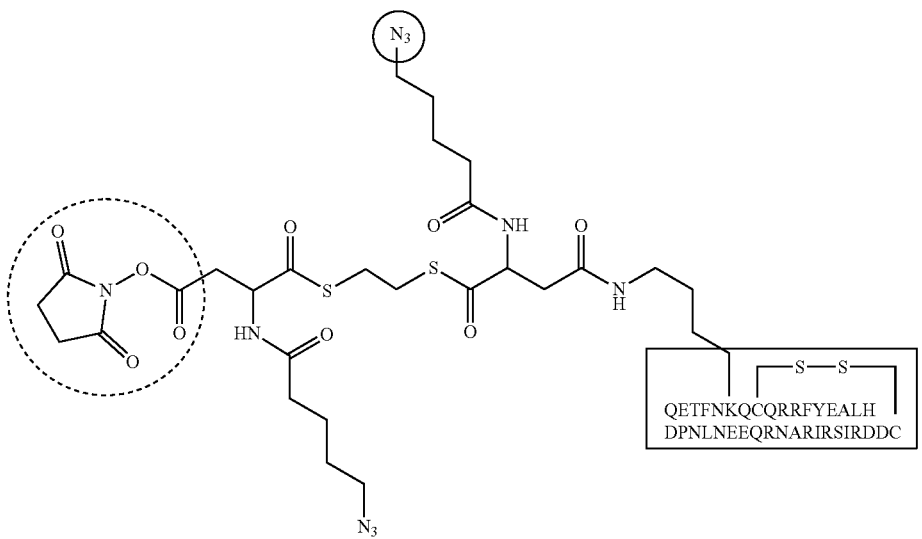

The above-amino acid sequence: SEQ ID NO: 10

Antibody having bioorthogonal functional groups which can be produced by using the compound*

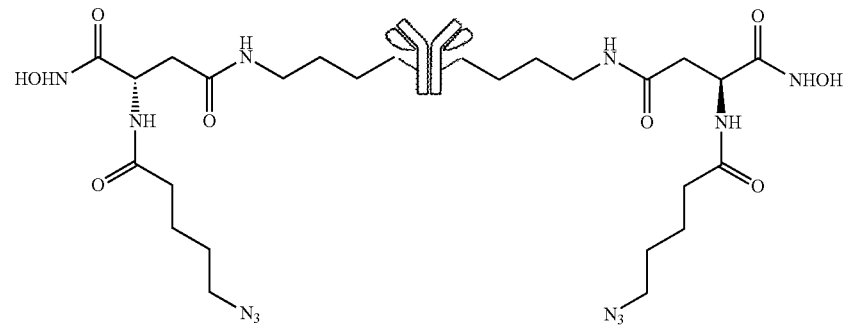

| Example | Specific Structure of Compound<br>□: Affinity substance (A)<br>⬚: Cleavable portion (in L)<br>○: Bioorthogonal functional group B(a) or L(ii)<br>◌: Reactive group (R) |
|---|---|
| 21 | 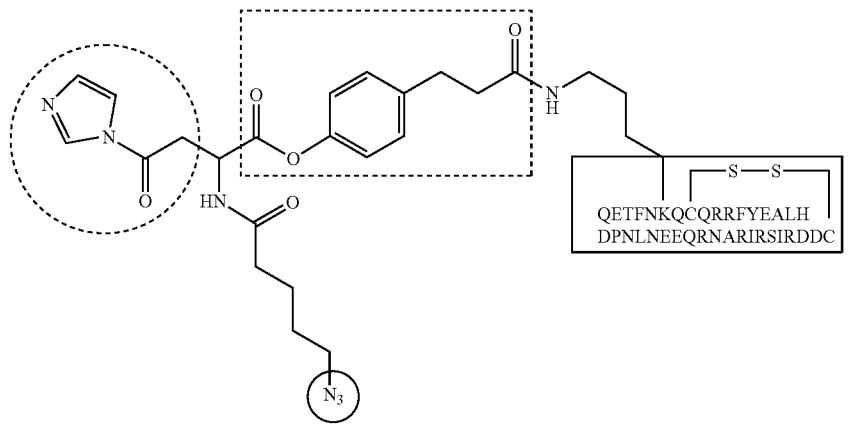 |
| | The above-amino acid sequence: SEQ ID NO: 10 |
| Antibody having bioorthogonal functional groups which can be produced by using the compound* | 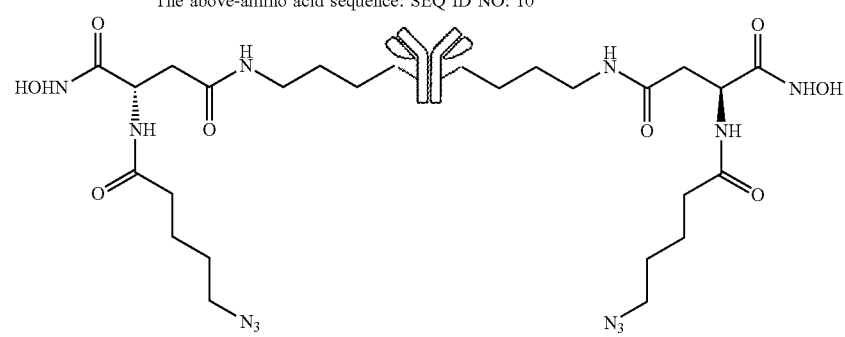 |
| 22 | 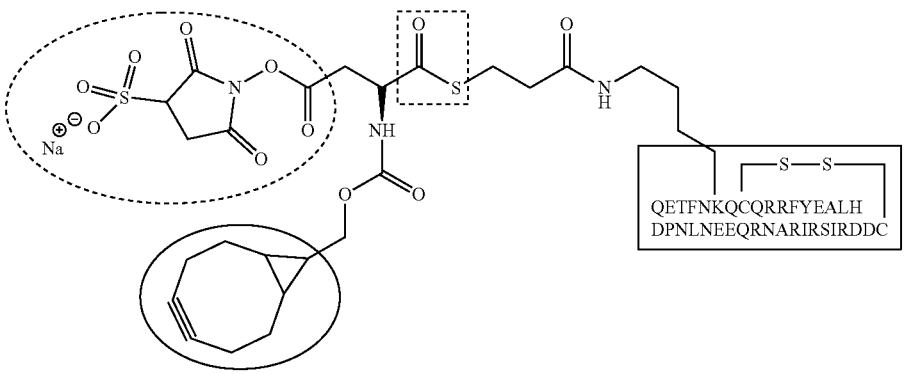 |
| | The above-amino acid sequence: SEQ ID NO: 10 |
| Antibody having bioorthogonal functional groups which can be produced by using the compound* | 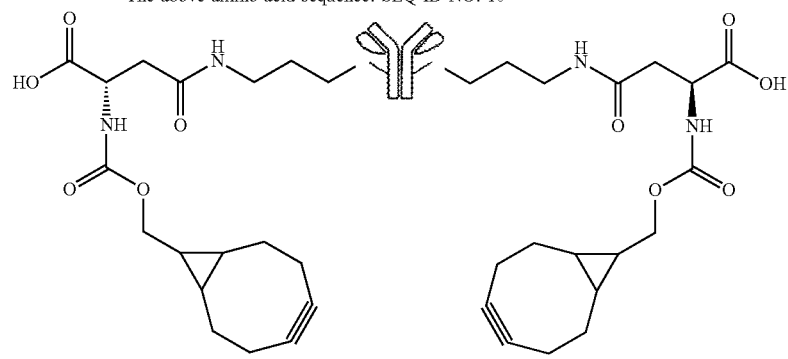 |

| Example | Specific Structure of Compound<br>□: Affinity substance (A)<br>⬚: Cleavable portion (in L)<br>○: Bioorthogonal functional group B(a) or L(ii)<br>◌: Reactive group (R) |
|---|---|
| 23 | 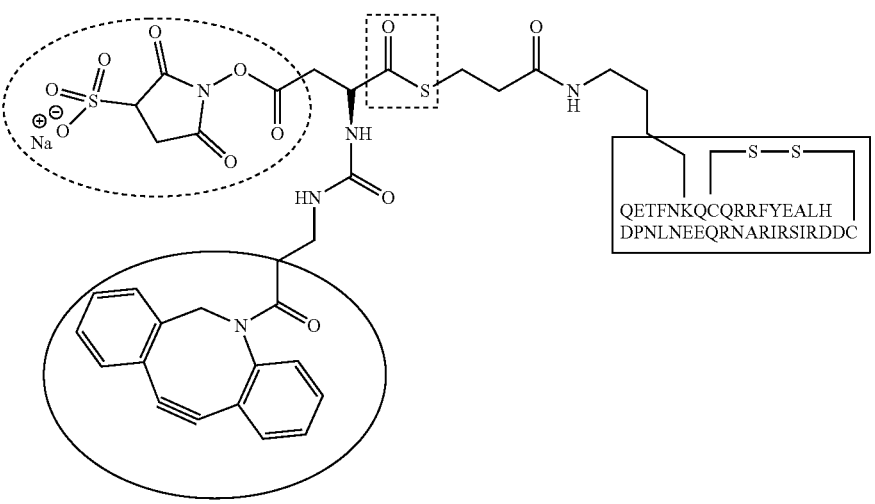
The above-amino acid sequence: SEQ ID NO: 10 |
| Antibody having bioorthogonal functional groups which can be produced by using the compound* | 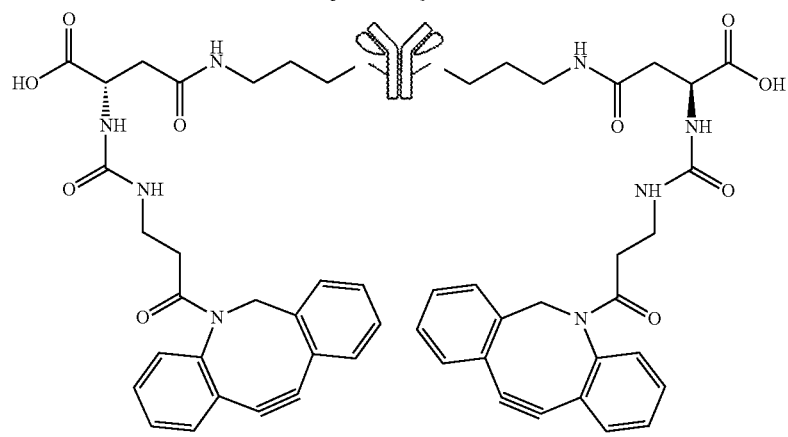 |
| 24 | 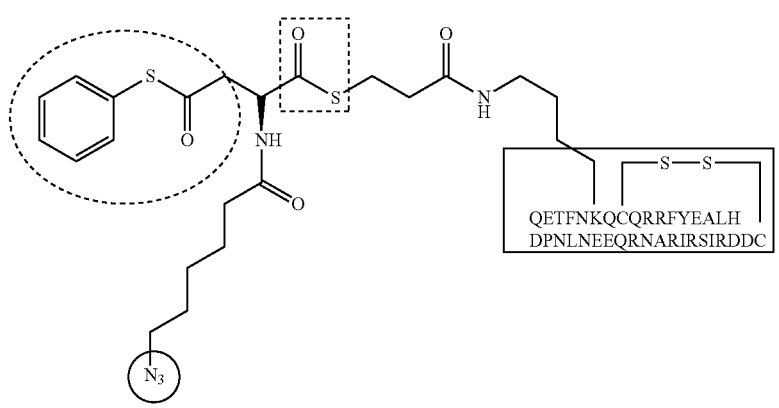
The above-amino acid sequence: SEQ ID NO: 10 |

-continued

Specific Structure of Compound
☐: Affinity substance (A)
⬚: Cleavable portion (in L)
○: Bioorthogonal functional group B(a) or L(ii)
◌: Reactive group (R)

| Example | |
|---|---|
| Antibody having bioorthogonal functional groups which can be produced by using the compound* | 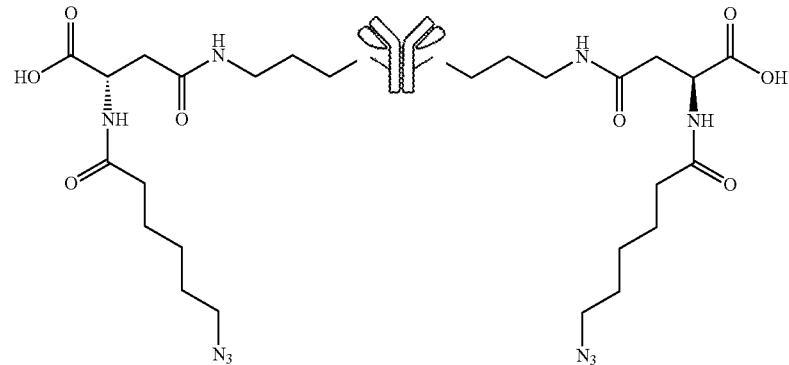 [SMILES: CCCCNC(=O)C[C@H](NC(=O)CCCCCN=[N+]=[N-])C(=O)O ; CCCCNC(=O)C[C@H](NC(=O)CCCCCN=[N+]=[N-])C(=O)O] |
| 25 | 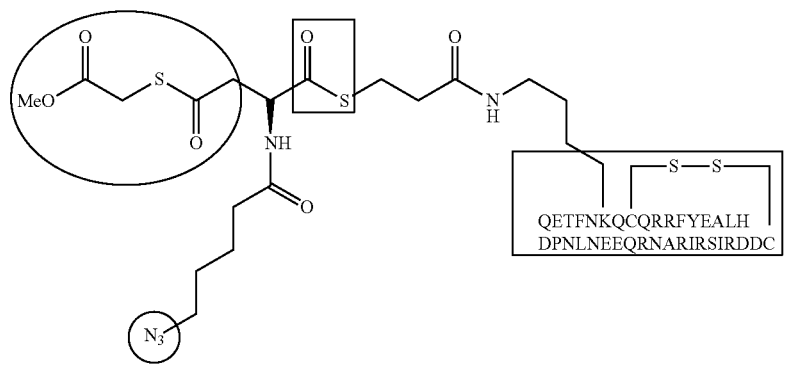<br>The above-amino acid sequence: SEQ ID NO: 10 |
| Antibody having bioorthogonal functional groups which can be produced by using the compound* | 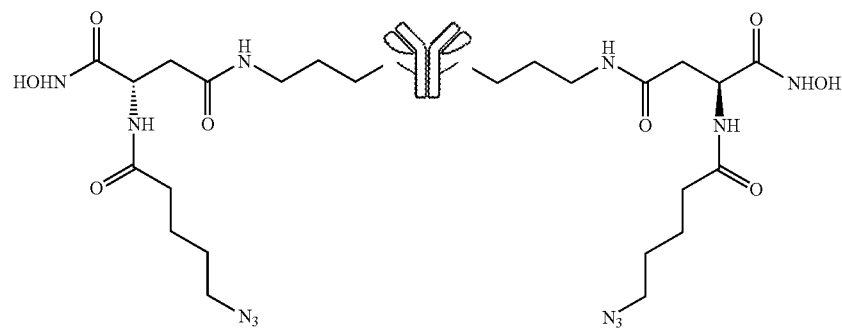 |

It has been indicated from the foregoing that in a compound having an affinity substance to an antibody (a polypeptide comprising a glutamine residue (Q) at an N-terminal), a cleavable portion, and a reactive group, the antibody can be modified regioselectively by adjusting factors such as the type of the affinity substance, the length of a linker between the affinity substance and the reactive group, and the position in the affinity substance to which the linker is introduced appropriately.

Reference Example 1: Synthesis of a Compound Having an Affinity Substance to a Soluble Protein, a Cleavable Portion, and a Reactive Group (Peptide- and Disulfide Linker-Coupled NHS-Activation Compound), and Modification and Analysis of Anti-HER2 IgG Antibody Trastuzumab Using the Compound (1-1) Synthesis of IgG1 Fc-Binding Peptide A sequence of Ac-FNMQCQRRFYEALHDPNLNK EQRNARIRSIRDDC-NH$_2$ (SEQ ID NO: 46) was synthesized by a Fmoc solid-phase synthesis method to obtain a desired product.

Fmoc Solid Phase Synthesis Method

As a peptide synthesizing device, Syro wave manufactured by Biotage was used. All reagents used were manufactured by Watanabe Chemical Industry. For Resin, Fmoc-NH-SAL-PEG Resin, HL was used, and arginine (R), cysteine (C), and histidine (H) were subjected to double coupling. Cutting from Resin was performed under condition of stirring in a solution of trifluoroacetic acid:water triisopropylsilane:ethanedithiol=94:2.5:1.0:2.5 for three hours. After cutting, Resin was removed by filtration to remove trifluoroacetic acid. Diethyl ether was added to the crystals thus formed to perform ether precipitation, and the white crystals thus formed were collected by filtration. These crystals were dissolved in a 0.1% aqueous trifluoroacetic acid solution, subjected to reverse phase high performance liquid chromatography using octadodecyl group chemical bond type silica gel as a filler, and eluted with a mixed solution of water and acetonitrile comprising 0.16 trifluoroacetic acid. Each fraction was determined by LC-MS. A fraction comprising a product was collected, and concentrated under reduced pressure to remove only acetonitrile. Then, the resulting residue was freeze-dried.

(1-2) Formation of Intramolecular Disulfide Bonds at Cys at Positions 5 and 34 of Ac-FNMQCQRRFYEALH DPNLNKEQRNARIRSIRDDC-NH$_2$ (SEQ ID NO: 46)

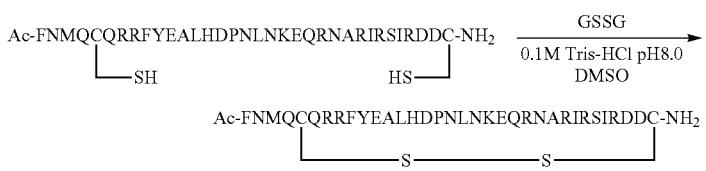

The above amino acid sequence is SEQ ID NO: 46.

The peptide synthesized in (1-1) was dissolved in DMSO, and 0.1 M Tris-HCl pH 8.0 was added thereto. An oxidized glutathione was added to this solution, and the resulting mixture was stirred at room temperature for 20 hours. A 2 M trifluoroacetic acid aqueous solution was added to the reaction solution to stop the reaction. The resulting solution was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05% trifluoroacetic acid. Each fraction was determined by LC-MS. A fraction comprising a product was collected and concentrated under reduced pressure to remove acetonitrile. Thereafter, the resulting residue was freeze-dried to obtain a desired product (23.0 mg, 5.38 µmol).

MS (ESI) D/z:4 1070.55[M+4H]$^{4+}$, z=5 856.55 [M+5H]$^{5+}$ (1-3) Coupling of disulfide linker with peptide

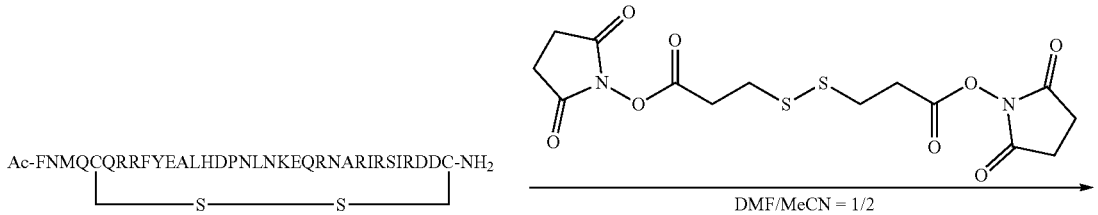

-continued

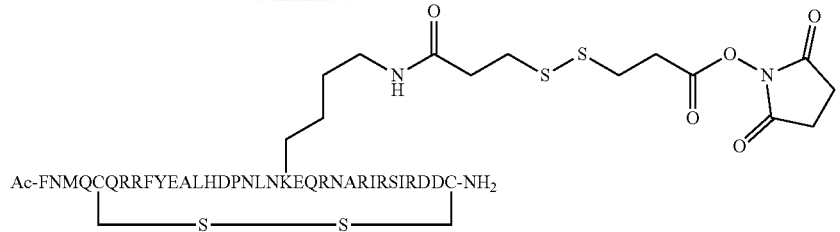

Ac-FNMQCQRRFYEALHDPNLNKEQRNARIRSIRDDC-NH2

The above amino acid sequence is SEQ ID NO: 46.

Ac-FNMQCQRRFYEALHDPNLNKEQRNARIRSIR DDC-NH$_2$ (SEQ ID NO: 46) (23.0 mg, 5.38 μmol, where the 5th and 34th cysteines form disulfide bonds in the molecule, respectively) synthesized in (1-2) was dissolved in N,N-dimethylformamide (1.00 mL). To the resulting solution, a solution obtained by dissolving 3,3'-dithiodipropionic acid di(N-succinimidyl) (87.0 mg, 215 mol) in acetonitrile (1.00 mL) was added, and the resulting mixture was stirred at room temperature for 24 hours. The resulting solution was concentrated under reduced pressure to remove acetonitrile. Thereafter, the resulting residue was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05 trifluoroacetic acid. Each fraction was determined by LC-MS. A fraction comprising a product was collected and concentrated under reduced pressure to remove acetonitrile. Thereafter, the resulting residue was freeze-dried to obtain the above peptide- and disulfide linker-coupled NHS-activation compound (16.0 mg, 3.50 μmol).

MS(ESI) D/z:z=5 914.45[M+5H]$^{5+}$, z=6 762.15[M+ 6H]$^{6+}$

HPLC purity: 83%

(1-4) Specific Modification of Anti-HER2 IgG Antibody Trastuzumab and Analysis Thereof by ESI-TOFMS The peptide- and disulfide linker-coupled NHS-activation compound synthesized in (1-3) was dissolved in N,N'-dimethylformamide to adjust the concentration to 4 mM. 500 μg of anti-HER2 IgG antibody trastuzumab (Chugai Pharmaceutical Co., Ltd.) was dissolved in 171 μL of 50 mM sodium acetate buffer (pH 5.5), 4.2 μL (5 equivalents to the antibody) of 4 mM peptide reagent was added thereto, and the resulting mixture was stirred at room temperature for one hour. The reaction solution was added to a NAP-5 column to stop the reaction and substituted with 20 mM PBS buffer. The mass was measured by ESI-TOFMS; for the raw material trastuzumab, a peak was observed at 148065, for a product with one binding peptide introduced, a peak was observed at 152525, and for a product with two binding peptides introduced, a peak was observed at 156978.

(1-5) HIC-UPLC Analysis of Specific Modification of Anti-HER2 IgG Antibody Trastuzumab The antibody-peptide conjugate formed in (1-4) and the raw material antibody were analyzed by HIC. As the column, Protein-Pak Hi Res HIC Column (Waters) 4.6×100 mm 2.5 μm was used. Detection was performed by using A_Buffer: 0.1 M PiNa, 2.3 M (NH$_4$)$_2$SO$_4$, pH 7.0 and B_Buffer: 0.1 M PiNa at pH 7.0 at a flow rate of 0.6 ml/min at gradient A60% B40%→A0% B100% for 16 min (data collection 20 min) at a column temperature of 40° C. at a thermostat temperature of 40° C. at a detector wavelength of 280 nm.

Figure 16:
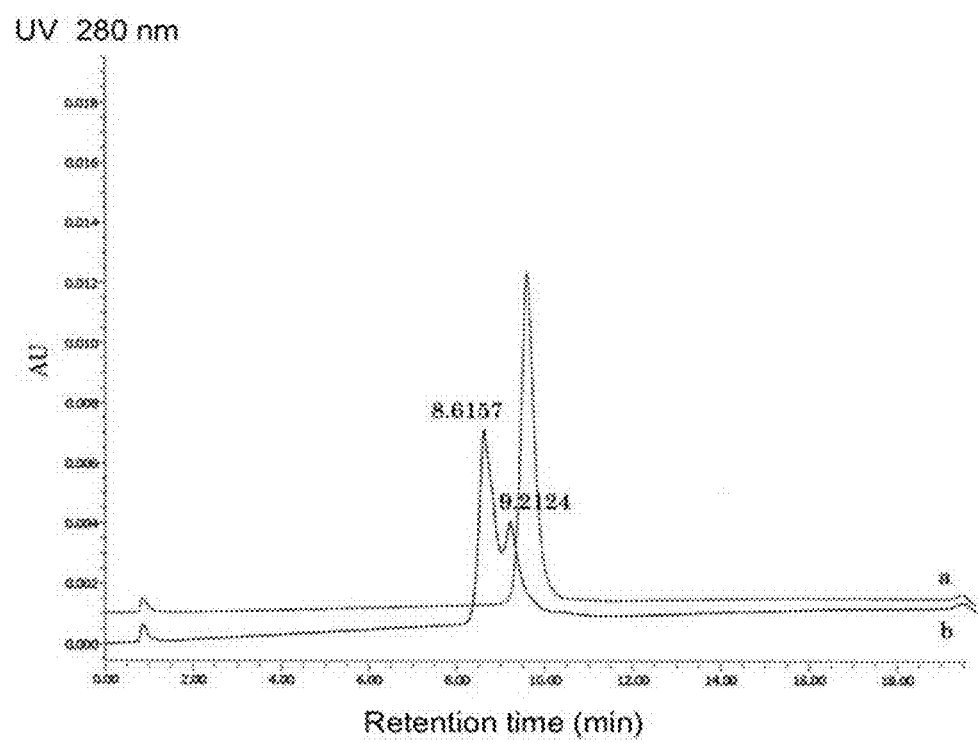
FIG. 16 is a diagram illustrating results of HIC-UPLC analysis of specific modification of trastuzumab (detection wavelength: UV 280 nm).

A sample was reacted under the following conditions.
a: Trastuzumab raw material
b: Trastuzumab+5 equivalents of peptide- and disulfide linker-coupled NHS-activation compound A compound having Retension Time of 9.2124 minutes is considered to be a compound with one peptide introduced, and a compound having Retension Time of 8.6157 minutes is considered to be a compound with two peptides introduced (FIG. 16).

Reference Example 2: Peptide Mapping of Thiol-Introduced Trastuzumab (2-1) Trypsin Treatment of Thiol-Introduced Trastuzumab To a 1.5 mL low-adsorption micro test tube, 10 μL of a sample solution (comprising the thiol-introduced trastuzumab prepared in Reference Example 1), a 50 mM ammonium hydrogencarbonate buffer, and 10 μL of a 20 mM aqueous dithiothreitol solution dissolved in 40% trifluoroethanol were added. The resulting mixture was heated at 65° C. for one hour, then 10 μL of a 50 mM aqueous iodoacetamide solution was added thereto, and the resulting mixture was reacted in a dark place at room temperature for 30 minutes while being shaken at 300 rpm. After the reaction, 40 μL of a 50 mM ammonium hydrogencarbonate buffer was added thereto, the resulting mixture was stirred, 10 μL of a 20 ng/μL aqueous trypsin solution (Proteomics Grade, Code No. T6567-5×20 μg(SIGMA)) was added thereto, and the resulting mixture was subjected to enzyme digestion at 37° C. for 18 hours. After the digestion, 2 μL of a 20% aqueous trifluoroacetic acid solution was added thereto to stop the reaction, and LC-MS/MS measurement was performed.

(2-2) LC-MS/MS Measurement Conditions for Trastuzumab Analyzer

Nano HPLC: EASY-nLC 1000 (Thermo Fisher Scientific)
Mass Spectrometer: Tribrid Mass Spectrometer Orbitrap Fusion (Thermo Fisher Scientific)
HPLC Analysis Conditions
Trap column: Acclaim PepMap (registered trademark) 100, 75 μm×2 cm, (Thermo Fisher Scientific)
Analysis column: ESI-column (NTCC-360/75-3-125, 75 μm×12.5 cm, 3 μm (Nikkyo Technos Co., Ltd.))
Mobile Phase A: a 0.1% aqueous formate solution
Mobile Phase B: a 0.1% formate acetonitrile solution
Loading solution: a 0.1% aqueous trifluoroacetic acid solution
Flow rate: 300 nL/min
Sample injection amount: 1 μL
Gradient condition (B %): 2% (0.0 minute to 0.5 minute), 2%→30% (0.5 minute to 23.5 minutes), 30%→75% (23.5 minutes to 25.5 minutes), and 75% (25.5 minutes to 35.0 minutes).

Mass Spectrometer Analysis Conditions
Ionization: ESI, Positive mode
Scan type: Data Dependent Acquisition
Activation Type: Collision Induced Dissociation (CID)
Data acquisition was performed using Xcalibur 3.0 (Thermo Fisher Scientific) and Thermo Orbitrap Fusion Tune Application 2.0 (Thermo Fisher Scientific) as accompanying software.

(2-3) Analysis Conditions for Modified Site of Trastuzumab

Modified site analysis of an LC-MS/MS measurement result was performed using Proteome Discoverer version 1.4 (Thermo Fisher Scientific).

For analysis with Proteome Discoverer, Sequest HT was used as a search engine, and a precursor ion range was set to 350 to 5000 Da, and Total Intensity Threshold was set to 50000. Trypsin was set as a digestive enzyme, and Maximum Missed Cleavage Sites was set to 3. Values of Mass Tolerance of precursor and fragment ions were 5 ppm and 0.5 Da, respectively. For Static Modification, Carbamidomethyl (+57.021 Da) was set as modification of a cysteine residue with iodoacetamide. For Dynamic Modifications, oxidation of methionine (+15.995 Da) and a modified compound to a lysine residue (thiol-introduced compound subjected to carbamidomethylation with iodoacetamide (+145.019 Da)) were set. Furthermore, a filter was set such that only those with High Peptide Confidence were observed.

In addition, (1) and (3) illustrated in FIG. 4 were used as data of an amino acid sequence to be searched for a modification site.

(2-4) Analysis Result of Modified Site of Trastuzumab by LC-MS/MS

Figure 17:
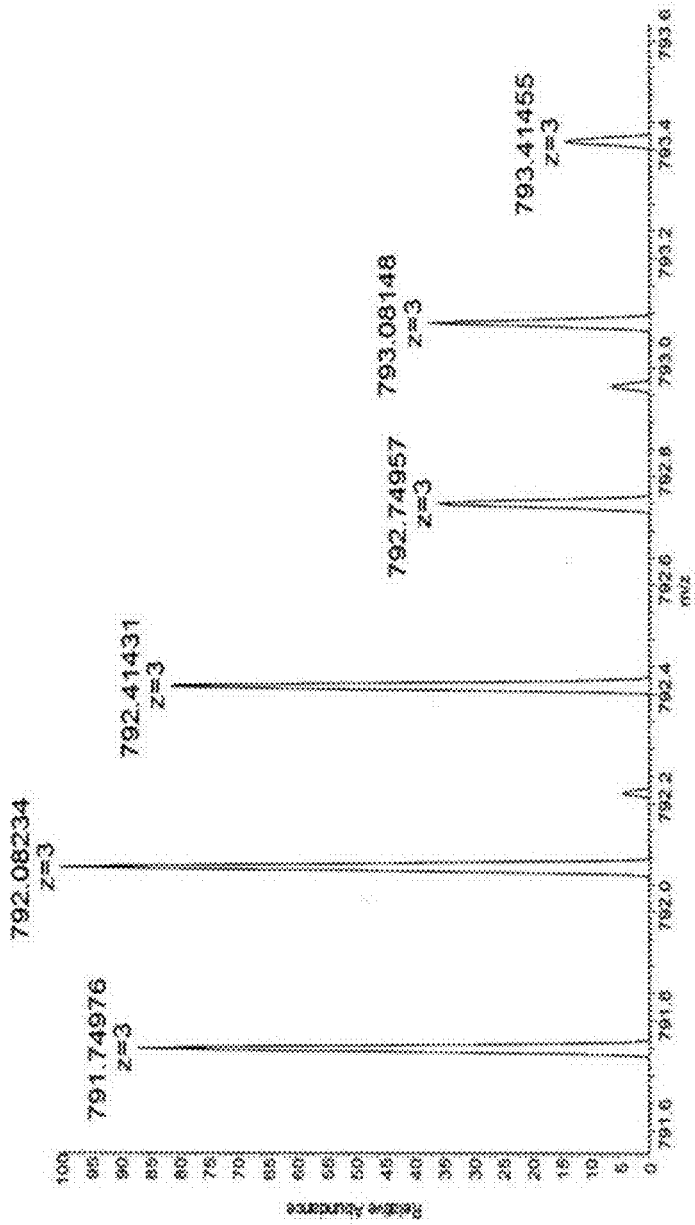
FIG. 17 is a diagram illustrating an MS spectrum of a peptide fragment of VVSVLTVLHQDWLNGKEYK (SEQ ID NO: 47) comprising a modified site to a lysine residue by trypsin digestion of trastuzumab (thiol-introduced compound (+145.019 Da) subjected to carbamidomethylation with iodoacetamide) modified with a binder peptide in Reference Example 1 (m/z 791.74872, trivalent).
Figure 18:
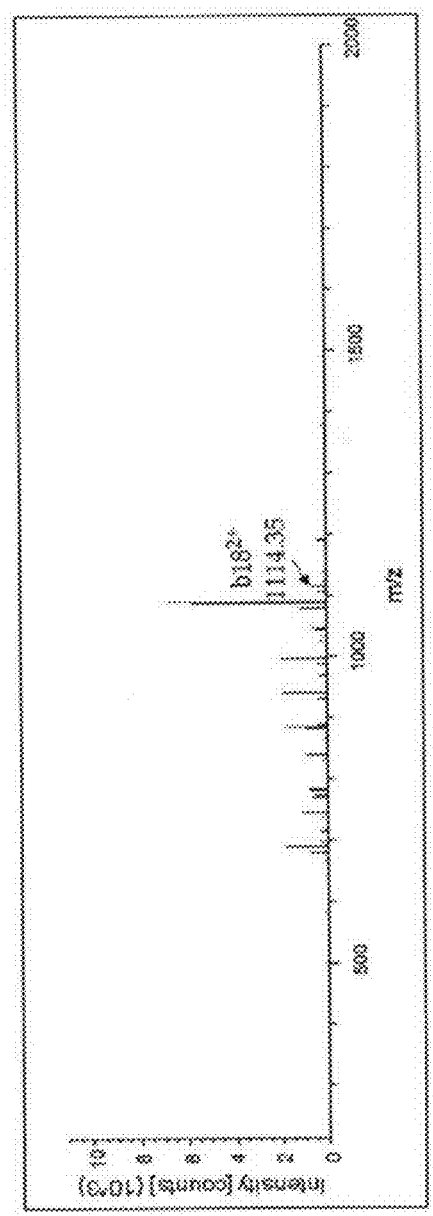
FIG. 18 is a diagram illustrating a CID spectrum of a peptide fragment of VVSVLTVLHQDWLNGKEYK (SEQ ID NO: 47) comprising a modified site to a lysine residue by trypsin digestion of trastuzumab (thiol-introduced compound (+145.019 Da) subjected to carbamidomethylation with iodoacetamide) modified with a binder peptide in Reference Example 1.
Figure 19:
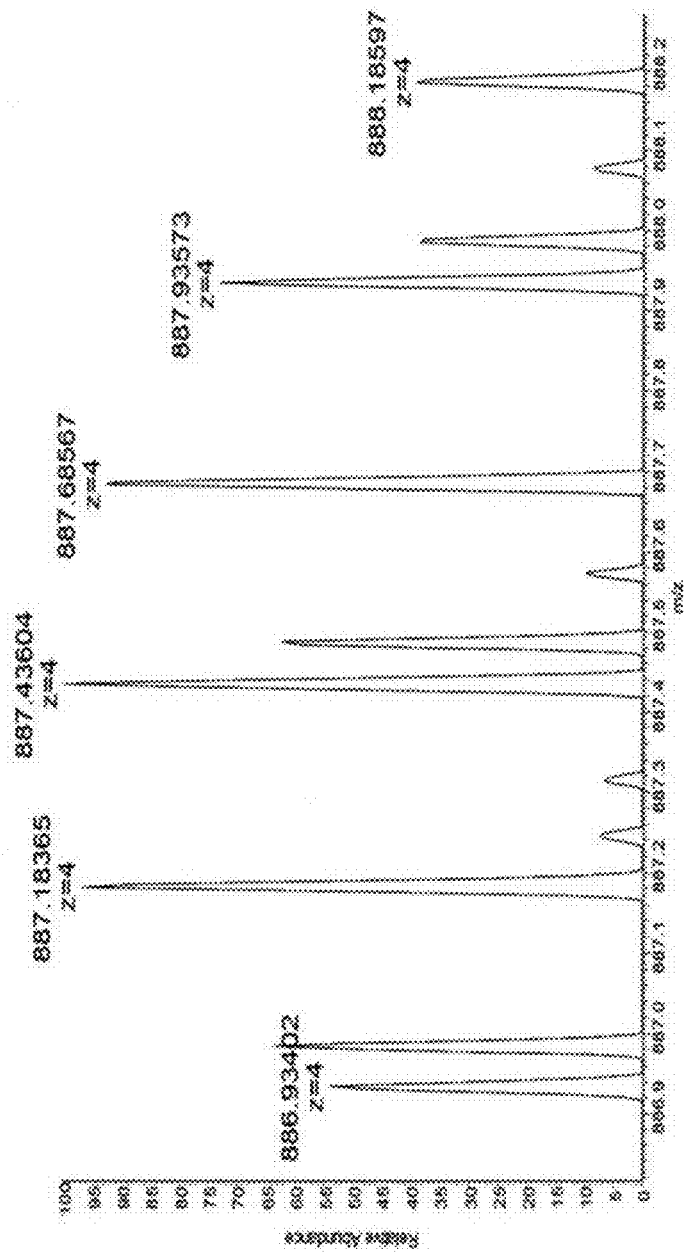
FIG. 19 is a diagram illustrating an MS spectrum of a peptide fragment of EEQYDSTYRVVSVLTVLHQDWLNGKEYK (SEQ ID NO: 48) comprising a modified site to a lysine residue by trypsin digestion of trastuzumab (thiol-introduced compound (+145.019 Da) subjected to carbamidomethylation with iodoacetamide) modified with a binder peptide in Reference Example 1 (m/z 886.93408, tetravalent).
Figure 20:
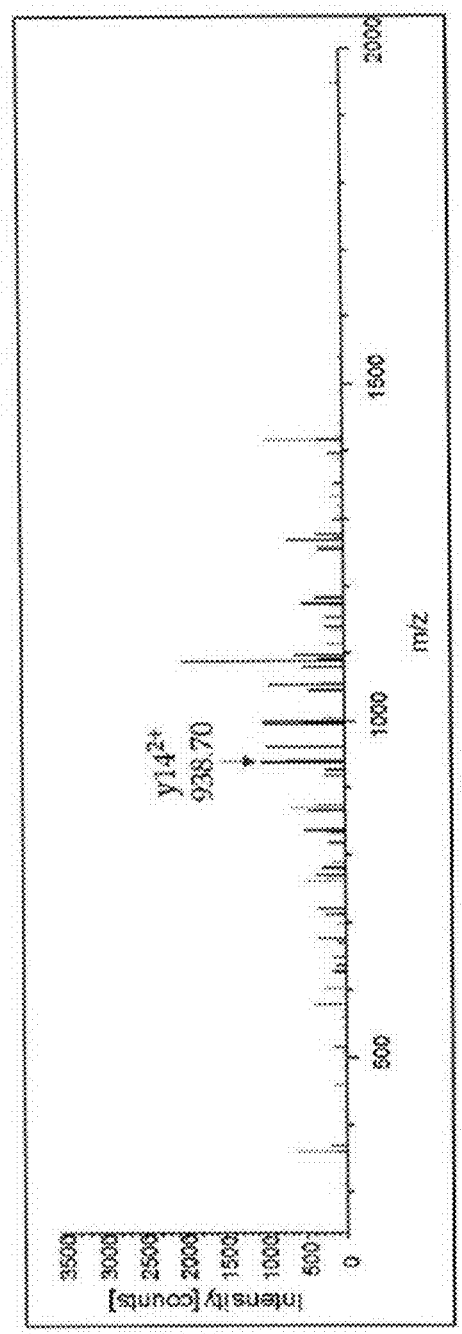
FIG. 20 is a diagram illustrating a CID spectrum of a peptide fragment of EEQYDSTYRVVSVLTVLHQDWLNGKEYK (SEQ ID NO: 48) comprising a modified site to a lysine residue by trypsin digestion of trastuzumab (thiol-introduced compound (+145.019 Da) subjected to carbamidomethylation with iodoacetamide) modified with a binder peptide in Reference Example 1.

As a result of analysis using LC-MS/MS, an MS spectrum of a peptide fragment of VVSVLTVLHQDWLNGKEYK (SEQ ID NO: 47), which is a peptide consisting of 19 amino acid residues comprising a modified site to a lysine residue by trypsin digestion of trastuzumab (thiol-introduced compound (+145.019 Da) subjected to carbamidomethylation with iodoacetamide) modified with the binder peptide in Reference Example 1 (measured value: m/z 791.74872; theoretical value: 791.74753; trivalent) was observed (FIG. 17); and from a CID spectrum, a product ion of m/z 1114.35 (theoretical value: 1114.06) corresponding to divalent b18 indicating modification of a lysine residue at position 317 of a heavy chain in EU numbering was determined (FIG. 18). In addition, an MS spectrum of a peptide fragment of EEQYDSTYRVVSVLTVLHQDWLNGKEYK (SEQ ID NO: 48), which is a peptide consisting of 28 amino acid residues comprising a modified site to a lysine residue by trypsin digestion (thiol-introduced compound (+145.019 Da) subjected to carbamidomethylation with iodoacetamide) (measured value: m/z 886.93408; theoretical value: 886.93215; tetravalent) was observed (FIG. 19); and from a CID spectrum, a product ion of m/z 938.70 (theoretical value: 938.46) corresponding to divalent y14 indicating modification of a lysine residue at position 317 of a heavy chain in EU numbering was determined (FIG. 20).

Reference Example 3: Synthesis of a Compound Having an Affinity Substance to a Soluble Protein, a Cleavable Portion, and a Reactive Group (Peptide- and Disulfide Linker-Coupled NHS-Activation Compound), and Modification and Analysis of Anti-HER2 IgG Antibody Trastuzumab Using the Compound (3-1) Synthesis of IgG1 Fc-Binding Peptide A sequence of Ac-FNMQCQRRFYEALHDPNLNE-EQRNARIRSIKDDC-NH$_2$ (SEQ ID NO: 49) was synthesized by an Fmoc solid-phase synthesis method in a similar manner to Reference Example 1. A desired product was obtained.

(3-2) Formation of Intramolecular Disulfide Bond at Cys at Positions 5 and 34 of Ac-FNMQCQRRFYEALHDPNLNE-EQRNARIRSIKDDC-NH$_2$ (SEQ ID NO: 49)

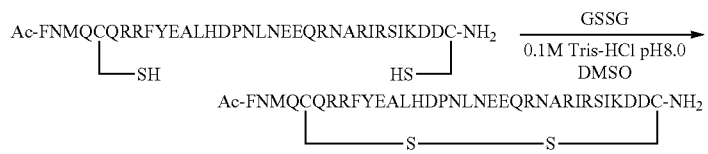

The amino acid sequence is SEQ ID NO: 49.

The peptide synthesized in (3-1) was dissolved in DMSO, and 0.1 M Tris-HCl pH 8.0 was added thereto. An oxidized glutathione was added to this solution, and the resulting mixture was stirred at room temperature for 20 hours. A 2 M trifluoroacetic acid aqueous solution was added to the reaction solution to stop the reaction. The resulting solution was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05% trifluoroacetic acid. Each fraction was determined by LC-MS. A fraction comprising a product was collected and concentrated under reduced pressure to remove acetonitrile. Thereafter, the resulting residue was freeze-dried to obtain a desired product (20.0 mg, 4.70 μmol).

MS(ESI) D/z:z=4 1063.65[M+4H]$^{4+}$, z=5 851.15 [M+5H]$^{5+}$ (3-3) Coupling of Disulfide Linker with Peptide

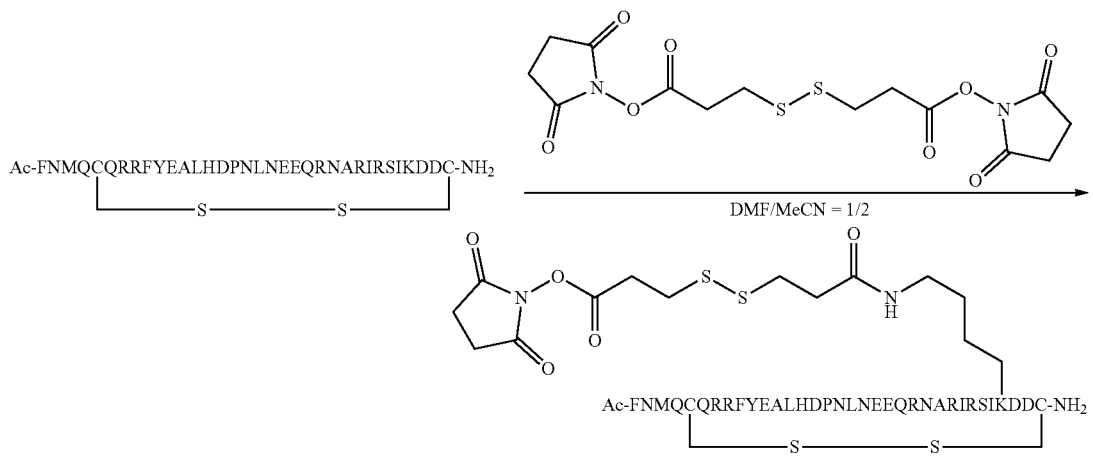

The amino acid sequence is SEQ ID NO: 49.

Ac-FNMQCQRRFYEALRDPNLNEEORNARIRSIK-DDC-NH$_2$ (SEQ ID NO: 49) (20.0 mg, 4.70 μmol, where the 5th and 34th cysteines form disulfide bonds in the molecule, respectively) synthesized in (3-2) was dissolved in N,N-dimethylformamide (1.00 mL). To the resulting solution, a solution obtained by dissolving 3,3'-dithiodipropionic acid di(N-succinimidyl) (76.0 mg, 1813 μmol) in acetonitrile (1.00 mL) was added, and the resulting mixture was stirred at room temperature for 24 hours. The resulting solution was concentrated under reduced pressure to remove acetonitrile. Thereafter, the resulting residue was dissolved in a 0.05% aqueous trifluoroacetic acid solution, subjected to reverse phase high performance liquid chromatography using octadodecyl group chemical bond type silica gel as a filler, and eluted with a mixed solution of water and acetonitrile comprising 0.05% trifluoroacetic acid. Each fraction was determined by LC-MS. A fraction comprising a product was collected and concentrated under reduced pressure to remove acetonitrile. Thereafter, the resulting residue was freeze-dried to obtain the above peptide- and disulfide linker-coupled NHS-activation compound (12.0 mg, 2.63 mol).

MS(ESI) D/z:z=5 908.95[M+5H]$^{5+}$, z=6 757.75[M+6H]$^{6+}$

HPLC purity: 83%

(3-4) Specific Modification of Anti-HER2 IgG Antibody Trastuzumab and Analysis Thereof by ESI-TOFMS The peptide- and disulfide linker-coupled NHS-activation compound synthesized in (3-3) was dissolved in N,N'-dimethylformamide to adjust the concentration to 4 mM. 500 μg of anti-HER2 IgG antibody trastuzumab (Chugai Pharmaceutical Co., Ltd.) was dissolved in 171 μL of 50 mM sodium acetate buffer (pH 5.5), 8.5 μL (10 equivalents to the antibody) of 4 mM peptide reagent was added thereto, and the resulting mixture was stirred at room temperature for one hour. The reaction solution was added to a NAP-5 column to stop the reaction and substituted with 20 mM PBS buffer. The mass was measured by ESI-TOFMS; for the raw material trastuzumab, a peak was observed at 148234, for a product with one binding peptide introduced, a peak was observed at 152648, and for a product with two binding peptides introduced, a peak was observed at 157083.

(3-5) Determination of Heavy Chain Selectivity of Specific Modified Compound of Trastuzumab Under Reduction Conditions by ESI-TOFMS Analysis To the antibody-peptide conjugate formed in (3-4), 5 μL of a 7 mM tris(2-carboxyethyl) phosphine hydrochloride solution (equivalent to the antibody) was added, and the resulting mixture was stirred at room temperature for 20 minutes. The mass was measured by ESI-TOFMS; for the product, heavy chain peaks were observed at 50686 and 50847 with a thiopropionyl group introduced into the heavy chain, and a light chain peak was observed at 23439, the same as that of the raw material.

(3-6) HIC-UPLC Analysis of Specific Modification of Anti-HER2 IgG Antibody Trastuzumab The antibody-peptide conjugate formed in (3-4) and the raw material antibody were analyzed by HIC. As the column, Protein-Pak Hi Res HIC Column (Waters) 4.6×100 mm 2.5 μm was used. Detection was performed by using A_Buffer: 0.1 M PiNa, 2.3 M (NH$_4$)$_2$SO$_4$, pH 7.0 and B_Buffer: 0.1 M PiNa at pH 7.0 at a flow rate of 0.6 ml/min at gradient A60% B40%→A0% B100% for 16 min (data collection 20 min) at a column temperature of 40° C. at a thermostat temperature of 40° C. at a detector wavelength of 280 nm.

Figure 21:
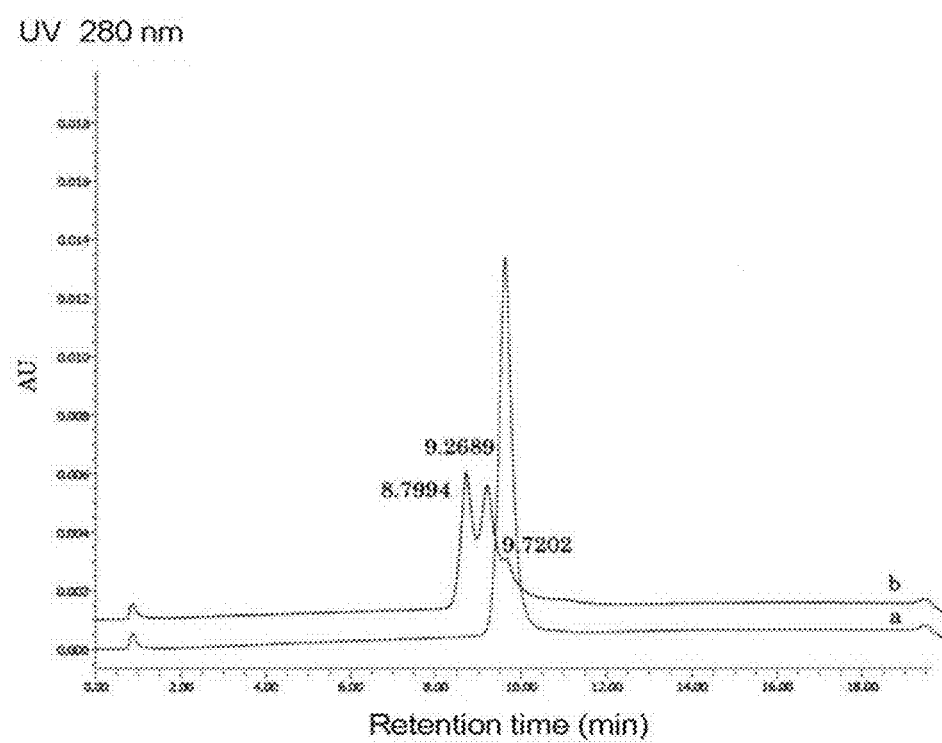
FIG. 21 is a diagram illustrating results of HIC-UPLC analysis of specific modification of trastuzumab (detection wavelength: UV 280 nm) (Reference Example 3).

A sample was reacted under the following conditions.
a: Trastuzumab raw material
b: Trastuzumab+10 equivalents of peptide- and disulfide linker-coupled NHS-activation compound A compound having Retension Time of 9.7202 minutes is considered to be the trastuzumab raw material, a compound having Retension Time of 9.2689 minutes is considered to be a compound with one peptide introduced, and a compound having Retension Time of 8.7994 minutes is considered to be a compound with two peptides introduced (FIG. 21).

Reference Example 4: Peptide Mapping of Thiol-Introduced Trastuzumab (4-1) Trypsin Treatment of Thiol-Introduced Trastuzumab
The same processing as in Reference Example (2-1) was performed.

(4-2) LC-MS/MS Measurement Conditions for Trastuzumab
The same measurement conditions as in Reference Example (2-2) were used.

(4-3) Analysis Conditions for the Modified Site of Trastuzumab

The same analysis conditions as in Reference Example (2-3) were used.

(4-4) Analysis Result of Modified Site of Trastuzumab by LC-MS/MS

Figure 22:
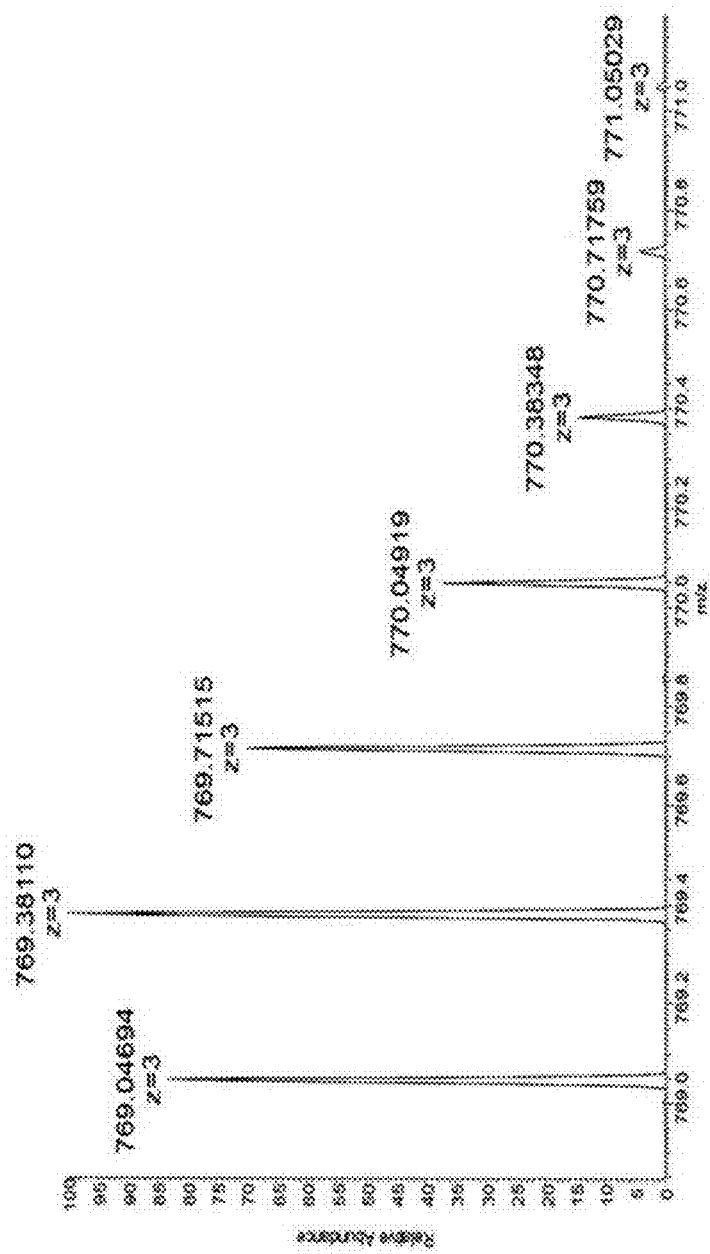
FIG. 22 is a diagram illustrating an MS spectrum of a peptide fragment of FNWYVDGVEVHNAKTKPR (SEQ ID NO: 50) comprising a modified site to a lysine residue by trypsin digestion of trastuzumab (thiol-introduced compound (+145.019 Da) subjected to carbamidomethylation with iodoacetamide) modified with a binder peptide in Reference Example 3 (m/z 769.04688, trivalent).
Figure 23:
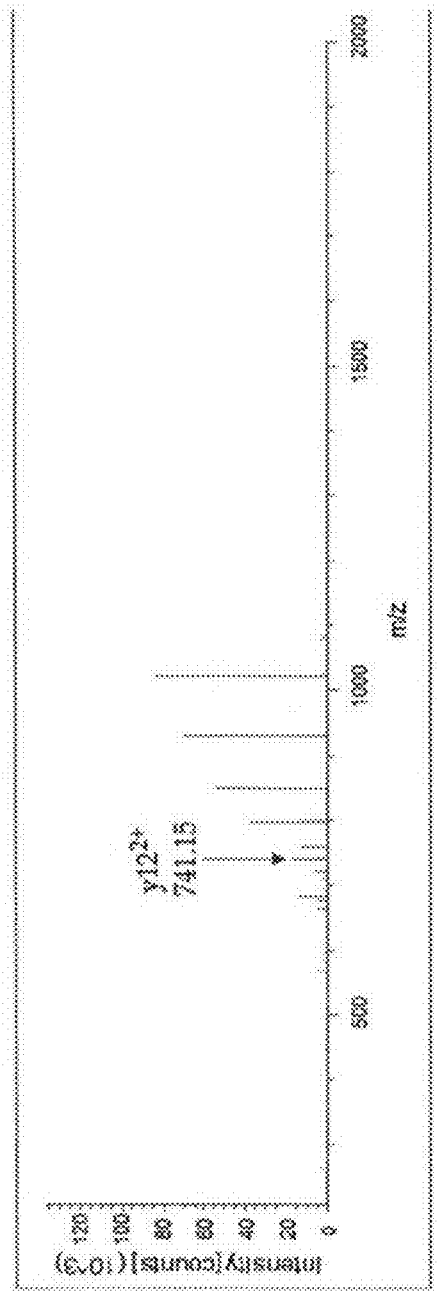
FIG. 23 is a diagram illustrating a CID spectrum of a peptide fragment of FNWYVDGVEVHNAKTKPR (SEQ ID NO: 50) comprising a modified site to a lysine residue by trypsin digestion of trastuzumab (thiol-introduced compound (+145.019 Da) subjected to carbamidomethylation with iodoacetamide) modified with a binder peptide in Reference Example 3.

As a result of analysis using LC-MS/MS, an MS spectrum of a peptide fragment of FNWYVDGVEVHNAKTKPR (SEQ ID NO: 50), which is a peptide consisting of 18 amino acid residues comprising a modified site to a lysine residue by trypsin digestion of trastuzumab (thiol-introduced compound (+145.019 Da) subjected to carbamidomethylation with iodoacetamide) modified with the binder peptide in Reference Example 3 (measured value: m/z 769.04688; theoretical value: 769.04457; trivalent) was observed (FIG. 22); and from a CID spectrum, a product ion of m/z 741.15 (theoretical value: 740.89) corresponding to divalent y12 indicating modification of a lysine residue at position 288 or 290 of a heavy chain in EU numbering was determined (FIG. 23).

INDUSTRIAL APPLICABILITY

For example, the present invention is useful for production of a regioselectively modified antibody.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

---

The invention claimed is:

1. A compound having an affinity substance to an antibody, a cleavable portion, and a reactive group, or a salt thereof, the compound being represented by the following Formula (I):

A-L-B—R    (I), wherein
A is the affinity substance to an antibody,
L is a cleavable linker that is a divalent group comprising the cleavable portion,
B is (a) a divalent group comprising a bioorthogonal functional group or (b) a divalent group comprising no bioorthogonal functional group, wherein the bioorthogonal functional group has a chemical structure selected from the group consisting of the following:

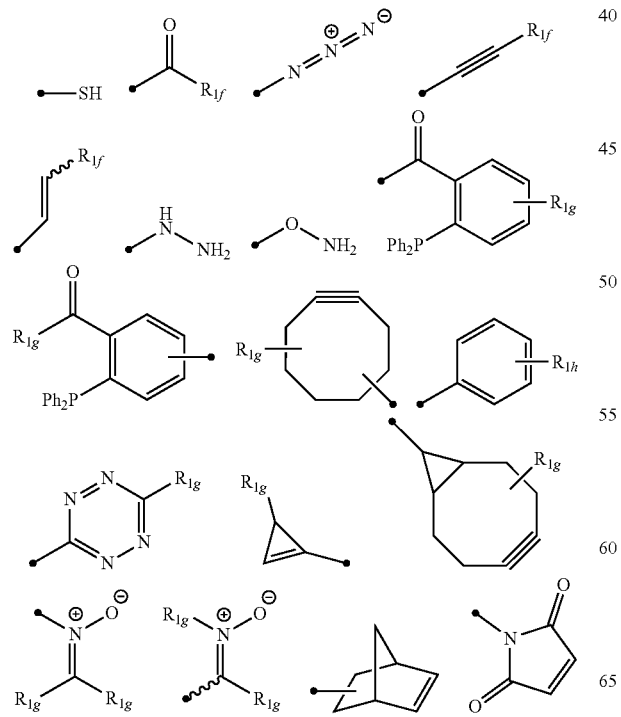

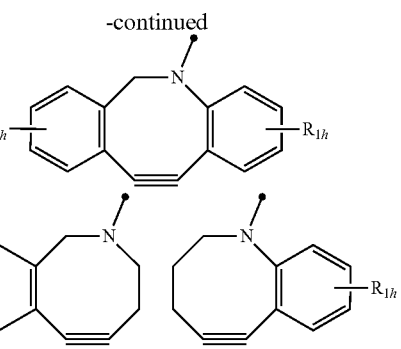

wherein
$R_{1f}$, one or a plurality of $R_{1g}$s, and one or a plurality of $R_{1h}$s are the same as or different from each other, and are each an atom or a group selected from the group consisting of the substituent (i) to (vii) or an electron-withdrawing group, and
● is a bond,
wherein the substituent (i) to (vii) are:
(i) a halogen atom;
(ii) a monovalent hydrocarbon group;
(iii) an aralkyl;
(iv) a monovalent heterocyclic group;
(v) $R_c$—O—, $R_c$—C(=O)—, $R_c$—O—C(=O)—, or $R_c$—C(=O)—O—, wherein $R_c$ represents a hydrogen atom or a monovalent hydrocarbon group;
(vi) $NR_dR_e$—, $NR_dR_e$—C(=O)—, $NR_dR_e$—C(=O)—O—, or $R_d$—C(=O)—$NR_e$—, wherein $R_d$ and $R_e$ are the same as or different from each other, and each represent a hydrogen atom or a monovalent hydrocarbon group; or
(vii) a nitro group, a sulfate group, a sulfonate group, a cyano group, or a carboxyl group, and
R is the reactive group to the antibody,
wherein the affinity substance to an antibody is a polypeptide comprising a glutamine residue (Q) at an N-terminal terminal and is selected from the group consisting of the following (1) to (4):

(1)

Q—[antibody-affinity polypeptide portion]

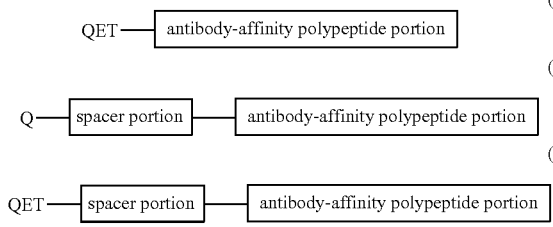

(2)

(3)

(4)

wherein Q is a glutamine residue at an N-terminal, E is a glutamic acid residue, T is a threonine residue, the solid line is a bond, the spacer portion consists of 1 to 50 amino acid residues, and the antibody-affinity polypeptide portion consists of 15 to 70 amino acid residues, wherein the antibody-affinity polypeptide portion is selected from the group consisting of protein A, protein G, protein L, protein Z, and a fragment thereof having affinity to an antibody, and a variant thereof having affinity to an antibody.

2. The compound or salt thereof according to claim 1, wherein the glutamine residue is pyroglutamylated.

3. The compound or salt thereof according to claim 1, wherein the antibody-affinity polypeptide portion comprises an amino acid sequence with any one amino acid residue substituted with a lysine residue in the amino acid sequence of FNMQCQRRFYEALHDPNLNEEQRNAXIXSIRDDC (SEQ ID NO: 5) and having at least 90% identity to the amino acid sequence of SEQ ID NO: 5, and
wherein two Xs are each independently one amino acid residue selected from the group consisting of an arginine residue, a glutamic acid residue, and a glutamine residue.

4. The compound or salt thereof according to claim 1, wherein the antibody-affinity polypeptide portion comprises an amino acid sequence with any one amino acid residue substituted with a lysine residue in the amino acid sequence of FNMQCQRRFYEALHDPNLNEEQRNARIRSIRDDC (SEQ ID NO: 6) and having at least 90% identity to the amino acid sequence of SEQ ID NO: 6.

5. The compound or salt thereof according to claim 1, wherein the affinity substance to an antibody comprises an amino acid sequence selected from the group consisting of the following:

(1)
(SEQ ID NO: 7)
QETNPTENLYFQQKNMQCQRRFYEALHDPNLNEEQRNARIRSIRDDC;

(2)
(SEQ ID NO: 8)
QTADNQKNMQCQRRFYEALHDPNLNEEQRNARIRSIRDDCSQSANLLAE
AQQLNDAQAPQA;

(3)
(SEQ ID NO: 9)
QETKNMQCQRRFYEALHDPNLNEEQRNARIRSIRDDC;

(4)
(SEQ ID NO: 10)
QETFNKQCQRRFYEALHDPNLNEEQRNARIRSIRDDC;

(5)
(SEQ ID NO: 22)
QETENMQCQRRFYEALHDPNLNKEQRNARIRSIRDDC;

(6)
(SEQ ID NO: 23)
QETENMQCQRRFYEALHDPNLNEEQRNARIRSIKDDC;

(7)
(SEQ ID NO: 51)
QETMQCQRRFYEALHDPNLNEEQRNARIRSIKDDC;

(8)
(SEQ ID NO: 52)
QETQCQRRFYEALHDPNLNEEQRNARIRSIKDDC;

(9)
(SEQ ID NO: 53)
QETCQRRFYEALHDPNLNEEQRNARIRSIKDDC;

(10)
(SEQ ID NO: 24)
QETRGNCAYHKGQLVWCTYH; and

(11)
(SEQ ID NO: 25)
QETRGNCAYHKGQIIWCTYH.

6. A reagent of regioselectively modifying an antibody, the reagent comprising a compound having an affinity substance to an antibody, a cleavable portion, and a reactive group, or a salt thereof, the compound being represented by the following Formula (I):

A-L-B—R  (I), wherein

A is the affinity substance to an antibody,

L is a cleavable linker that is a divalent group comprising the cleavable portion, B is (a) a divalent group comprising a bioorthogonal functional group or (b) a divalent group comprising no bioorthogonal functional group, wherein the bioorthogonal functional group corresponds to any one chemical structure selected from the group consisting of the following:

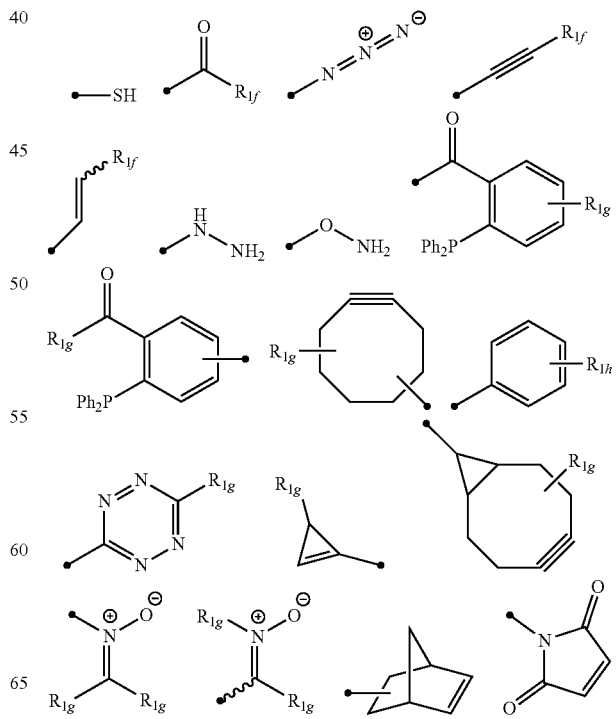

-continued

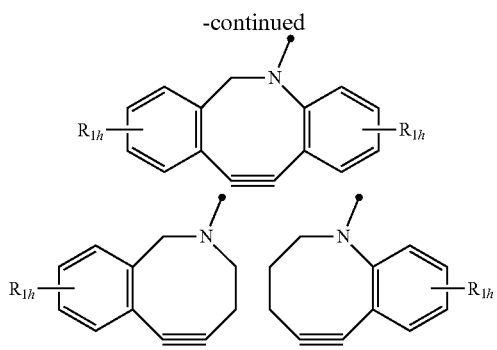

wherein $R_{1f}$, one or a plurality of $R_{1g}$s, and one or a plurality of $R_{1h}$s are the same as or different from each other, and are each an atom or a group selected from the group consisting of the substituent (i) to (vii) or an electron-withdrawing group, and ● is a bond, wherein the substituent (i) to (vii) are:
(i) a halogen atom;
(ii) a monovalent hydrocarbon group;
(iii) an aralkyl;
(iv) a monovalent heterocyclic group;
(v) $R_c$—O—, $R_c$—C(=O)—, $R_c$—O—C(=O)—, or $R_c$—C(=O)—O—, wherein $R_c$ represents a hydrogen atom or a monovalent hydrocarbon group;
(vi) $NR_dR_e$—, $NR_dR_e$—C(=O)—, $NR_dR_e$—C(=O)—O—, or $R_d$—C(=O)—$NR_e$—, wherein $R_d$ and $R_e$ are the same as or different from each other, and each represent a hydrogen atom or a monovalent hydrocarbon group; or
(vii) a nitro group, a sulfate group, a sulfonate group, a cyano group, or a carboxyl group, and R is the reactive group to the antibody, wherein the affinity substance to an antibody is a polypeptide comprising a glutamine residue (Q) at an N-terminal, and is selected from the group consisting of the following (1) to (4):

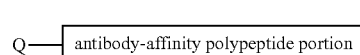 (1)

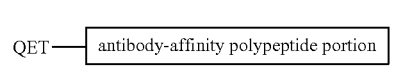 (2)

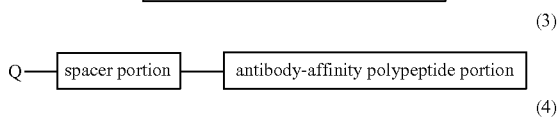 (3)

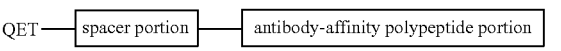 (4)

wherein Q is a glutamine residue at an N-terminal, E is a glutamic acid residue, T is a threonine residue, the solid line is a bond, the spacer portion consists of 1 to 50 amino acid residues, and the antibody-affinity polypeptide portion consists of 15 to 70 amino acid residues, wherein the antibody-affinity polypeptide portion is selected from the group consisting of protein A, protein G, protein L, protein Z, and a fragment thereof having affinity to an antibody, and a variant thereof having affinity to an antibody.

* * * * *